(12) United States Patent
Santamaria

(10) Patent No.: US 12,397,038 B2
(45) Date of Patent: Aug. 26, 2025

(54) UBIQUITOUS ANTIGENS FOR TREATMENT OF AUTOIMMUNE OR INFLAMMATORY DISEASES

(71) Applicant: UTI Limited Partnership, Calgary (CA)

(72) Inventor: Pedro Santamaria, Calgary (CA)

(73) Assignee: UTI Limited Partnership, Calgary (CA)

( * ) Notice: Subject to any disclaimer, the term of this patent is extended or adjusted under 35 U.S.C. 154(b) by 1002 days.

(21) Appl. No.: 16/767,392

(22) PCT Filed: Nov. 28, 2018

(86) PCT No.: PCT/IB2018/001520
§ 371 (c)(1),
(2) Date: May 27, 2020

(87) PCT Pub. No.: WO2019/106435
PCT Pub. Date: Jun. 6, 2019

(65) Prior Publication Data
US 2020/0390856 A1 Dec. 17, 2020

Related U.S. Application Data

(60) Provisional application No. 62/591,921, filed on Nov. 29, 2017, provisional application No. 62/636,520, filed on Feb. 28, 2018, provisional application No. 62/641,607, filed on Mar. 12, 2018.

(51) Int. Cl.

| | | |
|---|---|---|
| *A61K 38/17* | (2006.01) |
| *A61K 9/14* | (2006.01) |
| *A61K 33/26* | (2006.01) |
| *A61K 38/41* | (2006.01) |
| *A61K 39/00* | (2006.01) |
| *A61K 47/60* | (2017.01) |
| *A61P 25/00* | (2006.01) |
| *A61P 25/28* | (2006.01) |
| *C07K 14/47* | (2006.01) |
| *A61K 35/12* | (2015.01) |
| *C07K 14/74* | (2006.01) |

(52) U.S. Cl.
CPC .......... *A61K 38/1774* (2013.01); *A61K 9/143* (2013.01); *A61K 33/26* (2013.01); *A61K 38/1719* (2013.01); *A61K 38/415* (2013.01); *A61K 39/0008* (2013.01); *A61K 47/60* (2017.08); *A61P 25/00* (2018.01); *A61P 25/28* (2018.01); *C07K 14/4713* (2013.01); *A61K 2035/122* (2013.01); *A61K 2039/55555* (2013.01); *A61K 2039/605* (2013.01)

(58) Field of Classification Search
None
See application file for complete search history.

(56) References Cited

U.S. PATENT DOCUMENTS

| | | |
|---|---|---|
| 4,367,110 A | 1/1983 | Yoshikawa |
| 4,414,148 A | 11/1983 | Jansen |
| 4,452,901 A | 6/1984 | Gordon |
| 4,478,946 A | 10/1984 | Van der Merwe |
| 4,554,101 A | 11/1985 | Hopp |
| 4,569,789 A | 2/1986 | Blattler |
| 4,589,071 A | 5/1986 | Yamamuro |
| 4,589,330 A | 5/1986 | Teron |
| 4,659,839 A | 4/1987 | Nicolotti |
| 4,671,958 A | 6/1987 | Rodwell |
| 4,680,338 A | 7/1987 | Sundoro |
| 4,699,784 A | 10/1987 | Shih |
| 4,818,542 A | 4/1989 | Deluca |

(Continued)

FOREIGN PATENT DOCUMENTS

| | | |
|---|---|---|
| CA | 2517097 | 9/2004 |
| CA | 2717719 | 8/2009 |

(Continued)

OTHER PUBLICATIONS

Lieo, A., et al. Semin. Liver. Dis.; 34(3):273-284 (Year: 2014).*
Schaefer, W. et al., "Heavy and light chain pairing of bivalent quadroma and knobs-into-holes antibodies analyzed by UHR-ESI-QTOF mass spectrometry", MAbs., 8(1):49-55, (2016).
Umeshappa, C. et al., "Suppression of A Broad Spectrum of Liver Autoimmune Pathologies by Single Peptide-MHC-Based Nanomedicines", Nat Commun., 10(1):2150, (2019).
GenBank Accession No. AAC14923.1, "T cell receptor alpha chain [*Homo sapiens*]", retrieved from https://www.ncbi.nlm.nih.gov/protein/AAC14923.1?report=genbank&log$=protalign&blast, (1998).

(Continued)

*Primary Examiner* — Michael Szperka
*Assistant Examiner* — Marianne DiBrino
(74) *Attorney, Agent, or Firm* — Global Patent Group Inc.; Cynthia Hathaway; Gina Nellesen

(57) ABSTRACT

Described herein are methods for treating an autoimmune or inflammatory disease in a patient, comprising administering a composition comprising: a) a plurality of antigen-major histocompatibility class II complexes (antigen-MHCIIs), each antigen-MHCII of the plurality comprising a ubiquitous autoantigen associated with a binding groove of an MHC class II molecule, wherein the ubiquitous autoantigen is chosen from PDC-E2$_{353\text{-}367}$, PDC-E2$_{72\text{-}86}$, and PDC-E2$_{422\text{-}436}$ for DRB3*0202; PDC-E2$_{353\text{-}367}$, PDC-E2$_{80\text{-}94}$, and PDC-E2$_{535\text{-}549}$ for DRB5*0101; PDC-E2$_{629\text{-}648}$, PDC-E2$_{122\text{-}135}$, and PDC-E2$_{249\text{-}263}$ for DRB4*0101; and PDC-E2$_{249\text{-}263}$ for DRB1*0801; and b) a nanoparticle core possessing a diameter of between 1 and about 100 nanometers; wherein the antigen-MHCs are coupled to the nanoparticle core or a biocompatible layer surrounding the nanoparticle core; and wherein the autoimmune or inflammatory disease is chosen from multiple sclerosis and psoriasis.

16 Claims, 66 Drawing Sheets

Specification includes a Sequence Listing.

(56) References Cited

U.S. PATENT DOCUMENTS

| | | | |
|---|---|---|---|
| 4,859,839 A | 8/1989 | Tetelman | |
| 5,258,499 A | 11/1993 | Konigsberg | |
| 5,543,391 A | 8/1996 | Yatvin | |
| 5,676,926 A | 10/1997 | Platzek | |
| 5,676,928 A | 10/1997 | Klaveness | |
| 5,731,168 A | 3/1998 | Carter | |
| 5,807,706 A | 9/1998 | Carter | |
| 5,821,333 A | 10/1998 | Carter | |
| 5,840,839 A | 11/1998 | Wang | |
| 6,103,379 A | 8/2000 | Margel | |
| 6,387,498 B1 | 5/2002 | Coulter | |
| 6,651,655 B1 | 11/2003 | Licalsi | |
| 6,688,494 B2 | 2/2004 | Pozarnsky | |
| 6,712,997 B2 | 3/2004 | Won | |
| 6,797,514 B2 | 9/2004 | Berenson | |
| 6,846,474 B2 | 1/2005 | Nayfeh | |
| 6,929,675 B1 | 8/2005 | Bunge | |
| 7,060,121 B2 | 6/2006 | Lin | |
| 7,090,973 B1 | 8/2006 | Breton | |
| 7,183,065 B2 | 2/2007 | Braun | |
| 7,285,289 B2 | 10/2007 | Nagy | |
| 7,326,399 B2 | 2/2008 | Zhou | |
| 7,332,586 B2 | 2/2008 | Franzen | |
| 7,361,733 B2 | 4/2008 | Hershberg | |
| 7,572,631 B2 | 8/2009 | Berenson | |
| 7,642,228 B2 | 1/2010 | Carter | |
| 7,695,936 B2 | 4/2010 | Carter | |
| 7,785,801 B2 | 8/2010 | Tuereci | |
| 7,795,224 B2 | 9/2010 | Eisenbach | |
| 7,812,116 B2 | 10/2010 | Bae | |
| 7,816,814 B1 | 10/2010 | Hennessy | |
| 8,216,805 B2 | 7/2012 | Carter | |
| 8,354,110 B2 | 1/2013 | Santamaria | |
| 8,679,785 B2 | 3/2014 | Carter | |
| 8,835,144 B2 | 9/2014 | Jiang | |
| 9,149,440 B2 | 10/2015 | Turos | |
| 9,511,151 B2 | 12/2016 | Santamaria | |
| 9,603,948 B2 | 3/2017 | Santamaria | |
| 10,004,703 B2 | 6/2018 | Jacobson | |
| 10,012,045 B2 | 7/2018 | Lajesic | |
| 10,080,808 B2 | 9/2018 | Santamaria | |
| 10,124,045 B2 | 11/2018 | Santamaria | |
| 10,172,955 B2 | 1/2019 | Santamaria | |
| 10,441,556 B2 | 10/2019 | Jacobson | |
| 10,485,882 B2 | 11/2019 | Santamaria | |
| 10,632,193 B2 | 4/2020 | McCreedy | |
| 10,905,773 B2 | 2/2021 | Santamaria | |
| 10,988,516 B2 | 4/2021 | Santamaria | |
| 11,000,596 B2 | 5/2021 | Santamaria | |
| 11,338,024 B2 | 5/2022 | Santamaria | |
| 12,011,480 B2 | 6/2024 | Santamaria | |
| 2003/0068363 A1 | 4/2003 | Clark | |
| 2003/0124149 A1 | 7/2003 | Shalaby | |
| 2004/0115216 A1 | 6/2004 | Schneck | |
| 2004/0137642 A1 | 7/2004 | Erfle | |
| 2004/0197304 A1 | 10/2004 | Chen | |
| 2004/0224402 A1 | 11/2004 | Bonyhadi | |
| 2004/0265392 A1 | 12/2004 | Tovar | |
| 2005/0003431 A1 | 1/2005 | Wucherpfennig | |
| 2005/0118102 A1 | 6/2005 | Xiang | |
| 2005/0129617 A1 | 6/2005 | Tan | |
| 2005/0202032 A1 | 9/2005 | Kaufman | |
| 2005/0208120 A1 | 9/2005 | Albani | |
| 2006/0216239 A1 | 9/2006 | Zhang | |
| 2006/0219239 A1 | 10/2006 | Plaschkes | |
| 2006/0246524 A1* | 11/2006 | Bauer | B82Y 5/00 548/518 |
| 2007/0054337 A1 | 3/2007 | Ferning | |
| 2007/0059775 A1 | 3/2007 | Hultman | |
| 2007/0129307 A1 | 6/2007 | Tan | |
| 2007/0154953 A1 | 7/2007 | Brunner | |
| 2009/0155292 A1 | 6/2009 | Santamaria | |
| 2009/0258355 A1 | 10/2009 | Maye | |
| 2010/0061984 A1 | 3/2010 | Greene | |
| 2010/0095544 A1 | 4/2010 | Haseloh | |
| 2010/0104503 A1 | 4/2010 | Mellman |
| 2010/0303730 A1 | 12/2010 | Hegmann |
| 2010/0303866 A1 | 12/2010 | Saint-Remy |
| 2011/0029121 A1 | 2/2011 | Amit |
| 2011/0059121 A1 | 3/2011 | Santamaria |
| 2011/0250146 A1 | 10/2011 | Zhang |
| 2011/0318380 A1 | 12/2011 | Brix |
| 2012/0077686 A1 | 3/2012 | Weiner |
| 2012/0093934 A1 | 4/2012 | Santamaria |
| 2012/0121649 A1 | 5/2012 | Santamaria |
| 2012/0252742 A1 | 10/2012 | Kranz |
| 2013/0089553 A1 | 4/2013 | Carter |
| 2013/0128138 A1 | 5/2013 | Kuo |
| 2013/0171179 A1 | 7/2013 | Burrows |
| 2013/0302421 A1 | 11/2013 | Santamaria |
| 2013/0330414 A1 | 12/2013 | Santamaria |
| 2014/0105980 A1 | 4/2014 | Santamaria |
| 2014/0294982 A1 | 10/2014 | Freund |
| 2014/0341938 A1 | 11/2014 | Rademacher |
| 2014/0370099 A1 | 12/2014 | Green |
| 2015/0068613 A1 | 3/2015 | Taskar |
| 2015/0125536 A1 | 5/2015 | Santamaria |
| 2015/0150996 A1 | 6/2015 | Miller |
| 2015/0209446 A1 | 7/2015 | Santamaria |
| 2015/0250871 A1 | 9/2015 | Santamaria |
| 2015/0344586 A1 | 12/2015 | Georges |
| 2015/0374815 A1 | 12/2015 | Kishimoto |
| 2016/0068613 A1 | 3/2016 | Regula |
| 2016/0271237 A1 | 9/2016 | Santamaria |
| 2017/0095544 A1 | 4/2017 | Santamaria |
| 2017/0274096 A1 | 9/2017 | Santamaria |
| 2017/0312348 A1 | 11/2017 | Santamaria |
| 2017/0333540 A1 | 11/2017 | Santamaria |
| 2018/0127481 A1 | 5/2018 | Santamaria |
| 2019/0060427 A1 | 2/2019 | Santamaria |
| 2019/0060484 A1 | 2/2019 | Santamaria |
| 2019/0076545 A1 | 3/2019 | Santamaria |
| 2019/0134171 A1 | 5/2019 | Santamaria |
| 2020/0009265 A1 | 1/2020 | Santamaria |
| 2020/0057048 A1 | 2/2020 | Santamaria |
| 2021/0145949 A1 | 5/2021 | Santamaria |
| 2021/0205470 A1 | 7/2021 | Santamaria |
| 2021/0230237 A1 | 7/2021 | Santamaria |
| 2022/0401534 A1 | 12/2022 | Santamaria |
| 2023/0355730 A1 | 11/2023 | Santamaria |
| 2024/0201171 A1 | 6/2024 | Santamaria |
| 2024/0299536 A1 | 9/2024 | Santamaria |

FOREIGN PATENT DOCUMENTS

| | | |
|---|---|---|
| CA | 2868551 | 10/2013 |
| CN | 101678090 | 3/2010 |
| EP | 0188256 | 7/1986 |
| EP | 1088256 | 4/2001 |
| EP | 2131856 | 12/2009 |
| EP | 2614834 | 7/2013 |
| EP | 2621523 | 8/2013 |
| EP | 3065771 | 9/2016 |
| EP | 3067366 | 9/2016 |
| EP | 3269384 | 1/2018 |
| EP | 3291832 | 3/2018 |
| EP | 3539564 | 9/2019 |
| JP | 2003231698 | 8/2003 |
| JP | 2005538083 | 12/2005 |
| JP | 2006522319 | 9/2006 |
| JP | 2007508503 | 4/2007 |
| JP | 2008514686 | 5/2008 |
| JP | 2010522695 | 7/2010 |
| JP | 2012505249 | 3/2012 |
| JP | 2013538208 | 10/2013 |
| JP | 2015063616 | 4/2015 |
| KR | 20120100840 | 9/2012 |
| WO | 1990007339 | 7/1990 |
| WO | 1992018150 | 10/1992 |
| WO | 1993001716 | 2/1993 |
| WO | 1993016725 | 9/1993 |
| WO | 1994009823 | 5/1994 |
| WO | 1996018105 | 6/1996 |
| WO | 1998006749 | 2/1998 |

(56) References Cited

FOREIGN PATENT DOCUMENTS

| WO | 1999014236 | 3/1999 |
|---|---|---|
| WO | 1999042597 | 8/1999 |
| WO | 1999064926 | 12/1999 |
| WO | 2000043662 | 7/2000 |
| WO | 2000067788 | 11/2000 |
| WO | 2001024764 | 4/2001 |
| WO | 2002080963 | 10/2002 |
| WO | 2004006951 | 1/2004 |
| WO | 2004076909 | 9/2004 |
| WO | 2004078909 | 9/2004 |
| WO | 2005033267 | 4/2005 |
| WO | 2005036035 | 4/2005 |
| WO | 2006016113 | 2/2006 |
| WO | 2006037979 | 4/2006 |
| WO | 2006054806 | 5/2006 |
| WO | 2006080951 | 8/2006 |
| WO | 2007024026 | 3/2007 |
| WO | 2008051245 | 5/2008 |
| WO | 2008109852 | 9/2008 |
| WO | 2008118861 | 10/2008 |
| WO | 2009003492 | 1/2009 |
| WO | 2009031258 | 3/2009 |
| WO | 2009040811 | 4/2009 |
| WO | 2009064273 | 5/2009 |
| WO | 2009078799 | 6/2009 |
| WO | 2009094273 | 7/2009 |
| WO | 2009111588 | 9/2009 |
| WO | 2009126835 | 10/2009 |
| WO | 2010025324 | 3/2010 |
| WO | 2010027827 | 3/2010 |
| WO | 2010037395 | 4/2010 |
| WO | 2010037397 | 4/2010 |
| WO | 2010042876 | 4/2010 |
| WO | 2010080032 | 7/2010 |
| WO | 2010085509 | 7/2010 |
| WO | 2011073685 | 6/2011 |
| WO | 2011104497 | 9/2011 |
| WO | 2012012874 | 2/2012 |
| WO | 2012031258 | 3/2012 |
| WO | 2012041968 | 4/2012 |
| WO | 2012062904 | 5/2012 |
| WO | 2012121528 | 9/2012 |
| WO | 2013043662 | 3/2013 |
| WO | 2013072051 | 5/2013 |
| WO | 2013103438 | 7/2013 |
| WO | 2013144811 | 10/2013 |
| WO | 2014080286 | 5/2014 |
| WO | 2014096015 | 6/2014 |
| WO | 2015063616 | 5/2015 |
| WO | 2016081854 | 5/2016 |
| WO | 2016097334 | 6/2016 |
| WO | 2016145605 | 9/2016 |
| WO | 2016146505 | 9/2016 |
| WO | 2016160721 | 10/2016 |
| WO | 2016193299 | 12/2016 |
| WO | 2016198932 | 12/2016 |
| WO | 2017044672 | 3/2017 |
| WO | 2018087597 | 5/2018 |
| WO | 2018185564 | 10/2018 |
| WO | 2019106435 | 6/2019 |

OTHER PUBLICATIONS t Hart, B. et al., "Modelling of Multiple Sclerosis: Lessons Learned in a Non-Human Primate", Lancet Neurol., 3(10):588-97, (2004).
Aichele, P. et al., "Peptide-induced T-cell Tolerance to Prevent Autoimmune Diabetes in a Transgenic Mouse Model", Proc Natl Acad Sci USA, 91(2):444-8, (1994).
Altman, J. et al., "Phenotypic Analysis of Antigen-Specific T Lymphocytes", Science, 274(5284):94-6, (1996).
Altschul, S. et al., "Basic Local Alignment Search Tool", J Mol Biol., 215(3):403-10, (1990).

Amrani, A. et al., "Expansion of the Antigenic Repertoire of a Single T Cell Receptor Upon T Cell Activation", J Immunol., 167(2):655-66, (2001).
Amrani, A. et al., "Progression of Autoimmune Diabetes Driven by Avidity Maturation of a T-cell Population," Nature, 406(6797):739-42, (2000).
Anderson, B. et al., "Prevalent CD8(+) T Cell Response Against One peptide/MHC Complex in Autoimmune Diabetes", Proc Natl Acad Sci USA, 96(16):9311-6, (1999).
Anderton, S. et al., "Hierarchy in the Ability of T Cell Epitopes to Induce Peripheral Tolerance to Antigens From Myelin", Eur J Immunol., 28(4):1251-61, (1998).
Anonymous, Diabetes Prevention Trial—Type 1 Diabetes Study Group, "Effects of Insulin in Relatives of Patients With Type 1 Diabetes Mellitus", N Engl J Med., 346(22):1685-91, (2002).
Anonymous, Website article from kidshealth.org/PageManager.jsp?dn=KidsHealth&lic=1&ps=107&cat_id=139&article; downloaded Nov. 9, 2010: 2 pages total.
Appay, V. et al., "HIV-specific CD8(+) T Cells Produce Antiviral Cytokines but Are Impaired in Cytolytic Function", J Exp Med., 192(1):63-72, (2000).
Asai, H. et al., "Co-introduced Functional CCR2 Potentiates in Vivo Anti-Lung Cancer Functionality Mediated by T Cells Double Gene-Modified to Express WT1-specific T-cell", PLoS One, 8(2):e56820, (2013).
Azuma, M. et al., "T Cell Costimulation and Diseases," Kokubyo Gakkai Zasshi, 67(3):233-9, (2000).
Babbe, H. et al., "Clonal Expansions of CD8(+) T Cells Dominate the T Cell Infiltrate in Active Multiple Sclerosis Lesions as Shown by Micromanipulation and Single Cell Polymerase Chain Reaction", J Exp Med., 192(3):393-404, (2000).
Bacchetta, R. et al., "High Levels of Interleukin 10 Production in Vivo Are Associated With Tolerance in SCID Patients Transplanted With HLA Mismatched Hematopoietic Stem Cells ", J Exp Med., 179(2):493-502, (1994).
Bachmann, M. et al., "Developmental Regulation of Lck Targeting to the CD8 Coreceptor Controls Signaling in Naive and Memory T Cells", J Exp Med., 189(10):1521-30, (1999).
Bahcetepe, N. et al., "The Role of HLA Antigens in the Aetiology of Psoriasis", Med Glas (Zenica), 10(2):339-42, (2013).
Bailey-Bucktrout, S. et al., "Self-antigen-driven Activation Induces Instability of Regulatory T Cells During an Inflammatory Autoimmune Response", Immunity, 39(5):949-62, (2013).
Baker, D. et al., "Critical Appraisal of Animal Models of Multiple Sclerosis", Mult Scler., 17(6):647-57, (2011).
Bakker, A. et al., "MHC Multimer Technology: Current Status and Future Prospects", Curr Opin Immunol., 17(4):428-33, (2005).
Barber, D. et al., "Restoring Function in Exhausted CD8 T Cells During Chronic Viral Infection", Nature, 439(7077):682-7, (2006).
Becker, T. et al., "Interleukin 15 Is Required for Proliferative Renewal of Virus-Specific Memory CD8 T Cells", J Exp Med., 195(12):1541-8, (2002).
Behan, P. et al., "The Sad Plight of Multiple Sclerosis Research (Low on Fact, High on Fiction): Critical Data to Support It Being a Neurocristopathy", Inflammopharmacology, 18(6):265-90, (2010).
Chen, Q. et al., "IL-2 Controls the Stability of Foxp3 Expression in TGF-beta-induced Foxp3+ T Cells in Vivo", J Immunol., 186(11):6329-37, (2011).
Choudhuri, K. et al., "Signaling Microdomains in T Cells", FEBS Lett., 584(24):4823-31, (2010).
Cirillo, C. et al., "S100B Protein in the Gut: The Evidence for Enteroglial-Sustained Intestinal Inflammation", World J Gastroenterol., 17(10):1261-6, (2011).
Clemente Casares, J. "pMHC-Class II Nanovaccine to Treat Autoimmune Diseases", Doctor of Philosophy Thesis, Calgary University, Alberta, Canada, 391 pages, retrieved from: http://theses.ucalgary.ca/handle/11023/1589; (2014).
Clemente-Casares, X. et al., "Expanding Antigen-Specific Regulatory Networks to Treat Autoimmunity", Nature, 530(7591):434-40, (2016).
Clemente-Casares, X. et al., "Peptide-MHC-based Nanovaccines for the Treatment of Autoimmunity: A "One Size Fits All" Approach?", J Mol Med., 89(8):733-42, (2011).

(56) References Cited

OTHER PUBLICATIONS

Cnop, M. et al., "Mechanisms of Pancreatic Beta-Cell Death in Type 1 and Type 2 Diabetes: Many Differences, Few Similarities", Diabetes, 54(Suppl 2):S97-S107, (2005).
Constantinescu, C. et al., "Experimental Autoimmune Encephalomyelitis (EAE) as a Model for Multiple Sclerosis (MS)", Br J Pharmacol., 164(4):1079-106, (2011).
Corrigall, V. et al., "Autoantigens and Immune Pathways in Rheumatoid Arthritis", Grit Rev Immunol., 22(4):281-93, (2002).
Croxford, A. et al., "Mouse Models for Multiple Sclerosis: Historical Facts and Future Implications", Biochim Biophy Acta., 1812(2):177-83, (2011).
Cuív, P. et al., "Draft Genome Sequence of Bacteroides Vulgatus PC510, a Strain Isolated From Human Feces", J Bacteriol., 193(15):4025-6, (2011).
Culina, S. et al., "Antigen-Based Immune Therapeutics for Type 1 Diabetes: Magic Bullets or Ordinary Blanks?", Clin Dev Immunol., 2011:286248, (2011).
Daperno, M. et al., "Results of the 2nd Part Scientific Workshop of the ECCO. II: Measures and Markers of Prediction to Achieve, Detect, and Monitor Intestinal Healing in Inflammatory Bowel Disease", J Crohns Colitis., 5(5):484-98, (2011).
Dave, M. et al., "Mucosal Healing in Inflammatory Bowel Disease-A True Paradigm of Success?", Gastroenterol hepatol., 8(1):29-38, (2012).
Davies, R. et al., "Engineered Particle Surfaces", Adv Mat., 10(15):1264-70, (1998).
De Plaen, E. et al., "Immunogenic (Tum–) Variants of Mouse Tumor P815: Cloning of the Gene of Tum– Antigen P91A and Identification of the Tum– Mutation", Proc Natl Acad Sci USA, 85(7):2274-8, (1988).
Denic, A. et al., "The Relevance of Animal Models in Multiple Sclerosis Research", Pathophysiology, 18(1):21-9, (2011).
Desreumaux, P. et al., "Safety and Efficacy of Antigen-Specific Regulatory T-cell Therapy for Patients With Refractory Crohn's Disease", Gastroenterology, 143(5):1207-17, (2012).
Flad, T. et al., "Development of an MHC-class I Peptide Selection Assay Combining Nanoparticle Technology and Matrix-Assisted Laser Desorption/Ionisation Mass Spectrometry", J Immunol Methods, 283(1-2):205-13, (2003).
Jarchum, I. et al., "Identification of Novel IGRP Epitopes Targeted in Type 1 Diabetes Patients", Clin Immunol., 127(3):359-65, (2008).
Jarchum, I. et al., "In Vivo Cytotoxicity of Insulin-Specific CD8+ T-cells in HLA-A*0201 Transgenic NOD Mice", Diabetes, 56(10):2551-60, (2007).
Jarius, S. et al., "Mechanisms of Disease: Aquaporin-4 Antibodies in Neuromyelitis Optica", Nat Clin Pract Neurol., 4(4):202-14, (2008).
Jokerst, J. et al., "Nanoparticle PEGylation for Imaging and Therapy", Nanomedicine (Lond.), 6(4):715-28, (2011).
Judge, A. et al., "Interleukin 15 Controls Both Proliferation and Survival of a Subset of Memory-Phenotype CD8(+) T Cells", J Exp Med., 196(7):935-46, (2002).
Jun, H. et al., "A New Look at Viruses in Type 1 Diabetes", Diab Met Res., 19(1):8-31, (2003).
Jurewicz, A. et al., "MHC Class I-restricted Lysis of Human Oligodendrocytes by Myelin Basic Protein Peptide-Specific CD8 T Lymphocytes", J Immunol., 160(6):3056-9, (1998).
Kamanaka, M. et al., "Expression of interleukin-10 in Intestinal Lymphocytes Detected by an interleukin-10 Reporter Knockin Tiger Mouse", Immunity, 25(6):941-52, (2006).
Kamikura, Y. et al., "Adhesion, Costimulatory Molecule, Trafficking, Homing: Cancer Immunotherapy and Costimulatory Molecule", Ann Rev., Immunity, 162:2-13, (2004).
Kappos, L. et al., "Induction of a Non-Encephalitogenic Type 2 T Helper-Cell Autoimmune Response in Multiple Sclerosis After Administration of an Altered Peptide Ligand in a Placebo-Controlled, Randomized Phase II Trial. The Altered Peptide Ligand in Relapsing MS Study Group", Nat Med., 6(10):1176-82, (2000).

Karin, N. et al., "Reversal of Experimental Autoimmune Encephalomyelitis by a Soluble Peptide Variant of a Myelin Basic Protein Epitope: T Cell Receptor Antagonism and Reduction of Interferon Gamma and Tumor Necrosis Factor Alpha Production", J Exp Med., 180(6):2227-37, (1994).
Karlin, S. et al., "Applications and Statistics for Multiple High-Scoring Segments in Molecular Sequences", Proc Natl Acad Sci USA, 90(12):5873-7, (1993).
Karounos, D. et al., "Metabolically Inactive Insulin Analog Prevents Type I Diabetes in Prediabetic NOD Mice", J Clin Invest., 100(6):1344-8, (1997).
Kent, S. et al., "Expanded T Cells From Pancreatic Lymph Nodes of Type 1 Diabetic Subjects Recognize an Insulin Epitope", Nature, 435(7039):224-8, (2005).
Keymeulen, B. et al., "Insulin Needs After CD3-antibody Therapy in New-Onset Type 1 Diabetes", N Engl J Med., 352(25):2598-608, (2005).
Kim, S. et al., "Induction and Visualization of Mucosal Memory CD8 T Cells Following Systemic Virus Infection", J Immunol., 163(8):4125-32, (1999).
Kita, H. et al., "Quantitative and Functional Analysis of PDC-E2-specific Autoreactive Cytotoxic T Lymphocytes in Primary Biliary Cirrhosis", J Clin Invest., 109(9):1231-40, (2002).
Komai-Koma, M. et al., "TLR2 Is Expressed on Activated T Cells as a Costimulatory Receptor", Proc Natl Acad Sci USA, 181(9):3829-34, (2004).
Longhi, M. et al., "Autoantigen-specific Regulatory T Cells, a Potential Tool for Immune-Tolerance Reconstitution in type-2 Autoimmune Hepatitis", Hepatology, 53(2):536-47, (2011).
Lowery, A. et al., "Immunonanoshells for Targeted Photothermal Ablation of Tumor Cells", Int J Nanomedicine, 1(2):149-54, (2006).
Lupas, A., "Coiled Coils: New Structures and New Functions", TIB 21, 375-82, (1996).
Ma, Z. et al., "TCR Triggering by pMHC Ligands Tethered on Surfaces via Poly(ethylene Glycol) Depends on Polymer Length", PLoS One, 9(11):e112292, (2014).
Mallone, R. et al., "CD8+ T-cell Responses Identify Beta-Cell Autoimmunity in Human Type 1 Diabetes", Diabetes, 56(3):613-21, (2007).
Mallone, R. et al., "T Cell Recognition of Autoantigens in Human Type 1 Diabetes: Clinical Perspectives", Clin Dev Immunol., 2011:513210, (2011).
Marée, A. et al., "Modeling Competition Among Autoreactive CD8+ T Cells in Autoimmune Diabetes: Implications for Antigen-Specific Therapy", Int Immunol., 18(7):1067-77, (2006).
Mars, L. et al., "CD8 T Cell Responses to Myelin Oligodendrocyte Glycoprotein-Derived Peptides in Humanized HLA-A*0201-transgenic Mice". J Immunol., 179(8):5090-8, (2007).
Marsh, S. et al., "Nomenclature for Factors of the HLA System, Update Oct. 2010", Tissue Antigens, 77(4):349-54, (2011).
Martínez-Martín, N et al., "Cooperativity Between T Cell Receptor Complexes Revealed by Conformational Mutants of CD3epsilon", Sci Signal., 2(83):ra43, (2009).
Marwaha, A. et al., "Cutting Edge: Increased IL-17-secreting T Cells in Children With New-Onset Type 1 Diabetes", J Immunol., 185(7):3814-8, (2010).
Mazzarella, G., "Effector and Suppressor T Cells in Celiac Disease", World J Gastroenterol., 21(24):7349-56, (2015).
McCarthy, D. et al., "Mouse Models of Multiple Sclerosis: Experimental Autoimmune Encephalomyelitis and Theiler's Virus-Induced Demyelinating Disease", Methods Mol Biol., 900:281-401, (2012).
McClymont, S. et al., "Plasticity of Human Regulatory T Cells in Healthy Subjects and Patients With Type 1 Diabetes", J Immunol., 186(7):3918-26, (2011).
McKeithan, T., "Kinetic Proofreading in T-cell Receptor Signal Transduction", Proc Natl Acad Sci USA, 92(11):5042-6, (1995).
McLarnon, A., "IBD: Regulatory T-cell Therapy Is a Safe and Well-Tolerated Potential Approach for Treating Refractory Crohn's Disease", Nat Rev Gastroenterol Hepatol., 9(10):559, (2012).
Mei, X. et al., Chemical Industry Press, Biotechnology Pharmaceutic Preparation: Foundation and Application: 199, (2004).

(56) References Cited

OTHER PUBLICATIONS

Merchant, A. et al., "An Efficient Route to Human Bispecific IgG", Nat Biotechnol., 16(7):677-81, (1998).
Mescher, M. et al., "Signals Required for Programming Effector and Memory Development by CD8+ T Cells", Immunol Rev., 211:81-92, (2006).
Mestas, J. et al., "Of Mice and Not Men: Differences Between Mouse and Human Immunology", J Immunol., 172(5):2731-8, (2004).
Metzler, B. et al., "Inhibition of Experimental Autoimmune Encephalomyelitis by Inhalation but Not Oral Administration of the Encephalitogenic Peptide: Influence of MHC Binding Affinity", Int Immunol., 5(9):1159-65, (1993).
Miguel-Sancho, N. et al., "Development of Stable, Water-Dispersible, and Biofunctionalizable Superparamagnetic Iron Oxide Nanoparticles", Chem Mat., 23(11):2795-802, (2011).
Miller, S. et al., "The Induction of Cell-Mediated Immunity and Tolerance With Protein Antigens Coupled to Syngeneic Lymphoid Cells", J Exp Med., 149(3):758-66, (1979).
Miyara, M. et al., "Functional Delineation and Differentiation Dynamics of Human CD4+ T Cells Expressing the FoxP3 Transcription Factor", Immunity, 30(6):899-911, (2009).
Mondini, S. et al., "One-Step Synthesis and Functionalization of Hydroxyl-Decorated Magnetite Nanoparticles", J Colloid Interface Sci., 322(1):173-9, (2008).
Moore, A. et al., "Tracking the Recruitment of Diabetogenic CD8+ T-cells to the Pancreas in Real Time", Diabetes, 53(6):1459-66, (2004).
Mukherjee, R. et al., "Identification of CD4+ T Cell-Specific Epitopes of Islet-Specific glucose-6-phosphatase Catalytic Subunit-Related Protein: A Novel Beta Cell Autoantigen in Type 1 Diabetes", J Immunol., 174(9):5306-15, (2005).
Musacchio, T. et al., "PEG-PE Micelles Loaded With Paclitaxel and Surface-Modified by a PBR-ligand: Synergistic Anticancer Effect", Mol Pharm., 6(2):468-79, (2009).
Nakayama, M. et al., "Prime Role for an Insulin Epitope in the Development of Type 1 Diabetes in NOD Mice", Nature, 435(7039):220-3, (2005).
Nelson, J. et al., "6 Types of Asthma and How They're Treated", Mother Nature Network, mnn.com, 4 pages, (2015).
Noren, C. et al., "A General Method for Site-Specific Incorporation of Unnatural Amino Acids Into Proteins", Science, 244(4901):182-8, (1989).
Oh, S. et al., "IL-15/IL-15Ralpha-mediated Avidity Maturation of Memory CD8+ T Cells", Proc Natl Acad Sci USA, 101:15154-9, (2004).
Oleszak, E. et al., "Theiler's Virus Infection: A Model for Multiple Sclerosis," Clin Microbiol Rev., 17(1):174-207, (2004).
Onoda, T. et al., "Human CD4+ Central and Effector Memory T Cells Produce IL-21: Effect on Cytokine-Driven Proliferation of CD4+ T Cell Subsets", Int Immunol., 19(10):1191-9, (2007).
Ouyang, Q. et al., "Recognition of HLA Class I-restricted Beta-Cell Epitopes in Type 1 Diabetes", Diabetes, 55(11):3068-74, (2006).
Oyewumi, M. et al., Nano-microparticles as Immune Adjuvants: Correlating Particle Sizes and the Resultant Immune Responses, Expert Rev Vaccines, 9(9):1095-107, (2010).
Pachner, A., "Experimental Models of Multiple Sclerosis", Curr Opin Neurol., 24(3):291-9, (2011).
Packard, T. et al., "COPD Is Associated With Production of Autoantibodies to a Broad Spectrum of Self-Antigens, Correlative With Disease Phenotype", Immunol Res., 55(1-3):48-57, (2013).
Pakula, A. et al., "Genetic Analysis of Protein Stability and Function", Annu Rev Genet., 23:289-310, (1989).
Palmer, J. et al., "Insulin Antibodies in Insulin-Dependent Diabetics Before Insulin Treatment", Science, 222(4630):1337-9, (1983).
Partch, R. et al., "Aerosol and Solution Modification of Particle-Polymer Interfaces", J Adhesion, 67(1-4):259-76, (1998).
Pascolo, S. et al., "HLA-A2.1-restricted Education and Cytolytic Activity of CD8(+) T Lymphocytes From beta2 Microglobulin (beta2m) HLA-A2.1 Monochain Transgenic H-2Db beta2m Double Knockout Mice", J Exp Med., 185(12):2043-51, (1997).
Patel, J. et al., "Cationic Nanoparticles for Delivery of CpG Oligodeoxynucleotide and Ovalbumin: In Vitro and In Vivo Assessment", J Biomed Nanotechnol., 3(1):97-106, (2007).
Pekarek, K. et al., "Double-walled Polymer Microspheres for Controlled Drug Release", Nature, 367(6460):258-60, (1994).
Peng, S. et al., "Synthesis and Characterization of Monodisperse Hollow Fe3O4 Nanoparticles", Angew Chem Int Ed Engl., 46(22):4155-8, (2007).
Perrault, S. et al., "Mediating Tumor Targeting Efficiency of Nanoparticles Through Design", Nano Lett, 9(5):1909-15, (2009).
Petros, R. et al., Antibody Conjugation to PRINT Abstracts of Papers Am Chem Soc., 233(14):14, (2007).
Pinkse, G. et al., "Autoreactive CD8 T Cells Associated With Beta Cell Destruction in Type 1 Diabetes", Proc Natl Acad Sci USA, 102(51):18425-30, (2005).
Ponder, J. et al., "Tertiary Templates for Proteins. Use of Packing Criteria in the Enumeration of Allowed Sequences for Different Structural Classes", J Mol Biol., 193(4):775-91, (1987).
Pot, C. et al., "Cutting Edge: IL-27 Induces the Transcription Factor c-Maf, Cytokine IL-21, and the Costimulatory Receptor ICOS That Coordinately Act Together to Promote Differentiation of IL-10-producing Tr1 Cells", J Immunol., 183(2):797-801, (2009).
Purton, J. et al., "Antiviral CD4+ Memory T Cells Are IL-15 Dependent ," J Exp Med., 204(4):951-61, (2007).
Quinn, M. et al., "How Do You Diagnose Rheumatoid Arthritis Early?", Best Pract Res Clin Rheumatol., 15(1):49-66, (2001).
Ransohoff, R., "Animal Models of Multiple Sclerosis: The Good, the Bad and the Bottom Line", Nat Neurosci., 15(8):1074-7, (2012).
Reijonen, H. et al., "Detection of GAD65-specific T-cells by Major Histocompatibility Complex Class II Tetramers in Type 1 Diabetic Patients and At-Risk Subjects", Diabetes, 51(5):1375-82, (2002).
Report to Congress, "Progress in Auotimmune Diseases Research", U.S. DHHS, NIH, 146 pages, (2005).
Riemekasten, G. et al., "Key Autoantigens in SLE", Rheumatology (Oxford), 44(8):975-82, (2005).
Roncarolo, M. et al., "Clinical Tolerance in Allogeneic Hematopoietic Stem Cell Transplantation", Immunol Rev., 241(1):145-63, (2011).
Rossi, M. et al., "Intravenous or Intranasal Administration of Gliadin Is Able to Down-Regulate the Specific Immune Response in Mice", Scand J Immunol., 50(2):177-82, (1999). (1999).
Routsias, J. et al., "Autoimmune Response and Target Autoantigens in Sjogren's Syndrome", Eur J Clin Invest., 40(11):1026-36, (2010).
Saengruengrit, C. et al., "The Combined Magnetic Field and Iron oxide-PLGA Composite Particles: Effective Protein Antigen Delivery and Immune Stimulation in Dendritic Cells", J Colloid Interface Sci., 520:101-11, (2018).
Sahin, U. et al., "Human Neoplasms Elicit Multiple Specific Immune Responses in the Autologous Host", Proc Natl Acad Sci USA, 92(25):11810-3, (1995).
Sakaguchi, S. et al., "Foxp3+ CD25+ CD4+ Natural Regulatory T Cells in Dominant Self-Tolerance and Autoimmune Disease", Immunol Rev., 212:8-27, (2006).
Santamaria, P. et al., "Beta-cell-cytotoxic CD8+ T Cells From Nonobese Diabetic Mice Use Highly Homologous T Cell Receptor Alpha-Chain CDR3 Sequences", J Immunol., 154(5):2494-503, (1995).
Santamaria, P. et al., "Characterization of T Lymphocytes Infiltrating Human Pancreas Allograft Affected by Isletitis and Recurrent Diabetes", Diabetes, 41(1):53-61, (1992).
Santamaria, P. et al., "Skewed T-cell Receptor Usage and Junctional Heterogeneity Among Isletitis Alpha Beta and Gamma Delta T-cells in Human IDDM [Corrected]", Diabetes, 43(4):599-606, (1994).
Santamaria, P., "Effector Lymphocytes in Autoimmunity", Curr Opin Immunol., 13(6):663-9, (2001).
Santamaria, P., "The Long and Winding Road to Understanding and Conquering Type 1 Diabetes", Immunity, 32(4):437-45, (2010).
Saragovi, H. et al., "Small Molecule and Protein-Based Neurotrophic Ligands: Agonists and Antagonists as Therapeutic Agents", Exp Opin Ther Patents, 9(6):737-51, (1999).

(56) References Cited

OTHER PUBLICATIONS

Saraiva, M. et al., "Interleukin-10 Production by Th1 Cells Requires interleukin-12-induced STAT4 Transcription Factor and ERK MAP Kinase Activation by High Antigen Dose", Immunity, 31(2):209-19, (2009).
Sato, "Diabetes and Cytokines. Roles of Cytokines in Diabetes Mellitus, Separate Volume", J Clin Exp Med., cytokine-state of arts, 5 pages, (2004).
Sato, K. et al., "Marked Induction of c-Maf Protein During Th17 Cell Differentiation and Its Implication in Memory Th Cell Development", J Biol Chem . . . 286(17):14963-71, (2011).
Scaldaferri, F. et al., "Mucosal Biomarkers in Inflammatory Bowel Disease: Key Pathogenic Players or Disease Predictors?" World J Gastroenterol., 16(21 ):2616-25, (2010).
Schamel, W. et al., "Organization of the Resting TCR in Nanoscale Oligomers ", Immunol Rev., 251(1):13-20, (2013).
Schirle, M. et al., "Combining Computer Algorithms With Experimental Approaches Permits the Rapid and Accurate Identification of T Cell Epitopes From Defined Antigens", J Immunol Meth., 257(1-2):1-16, (2001).
Schlesinger, S. et al., "Alphavirus Vectors for Gene Expression and Vaccines", Curr Opin Biotechnol., 10(5):434-9, (Abstract only), (1999 ).
Schlichtholz, B. et al., The Immune Response to p53 in Breast Cancer Patients Is Directed Against Immunodominant Epitopes Unrelated to the Mutational Hot Spot, Cancer Res., 52(22):6380-4, (1992).
Schneider, K. et al., "The End of the Era of Generosity? Global Health Amid Economic Crisis", Philos Ethics Humanit Med., 4:1, (2009).
Schnütgen, F. et al., "A Directional Strategy for Monitoring Cre-mediated Recombination at the Cellular Level in the Mouse", Nat Biotechnol., 21(5):562-6, (2003).
Schreiber, H. et al., "Using Carbon Magnetic Nanoparticles to Target, Track, and Manipulate Dendritic Cells", J Immunol Methods, 356(1-2):47-59, (2010).
Scott, R. et al., "Synthesis, Characterization, and Applications of Dendrimer-Encapsulated Nanoparticles", J Phys Chem B., 109(2):692-704, (2005).
Serra, P. et al., "Nanoparticle-based Approaches to Immune Tolerance for the Treatment of Autoimmune Diseases", Eur J Immunol., 48(5):751-6, (2018).
Serreze, D. et al., "Autoreactive Diabetogenic T-cells in NOD Mice Can Efficiently Expand From a Greatly Reduced Precursor Pool", Diabetes, 50(9):1992-2000, (2001).
Shanks, N. et al., "Are Animal Models Predictive for Humans?", Philos Ethics Humanit Med., 4(2):1-20, (2009).
Shao, K. et al., "Nanoparticle-Based Immunotherapy for Cancer", ACS Nano., 9(1):16-30, (2015).
Sherman, E. et al., "Functional Nanoscale Organization of Signaling Molecules Downstream of the T Cell Antigen Receptor", Immunity, 35(5):705-20, (2011).
Shimoda, S. et al., "Identification and Precursor Frequency Analysis of a Common T Cell Epitope Motif in Mitochondrial Autoantigens in Primary Biliary Cirrhosis", J Clin Invest., 102(10):1831-40, (1998).
Shukla, S. et al., "Emerging Nanotechnologies for Cancer Immunotherapy", Exp Bioi Med (Maywood)., 241(10):1116-26, (2016).
Sibley. R. et al., "Recurrent Diabetes Mellitus in the Pancreas Iso– And Allograft. A Light and Electron Microscopic and Immunohistochemical Analysis of Four Cases", Lab Invest., 53(2):132-44, (1985).
Singha, S. et al., "Peptide-MHC-based Nanomedicines for Autoimmunity Function as T-cell Receptor Microclustering Devices", Nat Nanotechnol., 12(7):701-10, (2017).
Sollid, L. et al., "Nomenclature and Listing of Celiac Disease Relevant Gluten T-cell Epitopes Restricted by HLA-DQ Molecules", Immunogenetics, 64(6):455-60, (2012).

Somoza, N. et al., "Pancreas in Recent Onset Insulin-Dependent Diabetes Mellitus. Changes in HLA, Adhesion Molecules and Autoantigens, Restricted T Cell Receptor V Beta Usage, and Cytokine Profile", J Immunol., 153(3):1360-77, (1994).
Spada, F. et al., "Self-recognition of CD1 by Gamma/Delta T Cells: Implications for Innate Immunity", J Exp Med., 191(6):937-48, (2000).
Spensieri, F. et al., "Human Circulating influenza-CD4+ ICOS1+ IL-21+ T Cells Expand After Vaccination, Exert Helper Function, and Predict Antibody Responses", Proc Natl Acad Sci USA, 110(35):14330-5, (2013).
Sprent, J. et al., "T Cell Death and Memory", Science, 293(5528):245-8, (2001).
Sprent, J. et al., "T Cell Memory", Annu Rev Immunol., 20:551-79, (2002).
Standifer, N. et al., "Identification of Novel HLA-A*0201-restricted Epitopes in Recent-Onset Type 1 Diabetic Subjects and Antibody-Positive Relatives", Diabetes, 55(11):3061-7, (2006).
Steenblock, E. et al., "A Comprehensive Platform for Ex Vivo T-cell Expansion Based on Biodegradable Polymeric Artificial Antigen-Presenting Cells", Mol Ther., 16(4):765-72, (2008). (2008).
Stratmann, T. et al., "Susceptible MHC Alleles, Not Background Genes, Select an Autoimmune T Cell Reactivity", J Clin Invest., 112(6):902-14, (2003).
Stratmann, T. et al., "The I-Ag7 MHC Class II Molecule Linked to Murine Diabetes Is a Promiscuous Peptide Binder", J Immunol., 165(6):3214-25, (2000).
Sukhorukov, G. et al., Stepwise Polyelectrolyte Assembly on Particle Surfaces: A Novel Approach to Colloid Design, Polymers Adv Tech., 9(10-11):759-67, (1998).
Sutton, I. et al., "Primary Biliary Cirrhosis: Seeking the Silent Partner of Autoimmunity", Gut, 50(6):743-6), (2002).
Szczerkowska-Dobosz, A., "Human Leukocyte Antigens as Psoriasis Inheritance and Susceptibility Markers", Arch Immunol Ther Exp (Warsz)., 53(5):428-33, (2005).
Tait, B. et al., "HLA Antigens and Age at Diagnosis of Insulin-Dependent Diabetes Mellitus", Hum Immunol., 42(2):116-24, (1995).
Takahashi, F. et al., "Isolation and Characterization of a Colonic Autoantigen Specifically Recognized by Colon Tissue-Bound Immunoglobulin G From Idiopathic Ulcerative Colitis", J Clin Invest., 76(1):311-8, (1985).
Takaki, T. et al., "HLA-A*0201-restricted T Cells From Humanized NOD Mice Recognize Autoantigens of Potential Clinical Relevance to Type 1 Diabetes", J Immunol., 176(5):3257-65, (2006).
Tan, J. et al., "Interleukin (IL)-15 and IL-7 Jointly Regulate Homeostatic Proliferation of Memory Phenotype CD8+ Cells but Are Not Required for Memory Phenotype CD4+ Cells", J Exp Med., 195(12):1523-32, (2002).
Tanimura, K. et al., "B2-Glycoprotein I/HLA Class II Complexes Are Novel Autoantigens in Antiphospholipid Syndrome", Blood, 125(18):2835-44, (2015).
Tigges, M. et al., "Human Herpes Simplex Virus (HSV)-specific CD8+ CTL Clones Recognize HSV-2-infected Fibroblasts After Treatment With IFN-gamma or When Virion Host Shutoff Functions Are Disabled", J Immunol., 156(10):3901-10, (1996).
Toes, R. et al., "Peptide Vaccination Can Lead to Enhanced Tumor Growth Through Specific T-cell Tolerance Induction", Proc Natl Acad Sci USA, 93(15):7855-60, (1996).
Toma, A. et al., "Recognition of a Subregion of Human Proinsulin by Class I-restricted T Cells in Type 1 Diabetic Patients", Proc Natl Acad Sci USA, 102(30):10581-6, (2005).
Trenttham, D. et al., "Effects of Oral Administration of Type II Collagen on Rheumatoid Arthritis", Science, 261(5129):1727-30, (1993).
Trudeau, J. et al., "Prediction of Spontaneous Autoimmune Diabetes in NOD Mice by Quantification of Autoreactive T Cells in Peripheral Blood", J Clin Invest., 111(2):217-23, (2003).
Tsai, S. et al., "CD8+ T Cells in Type 1 Diabetes", Adv Immunol., 100:79-124, (2008).
Tsai, S. et al., "Reversal of Autoimmunity by Boosting Memory-Like Autoregulatory T Cells", Immunity, 32(4):568-80, (2010).

(56) References Cited

OTHER PUBLICATIONS

Tsuchida, T. et al., "Autoreactive CD8+ T-cell Responses to Human Myelin Protein-Derived Peptides", Proc Natl Acad Sci USA, 91(23):10859-63, (1994).
Tufveson, G. et al., "New Immunosuppressants: Testing and Development in Animal Models and the Clinic: With Special Reference to DSG", Immunological Rev., 136:99-109, (1993).
Ugel, S. et al., "In Vivo Administration of Artificial Antigen-Presenting Cells Activates Low-Avidity T Cells for Treatment of Cancer", Cancer Res., 69(24):9376-84, (2009).
Unger, W. et al., "Human Clonal CD8 Autoreactivity to an IGRP Islet Epitope Shared Between Mice and Men", Ann NY Acad Sci., 1103:192-5, (2007).
Vadasz, Z. et al., "B-regulatory Cells in Autoimmunity and Immune Mediated Inflammation", FEBS Lett., 587(13):2074-8, (2013).
Vakil, R. et al., "Effect of Cholesterol on the Release of Amphotericin B From PEG-phospholipid Micelles", Mol Pharm., 5(1):98-104, (2008).
Van Belle, T. et al., "Type 1 Diabetes: Etiology, Immunology, and Therapeutic Strategies", Physiol Rev., 91(1):79-118, (2011).
Van Boekel, M. et al., "Autoantibody Systems in Rheumatoid Arthritis: Specificity, Sensitivity and Diagnostic Value", Arthritis Res., 4(2):87-93, (2002).
Van Driel, I. et al., "Role of Regulatory T Cells in Gastrointestinal Inflammatory Disease", J Gastroenterol Hepatol., 23(2):171-7, (2008).
Vandenbark, A. et al., "Recombinant TCR Ligand Induces Tolerance to Myelin Oligodendrocyte Glycoprotein 35-55 Peptide and Reverses Clinical and Histological Signs of Chronic Experimental Autoimmune Encephalomyelitis in HLA-DR2 Transgenic Mice", J Immunol., 171(1):127-33, (2003).
Verdaguer, J. et al., "Acceleration of Spontaneous Diabetes in TCR-beta-transgenic Nonobese Diabetic Mice by Beta-Cell Cytotoxic CD8+ T Cells Expressing Identical Endogenous TCR-alpha Chains", J Immunol., 157(10):4726-35, (1996).
Verdaguer, J. et al., "Spontaneous Autoimmune Diabetes in Monoclonal T Cell Nonobese Diabetic Mice", J Exp Med., 186(10):1663-76, (1997).
Verdù, E. et al., "Oral Administration of Antigens From Intestinal Flora Anaerobic Bacteria Reduces the Severity of Experimental Acute Colitis in BALB/c Mice", Clin Exp Immunol., 120(1):46-50, (2000).
Vincent, M. et al., "Understanding the Function of CD1-restricted T Cells", Nat Immunol., 4(6):517-23, (2003).
Wainwright, S. et al., "HLA-F Is a Predominantly Empty, Intracellular, TAP-associated MHC Class lb Protein With a Restricted Expression Pattern", J Immunol., 164(1):319-28, (2000).
Walter, U. et al., "CD8+ T Cells in Autoimmunity", Curr Opin Immunol., 17(6):624-31, (2005).
Wang, J. et al., "In Situ Recognition of Autoantigen as an Essential Gatekeeper in Autoimmune CD8+ T Cell Inflammation ", Proc Natl Acad Sci USA, 107(20):9317-22, (2010).
Wang, X. et al., "Induction of Potent CD8 T-Cell Responses by Novel Biodegradable Nanoparticles Carrying Human Immunodeficiency Virus Type 1 gp120," J Virol., 81(18):10009-16, (2007).
Wang, Y. et al., "One-Pot Reaction to Synthesize Superparamagnetic Iron Oxide Nanoparticles by Adding Phenol as Reducing Agent and Stabilizer", J Nanoparticle Res., 14:755, (2012).
Warnock, G. et al., "Normoglycaemia After Transplantation of Freshly Isolated and Cryopreserved Pancreatic Islets in Type 1 (Insulin-Dependent) Diabetes Mellitus ", Diabetologia, 34(1): 55-8, (1991).
Wei, C. et al., "Facile Synthesis of Superparamagnetic Magnetite Nanoparticles in Liquid Polyols", J Colloid Interface Sci., 305(2):366-70, (2007).
Weiner, H. et al., "Double-blind Pilot Trial of Oral Tolerization With Myelin Antigens in Multiple Sclerosis", Science, 259(5099):1321-4, (1993).
Weiss, G. et al., "Covalent HLA-B27/peptide Complex Induced by Specific Recognition of an Aziridine Mimic of Arginine", Proc Natl Acad Sci USA, 93(20):10945-8, (1996).

Wekerle, H. et al., "Animal Models of Multiple Sclerosis", Drug Discov Today: Disease Models, 3(4):359-67, (2006).
Wen, Z., "Surface Effect of the Nanoparticles", Intro Nat Sci., Nanjing University Press, pp. 373-374, (2007).
Williams, M. et al., "Developing and Maintaining Protective CD8+ Memory T Cells", Immunol Rev., 211:146-53, (2006).
Wilson, J. et al., "pH-Responsive Nanoparticle Vaccines for Dual-Delivery of Antigens and Immunostimulatory Oligonucleotides", ASC Nano., 7(5):3912-25, (2013).
Winer, S. et al., "Autoimmune Islet Destruction in Spontaneous Type 1 Diabetes Is Not Beta-Cell Exclusive", Nat Med., 9(2):198-205, (2003).
Wong, F. et al., "Identification of an MHC Class I-restricted Autoantigen in Type 1 Diabetes by Screening an Organ-Specific cDNA Library", Nat Med., 5(9):1026-31, (1999).
Wraith, D. et al., "Antigen Recognition in Autoimmune Encephalomyelitis and the Potential for Peptide-Mediated Immunotherapy", Cell, 59(2):247-55, (1989).
Wu, W. et al., "Magnetic Iron Oxide Nanoparticles: Synthesis and Surface Functionalization Strategies", Nanoscale Res Lett., 3(11):397-415, (2008).
Wucherpfennig, K. et al., "Structural Basis for Major Histocompatibility Complex (MHC)-linked Susceptibility to Autoimmunity: Charged Residues of a Single MHC Binding Pocket Confer Selective Presentation of Self-Peptides in Pemphigus Vulgaris", Proc Natl Acad Sci USA, 92(25):11935-9, (1995).
Xie, J. et al., "Controlled PEGylation of Monodisperse $Fe_3O_4$ Nanoparticles for Reduced Non☐ Specific Uptake by Macrophage Cells", Adv Mat., 19(20):3163-6, (2007).
Xie, J. et al., "One-Pot Synthesis of Monodisperse Iron Oxide Nanoparticles for Potential Biomedical Applications", Pure Appl Chem., 78(5):1003-14, (2006).
Xu, C. et al., "Monodisperse Magnetic Nanoparticles for Biomedical Applications", Polymer Int., 56(7):821-6, (2007).
Xu, H., "13.3.3 Relationship Between Gene Transduction and Nanoparticle Size", Nano Med., 35S, 4 pages, (2004).
Xu, Z. et al., "Oleylamine as Both Reducing Agent and Stabilizer in a Facile Synthesis of Magnetite Nano Particles", Chem Mat., 21:1778-80, (2009).
Yadav, V. et al., "Recombinant T-Cell Receptor Ligand (RTL) for Treatment of Multiple Sclerosis: A Double-Blind, Placebo-Controlled, Phase 1, Dose-Escalation Study", Autoimmune Dis., 2012:954739, (2012).
Yamanouchi, J. et al., "Interleukin-2 Gene Variation Impairs Regulatory T Cell Function and Causes Autoimmunity", Nat Genet., 39(3):329-37, (2007).
Yanaba, K. et al., "The Development and Function of Regulatory B Cells Expressing IL-10 (B10 Cells) Requires Antigen Receptor Diversity and TLR Signals", J Immunol., 182(12):7459-72, (2009).
Yang, J. et al., "CD4+ T Cells From Type 1 Diabetic and Healthy Subjects Exhibit Different Thresholds of Activation to a Naturally Processed Proinsulin Epitope", J Autoimmun., 31(1):30-41, (2008).
Yang, J. et al., "Islet-specific glucose-6-phosphatase Catalytic Subunit-Related Protein-Reactive CD4+ T Cells in Human Subjects", J Immunol., 176(5):2781-9, (2006).
Yang, X. et al., "Opposing Regulation of the Locus Encoding IL-17 Through Direct, Reciprocal Actions of STAT3 and STAT5", Nat Immunol., 12(3):247-54, (2011).
Yeste, A. et al., "Nanoparticle-mediated Codelivery of Myelin Antigen and a Tolerogenic Small Molecule Suppresses Experimental Autoimmune Encephalomyelitis", Proc Natl Acad Sci USA, 109(28):11270-5, (2012).
Ying, H. et al., "Cancer Therapy Using a Self-Replicating RNA Vaccine", Nat Med., 5(7):823-7, (1999).
Yokosuka, T. et al., "Newly Generated T Cell Receptor Microclusters Initiate and Sustain T Cell Activation by Recruitment of Zap70 and SLP-76", Nat Immunol., 6(12):1253-62, (2005).
Yoshida, K. et al., "Evidence for Shared Recognition of a Peptide Ligand by a Diverse Panel of Non-Obese Diabetic Mice-Derived, Islet-Specific, Diabetogenic T Cell Clones", Int Immunol., 14(12)1439-47, (2002).

(56) References Cited

OTHER PUBLICATIONS

Yoshizaki, A. et al., "Regulatory B Cells Control T-cell Autoimmunity Through IL-21-dependent Cognate Interactions", Nature, 491(7423):264-8, (2012).
Yu, Y. et al., "Cutting Edge: Single-Chain Trimers of MHC Class I Molecules Form Stable Structures That Potently Stimulate Antigen-Specific T Cells and B Cells", J Immunol., 168(7):3145-9, (2002).
Zajac, A. et al., "Viral Immune Evasion Due to Persistence of Activated T Cells Without Effector Function", J Exp Med., 188(12):2205-13, (1998).
Zang, Y. et al., "Increased CD8+ Cytotoxic T Cell Responses to Myelin Basic Protein in Multiple Sclerosis", J Immunol., 172(8):5120-7, (2004).
Zhang, S. et al., "HMGB1, an Innate Alarmin, in the Pathogenesis of Type 1 Diabetes", Int J Clin Exp Pathol., 3(1):24-38, (2010).
Zhong, L. et al., "NSOM/QD-based Direct Visualization of CD3-induced and CD28-enhanced Nanospatial Coclustering of TCR and Coreceptor in Nanodomains in T Cell Activation", PLoS One, 4(6): e5945, (2009).
Zhou, L. et al., "Plasticity of CD4+ T Cell Lineage Differentiation", Immunity, 30(5):646-55, (2009).
Zhou, X. et al., "Instability of the Transcription Factor Foxp3 Leads to the Generation of Pathogenic Memory T Cells in Vivo", Nat Immunol., 10(9):1000-7, (2009).
Zufferey, R. et al., "Woodchuck Hepatitis Virus Posttranscriptional Regulatory Element Enhances Expression of Transgenes Delivered by Retroviral Vectors", J Virol., 73(4):2886-92, (1999).
AU Patent Application No. 2016203231; Examination Report No. 2, dated Nov. 30, 2017; 3 pages.
AU Patent Application No. 2016225913; Examination Report No. 1, dated Sep. 22, 2017; 4 pages.
Bibliographic data page from EPO website at espace.net.com/publication_Details/biblio?CC=WO&NR=2004078909A2&KC=..., downloaded Nov. 15, 2010, showing that W02004078909 was also published as US2007154953: 1 page total.
CA Patent Application No. 2,817,710; Office Action, dated Oct. 19, 2017; 4 pages.
CN Patent Application No. 201380022126.2; Office Action No. 4, dated Jul. 24, 2017; 2 pages.
Japan Intractable Diseases Information Center, "Crohn's Disease," retrieved from nanbyou.or.jp/entry/111, (2015).
JP Patent Application No. 2015-536240; Office Action, dated Aug. 16, 2017; 6 pages.
JP Patent Application No. 2016-159414; Office Action, dated Oct. 30, 2017; 4 pages.
JP Patent Application No. 2017-014194; Office Action, dated Sep. 13, 2017; 6 pages.
MX Patent Application No. MX/a/2013/003559; Office Action No. 3, dated Jul. 3, 2017; 5 pages.
MX Patent Application No. MX/a/2014/011623; Office Action, dated Jul. 28, 2017; 10 pages.
NZ Patent Application No. 706970; First Examination Report, dated Nov. 8, 2017; 4 pages.
RU Patent Application No. 2014141984; Second Office Action, dated Nov. 23, 2017; 6 pages.
RU Patent Application No. 2015116509; Office Action, dated Nov. 29, 2017; 9 pages.
Shaefer, W. et al., "Heavy and light chain pairing of bivalent quadroma and knobs-into-holes antibodies analyzed by UHR-ESI-QTOF mass spectrometry", MAbs., 8(1):49-55, (2015).
U.S. Appl. No. 12/044,435; Applicant-Initiated Interview Summary, dated Dec. 13, 2012; 4 pages.
U.S. Appl. No. 12/044,435; Applicant-Initiated Interview Summary, dated Sep. 12, 2012; 6 pages.
U.S. Appl. No. 12/044,435; Final Office Action, dated Jun. 8, 2011; 24 pages.
U.S. Appl. No. 12/044,435; Non-Final Office Action, dated May 2, 2012; 12 pages.
U.S. Appl. No. 12/044,435; Non-Final Office Action, dated Nov. 24, 2010; 39 pages.
U.S. Appl. No. 12/044,435; Notice of Allowance, dated Sep. 12, 2012; 8 pages.
U.S. Appl. No. 12/848,055; Final Office Action, dated Aug. 23, 2012; 13 pages.
U.S. Appl. No. 12/848,055; Final Office Action, dated Dec. 24, 2014; 19 pages.
U.S. Appl. No. 12/848,055; Final Office Action, dated Jul. 12, 2013; 17 pages.
U.S. Appl. No. 12/848,055; Non-Final Office Action, dated Apr. 4, 2012; 22 pages.
U.S. Appl. No. 12/848,055; Non-Final Office Action, dated Dec. 19, 2012; 14 pages.
U.S. Appl. No. 12/848,055; Non-Final Office Action, dated Jun. 6, 2014; 24 pages.
U.S. Appl. No. 12/848,055; Non-Final Office Action, dated May 13, 2016; 27 pages.
U.S. Appl. No. 13/249,105; 1.132 Declaration, dated Jun. 2, 2017; 26 pages.
U.S. Appl. No. 13/249,105; 1.132 Declaration, dated Sep. 4, 2015; 13 pages.
U.S. Appl. No. 13/249,105; Final Office Action, dated Apr. 11, 2018; 32 pages.
U.S. Appl. No. 13/249,105; Final Office Action, dated Nov. 30, 2015; 20 pages.
U.S. Appl. No. 13/249,105; Non-Final Office Action, dated Apr. 3, 2015; 31 pages.
U.S. Appl. No. 13/249,105; Non-Final Office Action, dated Sep. 8, 2017; 16 pages.
U.S. Appl. No. 13/294,109; 1.132 Declaration, dated Nov. 5, 2015; 21 pages.
U.S. Appl. No. 13/294,109; Examiner-Initiated Interview Summary, dated Apr. 4, 2016; 3 pages.
U.S. Appl. No. 13/294,109; Final Office Action, dated Jan. 12, 2015; 13 pages.
U.S. Appl. No. 13/294,109; Final Office Action, dated Nov. 13, 2013; 14 pages.
U.S. Appl. No. 13/294,109; Non-Final Office Action, dated Jun. 4, 2013; 23 pages.
U.S. Appl. No. 13/294,109; Notice of Allowance, dated Apr. 4, 2016; 15 pages.
U.S. Appl. No. 13/294,109; Notice of Allowance, dated Sep. 29, 2016; 31 pages.
U.S. Appl. No. 13/294,109; Notice of Appeal, dated Jul. 10, 2015; 4 pages.
U.S. Appl. No. 13/712,832; Non-Final Office Action, dated Feb. 27, 2015; 34 pages.
U.S. Appl. No. 13/830,521; 1.132 Declaration, dated Dec. 24, 2014; 8 pages.
U.S. Appl. No. 13/830,521; Final Office Action, dated Mar. 5, 2015; 15 pages.
U.S. Appl. No. 13/830,521; Non-Final Office Action, dated Jul. 25, 2014; 36 pages.
U.S. Appl. No. 13/830,521; Non-Final Office Action, dated Jun. 28, 2016; 13 pages.
U.S. Appl. No. 13/842,302; 1.132 Declaration, dated Feb. 17, 2016; 46 pages.
U.S. Appl. No. 13/842,302; 1.132 Declaration, dated Feb. 23, 2016; 2 pages.
U.S. Appl. No. 13/842,302; Examiner-Initiated Interview Summary, dated Oct. 22, 2020; 1 page.
U.S. Appl. No. 13/842,302; Final Office Action, dated Dec. 28, 2018; 21 pages.
U.S. Appl. No. 13/842,302; Final Office Action, dated Feb. 18, 2015; 25 pages.
U.S. Appl. No. 13/842,302; Final Office Action, dated May 3, 2017; 31 pages.
U.S. Appl. No. 13/842,302; Non-Final Office Action, dated Apr. 29, 2020; 22 pages.
U.S. Appl. No. 13/842,302; Non-Final Office Action, dated Apr. 30, 2014; 29 pages.
U.S. Appl. No. 13/842,302; Non-Final Office Action, dated Apr. 30, 2018; 46 pages.

(56) References Cited

OTHER PUBLICATIONS

U.S. Appl. No. 13/842,302; Non-Final Office Action, dated Jul. 6, 2016; 28 pages.
U.S. Appl. No. 13/842,302; Notice of Allowance, dated Oct. 22, 2020; 31 pages.
U.S. Appl. No. 14/531,707; Examiner-Initiated Interview Summary, dated Jun. 18, 2018; 1 page.
U.S. Appl. No. 14/531,707; Non-Final Office Action, dated Oct. 3, 2017; 14 pages.
U.S. Appl. No. 14/531,707; Notice of Allowance, dated Jul. 20, 2018; 4 pages.
U.S. Appl. No. 14/531,707; Notice of Allowance, dated Jun. 18, 2018; 58 pages.
U.S. Appl. No. 14/684,153; Non-Final Office Action, dated Jun. 30, 2016; 32 pages.
U.S. Appl. No. 14/684,153; Notice of Allowance, dated Jan. 26, 2017; 7 pages.
U.S. Appl. No. 15/348,959; Applicant-Initiated Interview Summary, dated Aug. 30, 2017; 2 pages.
U.S. Appl. No. 15/348,959; Applicant-Initiated Interview Summary, dated Jul. 3, 2019; 2 pages.
U.S. Appl. No. 15/348,959; Examiner-Initiated Interview Summary, dated Jul. 3, 2019; 2 pages.
U.S. Appl. No. 15/348,959; Final Office Action, dated Jan. 12, 2018; 30 pages.
U.S. Appl. No. 15/348,959; First-Action Interview Office Action, dated Aug. 30, 2017; 25 pages.
U.S. Appl. No. 15/348,959; Non-Final Office Action, dated Feb. 21, 2019; 7 pages.
U.S. Appl. No. 15/348,959; Notice of Allowance, dated Jul. 3, 2019; 12 pages.
U.S. Appl. No. 15/348,959; Pre-Interview First Office Action, dated Apr. 13, 2017; 20 pages.
U.S. Appl. No. 15/433,898; Non-Final Office Action, dated Sep. 28, 2017; 31 pages.
U.S. Appl. No. 15/433,898; Notice of Allowance, dated May 17, 2018; 34 pages.
U.S. Appl. No. 15/572,137; Final Office Action, dated Feb. 8, 2022; 17 pages.
U.S. Appl. No. 15/572,137; Final Office Action, dated Feb. 25, 2021; 23 pages.
U.S. Appl. No. 15/572,137; Non-Final Office Action, dated Jul. 23, 2021; 16 pages.
U.S. Appl. No. 15/572,137; Non-Final Office Action, dated Sep. 28, 2022; 26 pages.
U.S. Appl. No. 15/610,550; Applicant-Initiated Interview Summary, date of interview Mar. 25, 2020; 3 pages.
U.S. Appl. No. 15/610,550; Final Office Action, dated Jun. 19, 2020; 16 pages.
U.S. Appl. No. 15/610,550; Non-Final Office Action, dated Nov. 4, 2019; 50 pages.
U.S. Appl. No. 15/807,415; Final Office Action, dated Aug. 30, 2022; 26 pages.
U.S. Appl. No. 15/807,415; Final Office Action, dated Dec. 30, 2020; 33 pages.
U.S. Appl. No. 15/807,415; Non-Final Office Action, dated Aug. 19, 2021; 17 pages.
U.S. Appl. No. 15/807,415; Non-Final Office Action, dated Jul. 29, 2020; 74 pages.
U.S. Appl. No. 15/999,192; Non-Final Office Action, dated Apr. 15, 2020; 71 pages.
U.S. Appl. No. 15/999,192; Notice of Allowance, dated Oct. 13, 2020; 15 pages.
U.S. Appl. No. 16/132,000; Examiner-Initiated Interview Summary, dated Jan. 7, 2022; 1 page.
U.S. Appl. No. 16/132,000; Notice of Allowance, dated Jan. 21, 2022; 15 pages.
U.S. Appl. No. 16/156,326; Final Office Action, dated Apr. 20, 2022; 40 pages.
U.S. Appl. No. 16/200,199; Non-Final Office Action, dated Aug. 27, 2020; 54 pages.
U.S. Appl. No. 16/200,199; Notice of Allowance, dated Jan. 13, 2021; 11 pages.
U.S. Appl. No. 16/603,180; Final Office Action, dated Mar. 1, 2023; 29 pages.
U.S. Appl. No. 16/603,180; Non-Final Office Action, dated Jul. 19, 2022; 54 pages.
U.S. Appl. No. 17/153,212; Applicant-Initiated Interview Summary, dated Aug. 6, 2024; 2 pages.
U.S. Appl. No. 18/048,339; Application as filed, dated Oct. 20, 2022; 83 pages.
Betts, R. et al., "CDS(+) T Cells in Asthma: Friend or Foe?", Pharmacol Ther., 121(2):123-31, (2009).
Bianchi, A. et al., "Parenteral Vaccination of Mice and Piglets With F4+ *Escherichia coli* Suppresses the Enteric anti-F4 Response Upon Oral Infection", Vaccine, 14(3):199-206, (1996).
Bibliographic data page from EPO website at https://www.espace.net.com/publication_Details/biblio? CC=WO&NR=2004078909A2 &KC= ..., downloaded Nov. 15, 2010, showing that W02004078909 was also published as U.S. Pat. No. 2007154953: 1 page total.
Bielekova, B. et al., "Encephalitogenic Potential of the Myelin Basic Protein Peptide (Amino Acids 83-99) in Multiple Sclerosis: Results of a Phase II Clinical Trial With an Altered Peptide Ligand", Nat Med., 6(10):1167-75, (2000).
Blancou, P. et al., "Immunization of HLA Class I Transgenic Mice Identifies Autoantigenic Epitopes Eliciting Dominant Responses in Type 1 Diabetes Patients", J Immunol., 178(11):7458-66, (2007).
Bossuyt, X. et al., "Serologic Markers in Inflammatory Bowel Disease", Clin Chem., 52(2):171-81, (2006).
Bottazzo, G. et al., "In Situ Characterization of Autoimmune Phenomena and Expression of HLA Molecules in the Pancreas in Diabetic Insulitis", N Engl J Med., 313(6):353-60, (1985).
Bottini, M. et al., "Luminescent Silica Nanobeads: Characterization and Evaluation as Efficient Cytoplasmatic Transporters for T-lymphocytes", J Am Chem Soc., 129(25):7814-23, (2007).
Bour-Jordan, H. et al., "B Cell Depletion: A Novel Therapy for Autoimmune Diabetes?", J Clin Invest., 117(12):3642-5, (2007).
Braud, V. et al., "Functions of Nonclassical MHC and non-MHC-encoded Class I Molecules ", Curr Opin Immunol., 11(1):100-8, (1999).
Buenafe, A. et al., "Regulatory T Cells Play a Role in T-cell Receptor CDR2 Peptide Regulation of Experimental Autoimmune Encephalomyelitis", Immunology, 135(2):168-79, (2012).
Bunnell, S. et al., "T Cell Receptor Ligation Induces the Formation of Dynamically Regulated Signaling Assemblies", J Cell Biol., 158(7):1263-75, (2002).
Burke, R. et al., "The Influence of Adjuvant on the Therapeutic Efficacy of a Recombinant Genital Herpes Vaccine", J Inf Dis., 170(5):1110-9, (1994).
Burton, B. et al., "Sequential Transcriptional Changes Dictate Safe and Effective Antigen-Specific Immunotherapy", Nat Commun., 5:4741, (2014).
Cao, K. et al., "Analysis of the Frequencies of HLA-A, B, and C Alleles and Haplotypes in the Five Major Ethnic Groups of the United States Reveals High Levels of Diversity in These Loci and Contrasting Distribution Patterns in These Populations", Hum Immunol., 62(9):1009-30, (2001).
Caruso, F. et al., "Investigation of Electrostatic Interactions in Polyelectrolyte Multilayer Films: Binding of Anionic Fluorescent Probes to Layers Assembled onto Colloids", Macromol., 32(7):2317-28, (1999).
Caruso, F. et al., "Protein Multilayer Formation on Colloids Through a Stepwise Self-Assembly Technique", J Am Chem Soc., 121(25):6039-46, (1999).
Chang, J. et al., "Design, Engineering, and Production of Human Recombinant T Cell Receptor Ligands Derived From Human Leukocyte Antigen DR2", J Biol Chem., 276(26):24170-6, (2001).
Chatenoud, L., "Do NKT Cells Control Autoimmunity?", J Clin Invest., 110(6):747-8, (2002).
Dieterich, W. et al., "Identification of Tissue Transglutaminase as the Autoantigen of Celiac Disease", Nat Med., 3(7):797-801, (1997).

(56) References Cited

OTHER PUBLICATIONS

Dilorenzo, T. et al., "Major Histocompatibility Complex Class I-restricted T Cells Are Required for All but the End Stages of Diabetes Development in Nonobese Diabetic Mice and Use a Prevalent T Cell Receptor Alpha Chain Gene Rearrangement", Proc Natl Acad Sci USA, 95(21):12538-43, (1998).

Diwan, M. et al., "Biodegradable Nanoparticle Mediated Antigen Delivery to Human Cord Blood Derived Dendritic Cells for Induction of Primary T Cell Responses", J Drug Target, 11(8-10):495-507, (2003).

Dominguez, A. et al., "Targeting the Tumor Microenvironment With anti-neu/anti-CD40 Conjugated Nanoparticles for the Induction of Antitumor Immune Responses", Vaccine, 28(5):1383-90, (2010).

Dranoff, G., "Targets of Protective Tumor Immunity", Ann NY Acad Sci., 1174:74-80, (2009).

Dressel, A. et al., "Autoantigen Recognition by Human CD8 T Cell Clones: Enhanced Agonist Response Induced by Altered Peptide Ligands", J Immunol., 159(10):4943-51, (1997).

Edelman, G. et al., "The Covalent Structure of an Entire gammaG Immunoglobulin Molecule", Proc Natl Acad Sci USA, 63(1):78-85, (1969).

Eggena, M. et al., "Identification of Histone H1 as a Cognate Antigen of the Ulcerative Colitis-Associated Marker Antibody pANCA", J Autoimmun., 14(1):83-97, (2000).

Ellman, J. et al., "Biosynthetic Method for Introducing Unnatural Amino Acids Site-Specifically Into Proteins ", Methods Enzymol., 202:301-36, (1991).

Fennessy, M. et al., "A Gene in the HLA Class I Region Contributes to Susceptibility to IDDM in the Finnish Population. Childhood Diabetes in Finland (DiMe) Study Group", Diabetologia., 37(9):937-45, (1994).

Fifis, T. et al., "Short Peptide Sequences Containing MHC Class I and/or Class II Epitopes Linked to Nano-Beads Induce Strong Immunity and Inhibition of Growth of Antigen-Specific Tumour Challenge in Mice", Vaccine, 23(2):258-66, (2004).

Firestein, G., "Evolving Concepts of Rheumatoid Arthritis", Nature, 423(6937):356-61, (2003).

Flad, T. et al., "Development of an MHC-class I Peptide Selection Assay Combining Nanoparticle Technology and Matrix-Assisted Laser Desorption/Ionisation Mass Spectrometry", J Immunol Methods, 283(1-2):205-13, (2003).

Frankel, A. et al., "Characterization of Diphtheria Fusion Proteins Targeted to the Human interleukin-3 Receptor", Protein Eng., 13(8):575-81, (2000).

Friedman, A. et al., "The Smart Targeting of Nanoparticles", Curr Pharm Des., 19(35):6315-29, (2013).

Gagliani, N. et al., "Coexpression of CD49b and LAG-3 Identifies Human and Mouse T Regulatory Type 1 Cells", Nat Med., 19(6):739-46, (2013).

Garboczi, D. et al., "HLA-A2-peptide Complexes: Refolding and Crystallization of Molecules Expressed in *Escherichia coli* and Complexed With Single Antigenic Peptides", Proc Natl Acad Sci USA, 89(8):3429-33, (1992).

GenBank accession No. NM_001008228.2, accessed at https://www.ncbi.nlm.nih.gov/nuccore/281371473/?report=genbank on Jan. 16, 2018, 1 page.

Getts, D. et al., "Microparticles Bearing Encephalitogenic Peptides Induce T-cell Tolerance and Ameliorate Experimental Autoimmune Encephalomyelitis", Nat Biotechnol., 30(12):1217-24, (2012).

Gil, D. et al., "Recruitment of Nck by CD3 Epsilon Reveals a Ligand-Induced Conformational Change Essential for T Cell Receptor Signaling and Synapse Formation", Cell, 109(7):901-12, (2002).

Gill, R. et al., "Characterization of Primary T Cell Subsets Mediating Rejection of Pancreatic Islet Grafts", J Immunol., 143(7):2176-8, (1989).

Gimmi, C. et al., "Human T-cell Clonal Anergy Is Induced by Antigen Presentation in the Absence of B7 Costimulation", Proc Natl Acad Sci USA, 90(14):6586-90, (1993).

Giuliani, F. et al, "Additive Effect of the Combination of Glatiramer Acetate and Minocycline in a Model of MS", J Neuroimmunol., 158(1-2):213-21, (2005).

Gold, R. et al., "Understanding Pathogenesis and Therapy of Multiple Sclerosis via Animal Models: 70 Years of Merits and Culprits in Experimental Autoimmune Encephalomyelitis Research", Brain, 129(Pt 8):1953-71, (2006).

Golman, B. et al., "Fine Particle Coating by Chemical Vapor Deposition for Functional Materials", Trends Chem Engin., 6:1-16, (2000).

Gong, W. et al., "Immobilized MHC Class I Chain-Related Protein A Synergizes With IL-15 and Soluble 4-1BB Ligand to Expand NK Cells With High Cytotoxicity Ex Vivo", Cell Mol Immunol., 7(6):477-84, (2010).

Gregori, S. et al., "Re-establishing Immune Tolerance in Type 1 Diabetes via Regulatory T Cells", Novartis Found Symp., 292:174-83, (2008), (abstract), Abstract only.

Guarda, G. et al., "L-selectin-negative CCR7- Effector and Memory CD8+ T Cells Enter Reactive Lymph Nodes and Kill Dendritic Cells", Nat Immunol., 8(7):743-52, (2007).

Guidance for Industry, "Estimating the Maximum Safe Staring Dose in Initial Clinical Trials for Therapeutics in Adult Healthy Volunteers", U.S. DHHS, FDA, CDER, 27 pages, (2005).

Gunn, J. et al., "A Multimodal Targeting Nanoparticle for Selectively Labeling T Cells", Small, 4(6):712-5, (2008).

Guo, H. et al., "Protein Tolerance to Random Amino Acid Change," Proc Natl Acad Sci USA, 101 (25):9205-10, (2004).

Gupta, A. et al., "Synthesis and Surface Engineering of Iron Oxide Nanoparticles for Biomedical Applications", Biomaterials, 26(18):3995-4021, (2005).

Ha, J. et al., "Immunoglobulin Fc Heterodimer Platform Technology: From Design to Applications in Therapeutic Antibodies and Proteins", Front Immunol., 7(394):1-16, (2016).

Hale, J. et al., "Distinct Memory CD4+ T Cells With Commitment to T Follicular Helper- And T Helper 1-cell Lineages Are Generated After Acute Viral Infection", Immunity, 38(4):805-17, (2013).

Hall, C. et al., "Mapping Labeled Sites in *Escherichia coli* Ribosomal RNA: Distribution of Methyl Groups and Identification of a Photoaffinity-Labeled RNA Region Putatively at the Peptidyltransferase Center", Biochemistry, 24(21):5702-11, (1985).

Hamilton-Williams, E. et al., "Transgenic Rescue Implicates beta2-microglobulin as a Diabetes Susceptibility Gene in Nonobese Diabetic (NOD) Mice", Proc Natl Acad Sci USA, 98(20):11533-8, (2001).

Han, B. et al., "Developmental Control of CD8 T Cell-Avidity Maturation in Autoimmune Diabetes", J Clin Invest., 115(7):1879-87, (2005).

Han, B. et al., "Prevention of Diabetes by Manipulation of anti-IGRP Autoimmunity: High Efficiency of a Low-Affinity Peptide", Nat Med., 11(6):645-52, (2005).

Han, G. et al., "Interleukin-17-Producing Gammadelta+ T Cells Protect NOD Mice from Type 1 Diabetes Through a Mechanism Involving Transforming Growth Factor-Beta", Immunology, 129(2):197-206, (2010).

Hanprasopwattana, A. et al., "Titania Coatings on Monodisperse Silica Spheres (Characterization Using 2-Propanol Dehydration and TEM)", Langmuir, 12(13):3173-9, (1996).

Harris, S. et al., "Prediction of Murine MHC Class I Epitopes in a Major House Dust Mite Allergen and Induction of T1-type CD8+ T Cell Responses", Int Immunol., 9(2):273-80, (1997).

Hassainya, Y. et al., "Identification of Naturally Processed HLA-A2—restricted Proinsulin Epitopes by Reverse Immunology", Diabetes, 54(7):2053-9, (2006).

Herold, K. et al., "Anti-CD3 Monoclonal Antibody in New-Onset Type 1 Diabetes Mellitus", N Eng J Med., 346(22):1692-8, (2002).

Hirsch, D. et al., "Antigen-based Immunotherapy for Autoimmune Disease: Current Status", Immunotargets Ther., 4:1-11, (2014).

Hirschfield, G. et al., "The Immunobiology and Pathophysiology of Primary Biliary Cirrhosis", Annu Rev Pathol., 8:303-30, (2013).

HLA Nomenclature (2015) (Year: 2015), 2 pages.

Ho, K. et al., "The Clinical Relevance of Autoantibodies in Scleroderma", Arthritis Res Ther., 5(2):80-93, (2003).

(56) References Cited

OTHER PUBLICATIONS

Holgate, S. et al., "Treatment Strategies for Allergy and Asthma", Nat Rev Immunol., 8(3):218-30, (2008).
Holst, J. et al., "Generation of T-cell Receptor Retrogenic Mice", Nat Protoc., 1(1):406-17, (2006).
Honeyman, M. et al., "Analysis of Families at Risk for Insulin-Dependent Diabetes Mellitus Reveals That HLA Antigens Influence Progression to Clinical Disease", Mol Med., 1(5):576-82, (1995).
Hugues, S. et al., "Generation and use of alternative multimers of peptide/MHC complexes", J Immunol Methods, 268(1):83-92, (2002).
Huppa, J. et al., "TCR-peptide-MHC Interactions in Situ Show Accelerated Kinetics and Increased Affinity", Nature, 463(7283):963-7, (2010).
International Application No. PCT/EP2011/066994; International Preliminary Report on Patentability, date of issuance Apr. 2, 2013; 5 pages.
International Application No. PCT/EP2011/066994; International Search Report and Written Opinion of the International Searching Authority, date of mailing Nov. 21, 2011; 7 pages.
International Application No. PCT/IB2013/052352; International Preliminary Report on Patentability, date of issuance Oct. 1, 2014; 6 pages.
International Application No. PCT/IB2013/052352; International Search Report and Written Opinion of the International Searching Authority, date of mailing Oct. 2, 2013; 9 pages.
International Application No. PCT/EP2011 /069931; International Preliminary Report on Patentability (Ch. 2), date of issuance May 16, 2013; 21 pages.
International Application No. PCT/EP2011 /069931; International Search Report and Written Opinion of the International Searching Authority, date of mailing Jul. 10, 2012; 24 pages.
International Application No. PCT/IB2013/003033; International Preliminary Report on Patentability, date of issuance Apr. 14, 2015; 6 pages.
International Application No. PCT/IB2013/003033; International Search Report and Written Opinion of the International Searching Authority, date of mailing Jul. 14, 2014; 9 pages.
International Application No. PCT/IB2014/003014; International Preliminary Report on Patentability, date of issuance May 10, 2016; 9 pages.
International Application No. PCT/IB2014/003014; International Search Report and Written Opinion of the International Searching Authority, date of mailing May 12, 2015; 14 pages.
International Application No. PCT/IB2016/000691; International Preliminary Report on Patentability, date of issuance Nov. 7, 2017; 31 pages.
International Application No. PCT/IB2016/000691; International Search Report and Written Opinion of the International Searching Authority, date of mailing Mar. 7, 2017; 44 pages.
International Application No. PCT/IB2017/001508; International Search Report and Written Opinion of the International Searching Authority, date of mailing Mar. 26, 2018; 13 pages.
International Application No. PCT/IB2017/001508; International Preliminary Report on Patentability, date of issuance May 14, 2019; 9 pages.
International Application No. PCT/IB2018/000510; International Preliminary Report on Patentability, date of issuance Oct. 8, 2019; 4 pages.
International Application No. PCT/IB2018/000510; International Search Report and Written Opinion of the International Searching Authority, date of mailing Nov. 8, 2018; 8 pages.
International Application No. PCT/IB2018/001520; International Preliminary Report on Patentability, date of issuance Jun. 2, 2020; 6 pages.
International Application No. PCT/IB2018/001520; International Search Report and Written Opinion of the International Searching Authority, date of mailing, Apr. 15, 2019; 10 pages.
International Application No. PCT/US2008/056279; International Preliminary Report on Patentability, date of issuance Sep. 8, 2009; 11 pages.
Invernizzi, P. et al., "Classical HLA-DRB1 and DPB1 Alleles Account for HLA Associations With Primary Biliary Cirrhosis", Genes Immun., 13(6):461-8, ( 2012).
Itoh, N. et al., "Mononuclear Cell Infiltration and Its Relation to the Expression of Major Histocompatibility Complex Antigens and Adhesion Molecules in Pancreas Biopsy Specimens From Newly Diagnosed Insulin-Dependent Diabetes Mellitus Patients", J Clin Invest., 92(5):2313-22, (1993).
Komatsu, N. et al., "Heterogeneity of Natural Foxp3+ T Cells: A Committed Regulatory T-cell Lineage and an Uncommitted Minor Population Retaining Plasticity", Proc Natl Acad Sci USA, 106(6):1903-8, (2009).
Komatsu, N. et al., "Pathogenic Conversion of Foxp3+ T Cells Into TH17 Cells in Autoimmune Arthritis", Nat Med., 20(1):62-8, (2014).
Krishnamoorthy, G. et al., "Myelin-specific T Cells Also Recognize Neuronal Autoantigen in a Transgenic Mouse Model of Multiple Sclerosis", Nat Med., 15(6):626-33, (2009).
Kukreja, A. et al., "NKT Cells and Type-1 Diabetes and the "hygiene Hypothesis" to Explain the Rising Incidence Rate", Diabet Tech Ther., 4(3):323-33, (2002).
Kulmala, P., "Prediabetes in Children: Natural History, Diagnosis, and Preventive Strategies", Pediatr Drugs, 5(4):211-21, (2003).
Kwong, B. et al., "Synthesis and Characterization of Antibody-Nanoparticle Conjugates for Locally Sequestered Tumor Immunotherapy", Abstracts of Papers Am Chem Soc., 240:61, (2010).
Kyger, M. et al., "Effective Arrestin-Specific Immunotherapy of Experimental Autoimmune Uveitis with RTL: A Prospect for Treatment of Human Uveitis", Transl Vis Sci Technol., 2(2):1-15, (2013).
Kyung-Yu, M. et al., "Targeting Strategies for Multifunctional Nanoparticles in Cancer Imaging and Therapy", Theranostics, 2(1):3-44 , (2012).
Laurence, A. et al., "T(H)-17 Differentiation: Of Mice and Men", Nat Immunol., 8(9):903-5, (2007).
Leavenworth, J. et al., "Amelioration of Arthritis Through Mobilization of Peptide-Specific CD8+ Regulatory T Cells", J Clin Invest., 123(3):1382-9, (2013).
Lechner, F. et al., "Analysis of Successful Immune Responses in Persons Infected With Hepatitis C Virus", J Exp Med., 191(9):1499-510, (2000).
Lee, Y. et al., "Biodegradable Nanoparticles Containing TLR3 or TLR9 Agonists Together With Antigen Enhance MHC-restricted Presentation of the Antigen", Arch Pharm Res., 33(11):1859-66, (2010).
Levings, M. et al., "T-regulatory 1 Cells: A Novel Subset of CD4 T Cells With Immunoregulatory Properties", J Allergy Clin Immunol., 106(1 Pt 2):S109-12, (2000).
Liblau, R. et al., "Autoreactive CD8 T Cells in Organ-Specific Autoimmunity: Emerging Targets for Therapeutic Intervention", Immunity, 17(1):1-6, (2002).
Lieberman, S. et al., "A Comprehensive Guide to Antibody and T-cell Responses in Type 1 Diabetes", Tissue Antigens, 62(5):359-77, (2003).
Lieberman, S. et al., "Identification of the Beta Cell Antigen Targeted by a Prevalent Population of Pathogenic CD8+ T Cells in Autoimmune Diabetes", Proc Natl Acad Sci USA, 100(14):8384-8, (2003).
Lieberman, S. et al., "Individual Nonobese Diabetic Mice Exhibit Unique Patterns of CDS+ T Cell Reactivity to Three Islet Antigens, Including the Newly Identified Widely Expressed *Dystrophia myotonica* Kinase", J Immunol., 173(11):6727-34, (2004).
Lillemeier, B. et al., "TCR and Lat Are Expressed on Separate Protein Islands on T Cell Membranes and Concatenate During Activation", Nat Immunol., 11(1):90-6 (2010).
Lleo, A. et al., "Etiopathogenesis of Primary Biliary Cirrhosis", World J Gastroenterol., 14(21):3328-37, (2008).
Singh, N. et al., "Emerging Concepts in TCR Specificity: Rationalizing and (Maybe) Predicting Outcomes", J Immunol., 199(7):2203-13, (2017).
IL Patent Application No. 249165; Office Action, dated Dec. 17, 2017; 5 pages.
Kozono, H. et al., "Production of Soluble MHC Class II Proteins With Covalently Bound Single Peptides", 369 (6476): 151-4, (1994).

(56) References Cited

OTHER PUBLICATIONS

"Homology", Definition of homology by Merriam-Webster dictionary, 13 pages, (2019).
Celik, A. et al., "The diversity of the HLA-E-restricted peptide repertoire explains the immunological impact of the Arg107Gly mismatch", Immunogenetics, 68(1):29-41, (2016).
Cochran, J. et al., "The relationship of MHC-peptide binding and T cell activation probed using chemically defined MHC class II oligomers", Immunity, 12(3):241-50, (2000).
GenBank Accession No. AAC14923.1, "T cell receptor alpha chain [Homo sapiens]", retrieved from ncbi. hlm.nih.gov/protein/AAC14923.1?report=genbank&log$=protalign&blast, (1998).
Hemmer, B. et al., "Minimal Peptide Length Requirements for CD4(+) T Cell Clones—Implications for Molecular Mimicry and T Cell Survival", Int Immunol., 12(3):375-83, (2000).
Kalandadze, A. et al., "Replacement of the Hydrophopic Transmembrane Region by a Leucine Zipper Dimerization Motif Allows the Assembly and Secretion of Soluble DR αß Heterodimers", J Biol Chem., 271(33):20156-20162, (1996).
Kalergis, A. et al., "A simplified procedure for the preparation of MHC/peptide tetramers: chemical biotinylation of an unpaired cysteine engineered at the C-terminus of MHC-I", J Immunol Meth., 234(1-2):61-70, (2000).
Koonin, E. et al., "Chapter 2 Evolutionary Concept in Genetic and Genomics", NCBI Bookshelf, Bookshelf ID: NBK20255, 23 pages, (2003).
Nishioka, Y. et al., "CD1d-Restricted Type II NKT Cells Reactive With Endogenous Hydrophobic Peptides", Front Immunol., 9:548, 6 pages, (2018).
Pfister, D. et al., "Process for protein PEGylation", J Control Release, 180:134-49, (2014).
Schumacher, T. et al., "Neoantigens in cancer immunotherapy", Science, 348(6230):69-74, (2015).
Serra, P. et al., "Increased Yields and Biological Potency of Knob-Into-Hole-Based Soluble MHC Class II Molecules", Nat Commun., 10(1):4917, (2019).
Serra, P. et al., "Peptide-MHC-Based Nanomedicines for the Treatment of Autoimmunity: Engineering, Mechanisms, and Diseases", Front Immunol., 11:621774, (2021).
Shimoda, S. et al., "HLA DRB4 0101-restricted immunodominant T cell autoepitope of pyruvate dehydrogenase complex in primary biliary cirrhosis: evidence of molecular mimicry in human autoimmune diseases", J Exp Med., 181 (5):1835-45, (1995).
Wieczorek, M. et al., "Major Histocompatibility Complex (MHC) Class I and MHC Class II Proteins: Conformational Plasticity in Antigen Presentation", Front Immunol., 8(292):1-16, (2017).
Yang, Y. et al., "Antigen-specific nanomedicines for the treatment of autoimmune disease: target cell types, mechanisms and outcomes", Curr Opin Biotechnol., 74: 285-92, (2022).
CO Patent Application No. NC2017/0011437; Office Action, dated Nov. 19, 2017; 3 pages.
EP Patent Application No. 13856460.4; Communication, dated Nov. 15, 2017; 6 pages.
EP Patent Application No. 13856460.4; Extended European Search Report, mailed Feb. 26, 2016; 9 pages.
EP Patent Application No. 14184505.7; Communication, mailed Oct. 22, 2015; 4 pages.
EP Patent Application No. 17173410.6; Extended European Search Report, dated Dec. 15, 2017; 8 pages.
GenBank accession No. NM_001008228.2, accessed at ncbi.nlm.nih.gov/nuccore/281371473/?report=genbank on Jan. 16, 2018, 1 page.
GenBank accession No. NP_001008229.1, accessed at ncbi.nlm.nih.gov/protein/56788389/?report=genpept on Jan. 16, 2018, 3 pages.
Application No. PCT/EP2011 /069931; International Preliminary Report on Patentability (Ch. 2), date of issuance May 16, 2013; 21 pages.
Application No. PCT/EP2011 /069931; International Search Report and Written Opinion of the International Searching Authority, date of mailing Jul. 10, 2012; 24 pages.
Application No. PCT/EP2011/066994; International Preliminary Report on Patentability, date of issuance Apr. 2, 2013; 5 pages.
Application No. PCT/EP2011/066994; International Search Report and Written Opinion of the International Searching Authority, date of mailing Nov. 21, 2011; 7 pages.
Application No. PCT/IB2013/003033; International Preliminary Report on Patentability, date of issuance Apr. 14, 2015; 6 pages.
Application No. PCT/IB2013/003033; International Search Report and Written Opinion of the International Searching Authority, date of mailing Jul. 14, 2014; 9 pages.
Application No. PCT/IB2014/003014; International Preliminary Report on Patentability, date of issuance May 10, 2016; 9 pages.
Application No. PCT/IB2014/003014; International Search Report and Written Opinion of the International Searching Authority, date of mailing May 12, 2015; 14 pages.
Nanjundappa, R. et al., "A Gut Microbial Mimic that Hijacks Diabetogenic Autoreactivity to Suppress Colitis", Cell, 171(3):655-67, (2017).
Chen, C. et al., "Induction of autoantigen-specific Th2 and Tr1 regulatory T cells and modulation of autoimmune diabetes", J Immunol., 171(2):733-44, (2003).
Mallone, R. et al., "Functional avidity directs T-cell fate in autoreactive CD4+ T cells", Blood, 106(8):2798-805, (2005).
Matern, B. et al., "Insights into the polymorphism in HLA-DRA and its evolutionary relationship with HLA haplotypes", HLA, 95(2):117-27, (2020).
Rakoff-Nahoum, S. et al., "Role of toll-like receptors in spontaneous commensal-dependent colitis", Immunity, 25 (2):319-29, (2006).
U.S. Appl. No. 15/572,137; Notice of Allowance, dated Nov. 22, 2023; 66 pages.
U.S. Appl. No. 15/807,415; Applicant-Initiated Interview Summary, date of interview Aug. 23, 2023; 2 pages.
U.S. Appl. No. 15/807,415; Non-Final Office Action, dated May 25, 2023; 64 pages.
U.S. Appl. No. 17/097,682; Non-Final Office Action, dated Oct. 18, 2023; 60 pages.
U.S. Appl. No. 17/128,776; Non-Final Office Action, dated Dec. 8, 2023; 42 pages.
Clemente, J. et al., "The impact of the gut microbiota on human health: an integrative view", Cell, 148(6):1258-70, (2012).
Database Accession No. ADKO01000110, "Bacteroides vulgatus PC510 contig00041, whole genome shotgun sequence", Jul. 31, 2011; 6 pages.
Database Accession No. DVD94, "SubName: Full=Conserved domain protein", Database UniProtKB [online database] XP002712564; Jun. 15, 2010; retrieved Nov. 19, 2023; retrieved from www.uniprot.org/jobs/2013111951RNQ6FG0A.txt; 2 pages.
Diagnosis and Treatment Guidelines (for medical professionals): Japan Intractable Diseases Information Center, "Sjogren's Syndrome," Shengrensho University; retrieved Nov. 11, 2015; retrieved from https://www.nanbyou.or.jp/entry/111 ; 6 pages.
GenBank Accession No. AAC08954, T cell receptor beta chain, [Homo sapiens], [online database], originally retrieved 2001, retrieved Nov. 8, 2024; retrieved from ncbi.nlm.nih.gov/protein/AAC08954; 3 pages.
GenBank Accession No. NP_001008229.1, Myelin-oligodendrocyte glycoprotein isoform alpha3 precursor [Homo sapiens], [online database], originally retrieved on Jan. 16, 2018, accessed at ncbi.nlm.nih.gov/protein/56788389/?report=genpept, (document dated Dec. 11, 2017); 3 pages.
International Application No. PCT/US2008/056279; International Search Report and Written Opinion of the International Searching Authority, date of mailing Oct. 22, 2008; 14 pages.
Japan Intractable Diseases Information Center, "Crohn's Disease," retrieved from nanbyou.or.jp/entry/81, 6 pages (2015).
McKown, K. et al., "Lack of Efficacy of Oral Bovine Type II Collagen Added to Existing Therapy in Rheumatoid Arthritis," Arthritis Rheum., 42(6):1204-8, (1999).
Roncarolo, M. et al., "Interleukin-10-secreting Type 1 Regulatory T Cells in Rodents and Humans", Immunol Rev., 212:28-50, (2006).
U.S. Appl. No. 12/044,435; Advisory Action, dated Aug. 23, 2011; 4 pages.

(56) References Cited

OTHER PUBLICATIONS

U.S. Appl. No. 12/044,435; Applicant-Initiated Interview Summary, date of interview Dec. 11, 2012; 4 pages.
U.S. Appl. No. 12/044,435; Applicant-Initiated Interview Summary, date of interview Sep. 7, 2012; 6 pages.
U.S. Appl. No. 12/044,435; Applicant-Initiated Interview Summary, dated Jul. 16, 2012; 3 pages.
U.S. Appl. No. 12/044,435; Applicant-Initiated Interview Summary, dated Nov. 7, 2011; 3 pages.
U.S. Appl. No. 12/044,435; Examiner-Initiated Interview Summary, dated Mar. 18, 2011; 4 pages.
U.S. Appl. No. 12/044,435; Final Office Action, dated Jun. 8, 2011; 22 pages.
U.S. Appl. No. 12/044,435; Non-Final Office Action, dated May 2, 2012; 9 pages.
U.S. Appl. No. 12/044,435; Non-Final Office Action, dated Nov. 24, 2010; 28 pages.
U.S. Appl. No. 12/044,435; Notice of Allowance, dated Sep. 12, 2012; 9 pages.
U.S. Appl. No. 12/044,435; Supplemental Notice of Allowability, dated Dec. 13, 2012; 2 pages.
U.S. Appl. No. 12/848,055; 1.132 Declaration, dated May 21, 2013; 7 pages.
U.S. Appl. No. 12/848,055; Advisory Action, dated May 5, 2014; 3 pages.
U.S. Appl. No. 12/848,055; Applicant-Initiated Interview Summary, dated Nov. 5, 2012; 6 pages.
U.S. Appl. No. 12/848,055; Final Office Action, dated Aug. 23, 2012; 10 pages.
U.S. Appl. No. 12/848,055; Final Office Action, dated Dec. 24, 2014; 18 pages.
U.S. Appl. No. 12/848,055; Final Office Action, dated Jul. 12, 2013; 15 pages.
U.S. Appl. No. 12/848,055; Non-Final Office Action, dated Apr. 4, 2012; 10 pages.
U.S. Appl. No. 12/848,055; Non-Final Office Action, dated Dec. 19, 2012; 13 pages.
U.S. Appl. No. 12/848,055; Non-Final Office Action, dated Jun. 6, 2014; 18 pages.
U.S. Appl. No. 12/848,055; Non-Final Office Action, dated May 13, 2016; 23 pages.
U.S. Appl. No. 12/848,055; Notice of Appeal, dated Jan. 7, 2014; 2 pages.
U.S. Appl. No. 12/848,055; Notice of Appeal, dated Jun. 22, 2015; 2 pages.
U.S. Appl. No. 12/848,055; Notice of Appeal, dated Nov. 11, 2016; 2 pages.
U.S. Appl. No. 13/249,105; 1.132 Declaration, dated Apr. 24, 2017; 26 pages.
U.S. Appl. No. 13/249,105; 1.132 Declaration, dated Aug. 24, 2015; 13 pages.
U.S. Appl. No. 13/249,105; Applicant Summary of Interview, dated Mar. 6, 2017; 2 pages.
U.S. Appl. No. 13/249,105; Applicant Summary of Interview, dated Oct. 9, 2015; 1 page.
U.S. Appl. No. 13/249,105; Applicant-Initiated Interview Summary, dated Aug. 6, 2015; 3 pages.
U.S. Appl. No. 13/249,105; Applicant-Initiated Interview Summary, dated Feb. 7, 2017; 3 pages.
U.S. Appl. No. 13/249,105; Applicant-Initiated Interview Summary, dated Sep. 11, 2015; 3 pages.
U.S. Appl. No. 13/249,105; Final Office Action, dated Apr. 11, 2018; 7 pages.
U.S. Appl. No. 13/249,105; Final Office Action, dated Nov. 30, 2015; 17 pages.
U.S. Appl. No. 13/249,105; Non-Final Office Action, dated Apr. 3, 2015; 9 pages.
U.S. Appl. No. 13/249,105; Non-Final Office Action, dated Sep. 8, 2017; 11 pages.
U.S. Appl. No. 13/249,105; Notice of Appeal, dated May 31, 2016; 2 pages.
U.S. Appl. No. 13/294,109; 1.132 Declaration, dated Dec. 11, 2014; 12 pages.
U.S. Appl. No. 13/294,109; 1.132 Declaration, dated Oct. 20, 2015; 21 pages.
U.S. Appl. No. 13/294,109; Examiner-Initiated Interview Summary, date of interview Mar. 24, 2016; 3 pages.
U.S. Appl. No. 13/294,109; Final Office Action, dated Jan. 12, 2015; 11 pages.
U.S. Appl. No. 13/294,109; Final Office Action, dated Nov. 13, 2013; 10 pages.
U.S. Appl. No. 13/294,109; Non-Final Office Action, dated Jun. 4, 2013; 9 pages.
U.S. Appl. No. 13/294,109; Notice of Allowance, dated Apr. 4, 2016; 9 pages.
U.S. Appl. No. 13/294,109; Notice of Allowance, dated Sep. 29, 2016; 5 pages.
U.S. Appl. No. 13/294,109; Notice of Appeal, dated Jul. 10, 2015; 2 pages.
U.S. Appl. No. 13/712,832; Non-Final Office Action, dated Feb. 27, 2015; 11 pages.
U.S. Appl. No. 13/830,521; 1.132 Declaration, dated Apr. 4, 2016; 33 pages.
U.S. Appl. No. 13/830,521; 1.132 Declaration, dated Dec. 23, 2014; 8 pages.
U.S. Appl. No. 13/830,521; Applicant-Initiated Interview Summary, dated Dec. 19, 2016; 2 pages.
U.S. Appl. No. 13/830,521; Applicant-Initiated Interview Summary, dated May 27, 2015; 3 pages.
U.S. Appl. No. 13/830,521; Final Office Action, dated Mar. 5, 2015; 13 pages.
U.S. Appl. No. 13/830,521; Non-Final Office Action, dated Jul. 25, 2014; 21 pages.
U.S. Appl. No. 13/830,521; Non-Final Office Action, dated Jun. 28, 2016; 10 pages.
U.S. Appl. No. 13/830,521; Notice of Appeal, dated Sep. 4, 2015; 2 pages.
U.S. Appl. No. 13/842,302; 1.132 Declaration, dated Feb. 22, 2016; 2 pages.
U.S. Appl. No. 13/842,302; 1.132 Declaration, dated Jan. 29, 2016; 46 pages.
U.S. Appl. No. 13/842,302; Advisory Action, dated Jul. 10, 2019; 6 pages.
U.S. Appl. No. 13/842,302; Applicant-Initiated Interview Summary, dated Aug. 15, 2018; 4 pages.
U.S. Appl. No. 13/842,302; Applicant-Initiated Interview Summary, dated Jan. 25, 2017; 4 pages.
U.S. Appl. No. 13/842,302; Applicant-Initiated Interview Summary, dated Jun. 23, 2015; 5 pages.
U.S. Appl. No. 13/842,302; Examiner-Initiated Interview Summary, date of interview Oct. 15, 2020; 1 page.
U.S. Appl. No. 13/842,302; Final Office Action, dated Dec. 28, 2018; 18 pages.
U.S. Appl. No. 13/842,302; Final Office Action, dated Feb. 18, 2015; 22 pages.
U.S. Appl. No. 13/842,302; Final Office Action, dated May 3, 2017; 28 pages.
U.S. Appl. No. 13/842,302; Non-Final Office Action, dated Apr. 29, 2020; 18 pages.
U.S. Appl. No. 13/842,302; Non-Final Office Action, dated Apr. 30, 2014; 15 pages.
U.S. Appl. No. 13/842,302; Non-Final Office Action, dated Apr. 30, 2018; 18 pages.
U.S. Appl. No. 13/842,302; Non-Final Office Action, dated Jul. 6, 2016; 24 pages.
U.S. Appl. No. 13/842,302; Notice of Allowance, dated Oct. 22, 2020; 11 pages.
U.S. Appl. No. 13/842,302; Notice of Appeal, dated Aug. 17, 2015; 2 pages.
U.S. Appl. No. 14/531,707; Applicant-Initiated Interview Summary, dated Jan. 31, 2018; 3 pages.

(56) References Cited

OTHER PUBLICATIONS

U.S. Appl. No. 14/531,707; Corrected Notice of Allowability, dated Jul. 20, 2018; 2 pages.
U.S. Appl. No. 14/531,707; Examiner-Initiated Interview Summary, date of interview Jun. 5, 2018; 1 page.
U.S. Appl. No. 14/531,707; Non-Final Office Action, dated Oct. 3, 2017; 12 pages.
U.S. Appl. No. 14/531,707; Notice of Allowance, dated Jun. 18, 2018; 11 pages.
U.S. Appl. No. 14/684,153; Applicant-Initiated Interview Summary, dated Dec. 20, 2016; 2 pages.
U.S. Appl. No. 14/684,153; Non-Final Office Action, dated Jun. 30, 2016; 18 pages.
U.S. Appl. No. 14/684,153; Notice of Allowance, dated Jan. 26, 2017; 6 pages.
U.S. Appl. No. 14/723,268; Final Office Action, dated Mar. 30, 2016; 15 pages.
U.S. Appl. No. 14/723,268; Non-Final Office Action, dated Oct. 16, 2015; 23 pages.
U.S. Appl. No. 14/723,268; Notice of Appeal, dated Sep. 29, 2016; 2 pages.
U.S. Appl. No. 15/348,959; Applicant-Initiated Interview Summary, date of interview Apr. 4, 2019; 2 pages.
U.S. Appl. No. 15/348,959; Applicant-Initiated Interview Summary, date of interview Jun. 27, 2017; 2 pages.
U.S. Appl. No. 15/348,959; Applicant-Initiated Interview Summary, dated Mar. 29, 2018; 3 pages.
U.S. Appl. No. 15/348,959; Examiner-Initiated Interview Summary, date of interview Jun. 21, 2019; 2 pages.
U.S. Appl. No. 15/348,959; Final Office Action, dated Jan. 12, 2018; 18 pages.
U.S. Appl. No. 15/348,959; First-Action Interview Office Action, dated Aug. 30, 2017; 20 pages.
U.S. Appl. No. 15/348,959; Non-Final Office Action, dated Feb. 21, 2019; 6 pages.
U.S. Appl. No. 15/348,959; Notice of Allowance, dated Jul. 3, 2019; 8 pages.
U.S. Appl. No. 15/348,959; Pre-Interview First Office Action, dated Apr. 13, 2017; 5 pages.
U.S. Appl. No. 15/433,898; Non-Final Office Action, dated Sep. 28, 2017; 16 pages.
U.S. Appl. No. 15/433,898; Notice of Allowance, dated May 17, 2018; 6 pages.
U.S. Appl. No. 15/433,898; Notice of Allowance, dated May 31, 2018; 3 pages.
U.S. Appl. No. 15/572,137; Final Office Action, dated Feb. 8, 2022; 13 pages.
U.S. Appl. No. 15/572,137; Final Office Action, dated Feb. 25, 2021; 12 pages.
U.S. Appl. No. 15/572,137; Non-Final Office Action, dated Jul. 23, 2021; 14 pages.
U.S. Appl. No. 15/572,137; Non-Final Office Action, dated Sep. 28, 2022; 22 pages.
U.S. Appl. No. 15/572,137; Notice of Allowance, dated Nov. 22, 2023; 8 pages.
U.S. Appl. No. 15/610,550; Applicant-Initiated Interview Summary, dated Mar. 3, 2020; 3 pages.
U.S. Appl. No. 15/610,550; Final Office Action, dated Jun. 19, 2020; 10 pages.
U.S. Appl. No. 15/610,550; Non-Final Office Action, dated Nov. 4, 2019; 9 pages.
U.S. Appl. No. 15/807,415; Applicant-Initiated Interview Summary, dated Aug. 29, 2023; 2 pages.
U.S. Appl. No. 15/807,415; Final Office Action, dated Aug. 30, 2022; 20 pages.
U.S. Appl. No. 15/807,415; Final Office Action, dated Dec. 30, 2020; 20 pages.
U.S. Appl. No. 15/807,415; Non-Final Office Action, dated Aug. 19, 2021; 13 pages.
U.S. Appl. No. 15/807,415; Non-Final Office Action, dated Jul. 29, 2020; 21 pages.
U.S. Appl. No. 15/807,415; Non-Final Office Action, dated May 25, 2023; 47 pages.
U.S. Appl. No. 15/999,192; Non-Final Office Action, dated Apr. 15, 2020; 19 pages.
U.S. Appl. No. 15/999,192; Notice of Allowance, dated Oct. 13, 2020; 8 pages.
U.S. Appl. No. 16/132,000; Examiner-Initiated Interview Summary, date of interview Jan. 7, 2022; 1 page.
U.S. Appl. No. 16/132,000; Notice of Allowance, dated Jan. 21, 2022; 10 pages.
U.S. Appl. No. 16/156,326; Final Office Action, dated Apr. 20, 2022; 34 pages.
U.S. Appl. No. 16/200,199; Non-Final Office Action, dated Aug. 27, 2020; 5 pages.
U.S. Appl. No. 16/200,199; Notice of Allowance, dated Jan. 13, 2021; 6 pages.
U.S. Appl. No. 16/603,180; Final Office Action, dated Mar. 1, 2023; 14 pages.
U.S. Appl. No. 16/603,180; Non-Final Office Action, dated Jul. 19, 2022; 13 pages.
U.S. Appl. No. 17/097,682; Non-Final Office Action, dated Oct. 18, 2023; 17 pages.
U.S. Appl. No. 17/128,776; Non-Final Office Action, dated Dec. 8, 2023; 7 pages.
U.S. Appl. No. 17/153,212; Non-Final Office Action, dated Nov. 14, 2024; 17 pages.
U.S. Appl. No. 17/228,014; Application as filed, dated Apr. 12, 2021; 63 pages.
Xu, J et al., "Evolution of symbiotic bacteria in the distal human intestine", PLoS Biol., 5(7)e156:1574-86, (2007).

\* cited by examiner

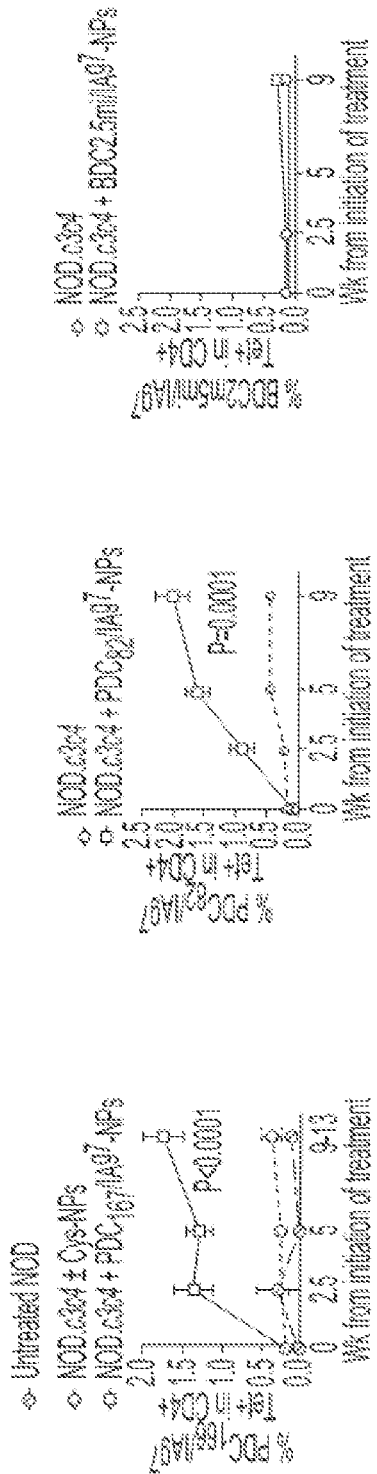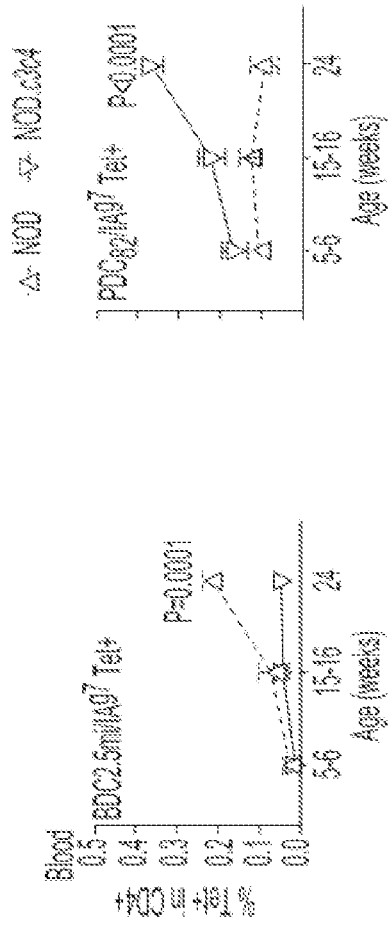
FIG. 1A
FIG. 1B

FIG. 6A  FIG. 6B left bar, PDC$_{166}$/IA$^{g7}$–NPs + rat IgG; middle bar, PDC$_{166}$/IA$^{g7}$–NPs + anti-IL10
right bar, PDC$_{166}$/IA$^{g7}$–NPs + anti-TGFb left bar, PDC$_{166}$/IA$^{g7}$–NPs + rat IgG; middle bar, PDC$_{166}$/IA$^{g7}$–NPs + anti-IL10
right bar, PDC$_{166}$/IA$^{g7}$–NPs + anti-TGFb left bar, PDC$_{166}$/IA$^{g7}$–NPs + rat IgG; middle bar, PDC$_{166}$/IA$^{g7}$–NPs + anti-IL10
right bar, PDC$_{166}$/IA$^{g7}$–NPs + anti-TGFb

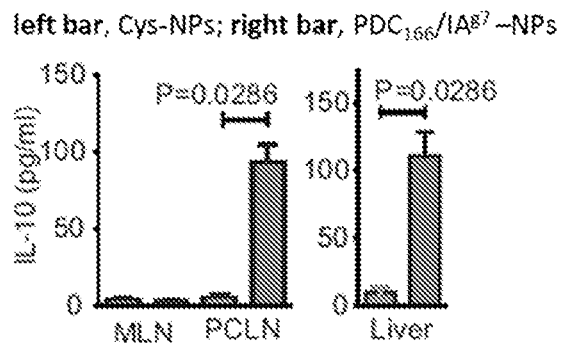
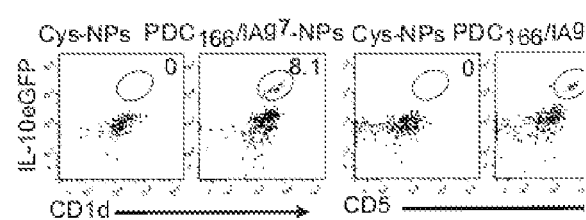
FIG. 7K    FIG. 7L
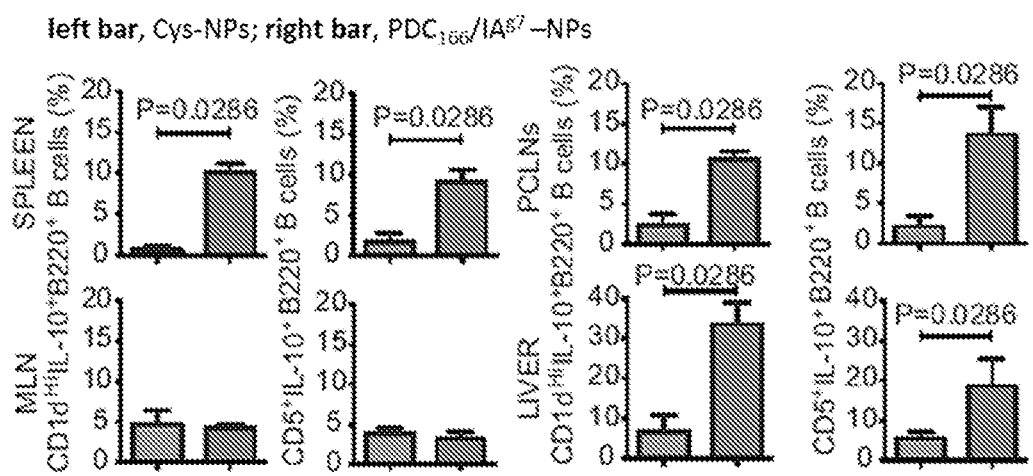
FIG. 7M

MAIYLLLFTAVRGIKEEHVYLIQAEFYLNPDQSGEFMFDFDGGDEIFHVDMAKKETVYWRLEEFGRFASFEAQGALANIAVDKAN
HA (Stem)                                                                      B5A LEIMTKRSNYTPITNVPPEVTVLTNSPVELREPNVLICFIDKFTPPVVNVTWLRNGKPVTTGVSETVFLPREDHLFRKFHYLPF
                                  B5A LPSTEDVYDCRVEHWGLDEPLLKHWEFDAPSPLPETTESGGGGDKTHTCPPCPAPEAAGG[PS]VFLFPPKPKDTLMISRTPEVT
                                          HINGE (truncated)  Leu Leu to Ala Ala CVVVDVSHEDPEVKFNWYVDGVEVHNAKTKPREEQYNSTYRVVSVLTVLHQDWLNGKEYKCKVSNKALPAPIEKTISKAKGQPR
                                                                         CH3 (knob)

EPQVYTLPPCRDELTKNQVSLWCLVKGFYPSDIAVEWESNGQPENNYKTTPPVLDSDGSFFLYSKLTVDKSRWQQGNVFSCSVM
                      CH3 (knob)

HEALHNHYTQKSLSLSPGKGGGGSGGGGSC (SEQ ID NO:103)
CH3 (knob)          448

UBIQUITOUS ANTIGENS FOR TREATMENT OF AUTOIMMUNE OR INFLAMMATORY DISEASES

CROSS REFERENCE TO RELATED APPLICATIONS

This application claims the benefit of U.S. provisional application 62/591,921 filed on Nov. 29, 2017; U.S. provisional application 62/636,520 filed on Feb. 28, 2018; and U.S. provisional application 62/641,607 filed on Mar. 12, 2018, all of which are incorporated by reference herein in their entirety.

INCORPORATION OF SEQUENCE LISTING

The sequence listing that is contained in the file named "PTI0010-505-US," which was created Mar. 8, 2024, and which has a file size of 29,798.4 bytes as measured in Microsoft Windows operating system, is filed electronically herewith and incorporated herein by reference.

SUMMARY

Provided herein are compositions comprising a plurality of antigen-major histocompatibility complexes coupled to a nanoparticle core. The compositions are useful for treating autoimmune and inflammatory disorders. Many autoimmune or inflammatory diseases are associated with an immune response directed to a particular tissue specific antigen or subset of antigens. This presents a problem for designing interventions that treat an autoimmune or inflammatory disease since each disease requires a specific medicament that targets that antigen or subset of antigens. Alternatively, nonspecific immune inhibitors can be used, but these are associated with significant systemic side-effects. Described herein are compositions comprising ubiquitous autoantigen-MHC complexes coupled to nanoparticles (uaMHC-NP), that are useful for treating autoimmune diseases or expanding populations of T regulatory cells that suppress autoreactive (i.e., autoimmune or inflammatory) T cells.

Primarily, the treatments described herein are multi-purpose in that a single composition can treat multiple-autoimmune or inflammatory disorders that are not mechanistically or pathologically linked. Many treatments, for example, corticosteroids or antibodies against general inflammatory mediators, that are multi-purpose in this way result in systemic immunosuppression, thus, increasing a treated patients risk for developing secondary infections and systemic immunological complications. The compositions described herein, while being multi-purpose, also spare systemic immunity leaving intact the ability of a patient to fight off viral, bacterial, fungal infection, or tumors. Surprisingly, the antigens utilized by the methods described herein are able to treat multiple diseases that are pathologically distinct (e.g., different autoimmune diseases of the same organ can be treated by a single antigen) and distinct with regard to tissue of origin (e.g., autoimmune diseases that afflict different organ systems). These antigens are antigens that are broadly expressed across many different tissue types, but are not the primary antigens associated with the disease, which generally display expression restricted to the particular tissue.

In certain aspects described herein is a composition comprising: (a) a plurality of antigen-major histocompatibility complexes (MHCs), each antigen-MHC of the plurality comprising a ubiquitous autoantigen, that is not a tissue specific antigen, associated with the binding groove of a MHC molecule; and (b) a nanoparticle core possessing a diameter of between 1 and 100 nanometers; wherein the antigen-MHCs are coupled to the nanoparticle core. In certain embodiments, the MHC molecule is a MHC class II molecule. In certain embodiments, the nanoparticle core is a metal or metal oxide. In certain embodiments, the metal is iron. In certain embodiments, the metal oxide is iron oxide. In certain embodiments, the diameter is between about 5 nanometers and about 50 nanometers. In certain embodiments, the diameter is between about 5 nanometers and about 25 nanometers. In certain embodiments, the plurality of antigen-MHCs is coupled to the nanoparticle core at an antigen-MHC to nanoparticle core ratio of at least 10:1. In certain embodiments, the plurality of antigen-MHCs is coupled to the nanoparticle core at an antigen-MHC to nanoparticle core ratio of no more than 150:1. In certain embodiments, the plurality of antigen-MHCs is coupled to the nanoparticle core at a density from about 0.4 to about 13 antigen-MHCs per 100 nm$^2$ of nanoparticle surface area. In certain embodiments, the antigen-MHCs are covalently coupled to the nanoparticle. In certain embodiments, the antigen-MHCs are covalently coupled to the nanoparticle core by a polyethylene glycol (PEG) linker having a mass of less than about 5 kilodaltons. In certain embodiments, the nanoparticle core further comprises a biocompatible coating. In certain embodiments, the ubiquitous autoantigen comprises a polypeptide derived from a protein that at steady-state exists in or on an intracellular compartment. In certain embodiments the intracellular compartment is cytosol, mitochondria, Golgi apparatus, endoplasmic reticulum, nucleus, or plasma membrane. In certain embodiments, the intracellular compartment is a mitochondrion. In certain embodiments, the ubiquitous autoantigen is pyruvate dehydrogenase complex-E2 component (PDC-E2). In certain embodiments, the ubiquitous autoantigen is Cytochrome P450 2D6 (CYP2D6). In certain embodiments, the ubiquitous autoantigen is soluble liver antigen (SLA). In certain embodiments, the ubiquitous autoantigen is actin (ACTB). In certain embodiments, the ubiquitous autoantigen is formimidoyltransferase-cyclodeaminase (FTCD). In certain embodiments, the ubiquitous autoantigen is myeloperoxidase (MPO). In certain embodiments, the intracellular compartment is a mitochondrion. In certain embodiments, the ubiquitous autoantigen is selected from the group consisting of: PDC-E2$_{353-367}$, PDC-E2$_{72-86}$ and PDC-E2$_{422-436}$ for DRB3*0202; PDC-E2$_{353-367}$, PDC-E2$_{80-94}$ and PDC-E2$_{535-549}$ for DRB5*0101; PDC-E2$_{629-648}$, PDC-E2$_{122-135}$ and PDC-E2$_{249-263}$ for DRB4*0101; and PDC-E2$_{249-263}$ for DRB1*0801. In certain embodiments, the ubiquitous autoantigen is selected from the group consisting of: PDC-E2$_{422-436}$ and PDC-E2$_{80-94}$. In certain embodiments, the ubiquitous autoantigen is selected from the group consisting of: CYP2D6$_{284-298}$, CYP2D6$_{289-303}$, CYP2D6$_{318-332}$, CYP2D6$_{313-332}$, CYP2D6$_{393-412}$, CYP2D6$_{192-206}$, CYP2D6$_{5-19}$, CYP2D6$_{293-307}$ (for DRB1*0301); CYP2D6$_{219-233}$, CYP2D6$_{237-251}$, CYP2D6$_{15-29}$ (for DRB3*0202); CYP2D6$_{235-249}$, CYP2D6$_{317-331}$, CYP2D6$_{293-307}$ (for DRB4*0101); CYP2D6$_{428-442}$, CYP2D6$_{237-251}$, CYP2D6$_{14-28}$ (for DRB5*0101); CYP2D6$_{199-213}$, CYP2D6$_{450-464}$, CYP2D6$_{301-315}$ (for DRB1*0401); CYP2D6$_{452-466}$, CYP2D6$_{59-73}$, CYP2D6$_{130-144}$, CYP2D6$_{193-212}$, CYP2D6$_{305-324}$, CYP2D6$_{15-29}$ (for DRB1*0701). In certain embodiments, the ubiquitous autoantigen is selected from the group consisting of: ACTB$_{202-216}$, ACTB$_{170-184}$, ACTB$_{245-259}$, (for DRB1*0301); $ACTB_{187-201}$, $ACTB_{172-186}$, $ACTB_{131-145}$ (for DRB3*0202); $ACTB_{131-145}$, $ACTB_{171-185}$, $ACTB_{129-143}$ (for DRB4*0101); $ACTB_{164-178}$, $ACTB_{25-39}$, $ACTB_{323-337}$ (for DRB5*0101). In certain embodiments, the ubiquitous autoantigen is selected from the group consisting of: $ACTB_{146-160}$, $ACTB_{18-32}$, and $ACTB_{171-185}$. In certain embodiments, the ubiquitous autoantigen is selected from the group consisting of: $SLA_{334-348}$, $SLA_{196-210}$, $SLA_{115-129}$, $SLA_{373-386}$, $SLA_{186-197}$ (for DRB1*0301); $SLA_{342-256}$, $SLA_{110-124}$, $SLA_{299-313}$ (for DRB3*0202); $SLA_{49-63}$, $SLA_{260-274}$, $SLA_{119-133}$ (for DRB4*0101); $SLA_{86-100}$, $SLA_{26-40}$, $SLA_{331-345}$ (for DRB5*0101); $SLA_{317-331}$, $SLA_{171-185}$, $SLA_{417-431}$ (for DRB1*0401); $SLA_{359-373}$, $SLA_{215-229}$, $SLA_{111-125}$ (for DRB1*0701). In certain embodiments, the ubiquitous autoantigen is selected from the group consisting of: $FTCD_{439-453}$, $FTCD_{381-395}$, $FTCD_{297-311}$ (for DRB3*0202); $FTCD_{525-539}$, $FTCD_{218-232}$, $FTCD$ 495-509 (for DRB1*0301); $FTCD_{262-276}$, $FTCD_{300-314}$, $FTCD_{259-273}$ (for DRB4*0101); $FTCD_{490-504}$, $FTCD_{389-403}$, $FTCD_{295-309}$ (for DRB5*0101). In certain embodiments, the ubiquitous autoantigen is selected from the group consisting of: $FTCD_{271-285}$, $FTCD_{498-512}$, and $FTCD_{301-315}$. In certain embodiments, the ubiquitous autoantigen is selected from the group consisting of: $MPO_{322-336}$, $MPO_{714-728}$, $MPO_{617-631}$ (for DRB3*0202); $MPO_{504-518}$, $MPO_{462-476}$, $MPO_{617-631}$ (for DRB1*0301); $MPO_{444-458}$, $MPO_{689-703}$, $MPO_{248-262}$ (for DRB4*0101); $MPO_{511-525}$, $MPO_{97-111}$, $MPO_{616-630}$ (for DRB5*0101). In certain embodiments, the complex further comprises a second plurality of antigen-major histocompatibility complexes (MHCs) coupled to the nanoparticle core, each antigen-MHC of the second plurality comprising an antigen. In certain embodiments, the antigen of the second plurality of antigen-major histocompatibility complexes (MHCs) is a second ubiquitous autoantigen. In certain embodiments, the second ubiquitous autoantigen comprises a polypeptide derived from a protein that at steady-state exists in or on an intracellular compartment. In certain embodiments, the intracellular compartment is cytosol, mitochondria, Golgi apparatus, endoplasmic reticulum, nucleus, or plasma membrane. In certain embodiments, the intracellular compartment is a mitochondrion. In certain embodiments, the intracellular compartment is a mitochondrion. In certain embodiments, the second ubiquitous autoantigen is selected from the group consisting of: $PDC\text{-}E2_{353-367}$, $PDC\text{-}E2_{72-86}$ and $PDC\text{-}E2_{422-436}$ for DRB3*0202; $PDC\text{-}E2_{353-367}$, $PDC\text{-}E2_{80-94}$ and $PDC\text{-}E2_{535-549}$ for DRB5*0101; $PDC\text{-}E2_{629-648}$, $PDC\text{-}E2_{122-135}$ and $PDC\text{-}E2_{249-263}$ for DRB4*0101; and $PDC\text{-}E2_{249-263}$ for DRB1*0801. In certain embodiments, the second ubiquitous autoantigen is selected from the group consisting of: PDC-E2422-436 and $PDC\text{-}E2_{80-94}$. In certain embodiments, the second ubiquitous autoantigen is selected from the group consisting of: $CYP2D6_{284-298}$, $CYP2D6_{289-303}$, $CYP2D6_{318-332}$, $CYP2D6_{313-332}$, $CYP2D6_{393-412}$, $CYP2D6_{192-206}$, $CYP2D65\text{-}19$, $CYP2D6_{293-307}$ (for DRB1*0301); $CYP2D6_{219-233}$, $CYP2D6_{237-251}$, $CYP2D6_{15-29}$ (for DRB3*0202); $CYP2D6_{235-249}$, $CYP2D6_{317-331}$, $CYP2D6_{293-307}$ (for DRB4*0101); $CYP2D6_{428-442}$, $CYP2D6_{237-251}$, $CYP2D6_{14-28}$ (for DRB5*0101); $CYP2D6_{199-213}$, $CYP2D6_{450-464}$, $CYP2D6_{301-315}$ (for DRB1*0401); $CYP2D6_{452-466}$, $CYP2D6_{59-73}$, $CYP2D6_{130-144}$, $CYP2D6_{193-212}$, $CYP2D6_{305-324}$, $CYP2D6_{15-29}$ (for DRB1*0701). In certain embodiments, the second ubiquitous autoantigen is selected from the group consisting of: $ACTB_{202-216}$, $ACTB_{170-184}$, $ACTB_{245-259}$, (for DRB1*0301); $ACTB_{187-201}$, $ACTB_{172-186}$, $ACTB_{131-145}$ (for DRB3*0202); $ACTB_{131-145}$, $ACTB_{171-185}$, $ACTB_{129-143}$ (for DRB4*0101); $ACTB_{164-178}$, $ACTB_{25-39}$, $ACTB_{323-337}$ (for DRB5*0101). In certain embodiments, the second ubiquitous autoantigen is selected from the group consisting of: $ACTB_{146-160}$, $ACTB_{18-32}$, and $ACTB_{171-185}$. In certain embodiments, the second ubiquitous autoantigen is selected from the group consisting of: $SLA_{334-348}$, $SLA_{196-210}$, $SLA_{115-129}$, $SLA_{373-386}$, $SLA_{186-197}$ (for DRB1*0301); $SLA_{342-256}$, $SLA_{110-124}$, $SLA_{299-313}$ (for DRB3*0202); $SLA_{49-63}$, $SLA_{260-274}$, $SLA_{119-133}$ (for DRB4*0101); $SLA_{86-100}$, $SLA_{26-40}$, $SLA_{331-345}$ (for DRB5*0101); $SLA_{317-331}$, $SLA_{171-185}$, $SLA_{417-431}$ (for DRB1*0401); $SLA_{359-373}$, $SLA_{215-229}$, $SLA_{111-125}$ (for DRB1*0701). In certain embodiments, the second ubiquitous autoantigen is selected from the group consisting of: $FTCD_{439-453}$, $FTCD_{381-395}$, $FTCD_{297-311}$ (for DRB3*0202); $FTCD_{525-539}$, $FTCD_{218-232}$, $FTCD_{495-509}$ (for DRB1*0301); $FTCD_{262-276}$, $FTCD_{300-314}$, $FTCD_{259-273}$ (for DRB4*0101); $FTCD_{490-504}$, $FTCD_{389-403}$, $FTCD_{295-309}$ (for DRB5*0101). In certain embodiments, the second ubiquitous autoantigen is selected from the group consisting of: $FTCD_{271-285}$, $FTCD_{498-512}$, and $FTCD_{301-315}$. In certain embodiments, the second ubiquitous autoantigen is selected from the group consisting of: $MPO_{322-336}$, $MPO_{714-728}$, $MPO_{617-631}$ (for DRB3*0202); $MPO_{504-518}$, $MPO_{462-476}$, $MPO_{617-631}$ (for DRB1*0301); $MPO_{444-458}$, $MPO_{689-703}$, $MPO_{248-262}$ (for DRB4*0101); $MPO_{511-525}$, $MPO_{97-111}$, $MPO_{616-630}$ (for DRB5*0101). In certain embodiments, the composition further comprises a pharmaceutically acceptable stabilizer, excipient, diluent, or combination thereof. In certain embodiments, the composition is formulated for intravenous administration. In certain embodiments, the composition is for use in a method of treating an autoimmune or inflammatory disease. In certain embodiments, the composition is for use in the manufacture of a medicament for treating an autoimmune or inflammatory disease. In certain embodiments, the autoimmune or inflammatory disease is selected from the group consisting of: type I diabetes, multiple sclerosis, relapsing-remitting multiple sclerosis, pemphigus, pemphigus foliaceus, pemphigus vulgaris, neuromyelitis optica spectrum disorder, rheumatoid arthritis, osteoarthritis, psoriatic arthritis, inflammatory bowel disease, Crohn's disease, celiac disease, allergic asthma, systemic lupus erythematosus, atherosclerosis, chronic obstructive pulmonary disease, emphysema, psoriasis, uveitis, Sjogren's Syndrome, scleroderma, anti-phospholipid syndrome, ANCA-associated vasculitis, primary biliary cirrhosis, autoimmune hepatitis, primary sclerosing cholangitis, and Stiff Man Syndrome. In certain embodiments, the autoimmune or inflammatory disease is multiple sclerosis. In certain embodiments, the ubiquitous autoantigen is not a polypeptide derived from myelin basic protein, myelin associated glycoprotein, myelin oligodendrocyte protein (MOG), proteolipid protein, oligodendrocyte myelin oligoprotein, myelin associated oligodendrocyte basic protein, oligodendrocyte specific protein, heat shock proteins, an oligodendrocyte specific protein, NOGO A, glycoprotein Po, peripheral myelin protein 22, or 2'3'-cyclic nucleotide 3'-phosphodiesterase. In certain embodiments, the autoimmune or inflammatory disease is type I diabetes. In certain embodiments, the ubiquitous autoantigen is a polypeptide derived from pre-proinsulin, proinsulin, islet-specific glucose-6-phosphatase (IGRP), glutamate decarboxylase (GAD), islet cell autoantigen-2 (ICA2), or insulin.

In certain aspects described herein is a method of treating an autoimmune or inflammatory disease comprising administering to an individual a therapeutically effective amount of a composition comprising: (a) a plurality of antigen-major histocompatibility complexes (MHCs), each antigen-MHC of the plurality comprising a ubiquitous autoantigen, that is not a tissue specific antigen, associated with the binding groove of an MHC molecule; and (b) a nanoparticle core possessing a diameter of between 1 and 100 nanometers; wherein the antigen-MHCs are coupled to the nanoparticle core. In certain embodiments, the MHC molecule is a MHC class II molecule. In certain embodiments, the nanoparticle core is a metal or metal oxide. In certain embodiments, the metal is iron. In certain embodiments, the metal oxide is iron oxide. In certain embodiments, the diameter is between about 5 nanometers and about 50 nanometers. In certain embodiments, the diameter is between about 5 nanometers and about 25 nanometers. In certain embodiments, the plurality of antigen-MHCs is coupled to the nanoparticle core at an antigen-MHC to nanoparticle core ratio of at least 10:1. In certain embodiments, the plurality of antigen-MHCs is coupled to the nanoparticle core at an antigen-MHC to nanoparticle core ratio of no more than 150:1. In certain embodiments, the plurality of antigen-MHCs is coupled to the nanoparticle core at a density from about 0.4 to about 13 antigen-MHCs per 100 nm$^2$ of nanoparticle core surface area. In certain embodiments, the antigen-MHCs are covalently coupled to the nanoparticle core. In certain embodiments, the antigen-MHCs are covalently coupled to the nanoparticle core by a polyethylene glycol (PEG) linker having a mass of less than about 5 kilodaltons. In certain embodiments, the nanoparticle core further comprises a biocompatible coating. In certain embodiments, the ubiquitous autoantigen comprises a polypeptide derived from a protein that at steady-state exists in or on an intracellular compartment. In certain embodiments, the intracellular compartment is cytosol, mitochondria, Golgi apparatus, endoplasmic reticulum, nucleus, or plasma membrane. In certain embodiments, the intracellular compartment is a mitochondrion. In certain embodiments, the ubiquitous autoantigen is pyruvate dehydrogenase complex-E2 component (PDC-E2). In certain embodiments, the ubiquitous autoantigen is Cytochrome P450 2D6 (CYP2D6). In certain embodiments, the ubiquitous autoantigen is soluble liver antigen (SLA). In certain embodiments, the ubiquitous autoantigen is actin (ACTB). In certain embodiments, the ubiquitous autoantigen is formimidoyltransferase-cyclodeaminase (FTCD). In certain embodiments, the ubiquitous autoantigen is myeloperoxidase (MPO). In certain embodiments, the intracellular compartment is a mitochondrion. In certain embodiments, the ubiquitous autoantigen is selected from the group consisting of: PDC-E2$_{353-367}$, PDC-E2$_{72-86}$ and PDC-E2$_{422-436}$ for DRB3*0202; PDC-E2$_{353-367}$, PDC-E2$_{80-94}$ and PDC-E2$_{535-549}$ for DRB5*0101; PDC-E2$_{629-648}$, PDC-E2$_{122-135}$ and PDC-E2$_{249-263}$ for DRB4*0101; and PDC-E2$_{249-263}$ for DRB1*0801. In certain embodiments, the ubiquitous autoantigen is selected from the group consisting of: PDC-E2422-436 and PDC-E2$_{80-94}$. In certain embodiments, the ubiquitous autoantigen is selected from the group consisting of: CYP2D6$_{284-298}$, CYP2D6$_{289-303}$, CYP2D6$_{318-332}$, CYP2D6$_{313-332}$, CYP2D6$_{393-412}$, CYP2D6$_{192-206}$, CYP2D65-19, CYP2D6$_{293-307}$ (for DRB1*0301); CYP2D6$_{219-233}$, CYP2D6$_{237-251}$, CYP2D6$_{15-29}$ (for DRB3*0202); CYP2D6$_{235-249}$, CYP2D6$_{317-331}$, CYP2D6$_{293-307}$ (for DRB4*0101); CYP2D6$_{428-442}$, CYP2D6$_{237-251}$, CYP2D6$_{14-28}$ (for DRB5*0101); CYP2D6$_{199-213}$, CYP2D6$_{450-464}$, CYP2D6$_{301-315}$ (for DRB1*0401); CYP2D6$_{452-466}$, CYP2D6$_{59-73}$, CYP2D6$_{130-144}$, CYP2D6$_{193-212}$, CYP2D6$_{305-324}$, CYP2D6$_{15-29}$ (for DRB1*0701). In certain embodiments, the ubiquitous autoantigen is selected from the group consisting of: ACTB$_{202-216}$, ACTB$_{170-184}$, ACTB$_{245-259}$, (for DRB1*0301); ACTB$_{187-201}$, ACTB$_{172-186}$, ACTB$_{131-145}$ (for DRB3*0202); ACTB$_{131-145}$, ACTB$_{171-185}$, ACTB$_{129-143}$ (for DRB4*0101); ACTB$_{164-178}$, ACTB$_{25-39}$, ACTB$_{323-337}$ (for DRB5*0101). In certain embodiments, the ubiquitous autoantigen is selected from the group consisting of: ACTB$_{146-160}$, ACTB$_{18-32}$, and ACTB$_{171-185}$. In certain embodiments, the ubiquitous autoantigen is selected from the group consisting of: SLA$_{334-348}$, SLA$_{196-210}$, SLA$_{115-129}$, SLA$_{373-386}$, SLA$_{186-197}$ (for DRB1*0301); SLA$_{342-256}$, SLA$_{110-124}$, SLA$_{299-313}$ (for DRB3*0202); SLA$_{49-63}$, SLA$_{260-274}$, SLA$_{119-133}$ (for DRB4*0101); SLA$_{86-100}$, SLA$_{26-40}$, SLA$_{331-345}$ (for DRB5*0101); SLA$_{317-331}$, SLA$_{171-185}$, SLA$_{417-431}$ (for DRB1*0401); SLA$_{359-373}$, SLA$_{215-229}$, SLA$_{111-125}$ (for DRB1*0701). In certain embodiments, the ubiquitous autoantigen is selected from the group consisting of: FTCD$_{439-453}$, FTCD$_{381-395}$, FTCD$_{297-311}$ (for DRB3*0202); FTCD$_{525-539}$, FTCD$_{218-232}$, FTCD$_{495-509}$ (for DRB1*0301); FTCD$_{262-276}$, FTCD$_{300-314}$, FTCD$_{259-273}$ (for DRB4*0101); FTCD$_{490-504}$, FTCD$_{389-403}$, FTCD$_{295-309}$ (for DRB5*0101). In certain embodiments, the ubiquitous autoantigen is selected from the group consisting of: FTCD$_{271-285}$, FTCD$_{498-512}$, and FTCD$_{301-315}$. In certain embodiments, the ubiquitous autoantigen is selected from the group consisting of: MPO$_{322-336}$, MPO$_{714-728}$, MPO$_{617-631}$ (for DRB3*0202); MPO$_{504-518}$, MPO$_{462-476}$, MPO$_{617-631}$ (for DRB1*0301); MPO$_{444-458}$, MPO$_{689-703}$, MPO$_{248-262}$ (for DRB4*0101); MPO$_{511-525}$, MPO$_{97-111}$, MPO$_{616-630}$ (for DRB5*0101). In certain embodiments, the complex further comprises a second plurality of antigen-major histocompatibility complexes (MHCs) coupled to the nanoparticle core, each antigen-MHC of the second plurality comprising an antigen. In certain embodiments, the antigen of the second plurality of antigen-major histocompatibility complexes (MHCs) is a second ubiquitous autoantigen. In certain embodiments, the second ubiquitous autoantigen comprises a polypeptide derived from a protein that at steady-state exists in or on an intracellular compartment. In certain embodiments, the intracellular compartment is cytosol, mitochondria, Golgi apparatus, endoplasmic reticulum, nucleus, or plasma membrane. In certain embodiments, the intracellular compartment is a mitochondrion. In certain embodiments, the intracellular compartment is a mitochondrion. In certain embodiments, the second ubiquitous autoantigen is selected from the group consisting of: PDC-E2$_{353-367}$, PDC-E2$_{72-86}$ and PDC-E2$_{422-436}$ for DRB3*0202; PDC-E2$_{353-367}$, PDC-E2$_{80-94}$ and PDC-E2$_{535-549}$ for DRB5*0101; PDC-E2$_{629-648}$, PDC-E2$_{122-135}$ and PDC-E2$_{249-263}$ for DRB4*0101; and PDC-E2$_{249-263}$ for DRB1*0801. In certain embodiments, the second ubiquitous autoantigen is selected from the group consisting of: PDC-E2$_{422-436}$ and PDC-E2$_{80-94}$. In certain embodiments, the second ubiquitous autoantigen is selected from the group consisting of: CYP2D6$_{284-298}$, CYP2D6$_{289-303}$, CYP2D6$_{318-332}$, CYP2D6$_{313-332}$, CYP2D6$_{393-412}$, CYP2D6$_{192-206}$, CYP2D65-19, CYP2D6$_{293-307}$ (for DRB1*0301); CYP2D6$_{219-233}$, CYP2D6$_{237-251}$, CYP2D6$_{15-29}$ (for DRB3*0202); CYP2D6$_{235-249}$, CYP2D6$_{317-331}$, CYP2D6$_{293-307}$ (for DRB4*0101); CYP2D6$_{428-442}$, CYP2D6$_{237-251}$, CYP2D6$_{14-28}$ (for DRB5*0101); CYP2D6$_{199-213}$, CYP2D6$_{450-464}$, CYP2D6$_{301-315}$ (for DRB1*0401); CYP2D6$_{452-466}$, CYP2D6$_{59-73}$, CYP2D6$_{130-144}$, CYP2D6$_{193-212}$, CYP2D6$_{305-324}$, CYP2D6$_{15-29}$ (for DRB1*0701). In certain embodiments, the second ubiquitous autoantigen is selected from the group consisting of: ACTB$_{202-216}$, ACTB$_{170-184}$, ACTB$_{245-259}$, (for DRB1*0301); ACTB$_{187-201}$, ACTB$_{172-186}$, ACTB$_{131-145}$ (for DRB3*0202); ACTB$_{131-145}$, ACTB$_{171-185}$, ACTB$_{129-143}$ (for DRB4*0101); ACTB$_{164-178}$, ACTB$_{25-39}$, ACTB$_{323-337}$ (for DRB5*0101). In certain embodiments, the second ubiquitous autoantigen is selected from the group consisting of: ACTB$_{146-160}$, ACTB$_{18-32}$, and ACTB$_{171-185}$. In certain embodiments, the second ubiquitous autoantigen is selected from the group consisting of: SLA$_{334-348}$, SLA$_{196-210}$, SLA$_{115-129}$, SLA$_{373-386}$, SLA$_{186-197}$ (for DRB1*0301); SLA$_{342-256}$, SLA$_{110-124}$, SLA$_{299-313}$ (for DRB3*0202); SLA$_{49-63}$, SLA$_{260-274}$, SLA$_{119-133}$ (for DRB4*0101); SLA$_{86-100}$, SLA$_{26-40}$, SLA$_{331-345}$ (for DRB5*0101); SLA$_{317-331}$, SLA$_{171-185}$, SLA$_{417-431}$ (for DRB1*0401); SLA$_{359-373}$, SLA$_{215-229}$, SLA$_{111-125}$ (for DRB1*0701). In certain embodiments, the second ubiquitous autoantigen is selected from the group consisting of: FTCD$_{439-453}$, FTCD$_{381-395}$, FTCD$_{297-311}$ (for DRB3*0202); FTCD$_{525-539}$, FTCD$_{218-232}$, FTCD$_{495-509}$ (for DRB1*0301); FTCD$_{262-276}$, FTCD$_{300-314}$, FTCD$_{259-273}$ (for DRB4*0101); FTCD$_{490-504}$, FTCD$_{389-403}$, FTCD$_{295-309}$ (for DRB5*0101). In certain embodiments, the second ubiquitous autoantigen is selected from the group consisting of: FTCD$_{271-285}$, FTCD$_{498-512}$, and FTCD$_{301-315}$. In certain embodiments, the second ubiquitous autoantigen is selected from the group consisting of: MPO$_{322-336}$, MPO$_{714-728}$, MPO$_{617-631}$ (for DRB3*0202); MPO$_{504-518}$, MPO$_{462-476}$, MPO$_{617-631}$ (for DRB1*0301); MPO$_{444-458}$, MPO$_{689-703}$, MPO$_{248-262}$ (for DRB4*0101); MPO$_{511-525}$, MPO$_{97-111}$, MPO$_{616-630}$ (for DRB5*0101). In certain embodiments, the composition further comprises a pharmaceutically acceptable stabilizer, excipient, diluent, or combination thereof. In certain embodiments, the composition is formulated for intravenous administration. In certain embodiments, the autoimmune or inflammatory disease is selected from the group consisting of type I diabetes, multiple sclerosis, relapsing-remitting multiple sclerosis, pemphigus, pemphigus foliaceus, pemphigus vulgaris, neuromyelitis optica spectrum disorder, rheumatoid arthritis, osteoarthritis, psoriatic arthritis, inflammatory bowel disease, Crohn's disease, celiac disease, allergic asthma, systemic lupus erythematosus, atherosclerosis, chronic obstructive pulmonary disease, emphysema, psoriasis, uveitis, Sjogren's Syndrome, scleroderma, anti-phospholipid syndrome, ANCA-associated vasculitis, primary biliary cirrhosis, autoimmune hepatitis, primary sclerosing cholangitis, and Stiff Man Syndrome. In certain embodiments, the autoimmune or inflammatory disease is multiple sclerosis. In certain embodiments, the ubiquitous autoantigen is not a polypeptide derived from myelin basic protein, myelin associated glycoprotein, myelin oligodendrocyte protein (MOG), proteolipid protein, oligodendrocyte myelin oligoprotein, myelin associated oligodendrocyte basic protein, oligodendrocyte specific protein, heat shock proteins, an oligodendrocyte specific protein, NOGO A, glycoprotein Po, peripheral myelin protein 22, or 2'3'-cyclic nucleotide 3'-phosphodiesterase. In certain embodiments, the autoimmune or inflammatory disease is type I diabetes. In certain embodiments, the ubiquitous autoantigen is a polypeptide derived from pre-proinsulin, proinsulin, islet-specific glucose-6-phosphatase (IGRP), glutamate decarboxylase (GAD), islet cell autoantigen-2 (ICA2), or insulin.

In another aspect described herein is a method of treating multiple sclerosis comprising administering to an individual a therapeutically effective amount of a composition comprising: (a) a plurality of antigen-major histocompatibility complexes (MHCs), each antigen-MHC of the plurality comprising a ubiquitous autoantigen, which is not a multiple sclerosis specific antigen, associated with the binding groove of an MHC molecule; and (a) a nanoparticle core, the nanoparticle core possessing a diameter of between 1 and 100 nanometers; wherein the antigen-MHCs are coupled to the nanoparticle core. In certain embodiments, the MHC molecule is a MHC class II molecule. In certain embodiments, the nanoparticle core is a metal or metal oxide. In certain embodiments, the metal is iron. In certain embodiments, the metal oxide is iron oxide. In certain embodiments, the diameter is between about 5 nanometers and about 50 nanometers. In certain embodiments, the diameter is between about 5 nanometers and about 25 nanometers. In certain embodiments, the plurality of antigen-MHCs is coupled to the nanoparticle core at an antigen-MHC to nanoparticle core ratio of at least 10:1. In certain embodiments, the plurality of antigen-MHCs is coupled to the nanoparticle core at an antigen-MHC to nanoparticle core ratio of no more than 150:1. In certain embodiments, the plurality of antigen-MHCs is coupled to the nanoparticle core at a density from about 0.4 to about 13 antigen-MHCs per 100 nm$^2$ of nanoparticle core surface area. In certain embodiments, the antigen-MHCs are covalently coupled to the nanoparticle core. In certain embodiments, the antigen-MHCs are covalently coupled to the nanoparticle core by a polyethylene glycol (PEG) linker having a mass of less than about 5 kilodaltons. In certain embodiments, the nanoparticle core further comprises a biocompatible coating. In certain embodiments, the ubiquitous autoantigen comprises a polypeptide derived from a protein that at steady-state exists in or on an intracellular compartment. In certain embodiments, the intracellular compartment is cytosol. In certain embodiments, the intracellular compartment is a mitochondrion. In certain embodiments, the ubiquitous autoantigen is pyruvate dehydrogenase complex-E2 component (PDC-E2). In certain embodiments, the ubiquitous autoantigen is Cytochrome P450 2D6 (CYP2D6). In certain embodiments, the ubiquitous autoantigen is soluble liver antigen (SLA). In certain embodiments, the ubiquitous autoantigen is actin (ACTB). In certain embodiments, the ubiquitous autoantigen is formimidoyltransferase-cyclodeaminase (FTCD). In certain embodiments, the ubiquitous autoantigen is myeloperoxidase (MPO). In certain embodiments, the intracellular compartment is a mitochondrion. In certain embodiments, the ubiquitous autoantigen is selected from the group consisting of: PDC-E2$_{353-367}$, PDC-E2$_{72-86}$ and PDC-E2$_{422-436}$ for DRB3*0202; PDC-E2$_{353-367}$, PDC-E2$_{80-94}$ and PDC-E2$_{535-549}$ for DRB5*0101; PDC-E2$_{629-648}$, PDC-E2$_{122-135}$ and PDC-E2$_{249-263}$ for DRB4*0101; and PDC-E2$_{249-263}$ for DRB1*0801. In certain embodiments, the ubiquitous autoantigen is selected from the group consisting of: PDC-E2422-436 and PDC-E2$_{80-94}$. In certain embodiments, the ubiquitous autoantigen is selected from the group consisting of: CYP2D6$_{284-298}$, CYP2D6$_{289-303}$, CYP2D6$_{318-332}$, CYP2D6$_{313-332}$, CYP2D6$_{393-412}$, CYP2D6$_{192-206}$, CYP2D65-19, CYP2D6$_{293-307}$ (for DRB1*0301); CYP2D6$_{219-233}$, CYP2D6$_{237-251}$, CYP2D6$_{15-29}$ (for DRB3*0202); CYP2D6$_{235-249}$, CYP2D6$_{317-331}$, CYP2D6$_{293-307}$ (for DRB4*0101); CYP2D6$_{428-442}$, CYP2D6$_{237-251}$, CYP2D6$_{14-28}$ (for DRB5*0101); CYP2D6$_{199-213}$, CYP2D6$_{450-464}$, CYP2D6$_{301-315}$ (for DRB1*0401); CYP2D6$_{452-466}$, CYP2D6$_{59-73}$, CYP2D6$_{130-144}$, CYP2D6$_{193-212}$, CYP2D6$_{305-324}$, CYP2D6$_{15-29}$ (for DRB1*0701). In certain embodiments, the ubiquitous autoantigen is selected from the group consisting of: ACTB$_{202-216}$, ACTB$_{170-184}$, ACTB$_{245-259}$, (for DRB1*0301); ACTB$_{187-201}$, ACTB$_{172-186}$, ACTB$_{131-145}$ (for DRB3*0202); ACTB$_{131-145}$, ACTB$_{171-185}$, ACTB$_{129-143}$ (for DRB4*0101); $ACTB_{164-178}$, $ACTB_{25-39}$, $ACTB_{323-337}$ (for DRB5*0101). In certain embodiments, the ubiquitous autoantigen is selected from the group consisting of: $ACTB_{146-160}$, $ACTB_{18-32}$, and $ACTB_{171-185}$. In certain embodiments, the ubiquitous autoantigen is selected from the group consisting of: $SLA_{334-348}$, $SLA_{196-210}$, $SLA_{115-129}$, $SLA_{373-386}$, $SLA_{186-197}$ (for DRB1*0301); $SLA_{342-256}$, $SLA_{110-124}$, $SLA_{299-313}$ (for DRB3*0202); $SLA_{49-63}$, $SLA_{260-274}$, $SLA_{119-133}$ (for DRB4*0101); $SLA_{86-100}$, $SLA_{26-40}$, $SLA_{331-345}$ (for DRB5*0101); $SLA_{317-331}$, $SLA_{171-185}$, $SLA_{417-431}$ (for DRB1*0401); $SLA_{359-373}$, $SLA_{215-229}$, $SLA_{111-125}$ (for DRB1*0701). In certain embodiments, the ubiquitous autoantigen is selected from the group consisting of: $FTCD_{439-453}$, $FTCD_{381-395}$, $FTCD_{297-311}$ (for DRB3*0202); $FTCD_{525-539}$, $FTCD_{218-232}$, $FTCD_{495-509}$ (for DRB1*0301); $FTCD_{262-276}$, $FTCD_{300-314}$, $FTCD_{259-273}$ (for DRB4*0101); $FTCD_{490-504}$, $FTCD_{389-403}$, $FTCD_{295-309}$ (for DRB5*0101). In certain embodiments, the ubiquitous autoantigen is selected from the group consisting of: $FTCD_{271-285}$, $FTCD_{498-512}$, and $FTCD_{301-315}$. In certain embodiments, the ubiquitous autoantigen is selected from the group consisting of: $MPO_{322-336}$, $MPO_{714-728}$, $MPO_{617-631}$ (for DRB3*0202); $MPO_{504-518}$, $MPO_{462-476}$, $MPO_{617-631}$ (for DRB1*0301); $MPO_{444-458}$, $MPO_{689-703}$, $MPO_{248-262}$ (for DRB4*0101); $MPO_{511-525}$, $MPO_{97-111}$, $MPO_{616-630}$ (for DRB5*0101). In certain embodiments, the complex further comprises a second plurality of antigen-major histocompatibility complexes (MHCs) coupled to the nanoparticle core, each antigen-MHC of the second plurality comprising an antigen. In certain embodiments, the antigen of the second plurality of antigen-major histocompatibility complexes (MHCs) is a second ubiquitous autoantigen. In certain embodiments, the second ubiquitous autoantigen comprises a polypeptide derived from a protein that at steady-state exists in or on an intracellular compartment. In certain embodiments, the intracellular compartment is cytosol. In certain embodiments, the intracellular compartment is a mitochondrion. In certain embodiments, the second ubiquitous autoantigen is selected from the group consisting of: $PDC-E2_{353-367}$, $PDC-E2_{72-86}$ and $PDC-E2_{422-436}$ for DRB3*0202; $PDC-E2_{353-367}$, $PDC-E2_{80-94}$ and $PDC-E2_{535-549}$ for DRB5*0101; $PDC-E2_{629-648}$, $PDC-E2_{122-135}$ and PDC-E2249-263 for DRB4*0101; and $PDC-E2_{249-263}$ for DRB1*0801. In certain embodiments, the second ubiquitous autoantigen is selected from the group consisting of: $PDC-E2_{422-436}$ and PDC-E280-94. In certain embodiments, the second ubiquitous autoantigen is selected from the group consisting of: $CYP2D6_{284-298}$, $CYP2D6_{289-303}$, $CYP2D6_{318-332}$, $CYP2D6_{313-332}$, $CYP2D6_{393-412}$, $CYP2D6_{192-206}$, CYP2D65-19, $CYP2D6_{293-307}$ (for DRB1*0301); $CYP2D6_{219-233}$, $CYP2D6_{237-251}$, $CYP2D6_{15-29}$ (for DRB3*0202); $CYP2D6_{235-249}$, $CYP2D6_{317-331}$, $CYP2D6_{293-307}$ (for DRB4*0101); $CYP2D6_{428-442}$, $CYP2D6_{237-251}$, $CYP2D6_{14-28}$ (for DRB5*0101); $CYP2D6_{199-213}$, $CYP2D6_{450-464}$, $CYP2D6_{301-315}$ (for DRB1*0401); $CYP2D6_{452-466}$, $CYP2D6_{59-73}$, $CYP2D6_{130-144}$, $CYP2D6_{193-212}$, $CYP2D6_{305-324}$, $CYP2D6_{15-29}$ (for DRB1*0701). In certain embodiments, the second ubiquitous autoantigen is selected from the group consisting of: $ACTB_{202-216}$, $ACTB_{170-184}$, $ACTB_{245-259}$, (for DRB1*0301); $ACTB_{187-201}$, $ACTB_{172-186}$, $ACTB_{131-145}$ (for DRB3*0202); $ACTB_{131-145}$, $ACTB_{171-185}$, $ACTB_{129-143}$ (for DRB4*0101); $ACTB_{164-178}$, $ACTB_{25-39}$, $ACTB_{323-337}$ (for DRB5*0101). In certain embodiments, the second ubiquitous autoantigen is selected from the group consisting of: $ACTB_{146-160}$, $ACTB_{18-32}$, and $ACTB_{171-185}$. In certain embodiments, the ubiquitous autoantigen is selected from the group consisting of: $SLA_{334-348}$, $SLA_{196-210}$, $SLA_{115-129}$, $SLA_{373-386}$, $SLA_{186-197}$ (for DRB1*0301); $SLA_{342-256}$, $SLA_{110-124}$, $SLA_{299-313}$ (for DRB3*0202); $SLA_{49-63}$, $SLA_{260-274}$, $SLA_{119-133}$ (for DRB4*0101); $SLA_{86-100}$, $SLA_{26-40}$, $SLA_{331-345}$ (for DRB5*0101); $SLA_{317-331}$, $SLA_{171-185}$, $SLA_{417-431}$ (for DRB1*0401); $SLA_{359-373}$, $SLA_{215-229}$, $SLA_{111-125}$ (for DRB1*0701). In certain embodiments, the second ubiquitous autoantigen is selected from the group consisting of: $FTCD_{439-453}$, $FTCD_{381-395}$, $FTCD_{297-311}$ (for DRB3*0202); $FTCD_{525-539}$, $FTCD_{218-232}$, $FTCD_{495-509}$ (for DRB1*0301); $FTCD_{262-276}$, $FTCD_{300-314}$, $FTCD_{259-273}$ (for DRB4*0101); $FTCD_{490-504}$, $FTCD_{389-403}$, $FTCD_{295-309}$ (for DRB5*0101). In certain embodiments, the second ubiquitous autoantigen is selected from the group consisting of: $FTCD_{271-285}$, $FTCD_{498-512}$, and $FTCD_{301-315}$. In certain embodiments, the ubiquitous autoantigen is selected from the group consisting of: $MPO_{322-336}$, $MPO_{714-728}$, $MPO_{617-631}$ (for DRB3*0202); $MPO_{504-518}$, $MPO_{462-476}$, $MPO_{617-631}$ (for DRB1*0301); $MPO_{444-458}$, $MPO_{689-703}$, $MPO_{248-262}$ (for DRB4*0101); $MPO_{511-525}$, $MPO_{97-111}$, $MPO_{616-630}$ (for DRB5*0101). In certain embodiments, the composition further comprises a pharmaceutically acceptable stabilizer, excipient, diluent, or combination thereof. In certain embodiments, the composition is formulated for intravenous administration. In certain embodiments, the ubiquitous autoantigen is not a polypeptide derived from myelin basic protein, myelin associated glycoprotein, myelin oligodendrocyte protein (MOG), proteolipid protein, oligodendrocyte myelin oligoprotein, myelin associated oligodendrocyte basic protein, oligodendrocyte specific protein, heat shock proteins, an oligodendrocyte specific protein, NOGO A, glycoprotein Po, peripheral myelin protein 22, or 2'3'-cyclic nucleotide 3'-phosphodiesterase.

In another aspect described herein is a method of treating type I diabetes comprising administering to an individual a therapeutically effective amount of a composition comprising: (a) a plurality of antigen-major histocompatibility complexes (MHCs), each antigen-MHC of the plurality comprising a ubiquitous autoantigen, which is not a type I diabetes specific antigen, associated with the binding groove of an MHC molecule; and (b) a nanoparticle core, the nanoparticle core possessing a diameter of between 1 and 100 nanometers; wherein the plurality of antigen-MHCs is coupled to the nanoparticle core. In certain embodiments, the MHC molecule is a MHC class II molecule. In certain embodiments, the nanoparticle core is a metal or metal oxide. In certain embodiments, the metal is iron. In certain embodiments, the metal oxide is iron oxide. In certain embodiments, the diameter is between about 5 nanometers and about 50 nanometers. In certain embodiments, the diameter is between about 5 nanometers and about 25 nanometers. In certain embodiments, the plurality of antigen-MHCs is coupled to the nanoparticle core at an antigen-MHC to nanoparticle core ratio of at least 10:1. In certain embodiments, the plurality of antigen-MHCs is coupled to the nanoparticle core at an antigen-MHC to nanoparticle core ratio of no more than 150:1. In certain embodiments, the plurality of antigen-MHCs is coupled to the nanoparticle at a density from about 0.4 to about 13 antigen-MHCs per 100 nm² of nanoparticle surface area. In certain embodiments, the antigen-MHCs are covalently coupled to the nanoparticle core. In certain embodiments, the antigen-MHCs are covalently coupled to the nanoparticle core by a polyethylene glycol (PEG) linker having a mass of less than about 5 kilodaltons. In certain embodiments, the nanoparticle core further comprises a biocompatible coating. In certain embodiments, the ubiquitous autoantigen comprises a polypeptide derived from a protein that at steady-state exists in or on an intracellular compartment. In certain embodiments, the intracellular compartment is cytosol. In certain embodiments, the intracellular compartment is a mitochondrion. In certain embodiments, the ubiquitous autoantigen is pyruvate dehydrogenase complex-E2 component (PDC-E2). In certain embodiments, the ubiquitous autoantigen is Cytochrome P450 2D6 (CYP2D6). In certain embodiments, the ubiquitous autoantigen is soluble liver antigen (SLA). In certain embodiments, the ubiquitous autoantigen is actin (ACTB). In certain embodiments, the ubiquitous autoantigen is formimidoyltransferase-cyclodeaminase (FTCD). In certain embodiments, the ubiquitous autoantigen is myeloperoxidase (MPO). In certain embodiments, the intracellular compartment is a mitochondrion. In certain embodiments, the ubiquitous autoantigen is selected from the group consisting of: $PDC\text{-}E2_{353\text{-}367}$, $PDC\text{-}E2_{72\text{-}86}$ and $PDC\text{-}E2_{422\text{-}436}$ for DRB3*0202; $PDC\text{-}E2_{353\text{-}367}$, $PDC\text{-}E2_{80\text{-}94}$ and $PDC\text{-}E2_{535\text{-}549}$ for DRB5*0101; $PDC\text{-}E2_{629\text{-}648}$, $PDC\text{-}E2_{122\text{-}135}$ and $PDC\text{-}E2_{249\text{-}263}$ for DRB4*0101; and $PDC\text{-}E2_{249\text{-}263}$ for DRB1*0801. In certain embodiments, the ubiquitous autoantigen is selected from the group consisting of: $PDC\text{-}E2_{422\text{-}436}$ and $PDC\text{-}E2_{80\text{-}94}$. In certain embodiments, the ubiquitous autoantigen is selected from the group consisting of: $CYP2D6_{284\text{-}298}$, $CYP2D6_{289\text{-}303}$, $CYP2D6_{318\text{-}332}$, $CYP2D6_{313\text{-}332}$, $CYP2D6_{393\text{-}412}$, $CYP2D6_{192\text{-}206}$, $CYP2D65\text{-}19$, $CYP2D6_{293\text{-}307}$ (for DRB1*0301); $CYP2D6_{219\text{-}233}$, $CYP2D6_{237\text{-}251}$, $CYP2D6_{15\text{-}29}$ (for DRB3*0202); $CYP2D6_{235\text{-}249}$, $CYP2D6_{317\text{-}331}$, $CYP2D6_{293\text{-}307}$ (for DRB4*0101); $CYP2D6_{428\text{-}442}$, $CYP2D6_{237\text{-}251}$, $CYP2D6_{14\text{-}28}$ (for DRB5*0101); $CYP2D6_{199\text{-}213}$, $CYP2D6_{450\text{-}464}$, $CYP2D6_{301\text{-}315}$ (for DRB1*0401); $CYP2D6_{452\text{-}466}$, $CYP2D6_{59\text{-}73}$, $CYP2D6_{130\text{-}144}$, $CYP2D6_{193\text{-}212}$, $CYP2D6_{305\text{-}324}$, $CYP2D6_{15\text{-}29}$ (for DRB1*0701). In certain embodiments, the ubiquitous autoantigen is selected from the group consisting of: $ACTB_{202\text{-}216}$, $ACTB_{170\text{-}184}$, $ACTB_{245\text{-}259}$, (for DRB1*0301); $ACTB_{187\text{-}201}$, $ACTB_{172\text{-}186}$, $ACTB_{131\text{-}145}$ (for DRB3*0202); $ACTB_{131\text{-}145}$, $ACTB_{171\text{-}185}$, $ACTB_{129\text{-}143}$ (for DRB4*0101); $ACTB_{164\text{-}178}$, $ACTB_{25\text{-}39}$, $ACTB_{323\text{-}337}$ (for DRB5*0101). In certain embodiments, the ubiquitous autoantigen is selected from the group consisting of: $ACTB_{146\text{-}160}$, $ACTB_{18\text{-}32}$, and $ACTB_{171\text{-}185}$. In certain embodiments, the ubiquitous autoantigen is selected from the group consisting of: $SLA_{334\text{-}348}$, $SLA_{196\text{-}210}$, $SLA_{115\text{-}129}$, $SLA_{373\text{-}386}$, $SLA_{186\text{-}197}$ (for DRB1*0301); $SLA_{342\text{-}256}$, $SLA_{110\text{-}124}$, $SLA_{299\text{-}313}$ (for DRB3*0202); $SLA_{49\text{-}63}$, $SLA_{260\text{-}274}$, $SLA_{119\text{-}133}$ (for DRB4*0101); $SLA_{86\text{-}100}$, $SLA_{26\text{-}40}$, $SLA_{331\text{-}345}$ (for DRB5*0101); $SLA_{317\text{-}331}$, $SLA_{171\text{-}185}$, $SLA_{417\text{-}431}$ (for DRB1*0401); $SLA_{359\text{-}373}$, $SLA_{215\text{-}229}$, $SLA_{111\text{-}125}$ (for DRB1*0701). In certain embodiments, the ubiquitous autoantigen is selected from the group consisting of: $FTCD_{439\text{-}453}$, $FTCD_{381\text{-}395}$, $FTCD_{297\text{-}311}$ (for DRB3*0202); $FTCD_{525\text{-}539}$, $FTCD_{218\text{-}232}$, $FTCD_{495\text{-}509}$ (for DRB1*0301); $FTCD_{262\text{-}276}$, $FTCD_{300\text{-}314}$, $FTCD_{259\text{-}273}$ (for DRB4*0101); $FTCD_{490\text{-}504}$, $FTCD_{389\text{-}403}$, $FTCD_{295\text{-}309}$ (for DRB5*0101). In certain embodiments, the ubiquitous autoantigen is selected from the group consisting of: $FTCD_{271\text{-}285}$, $FTCD_{498\text{-}512}$, and $FTCD_{301\text{-}315}$. In certain embodiments, the ubiquitous autoantigen is selected from the group consisting of: $MPO_{322\text{-}336}$, $MPO_{714\text{-}728}$, $MPO_{617\text{-}631}$ (for DRB3*0202); $MPO_{504\text{-}518}$, $MPO_{462\text{-}476}$, $MPO_{617\text{-}631}$ (for DRB1*0301); $MPO_{444\text{-}458}$, $MPO_{689\text{-}703}$, $MPO_{248\text{-}262}$ (for DRB4*0101); $MPO_{511\text{-}525}$, $MPO_{97\text{-}111}$, $MPO_{616\text{-}630}$ (for DRB5*0101). In certain embodiments, the complex further comprises a second plurality of antigen-major histocompatibility complexes (MHCs) coupled to the nanoparticle core, each antigen-MHC of the second plurality comprising an antigen. In certain embodiments, the antigen of the second plurality of antigen-major histocompatibility complexes (MHCs) is a second ubiquitous autoantigen. In certain embodiments, the second ubiquitous autoantigen comprises a polypeptide derived from a protein that at steady-state exists in or on an intracellular compartment. In certain embodiments, the intracellular compartment is cytosol. In certain embodiments, the intracellular compartment is a mitochondrion. In certain embodiments, the intracellular compartment is a mitochondrion. In certain embodiments, the second ubiquitous autoantigen is selected from the group consisting of: $PDC\text{-}E2_{353\text{-}367}$, $PDC\text{-}E2_{72\text{-}86}$ and $PDC\text{-}E2_{422\text{-}436}$ for DRB3*0202; $PDC\text{-}E2_{353\text{-}367}$, $PDC\text{-}E2_{80\text{-}94}$ and $PDC\text{-}E2_{535\text{-}549}$ for DRB5*0101; $PDC\text{-}E2_{629\text{-}648}$, $PDC\text{-}E2_{122\text{-}135}$ and $PDC\text{-}E2_{249\text{-}263}$ for DRB4*0101; and $PDC\text{-}E2_{249\text{-}263}$ for DRB1*0801. In certain embodiments, the ubiquitous autoantigen is selected from the group consisting of: $PDC\text{-}E2_{422\text{-}436}$ and $PDC\text{-}E2_{80\text{-}94}$. In certain embodiments, the second ubiquitous autoantigen is selected from the group consisting of: $CYP2D6_{284\text{-}298}$, $CYP2D6_{289\text{-}303}$, $CYP2D6_{318\text{-}332}$, $CYP2D6_{313\text{-}332}$, $CYP2D6_{393\text{-}412}$, $CYP2D6_{192\text{-}206}$, $CYP2D65\text{-}19$, $CYP2D6_{293\text{-}307}$ (for DRB1*0301); $CYP2D6_{219\text{-}233}$, $CYP2D6_{237\text{-}251}$, $CYP2D6_{15\text{-}29}$ (for DRB3*0202); $CYP2D6_{235\text{-}249}$, $CYP2D6_{317\text{-}331}$, $CYP2D6_{293\text{-}307}$ (for DRB4*0101); $CYP2D6_{428\text{-}442}$, $CYP2D6_{237\text{-}251}$, $CYP2D6_{14\text{-}28}$ (for DRB5*0101); $CYP2D6_{199\text{-}213}$, $CYP2D6_{450\text{-}464}$, $CYP2D6_{301\text{-}315}$ (for DRB1*0401); $CYP2D6_{452\text{-}466}$, $CYP2D6_{59\text{-}73}$, $CYP2D6_{130\text{-}144}$, $CYP2D6_{193\text{-}212}$, $CYP2D6_{305\text{-}324}$, $CYP2D6_{15\text{-}29}$ (for DRB1*0701). In certain embodiments, the second ubiquitous autoantigen is selected from the group consisting of: $ACTB_{202\text{-}216}$, $ACTB_{170\text{-}184}$, $ACTB_{245\text{-}259}$, (for DRB1*0301); $ACTB_{187\text{-}201}$, $ACTB_{172\text{-}186}$, $ACTB_{131\text{-}145}$ (for DRB3*0202); $ACTB_{131\text{-}145}$, $ACTB_{171\text{-}185}$, $ACTB_{129\text{-}143}$ (for DRB4*0101); $ACTB_{164\text{-}178}$, $ACTB_{25\text{-}39}$, $ACTB_{323\text{-}337}$ (for DRB5*0101). In certain embodiments, the second ubiquitous autoantigen is selected from the group consisting of: $ACTB_{146\text{-}160}$, $ACTB_{18\text{-}32}$, and $ACTB_{171\text{-}185}$. In certain embodiments, the second ubiquitous autoantigen is selected from the group consisting of: $SLA_{334\text{-}348}$, $SLA_{196\text{-}210}$, $SLA_{115\text{-}129}$, $SLA_{373\text{-}386}$, $SLA_{186\text{-}197}$ (for DRB1*0301); $SLA_{342\text{-}256}$, $SLA_{110\text{-}124}$, $SLA_{299\text{-}313}$ (for DRB3*0202); $SLA_{49\text{-}63}$, $SLA_{260\text{-}274}$, $SLA_{119\text{-}133}$ (for DRB4*0101); $SLA_{86\text{-}100}$, $SLA_{26\text{-}40}$, $SLA_{331\text{-}345}$ (for DRB5*0101); $SLA_{317\text{-}331}$, $SLA_{171\text{-}185}$, $SLA_{417\text{-}431}$ (for DRB1*0401); $SLA_{359\text{-}373}$, $SLA_{215\text{-}229}$, $SLA_{111\text{-}125}$ (for DRB1*0701). In certain embodiments, the second ubiquitous autoantigen is selected from the group consisting of: $FTCD_{439\text{-}453}$, $FTCD_{381\text{-}395}$, $FTCD_{297\text{-}311}$ (for DRB3*0202); $FTCD_{525\text{-}539}$, $FTCD_{218\text{-}232}$, $FTCD\ 495\text{-}509$ (for DRB1*0301); $FTCD_{262\text{-}276}$, $FTCD_{300\text{-}314}$, $FTCD_{259\text{-}273}$ (for DRB4*0101); $FTCD_{490\text{-}504}$, $FTCD_{389\text{-}403}$, $FTCD_{295\text{-}309}$ (for DRB5*0101). In certain embodiments, the second ubiquitous autoantigen is selected from the group consisting of: $FTCD_{271\text{-}285}$, $FTCD_{498\text{-}512}$, and $FTCD_{301\text{-}315}$. In certain embodiments, the second ubiquitous autoantigen is selected from the group consisting of: $MPO_{322\text{-}336}$, $MPO_{714\text{-}728}$, $MPO_{617\text{-}631}$ (for DRB3*0202); $MPO_{504\text{-}518}$, $MPO_{462\text{-}476}$, $MPO_{617\text{-}631}$ (for DRB1*0301); $MPO_{444\text{-}458}$, $MPO_{689\text{-}703}$, $MPO_{248\text{-}262}$ (for DRB4*0101); $MPO_{511\text{-}525}$, $MPO_{97\text{-}111}$, $MPO_{616\text{-}630}$ (for DRB5*0101). In certain embodiments, the composition further comprises a pharmaceutically acceptable stabilizer, excipient, diluent, or combination thereof. In certain embodiments, the autoimmune or inflammatory disease is type I diabetes. In certain embodiments, the ubiquitous autoantigen is not a polypeptide derived from pre-proinsulin, proinsulin, islet-specific glucose-6-phosphatase (IGRP), glutamate decarboxylase (GAD), islet cell autoantigen-2 (ICA2), or insulin.

BRIEF DESCRIPTION OF THE DRAWINGS

The novel features described herein are set forth with particularity in the appended claims. A better understanding of the features and advantages of the features described herein will be obtained by reference to the following detailed description that sets forth illustrative examples, in which the principles of the features described herein are utilized, and the accompanying drawings of which:

FIG. 1 illustrates the expansion of Primary Biliary Cirrhosis (PBC) relevant regulatory T cells by nanoparticles coupled to MHC class II associated with peptides derived from pyruvate dehydrogenase complex-E2 component (PDC-E2) (PBC-relevant peptide-major histocompatibility complex-nanoparticles (pMHC-NPs)). FIG. 1A shows percentage of tetramer+ CD4+ T-cells in blood of NOD vs. NOD.c3c4 mice as a function of age. FIG. 1B shows percentage of tetramer+ CD4+ T-cells in peripheral blood of pMHC-NP-treated NOD.c3c4 mice as compared to untreated NOD or NOD.c3c4 mice or NOD.c3c4 mice treated with control Cys-NPs.

FIG. 2 illustrates the expansion of PBC relevant regulatory T cells by PBC-relevant pMHC-NPs. FIG. 2A is a representative FACS profiles; FIG. 2B shows average mean fluorescence intensity values.

FIG. 3 illustrates clinical, phenotypic, immunological and pathological features of liver disease in NOD.c3c4 mice.

FIG. 4 illustrates reversal of disease in a mouse model of PBC using PBC-relevant pMHC-NPs.

FIG. 5 illustrates changes in the circulating frequency of tetramer+CD4+ T-cells in response to periodic re-treatment with PBC relevant nanoparticles.

FIG. 8 illustrates that PBC-relevant pMHC-NPs spare systemic immunity.

FIG. 9 illustrates expansion of T regulatory cells by PBC-relevant pMHC-NPs in humanized mice.

FIG. 10 illustrates that PBC-relevant pMHC-NPs are able to treat disease in models of liver autoimmunity distinct from PBC, in particular, primary sclerosing cholangitis (PSC) and autoimmune hepatitis (AIH).

FIG. 11 illustrates that PBC and AIH-relevant pMHC-NPs expand T regulatory cells in a mouse model of PSC.

FIG. 12 illustrates that PBC relevant pMHC-NPs expand T regulatory cells in a mouse model of AIH.

FIG. 13. illustrates the ability of ubiquitous autoantigen based pMHC-NPs to blunt liver autoimmune disease in an organ rather than disease-specific manner.

FIG. 14 illustrates therapeutic effects of PBC-relevant pMHCII-NPs in (NODxB6.Ifng-ARE-Del-/-) F1 mice.

FIG. 15 illustrates that disease-relevant pMHCII-NPs spare general immunity despite harboring PDC-E2 autoreactive TR1-like CD4+ T-cells.

FIG. 16 illustrates that pMHCII-based nanomedicines displaying epitopes from ubiquitous autoantigens blunt relapsing-remitting EAE in NOD mice.

PDC$_{166-181}$/IA$^{g7}$-NP- and 14 BDC$_{2.5mi}$/IA$^{g7}$-NP-treated mice.

FIG. 17 illustrates pMHCII-based nanomedicines displaying epitopes from ubiquitous autoantigens blunt chronic progressive EAE in C57BL/6 mice.

FIG. 18 D shows mean fluorescence intensity (MFI) for TR1 markers in splenic tetramer+CD4+ cells. Data are presented as mean±SEM. P values were calculated using ANOVA (FIG. 18A) or Mann-Whitney U test (FIGS. 18B, C and D).

FIG. 19 illustrates that a mouse model of psoriasis can prime ubiquitous autoantigen, and that administration of ubiquitous autoantigen pMHCII-NP therapy can reduce signs of psoriasis.

FIG. 20 illustrates a non-limiting embodiment of a pMHC-NP of this disclosure. FIG. 20A shows an alpha chain of an MHC class II dimer fused to the CH2 and CH3 domain of an immunoglobulin molecule comprising an engineered knob (SEQ ID NO:103). FIG. 20B shows a beta chain of an MHC class II with an N-terminal ubiquitous polypeptide (E2$_{122-135}$), fused to the beta chain of the MHC class II, and fused to the CH2 and CH3 domains of an immunoglobulin molecule comprising an engineered hole (SEQ ID NO:104).

Figure 1C:
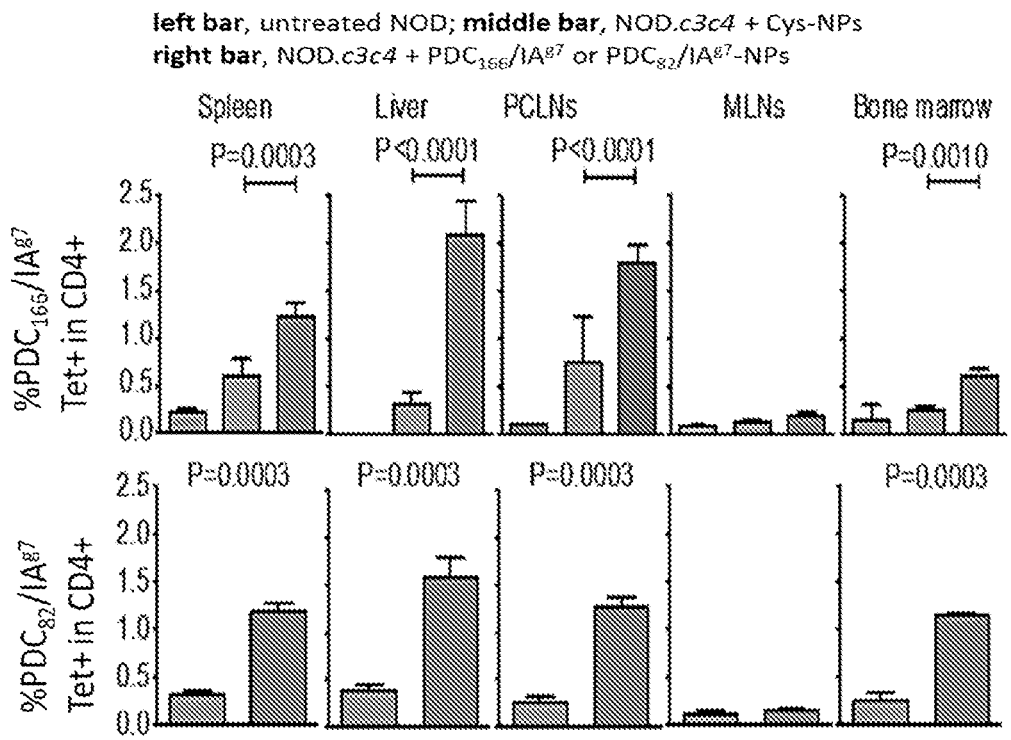
FIG. 1C shows percentages of tetramer+CD4+ T-cells in mice from panel B in various organs at the end of pMHC-NP therapy.

TABLE 1 illustrates linkers useful for coupling ubiquitous autoantigen-MHCs to nanoparticles.

TABLES 2, 3, and 4 illustrate percentages and absolute numbers of tetramer+CD4+ T-cells in NSG mice engrafted with PBMCs from DRB4*0101+ PBC patients, upon treatment with three different human PBC-relevant pMHC-NP types.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

"Antigen" as used herein refers to all, part, fragment, or segment of a molecule that can induce an immune response in a subject or an expansion of an immune cell, preferably a T or B cell. Antigens can be polypeptides, lipids, carbohydrates, or nucleic acids.

As used herein "individual" is synonymous with "subject" or "patient". The individual can be diagnosed with a disease. The individual can suspected of having a particular disease based on manifesting at least one symptom of said disease, having a family history of said disease, having a genotype relevant to define risk for said disease, or having one or more phenotypic measurements or "lab tests" at or near a level that would place an individual at risk for the disease. The individual can be a mammal, such as a horse, cat, dog, pig, cow, goat, or sheep. The individual can in certain instances be a human person.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, "polypeptide" refers to a plurality of amino acids joined by peptide bonds having more than about eight amino acid residues. The amino acids of the polypeptide can be naturally occurring or unnatural amino acid residues.

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are known for instance, using publicly available computer software such as BLAST, BLAST-2, ALIGN or Megalign (DNASTAR) software. Appropriate parameters for aligning sequences are able to be determined, including algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The uaMHC of the uaMHC-NP of the current disclosure, described herein, can be encoded by a nucleic acid. A nucleic acid is a type of polynucleotide comprising two or more nucleotide bases. In certain embodiments, the nucleic acid is a component of a vector that can be used to transfer the polypeptide encoding polynucleotide into a cell. As used herein, the term "vector" refers to a nucleic acid molecule capable of transporting another nucleic acid to which it has been linked. One type of vector is a genomic integrated vector, or "integrated vector," which can become integrated into the chromosomal DNA of the host cell. Another type of vector is an "episomal" vector, e.g., a nucleic acid capable of extra-chromosomal replication. Vectors capable of directing the expression of genes to which they are operatively linked are referred to herein as "expression vectors." Suitable vectors comprise plasmids, bacterial artificial chromosomes, yeast artificial chromosomes, viral vectors and the like. In the expression vectors regulatory elements such as promoters, enhancers, polyadenylation signals for use in controlling transcription can be derived from mammalian, microbial, viral or insect genes. The ability to replicate in a host, usually conferred by an origin of replication, and a selection gene to facilitate recognition of transformants may additionally be incorporated. Vectors derived from viruses, such as lentiviruses, retroviruses, adenoviruses, adeno-associated viruses, and the like, may be employed. Plasmid vectors can be linearized for integration into a chromosomal location. Vectors can comprise sequences that direct site-specific integration into a defined location or restricted set of sites in the genome (e.g., AttP-AttB recombination). Additionally, vectors can comprise sequences derived from transposable elements.

Any of the nucleic acids encoding the uaMHC or the vectors comprising said nucleic acids can be transferred to a suitable cell line for the production of uaMHC. In certain embodiments, the nucleic acid or vector is stably integrated into the genome of the cell line. Suitable cell lines can be as Vero (ATCC CRL 81) or CHO-K1 (ATCC CRL 61) cells, HeLa cells and L cells. Exemplary eukaryotic cells that can be used to express polypeptides include, but are not limited to, COS cells, including COS 7 cells; 293 cells, including 293-6E cells; CHO cells, including CHO—S and DG44 cells; PER.C6™ cells (Crucell); and NSO cells.

Described herein in certain embodiments, is a composition comprising: a plurality of antigen-major histocompatibility complexes (MHCs), each antigen-MHC of the plurality comprising a ubiquitous autoantigen, that is not a tissue specific antigen, associated with the binding groove of an MHC molecule; and a nanoparticle core possessing a diameter of between 1 and 100 nanometers; wherein the antigen-MHCs are coupled to the nanoparticle core.

Described herein in certain embodiments, is a method of treating an autoimmune or inflammatory disease comprising administering to an individual a therapeutically effective amount of a composition comprising: (a) a plurality of antigen-major histocompatibility complexes (MHCs), each antigen-MHC of the plurality comprising a ubiquitous autoantigen, that is not a tissue specific antigen, associated with the binding groove of an MHC molecule; (b) and a nanoparticle core possessing a diameter of between 1 and 100 nanometers; wherein the antigen-MHCs are coupled to the nanoparticle core.

Described herein in certain embodiments, is a method of treating multiple sclerosis comprising administering to an individual a therapeutically effective amount of a composition comprising: (a) a plurality of antigen-major histocompatibility complexes (MHCs), each antigen-MHC of the plurality comprising a ubiquitous autoantigen, which is not a multiple sclerosis specific antigen, associated with the binding groove of an MHC molecule; (b) and a nanoparticle core, the nanoparticle core possessing a diameter of between 1 and 100 nanometers; wherein the antigen-MHCs are coupled to the nanoparticle core.

Described herein in certain embodiments, is a method of treating type I diabetes comprising administering to an individual a therapeutically effective amount of a composition comprising: (a) a plurality of antigen-major histocompatibility complexes (MHCs), each antigen-MHC of the plurality comprising a ubiquitous autoantigen, which is not a type I diabetes specific antigen, associated with the binding groove of an MHC molecule; and (b) a nanoparticle core, the nanoparticle core possessing a diameter of between 1 and 100 nanometers; wherein the plurality of antigen-MHCs is coupled to the nanoparticle core.

Ubiquitous Autoantigens

Described herein are nanoparticle compositions and methods useful for treating autoimmune diseases and inflammatory disorders. The nanoparticle compositions comprise a plurality of antigens associated with MHCs coupled to a nanoparticle. The nanoparticle compositions and methods utilize broadly expressed ubiquitous autoantigens to elicit the generation of regulatory T and B lymphocytes.

In a certain aspect, the antigens that are associated with the MHC molecules are ubiquitous autoantigens. Ubiquitous autoantigens are differentiated from tissue specific antigens at least in that they are antigens commonly expressed by a plurality of different cell types that are unrelated. In certain embodiments, a ubiquitous autoantigen is one that is commonly expressed by ontogenically distinct tissues. In certain embodiments, a ubiquitous autoantigen that is one that is expressed in at least two cell types derived from a tissue originating from the list consisting of ectoderm, mesoderm, and endoderm. In certain embodiments, a ubiquitous autoantigen is one that is commonly expressed by functionally distinct tissues. In certain embodiments, a ubiquitous autoantigen is one that is expressed in at least two tissues selected from the list consisting of neural tissue, endocrine tissue, connective tissue, hematopoietic cells, liver issue, cardiac tissue, skin tissue, lung tissue, vascular tissue, intestinal tissue, and stomach tissue. In certain embodiments, a ubiquitous autoantigen is one that is expressed in both neural tissue and liver tissue. In certain embodiments, a ubiquitous autoantigen is one that is expressed in both neural tissue and pancreatic tissue. In a certain embodiment, the ubiquitous autoantigen is a polypeptide derived from a protein that participates in a cellular process common to at least 1, 2, 3, 4, 5, 6, 7, 8, 9, 10, or more cell types. Ubiquitous autoantigens may be sequences that are common to two or more closely related proteins that are recognized as being paralogs or homologs in the same family, yet display differential expression across various tissues. In certain embodiments, the two or more closely related proteins can for example, perform the same or similar function in two different unrelated tissues. In a certain embodiment, the ubiquitous autoantigen is a polypeptide derived from a protein that participates in a cellular process, wherein the cellular process is a metabolic process selected from glycolysis, oxidative phosphorylation, glycogenesis, nucleotide biosynthesis, beta oxidation, and omega oxidation. In certain embodiments, the ubiquitous autoantigen is selected from the list consisting of pyruvate dehydrogenase complex-E2 component (PDC-E2), Cytochrome P450 2D6 (CYP2D6), formim- idoyltransferase-cyclodeaminase (FTCD), soluble liver antigen (SLA), actin (ACTB), and myeloperoxidase (MPO).

Ubiquitous autoantigens are often encoded by housekeeping genes that are utilized in a variety of cell types. For example, actin is a cytoskeletal protein that contributes to cell structure, motility, cell division, and vesicle motility and is also ubiquitously expressed. As such, many ubiquitous autoantigens are intracellular and reside in a particular intracellular compartment at a steady-state. An antigen exists at steady-state in the cellular location where the antigen can be found at its highest quantities, determined, for example, by microscopy or cell fractionation. For example, despite the fact that actin can be found extracellularly associated with exosomes the vast majority of actin is found in the cytosol of the cell. Likewise, many antigens may transit through different organelles but reside primarily in a single organelle. For example, many endoplasmic reticulum (ER) resident proteins will transiently transit through the cis-Golgi, but are immediately returned to the ER, where they reside at steady-state.

In certain embodiments, the ubiquitous autoantigens for use with the nanoparticle compositions described herein are polypeptides derived from pyruvate dehydrogenase complex-E2 component (PDC-E2). In certain embodiments, the polypeptide derived from PDC-E2 is any one or more of: $PDC\text{-}E2_{353\text{-}367}$, $PDC\text{-}E2_{72\text{-}86}$ and $PDC\text{-}E2_{422\text{-}436}$ for DRB3*0202; $PDC\text{-}E2_{353\text{-}367}$, $PDC\text{-}E2_{80\text{-}94}$ and $PDC\text{-}E2_{535\text{-}549}$ for DRB5*0101; $PDC\text{-}E2_{629\text{-}648}$, $PDC\text{-}E2_{122\text{-}135}$ and $PDC\text{-}E2_{249\text{-}263}$ for DRB4*0101; and $PDC\text{-}E2_{249\text{-}263}$ for DRB1*0801. In certain embodiments, the polypeptide derived from PDC-E2 is any one or more of: $PDC\text{-}E2_{422\text{-}436}$ and $PDC\text{-}E2_{80\text{-}94}$. In certain embodiments, the polypeptide derived from PDC-E2 is any one or more of: SEQ ID NOs: 1 to 12.

In certain embodiments, the ubiquitous autoantigens for use with the nanoparticle compositions described herein are polypeptides derived from Cytochrome P450 2D6 (CYP2D6). In certain embodiments, the polypeptide derived from CYP2D6 is any one or more of: $CYP2D6_{284\text{-}298}$, $CYP2D6_{289\text{-}303}$, $CYP2D6_{318\text{-}332}$, $CYP2D6_{313\text{-}332}$, $CYP2D6_{393\text{-}412}$, $CYP2D6_{192\text{-}206}$, $CYP2D6\text{5-}19$, $CYP2D6_{293\text{-}307}$ (for DRB1*0301); $CYP2D6_{219\text{-}233}$, $CYP2D6_{237\text{-}251}$, $CYP2D6_{15\text{-}29}$ (for DRB3*0202); $CYP2D6_{235\text{-}249}$, $CYP2D6_{317\text{-}331}$, $CYP2D6_{293\text{-}307}$ (for DRB4*0101); $CYP2D6_{428\text{-}442}$, $CYP2D6_{237\text{-}251}$, $CYP2D6_{14\text{-}28}$ (for DRB5*0101); $CYP2D6_{199\text{-}213}$, $CYP2D6_{450\text{-}464}$, $CYP2D6_{301\text{-}315}$ (for DRB1*0401); $CYP2D6_{452\text{-}466}$, $CYP2D6_{59\text{-}73}$, $CYP2D6_{130\text{-}144}$, $CYP2D6_{193\text{-}212}$, $CYP2D6_{305\text{-}324}$, $CYP2D6_{15\text{-}29}$ (for DRB1*0701). In certain embodiments, the polypeptide derived from CYP2D6 is any one or more of: SEQ ID NOs: 13 to 37.

In certain embodiments, the ubiquitous autoantigens for use with the nanoparticle compositions described herein are polypeptides derived from soluble liver antigen (SLA). In certain embodiments, the polypeptide derived from SLA is any one or more of: $SLA_{334\text{-}348}$, $SLA_{196\text{-}210}$, $SLA_{115\text{-}129}$, $SLA_{373\text{-}386}$, $SLA_{186\text{-}197}$ (for DRB1*0301); $SLA_{342\text{-}256}$, $SLA_{110\text{-}124}$, $SLA_{299\text{-}313}$ (for DRB3*0202); $SLA_{49\text{-}63}$, $SLA_{260\text{-}274}$, $SLA_{119\text{-}133}$ (for DRB4*0101); $SLA_{86\text{-}100}$, $SLA_{26\text{-}40}$, $SLA_{331\text{-}345}$ (for DRB5*0101); $SLA_{317\text{-}331}$, $SLA_{171\text{-}185}$, $SLA_{417\text{-}431}$ (for DRB1*0401); $SLA_{359\text{-}373}$, $SLA_{215\text{-}229}$, $SLA_{111\text{-}125}$ (for DRB1*0701). In certain embodiments, the polypeptide derived from SLA is any one or more of: SEQ ID NOs: 53 to 72.

In certain embodiments, the ubiquitous autoantigens for use with the nanoparticle compositions described herein are polypeptides derived from actin (ACTB). In certain embodiments, the polypeptide derived from ACTB is any one or more of: $ACTB_{202-216}$, $ACTB_{170-184}$, $ACTB_{245-259}$, (for DRB1*0301); $ACTB_{187-201}$, $ACTB_{172-186}$, $ACTB_{131-145}$ (for DRB3*0202); $ACTB_{131-145}$, $ACTB_{171-185}$, $ACTB_{129-143}$ (for DRB4*0101); $ACTB_{164-178}$, $ACTB_{25-39}$, $ACTB_{323-337}$ (for DRB5*0101). In certain embodiments, the polypeptide derived from ACTB is any one or more of: $ACTB_{146-160}$, $ACTB_{18-32}$, and $ACTB_{171-185}$. In certain embodiments, the polypeptide derived from ACTB is any one or more of: SEQ ID NOs: 38 to 52.

In certain embodiments, the ubiquitous autoantigens for use with the nanoparticle compositions described herein are polypeptides derived from formimidoyltransferase-cyclodeaminase (FTCD). In certain embodiments, the polypeptide derived from FTCD is any one or more of: $FTCD_{439-453}$, $FTCD_{381-395}$, $FTCD_{297-311}$ (for DRB3*0202); $FTCD_{525-539}$, $FTCD_{218-232}$, $FTCD_{495-509}$ (for DRB1*0301); $FTCD_{262-276}$, $FTCD_{300-314}$, $FTCD_{259-273}$ (for DRB4*0101); $FTCD_{490-504}$, $FTCD_{389-403}$, $FTCD_{295-309}$ (for DRB5*0101). In certain embodiments, the polypeptide derived from FTCD is any one or more of: $FTCD_{271-285}$, FTCD 498-512, and $FTCD_{301-315}$. In certain embodiments, the polypeptide derived from FTCD is any one or more of: SEQ ID NOs: 73 to 87.

In certain embodiments, the ubiquitous autoantigens for use with the nanoparticle compositions described herein are polypeptides derived from myeloperoxidase (MPO). In certain embodiments, the polypeptide derived from MPO is any one or more of: $MPO_{322-336}$, $MPO_{714-728}$, $MPO_{617-631}$ (for DRB3*0202); $MPO_{504-518}$, $MPO_{462-476}$, $MPO_{617-631}$ (for DRB1*0301); $MPO_{444-458}$, $MPO_{689-703}$, $MPO_{248-262}$ (for DRB4*0101); $MPO_{511-525}$, $MPO_{97-111}$, $MPO_{616-630}$ (for DRB5*0101). In certain embodiments, the polypeptide derived from MPO is any one or more of: SEQ ID NOs: 88 to 99.

Additional ubiquitous autoantigens are listed in Table 5 at the end of this disclosure. In certain embodiments, the ubiquitous autoantigens for use with the nanoparticle compositions described herein are derived from a protein or polypeptide listed in Table 5. In certain embodiments, the ubiquitous autoantigens for use with the nanoparticle compositions described herein is derived from a human homolog to protein or polypeptide listed in Table 5. In certain embodiments, a homologue or human homologue is a protein or polypeptide that displays at least about 75%, 80%, 85%, 90%, 95%, or 98% identity to a protein listed in Table 5.

Tissue Specific Antigens

The nanoparticle compositions and methods described herein utilize ubiquitous autoantigens that are not tissue specific antigens. Many autoimmune or inflammatory diseases are associated with an immune response directed to a tissue specific antigen. This presents a problem for the production of a medicament to treat an autoimmune or inflammatory disease, since each disease requires a specific medicament that targets that antigen. Alternatively, nonspecific immune inhibitors can be used, but these are associated with significant systemic side-effects.

Tissue specific antigens are often expressed by a tissue or cell type affected by the autoimmune disease, for example a main pathological consequence of multiple sclerosis is demyelination of nervous system tissue, as a consequence tissue specific antigens for multiple sclerosis are largely restricted to the nervous system (e.g., myelin basic protein). Tissue specific antigens are those antigens that are associated with a specific cell or cell type. Tissue specific antigens can perform specialized functions or contribute to specialized tissue structures. In certain embodiments, a tissue specific antigen has expression restricted to any one of the following tissues: neural, kidney, cardiac, lung, liver, small intestine, colon, stomach, muscle, connective, and bloodvessel. In certain embodiments, a tissue specific antigen is restricted to expression of any one of the following cell types: beta cells, alpha cells, B lymphocytes, T lymphocytes, Schwann cells, adrenocortical cells.

Many tissue specific antigens may be expressed at a very low level in other cell or tissue types, but the main source of expression is one specific cell or tissue type. For example, a single cell or tissue type that displays cell specific or tissue type specific expression of a certain gene will express at least 10-fold, 50-fold, 100-fold, 500-fold, 1,000 fold or more of the gene at the mRNA or protein level than any other unrelated cell-type. Additionally, some tissue specific antigens will gain ectopic expression of a cell specific antigen under a pathogenic condition or by an exogenous stimulation. It is intended that merely because a different cell-type may gain ectopic expression under pathological or exogenous conditions the tissue specific nature of the antigen is not lost. For example, insulin is a tissue specific antigen produced by beta cells, yet due to genetic instability, some tumors (known as insulinomas) will express insulin, and under these types of circumstances insulin is still considered tissue specific.

Tissue specific antigens that are not ubiquitous autoantigens are primarily antigens associated with a particular tissue specific autoimmune or inflammatory disease.

In certain embodiments, the autoimmune or inflammatory disease is multiple sclerosis. In certain embodiments, the tissue specific antigen that is not a ubiquitous autoantigen is a polypeptide derived from myelin basic protein, myelin associated glycoprotein, myelin oligodendrocyte protein (MOG), proteolipid protein, oligodendrocyte myelin oligoprotein, myelin associated oligodendrocyte basic protein, oligodendrocyte specific protein, heat shock proteins, an oligodendrocyte specific protein, NOGO A, glycoprotein Po, peripheral myelin protein 22, and/or 2'3'-cyclic nucleotide 3'-phosphodiesterase.

In certain embodiments, the autoimmune or inflammatory disease is type I diabetes. In certain embodiments, the tissue specific antigen that is not a ubiquitous autoantigen is a polypeptide derived from pre-proinsulin, proinsulin, isletspecific glucose-6-phosphatase (IGRP), glutamate decarboxylase (GAD), islet cell autoantigen-2 (ICA2), and/or insulin.

In certain embodiments, the autoimmune or inflammatory disease is Pemphigus foliaceus (PF) or Pemphigus vulgaris (PV). In certain embodiments, the tissue specific antigen that is not a ubiquitous autoantigen is a polypeptide derived from desmoglein 3 (DG3) and/or desmoglein 1 (DG1).

In certain embodiments, the autoimmune or inflammatory disease is Neuromyelitis optica spectrum disorder (NMO). In certain embodiments, the tissue specific antigen that is not a ubiquitous autoantigen is a polypeptide derived from aquaporin 4 (AQP4).

In certain embodiments, the autoimmune or inflammatory disease is Arthritis. In certain embodiments, the tissue specific antigen that is not a ubiquitous autoantigen is a polypeptide derived from a heat shock protein, immunoglobulin binding protein, heterogeneous nuclear RNPs, annexin V, calpastatin, type II collagen, glucose-6-phosphate isomerase, elongation factor human cartilage gp39, mannose binding lectin, citrullinated vimentin, type II collagen, fibrinogen, alpha enolase, anti-carbamylated protein (anti-CarP), peptidyl arginine deiminase type 4 (PAD4), BRAF, fibrinogen gamma chain, inter-alpha-trypsin inhibitor heavy chain H1, alpha-1-antitrypsin, plasma protease C1 inhibitor, gelsolin, alpha 1-B glycoprotein, ceruloplasmin, inter-alpha-trypsin inhibitor heavy chain H4, complement factor H, alpha 2 macroglobulin, serum amyloid, C-reactive protein, serum albumin, fibrogen beta chain, serotransferin, alpha 2 HS glycoprotein, vimentin, and/or Complement C3

In certain embodiments, the autoimmune or inflammatory disease is allergic asthma. In certain embodiments, the tissue specific antigen that is not a ubiquitous autoantigen is a polypeptide derived from DERP1 and/or DERP2.

In certain embodiments, the autoimmune or inflammatory disease is inflammatory bowel disease. In certain embodiments, the tissue specific antigen that is not a ubiquitous autoantigen is a polypeptide derived from bacteroides integrase, flagelin, flagellin 2 (Fla-2/Fla-X), or uncharacterized E. coli protein (YIDX).

In certain embodiments, the autoimmune or inflammatory disease is systemic lupus erythematosus disease. In certain embodiments, the tissue specific antigen that is not a ubiquitous autoantigen is a polypeptide H4, H2B, H1', dsDNA, RNP, Smith (Sm), Sjogren's Syndrome-related Antigen A (SS-A)/Ro, Sjogren's Syndrome-related Antigen B (SS-B)/La, and/or histones. In some embodiments, SS-A includes, but is not limited to, RO60 and RO52. In some embodiments, histones include but are not limited to H4, H2B, H1.

In certain embodiments, the autoimmune or inflammatory disease is atherosclerosis. In certain embodiments, the tissue specific antigen that is not a ubiquitous autoantigen is a polypeptide derived from Apolipoprotein B (ApoB) and/or Apolipoprotein E (ApoE).

In certain embodiments, the autoimmune or inflammatory disease is chronic obstructive pulmonary disease (COPD). In certain embodiments, the tissue specific antigen that is not a ubiquitous autoantigen is a polypeptide derived from elastin.

In certain embodiments, the autoimmune or inflammatory disease is psoriasis. In certain embodiments, the tissue specific antigen that is not a ubiquitous autoantigen is a polypeptide derived from human adamis-like protein 5 (ATL5), cathelicidin antimicrobial peptide (CAP18), and/or ADAMTS-like protein 5 (ADMTSL5).

In certain embodiments, the autoimmune or inflammatory disease is uveitis. In certain embodiments, the tissue specific antigen that is not a ubiquitous autoantigen is a polypeptide derived from arrestin, human retinal S-antigen, and/or inter-photoreceptor retinoid-binding protein (IRBP).

In certain embodiments, the autoimmune or inflammatory disease is Sjogren's syndrome. In certain embodiments, the tissue specific antigen that is not a ubiquitous autoantigen is a polypeptide derived from (SS-A)/Ro, (SS-B)/La, RO60, RO52, and/or muscarinic receptor 3 (MR3).

In certain embodiments, the autoimmune or inflammatory disease is scleroderma. In certain embodiments, the tissue specific antigen that is not a ubiquitous autoantigen is a polypeptide derived from centromere autoantigen centromere protein C (CENP-C), DNA topoisomerase I (TOP1), and/or RNA polymerase III.

In certain embodiments, the autoimmune or inflammatory disease is anti-phospholipid syndrome. In certain embodiments, the tissue specific antigen that is not a ubiquitous autoantigen is a polypeptide derived from beta-2-glycoprotein 1 (BG2P1 or APOH).

In certain embodiments, the autoimmune or inflammatory disease is stiff man syndrome. In certain embodiments, the tissue specific antigen that is not a ubiquitous autoantigen is a polypeptide derived from GAD65.

Antigen-Major Histocompatibility Complexes (MHCs)

The nanoparticle complexes of this disclosure comprise a nanoparticle core, with or without layers and/or coatings, coupled to a ubiquitous autoantigen-MHC. The individual MHC polypeptide(s) and the antigenic (e.g., polypeptide) components form a complex through covalent or non-covalent binding (e.g. through hydrogen bonds, ionic bonds, or hydrophobic bonds). The preparation of such complexes may require varying degrees of manipulation and such methods are well known in the literature. In some aspects, antigenic components can be associated non-covalently with the pocket portion of the MHC component by, for instance, mixing the MHC and antigenic components; this relies on the natural binding affinity between an MHC and an antigen. Alternatively, in some aspects, the MHC component may be covalently associated with the antigenic component using standard procedures, such as, but not limited to, the introduction of known coupling agents or photo affinity labelling (see e.g., Hall et al., Biochemistry 24:5702-5711 (1985)). In certain aspects, an antigenic component may be operatively coupled to the MHC component via peptide linkages or other methods discussed in the literature, including but not limited to, attachment via carbohydrate groups on the glycoproteins, including, e.g., the carbohydrate moieties of the alpha- and/or beta-chains. In particular embodiments, the antigenic component may be attached to the N-terminal or C-terminal end of an appropriate MHC molecule. Alternatively, in certain embodiments, the MHC complex may be recombinantly formed by incorporating the sequence of the antigenic component into a sequence encoding an MHC, such that both retain their functional properties.

Multiple ubiquitous autoantigen-MHCs may be coupled to the same nanoparticle core; these complexes, MHCs, and/or antigens may be the same or different from one another.

Major Histocompatibility Molecules

The ubiquitous autoantigens described herein are associated with MHC molecules (to form the ubiquitous autoantigen-MHC), and coupled to nanoparticles. The antigens are bound to the binding grove of the MHC molecule. MHC molecules primarily bind antigens that are polypeptides, but polypeptides can comprise modifications such as lipidation, glycosylation, phosphorylation and the like. The MHC molecule can be an MHC class I molecule (MHCI) or an MHC class II molecule (MHCII). MHC class I molecules bind polypeptides between 8-10 amino acid residues in their binding groove, as the binding groove is closed on either side. MHC class II molecules, including those described herein, bind polypeptides at least 8 amino acids residues in length, but can bind longer peptides, with lengths of 9, 10, 11, 12, 13, 14, 15, 16, 17, 18, 19 amino acid residues or longer, as the binding groove is open on either side.

For use with human individuals the MHC molecules utilized herein are human (also referred to as human leukocyte antigens, abbreviated "HLA"). In certain embodiments, the MHC class I molecule is a classical or a non-classical MHC class I molecule HLA-A, HLA-B, HLA-C, HLA-E, CD1d, or a fragment or biological equivalent thereof. In certain embodiments, the MHC class II molecule is an HLA-DRB1, HLA-DRB3, HLA-DRB4, HLA-DRB5, HLA-DQB1, or HLA-DPB1, or a fragment or biological equivalent thereof. In some embodiments, the antigen-MHC (pMHC) can be a single chain construct. In some embodiments, the pMHC can be a dual-chain construct. In the case of a class II MHC, the beta chain of HLA will generally be non-covalently bound with an appropriate alpha chain to form a dual chain heterodimer with the alpha chain paired to the beta chain. Generally, the alpha chain of the MHC class II exhibits a much lower degree of polymorphism, for example, the DR alpha chain.

Since MHC class II complexes are heterodimers comprising an alpha and a beta chain, the heterodimers can have problems forming under some conditions, or are inherently unstable in some circumstances. When MHC class II molecules are deployed in a method or composition herein, the MHC molecules can further comprise a knob-in-hole architecture. In general, the alpha or beta chain is fused to an antibody $C_H2$ and $C_H3$ domain that has been modified to comprise a protuberance, while the corresponding other alpha or beta chain of the heterodimer is fused to an antibody $C_H2$ and $C_H3$ domain that has been modified to comprise a cavity.

As used herein, "knob-in-hole" or "knob-into-hole" refers to a polypeptidyl architecture requiring a protuberance (or "knob") at an interface of a first polypeptide and a corresponding cavity (or a "hole") at an interface of a second polypeptide, such that the protuberance can be positioned in the cavity so as to promote heterodimer formation. Protuberances may be constructed by replacing small amino acid side chains from the interface of the first polypeptide with larger side chains (e.g., phenylalanine or tyrosine). Cavities of identical or similar size to the protuberances may be created in the interface of the second polypeptide by replacing large amino acid side chains with smaller ones (e.g., alanine or threonine). The protuberances and cavities can be made by synthetic means such as by altering the nucleic acid encoding the polypeptides or by peptide synthesis, using routine methods by one skilled in the art. In some embodiments, the interface of the first polypeptide is located on an Fc domain in the first polypeptide; and the interface of the second polypeptide is located on an Fc domain on the second polypeptide. Knob-in-hole heterodimers and methods of their preparation and use are disclosed in U.S. Pat. Nos. 5,731,168; 5,807,706; 5,821,333; 7,642,228; 7,695,936; 8,216,805; and 8,679,785; and in Merchant et al., Nature Biotechnology, 1998, 16:677-681, all of which are incorporated by reference herein in their entirety.

Alternatively or in addition any of the antigens described herein can comprise a cysteine residue that interacts with a cysteine residue (engineered or natural) of an MHC class II alpha or beta chain. This is commonly known as a cysteine trap.

A cysteine trap can be utilized to stabilize a heterodimer described herein. Cysteine trapping involves forming covalently joined polypeptide complexes from unbound polypeptide partners. In some embodiments, cysteine trapping comprises introducing a cysteine at a strategically selected position within the interaction interface of the polypeptide partners to form a stabilized polypeptide complex. In some embodiments, cysteine trapping may stabilize the polypeptide complex to favor a specific conformation and to prevent dissociation. Cysteine trapping is also referred to as disulfide trapping and disulfide crosslinking. Examples of methods and applications of cysteine trapping are reviewed in Kufareva, et al., Methods Enzymol. 570:389-420 (2016). In the context of MHC, a cysteine is engineered into a polypeptide that is known or suspected to associate in the binding groove of an MHC class II dimer. A cysteine is then engineered in or near the binding groove such that, when the polypeptide associates with the binding groove, the binding groove cysteine can come into proximity and form a disulfide linkage with a polypeptide cysteine.

Provided herein, in one aspect, are isolated heterodimers comprising at least one first polypeptide and at least one second polypeptide, wherein the first polypeptide and the second polypeptide meet at an interface, wherein the interface of the first polypeptide comprises an engineered protuberance which is positionable in an engineered cavity in the interface of the second polypeptide; and (i) the first polypeptide comprises an MHC class II α1 domain, an MHC class II α2 domain, or a combination thereof; and the second polypeptide comprises an MHC class II β1 domain, an MHC class II β2 domain, or a combination thereof; or (ii) the first polypeptide comprises an MHC class II β1 domain, an MHC class II β2 domain, or a combination thereof; and the second polypeptide comprises an MHC class II α1 domain, an MHC class II α2 domain, or a combination thereof. The first polypeptide, the second polypeptide, or both can comprise an antibody $C_H3$ domain fused to the polypeptide. Optionally, the first polypeptide, the second polypeptide, or both comprise an antibody $C_H2$ domain located between the MHC (α or β chain) and the $C_H3$ domain. In certain embodiments, the first polypeptide comprises an antibody $C_H3$ domain, and the antibody $C_H3$ domain comprises at least one mutation selected from the list consisting of S354C, T366W, and both S354C and T366W (EU numbering). In certain embodiments, the second polypeptide comprises an antibody $C_H3$ domain, and the antibody $C_H3$ domain comprises at least one mutation selected from the list consisting of Y349C, T366S, L368A, Y407V (EU numbering), and combinations thereof. In further embodiments, the isolated heterodimer comprises a ubiquitous autoantigen, optionally covalently bound to either the first or the second polypeptide. Optionally, the ubiquitous autoantigen comprises a cysteine residue that interacts with a cysteine residue in either the first or second polypeptide to create a cysteine trap.

In one aspect, one polypeptide of the heterodimer comprises an MHC class II α1 domain, an MHC class II α2 domain, or a combination thereof; and at least one engineered protuberance. In some embodiments, the at least one engineered protuberance is not located at the MHC class II α1 domain or the MHC class II α2 domain. In some embodiments, the engineered protuberance is located at an antibody $C_H3$ domain fused to the polypeptide. In some embodiments, the polypeptide optionally comprises an antibody $C_H2$ domain located between an MHC class II α2 domain and the $C_H3$ domain with an engineered protuberance. In certain embodiments, the polypeptide comprises an antibody $C_H3$ domain, and the antibody $C_H3$ domain comprises at least one mutation selected from the list consisting of S354C, T366W, and both S354C and T366W (EU numbering). In further embodiments, the polypeptide comprises a ubiquitous autoantigen. Optionally, the ubiquitous autoantigen comprises a cysteine residue that interacts with a cysteine residue in either an MHC α1 or β1 domain to create a cysteine trap.

In one aspect, one polypeptide of the heterodimer comprises an MHC class II β1 domain, an MHC class II β2 domain, or a combination thereof; and at least one engineered protuberance. In some embodiments, the at least one engineered protuberance is not located at the MHC class II β1 domain or the MHC class II β2 domain. In some embodiments, the engineered protuberance is located at an antibody $C_H3$ domain fused to the polypeptide. In some embodiments, the polypeptide optionally comprises an antibody $C_H2$ domain located between an MHC class II β2 domain and the $C_H3$ domain with an engineered protuberance. In certain embodiments, the polypeptide comprises an antibody $C_H3$ domain, and the antibody $C_H3$ domain comprises at least one mutation selected from the list consisting of S354C, T366W, and both S354C and T366W (EU numbering). In further embodiments, the polypeptide comprises a ubiquitous autoantigen. Optionally, the ubiquitous autoantigen comprises a cysteine residue that interacts with a cysteine residue in either an MHC α1 or β1 domain to create a cysteine trap.

In one aspect, one polypeptide of the heterodimer comprises an MHC class II α1 domain, an MHC class II α2 domain, or a combination thereof; and at least one engineered cavity. In some embodiments, the at least one engineered cavity is not located at the MHC class II α1 domain or the MHC class II α2 domain. In some embodiments, the engineered cavity is located at an antibody $C_H3$ domain fused to the polypeptide. In some embodiments, the polypeptide optionally comprises an antibody $C_H2$ domain located between an MHC class II α2 domain and the $C_H3$ domain with an engineered cavity. In certain embodiments, the polypeptide comprises an antibody $C_H3$ domain, and the antibody $C_H3$ domain comprises at least one mutation selected from the list consisting of Y349C, T366S, L368A, Y407V (EU numbering), and combinations thereof. In further embodiments, the polypeptide comprises a ubiquitous autoantigen. Optionally, the ubiquitous autoantigen comprises a cysteine residue that interacts with a cysteine residue in either an MHC α1 or β1 domain to create a cysteine trap.

In one aspect, one polypeptide of the heterodimer comprises an MHC class II β1 domain, an MHC class II β2 domain, or a combination thereof; and at least one engineered cavity. In some embodiments, the at least one engineered cavity is not located at the MHC class II β1 domain or the MHC class II β2 domain. In some embodiments, the engineered cavity is located at an antibody $C_H3$ domain fused to the polypeptide. In some embodiments, the polypeptide optionally comprises an antibody $C_H2$ domain located between an MHC class II β2 domain and the $C_H3$ domain with an engineered cavity. In certain embodiments, the polypeptide comprises an antibody $C_H3$ domain, and the antibody $C_H3$ domain comprises at least one mutation selected from the list consisting of Y349C, T366S, L368A, Y407V (EU numbering), and combinations thereof. In further embodiments, the polypeptide comprises a ubiquitous autoantigen. Optionally, the ubiquitous autoantigen comprises a cysteine residue that interacts with a cysteine residue in either an MHC α1 or β1 domain to create a cysteine trap.

Figure 20B:
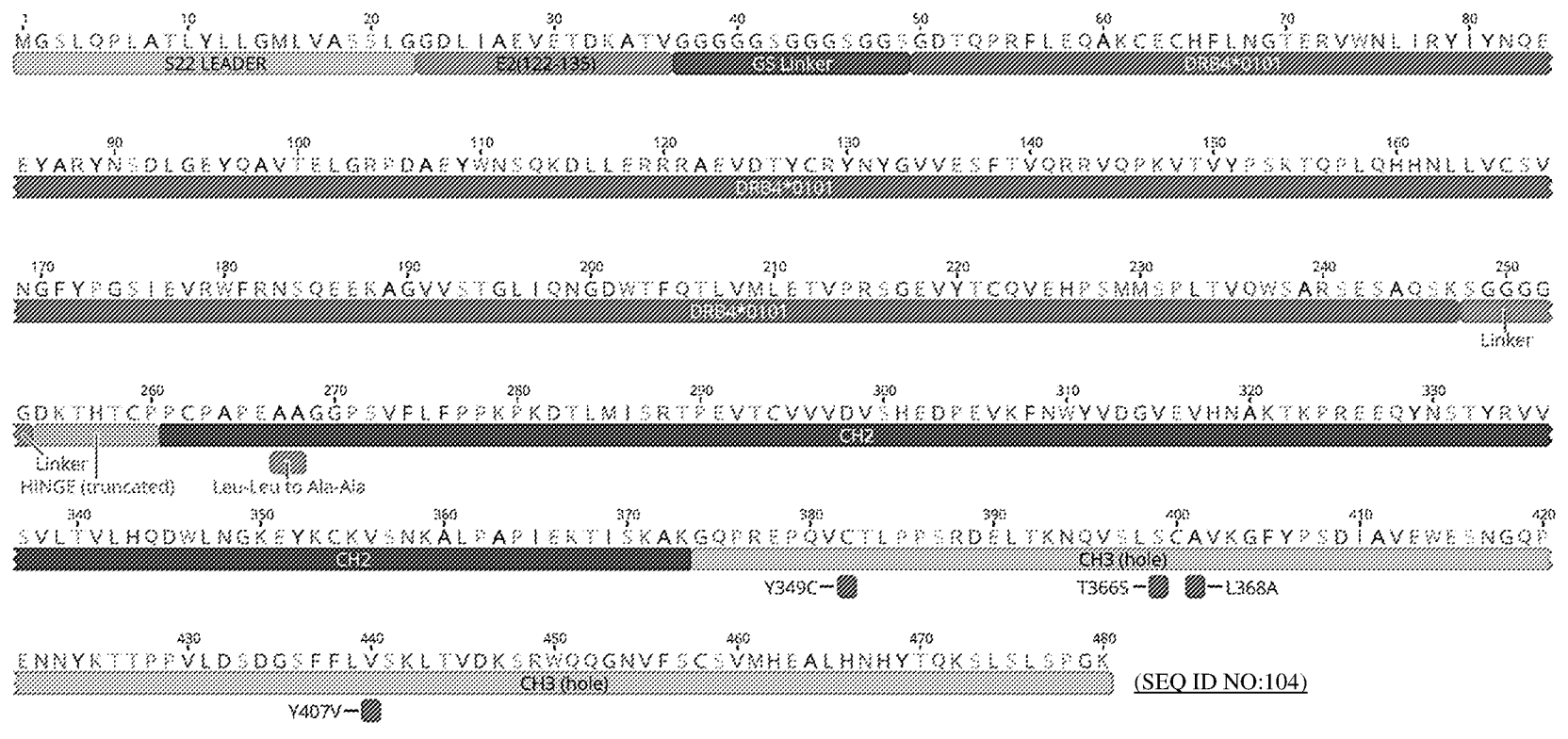

FIG. 20A and FIG. 20B show non-limiting embodiments of an engineered uaMHC comprising an engineered cavity and an engineered protuberance. FIG. 20A shows a human MHC class II alpha chain fused to an immunoglobulin CH2 and CH3 domain, SEQ ID NO: 103. The CH3 domain comprises an engineered knob that has been created by substituting two amino acids S354C and T366W. The alpha chain comprises an optional c-terminal cysteine to allow for conjugation to a functionalized linker, however this c-terminal cysteine can be alternatively included on the beta chain. FIG. 20B shows a human MHC class II beta chain fused to an immunoglobulin CH2 and CH3 domain, SEQ ID NO: 104. The CH3 domain comprises an engineered hole that has been created by substituting four amino acids Y349C, T366S, L368A and Y407V. The beta chain also comprises a ubiquitous autoantigen (PDC-E2$_{122-135}$) that is covalently coupled to the beta chain by a peptide linker. The protuberance-cavity interaction favors assembly and allows for purification of intact uaMHC heterodimers using standard techniques to purify immunoglobulin. Once purified the uaMHC can be coupled to a suitable nanoparticle through a functionalized linker molecule (E.g., functionalized PEG molecules). In certain embodiments, the alpha chain of MHC heterodimer comprises an amino acid sequence at least about 90%, 95%, 97%, 98%, 99%, or 100% identical to SEQ ID NO: 103. In certain embodiments, the beta chain of MHC heterodimer comprises an amino acid sequence at least about 90%, 95%, 97%, 98%, 99%, or 100% identical to SEQ ID NO: 104. In certain embodiments, the MHC heterodimer comprises an alpha chain at least about 90%, 95%, 97%, 98%, 99%, or 100% identical to SEQ ID NO: 103; and a beta chain at least about 90%, 95%, 97%, 98%, 99%, or 100% identical to SEQ ID NO: 104. In certain embodiments the alpha chain and the beta chain are at least about 90%, 95%, 97%, 98%, 99%, or 100% identical to SEQ ID NO: 103 or 104, and any one or more of the CH2 and CH3 domain of SEQ ID NO: 103, the CH2 and CH3 domain of SEQ ID NO: 103, and/or the ubiquitous autoantigen is identical to that disclosed in SEQ ID NO: 104. In certain embodiments the alpha chain and the beta chain are at least about 90%, 95%, 97%, 98%, 99%, or 100% identical to SEQ ID NO: 103 or 104, and the ubiquitous autoantigen is identical to that disclosed in SEQ ID NO: 104. Those of skill in the art will recognize that the alpha and beta chains of human MHC are highly polymorphic, and thus can tolerate a relatively high degree of variability. One of skill in the art will also be able to substitute the alpha and beta chains of the MHC shown in SEQ ID NOs: 102 and 104 for a different HLA allele, and an appropriate ubiquitous autoantigen that is able to bind the specific substituted allele. Such HLA allele and ubiquitous autoantigen pairings are disclosed elsewhere in the application, for example, at the sequence listing at the end of this application.

Nanoparticles

The ubiquitous autoantigen-MHCs are coupled to a nanoparticle core (uaMHC-NP). The nanoparticle can be made from a variety of materials. In certain embodiments, the nanoparticle is non-liposomal and/or has a solid core. In certain embodiments, the solid core can be a metal or a metal oxide. In certain embodiments, the solid core can be iron, iron oxide, or gold. The solid core can be a high density core such that the density is greater than about 2.0 $g/cm^3$, about 3.0 $g/cm^3$, about 4.0 $g/cm^3$, about 5.0 $g/cm^3$, about 6.0 $g/cm^3$, or about 7.0 $g/cm^3$. In certain embodiments, the density of the solid core is between about 4.0 $g/cm^3$ and about 8.0 $g/cm^3$. In certain embodiments, the density of the solid core is between about 5.0 $g/cm^3$ and about 8.0 $g/cm^3$. In certain embodiments, the density of the solid core is between about 5.0 $g/cm^3$ and about 7.0 $g/cm^3$. In certain embodiments, the density of the solid core is between about 5.0 $g/cm^3$ and about 6.0 $g/cm^3$.

The nanoparticle core of the uaMHC-NP comprises, or consists essentially of, or yet further consists of a core, for example a solid core, a metal core, a dendrimer core, a polymeric micelle nanoparticle core, a nanorod, a fullerene, a nanoshell, a coreshell, a protein-based nanostructure or a lipid-based nanostructure. In some aspects, the nanoparticle core is bioabsorbable and/or biodegradable. In some aspects, the nanoparticle core is a dendrimer nanoparticle core comprising, or alternatively consisting essentially thereof, or yet further consisting of a highly branched macromolecule having a tree-like structure growing from a core. In further aspects, the dendrimer nanoparticle core may comprise, or alternatively consist essentially thereof, or yet further consist of a poly(amidoamine)-based dendrimer or a poly-L-lysine-based dendrimer. In certain aspects, the nanoparticle core is a polymeric micelle core comprising, or alternatively consisting essentially thereof, or yet further consisting of an amphiphilic block co-polymer assembled into a nano-scaled core-shell structure. In further aspects, the polymeric micelle core comprises, or alternatively consists essentially thereof, or yet further consists of a polymeric micelle produced using polyethylene glycol-diastearoylphosphatidylethanolamine block copolymer. In a further aspect, the nanoparticle core comprises, or alternatively consists essentially of, or yet further consists of a metal. In another aspect, the nanoparticle core is not a liposome. Additional examples of core materials include but are not limited to, standard and specialty glasses, silica, polystyrene, polyester, polycarbonate, acrylic polymers, polyacrylamide, polyacrylonitrile, polyamide, fluoropolymers, silicone, celluloses, silicon, metals (e.g., iron, gold, silver), minerals (e.g., ruby), nanoparticles (e.g., gold nanoparticles, colloidal particles, metal oxides, metal sulfides, metal selenides, and magnetic materials such as iron oxide), and composites thereof. In some embodiments, an iron oxide nanoparticle core comprises iron (II, III) oxide. The core could be of homogeneous composition, or a composite of two or more classes of material depending on the properties desired. In certain aspects, metal nanoparticles will be used. These metal particles or nanoparticles can be formed from Au, Pt, Pd, Cu, Ag, Co, Fe, Ni, Mn, Sm, Nd, Pr, Gd, Ti, Zr, Si, and In, precursors, their binary alloys, their ternary alloys and their intermetallic compounds. See U.S. Pat. No. 6,712,997, which is incorporated herein by reference for such disclosure. In certain embodiments, the compositions of the core and layers (described below) may vary provided that the nanoparticles are biocompatible and bioabsorbable. The core could be of homogeneous composition, or a composite of two or more classes of material depending on the properties desired. In certain aspects, metal nanospheres will be used. These metal nanoparticles can be formed from Fe, Ca, Ga and the like. In certain embodiments, the nanoparticle comprises, or alternatively consists essentially of, or yet further consists of a core comprising metal or metal oxide such as gold or iron oxide.

In another aspect, provided herein are uaMHC-NPs comprising at least one ubiquitous autoantigen-MHC described herein and a nanoparticle, wherein the nanoparticle is non-liposomal and has an iron oxide core.

In another aspect, provided herein are uaMHC-NPs comprising at least one ubiquitous autoantigen-MHC described herein and a nanoparticle, wherein the nanoparticle is non-liposomal and has a gold core.

In another aspect, provided herein are uaMHC-NPs comprising at least one ubiquitous autoantigen-MHC herein and a nanoparticle, wherein the nanoparticle is non-liposomal and has an iron oxide core; and the at least one ubiquitous autoantigen-MHC is covalently linked to the nanoparticle through a linker.

In some aspects, the nanoparticle core has a diameter selected from the group of from about 1 nm to about 100 nm; from about 1 nm to about 75 nm; from about 1 nm to about 50 nm; from about 1 nm to about 25 nm; from about 5 nm to about 100 nm; from about 5 nm to about 50 nm; from about 5 nm to about 40 nm; from about 5 nm to about 30 nm; from about 5 nm to about 25 nm; or from about 5 nm to about 20 nm. In some embodiments, the nanoparticle core has a dimeter from about 10 nm to about 100 nm; from about 10 nm to about 50 nm; from about 10 nm to about 40 nm; from about 10 nm to about 30 nm; from about 10 nm to about 25 nm; or from about 10 nm to about 20 nm. In certain embodiments, the nanoparticle core has a diameter greater than about 1 nm, 2 nm, 5 nm, 10 nm, 15 nm, 20 nm, 25 nm, 30 nm, 40 nm, or 50 nm. In certain embodiments, the nanoparticle core has a diameter less than about 100 nm, 75 nm, 50 nm, 40 nm, 30 nm, 20 nm, or 15 nm.

In some aspects, the nanoparticle core is a dendrimer nanoparticle core comprising, or alternatively consisting essentially thereof, or yet further consisting of a highly branched macromolecule having a tree-like structure growing from a core. In further aspects, the dendrimer nanoparticle may comprise, or alternatively consist essentially thereof, or yet further consist of a poly(amidoamine)-based dendrimer or a poly-L-lysine-based dendrimer. In certain aspects, the nanoparticle core is a polymeric micelle core comprising, or alternatively consisting essentially thereof, or yet further consisting of an amphiphilic block co-polymer assembled into a nano-scaled core-shell structure. In further aspects, the polymeric micelle core may comprise, or alternatively consist essentially thereof or yet further consist of, a polymeric micelle produced using polyethylene glycol-diastearoylphosphatidylethanolamine block copolymer. The dendrimer core or polymeric micelle core may further comprise an outer coating or layer as described herein.

In certain embodiments, specific means of synthesis of dendrimer nanoparticles or nanoparticles with a dendrimer nanoparticle core may require that metal ions are extracted into the interior of dendrimers and then subsequently chemically reduced to yield nearly size-monodispersed particles having dimensions of less than 3 nm, such as the method disclosed in Crooks et al., "Synthesis, Characterization, and Applications of Dendrimer-Encapsulated Nanoparticles". *The Journal of Physical Chemistry B* (109): 692-704 (2005), wherein the resulting dendrimer core component serves not only as a template for preparing the nanoparticle but also to stabilize the nanoparticle, making it possible to tune solubility, and provides a means for immobilization of the nanoparticle on solid supports.

The nanoparticle cores typically consist of a substantially spherical core and optionally one or more layers or coatings. The core may vary in size and composition as described herein. In addition to the core, the particle may have one or more layers to provide functionalities appropriate for the applications of interest. The thicknesses of layers, if present, may vary depending on the needs of the specific applications. For example, layers may impart useful optical properties.

Layers may also impart chemical or biological functionalities, referred to herein as chemically active or biologically active layers. These layers typically are applied on the outer surface of the particle and can impart functionalities to the pMHC-NPs. The layer or layers may typically range in thickness from about 0.001 micrometers (1 nanometer) to about 10 micrometers or more (depending on the desired particle diameter) or from about 1 nm to 5 nm, from about 1 nm to about 10 nm, from about 1 nm to about 40 nm, from about 15 nm to about 25 nm, or about 20 nm, and ranges in between.

The layer or coating may comprise, or alternatively consist essentially of, or yet further consist of a biodegradable sugar or other polymer. Examples of biodegradable layers include but are not limited to dextran; poly(ethylene glycol); poly(ethylene oxide); mannitol; poly(esters) based on polylactide (PLA), polyglycolide (PGA), polycaprolactone (PCL); poly(hydroxalkanoate) of the PHB-PHV class; and other modified poly(saccharides) such as starch, cellulose and chitosan. Additionally, the nanoparticle may include a layer with suitable surfaces for attaching chemical functionalities for chemical binding or coupling sites.

Surface Valency and Density of Antigen-MHCs

The ubiquitous autoantigen-MHCs described herein are coupled to the nanoparticle at a certain valency. Valency is the number of pMHCs per nanoparticle core. In certain embodiments, the valency of the nanoparticle may range between about 1 pMHC per nanoparticle core to about 6,000 pMHCs per nanoparticle core. In certain embodiments, the valency of the nanoparticle may range between about 10 pMHCs per nanoparticle core to about 6,000 pMHCs per nanoparticle core. In certain embodiments, the valency of the nanoparticle may range between about 50 pMHCs per nanoparticle core to about 6,000 pMHCs per nanoparticle core. In certain embodiments, the valency of the nanoparticle may range between about 1 pMHC per nanoparticle core to about 5000, about 4000, about 3000, about 2000, or about 1000 pMHCs per nanoparticle core. In certain embodiments, the valency of the nanoparticle may range between about 10 pMHCs per nanoparticle core to about 5000, about 4000, about 3000, about 2000, or about 1000 pMHCs per nanoparticle core. In certain embodiments, the valency of the nanoparticle may range between about 50 pMHC per nanoparticle core to about 5000, about 4000, about 3000, about 2000, or about 1000 pMHCs per nanoparticle core. In certain embodiments, the valency of the nanoparticle may range between about 1 pMHC to per nanoparticle core to about 1000 pMHCs per nanoparticle core, or between about 10:1 to about 1000:1, or between about 11:1 to about 1000:1, or between about 12:1 to about 1000:1. In certain embodiments, the valency (antigen-MHC to nanoparticle core) may range between about 10:1 to about 500:1, or between about 11:1 to about 500:1, or between about 12:1 to about 500:1. In certain embodiments, the valency (antigen-MHC to nanoparticle core) may range between about 10:1 to about 200:1, or between about 11:1 to about 200:1, or between about 12:1 to about 200:1. In certain embodiments, the valency (antigen-MHC to nanoparticle core) may range between about 10:1 to about 150:1, or between about 11:1 to about 150:1, or between about 12:1 to about 150:1. In certain embodiments, the valency (antigen-MHC to nanoparticle core) may range between about 10:1 to about 100:1, or between about 11:1 to about 100:1, or between about 12:1 to about 100:1. In certain embodiments, the valency (antigen-MHC to nanoparticle core) may range between about 10:1 to about 200:1, between about 20:1 to about 200:1, between about 30:1 to about 200:1, between about 40:1 to about 200:1, or between about 50:1 to about 200:1. In certain embodiments, the valency (antigen-MHC to nanoparticle core) may range between about 10:1 to about 150:1, between about 20:1 to about 150:1, between about 30:1 to about 200:1, between about 40:1 to about 150:1, or between about 50:1 to about 150:1. In certain embodiments, the valency (antigen-MHC to nanoparticle core) may range between about 10:1 to about 100:1, between about 20:1 to about 100:1, between about 30:1 to about 100:1, between about 40:1 to about 100:1, or between about 50:1 to about 100:1.

In some aspects, the nanoparticle core has a defined valency per surface area of the core, also referred to herein as "density." In these aspects, the pMHC density per nanoparticle is from about 0.025 pMHC/100 $nm^2$ to about 100 pMHC/100 $nm^2$ of the surface area of the nanoparticle core, or alternatively from about 0.406 pMHC/100 $nm^2$ to about 50 pMHC/100 $nm^2$; or alternatively from about 0.05 pMHC/100 $nm^2$ to about 25 pMHC/100 $nm^2$. In certain aspects, the pMHC density per nanoparticle is from about 0.4 pMHC/100 $nm^2$ to about 25 pMHC/100 $nm^2$, or from about 0.4 pMHC/100 $nm^2$ to about 20 pMHC/100 $nm^2$, or from about 0.4 pMHC/100 $nm^2$ to about 15 pMHC/100 $nm^2$, or from about 0.4 pMHC/100 $nm^2$ to about 14 pMHC/100 $nm^2$, or from about 0.4 pMHC/100 $nm^2$ to about 13 pMHC/100 $nm^2$, or from about 0.4 pMHC/100 $nm^2$ to about 12 pMHC/100 $nm^2$, or from about 0.4 pMHC/100 $nm^2$ to about 11.6 pMHC/100 $nm^2$, or from about 0.4 pMHC/100 $nm^2$ to about 11.5 pMHC/100 $nm^2$, or from about 0.4 pMHC/100 $nm^2$ to about 11 pMHC/100 $nm^2$, or from about 0.4 pMHC/100 $nm^2$ to about 10 pMHC/100 $nm^2$, or from about 0.4 pMHC/100 $nm^2$ to about 9 pMHC/100 $nm^2$, or from about 0.4 pMHC/100 $nm^2$ to about 8 pMHC/100 $nm^2$, or from about 0.4 pMHC/100 $nm^2$ to about 7 pMHC/100 $nm^2$, or from about 0.4 pMHC/100 $nm^2$ to about 6 pMHC/100 $nm^2$, or from about 0.4 pMHC/100 $nm^2$ to about 5 pMHC/100 $nm^2$, or from about 0.4 pMHC/100 $nm^2$ to about 4 pMHC/100 $nm^2$, or from about 0.4 pMHC/100 $nm^2$ to about 3 pMHC/100 $nm^2$, or from about 0.4 pMHC/100 $nm^2$ to about 2.5 pMHC/100 $nm^2$, or from about 0.4 pMHC/100 $nm^2$ to about 2 pMHC/100 $nm^2$, or from about 0.4 pMHC/100 $nm^2$ to about 1.5 pMHC/100 $nm^2$.

In another aspect, the nanoparticle may have a pMHC density of from about 0.22 pMHC/100 $nm^2$ to about 10 pMHC/100 $nm^2$, or from about 0.22 pMHC/100 $nm^2$ to about 9 pMHC/100 $nm^2$, or from about 0.22 pMHC/100 $nm^2$ to about 8 pMHC/100 $nm^2$, or from about 0.22 pMHC/100 $nm^2$ to about 7 pMHC/100 $nm^2$, or from about 0.22 pMHC/100 $nm^2$ to about 6 pMHC/100 $nm^2$, or from about 0.22 pMHC/100 $nm^2$ to about 5 pMHC/100 $nm^2$, or from about 0.22 pMHC/100 $nm^2$ to about 4 pMHC/100 $nm^2$, or from about 0.22 pMHC/100 $nm^2$ to about 3 pMHC/100 $nm^2$, or from about 0.22 pMHC/100 $nm^2$ to about 2 pMHC/100 $nm^2$, or from about 0.22 pMHC/100 $nm^2$ to about 1.5 pMHC/100 $nm^2$. In some aspects, the nanoparticle has a pMHC density of from about 0.22 pMHC/100 $nm^2$ to about 10 pMHC/100 $nm^2$, or 0.24 pMHC/100 $nm^2$ to about 9 pMHC/100 $nm^2$, or from about 0.26 pMHC/100 $nm^2$ to about 8 pMHC/100 $nm^2$, or from about 0.28 pMHC/100 $nm^2$ to about 7 pMHC/100 $nm^2$, or from about 0.24 pMHC/100 $nm^2$ to about 4 pMHC/100 $nm^2$, or from about 0.5 pMHC/100 $nm^2$ to about 3 pMHC/100 $nm^2$, or from about 0.6 pMHC/100 $nm^2$ to about 1.5 pMHC/100 $nm^2$. In a further aspect, the nanoparticle has a pMHC density of from about 0.4 pMHC/100 $nm^2$ to about 1.3 pMHC/100 $nm^2$, or alternatively from about 0.5 pMHC/100 $nm^2$ to about 0.9 pMHC/100 $nm^2$, or alternatively from about 0.6 pMHC/100 $nm^2$ to about 0.8 pMHC/100 $nm^2$.

Linkers

In certain aspects, ubiquitous autoantigen-MHC can be coupled to the nanoparticle core by one or more of covalently, non-covalently, or cross-linked and optionally coupled through a linker. In aspects involving a linker or linkers, the linkers may be the same or different from each other on a single nanoparticle core. In some embodiments, the ubiquitous autoantigen-MHC comprises at least one ubiquitous autoantigen-MHC described herein and a nanoparticle, wherein the nanoparticle is non-liposomal and has metal or metal oxide core; and the at least one ubiquitous autoantigen-MHC is covalently linked to the nanoparticle through a linker comprising polyethylene glycol with a molecular weight of less than 5 kilodaltons (kD). In some embodiments, polyethylene glycol has a molecular weight of less than 1 kD, 2 kD, 3 kD, 4 kD, 5 kD, 6 kD, 7 kD, 8 kD, 9 kD, or 10 kD. In some embodiments, polyethylene glycol is functionalized with maleimide. In some embodiments, polyethylene glycol has a molecular weight of between about 1 kD and about 5 kD, between about 2 kD and about 5 kD, between about 3 kD and about 5 kD. In some embodiments, polyethylene glycol is functionalized with maleimide. In certain embodiments, the end of the linker that is in contact with the solid core is embedded in the solid core. In further aspects, the linker may be less than 5 kD in size, and is optionally polyethylene glycol. The linker can be any of the linkers described in Table 1.

so-called "linking molecules," followed by reacting the MHC or MHC complex with the particles obtained.

TABLE 1

Exemplary linker molecules

| Types of Nanoparticle | PEG linkers | M.W. (kD) | Functional group | Structure |
|---|---|---|---|---|
| Gold nano-particle (GNP-C) | Thiol-PEG-carboxyl | 3.5 | Carboxyl (—COOH) | 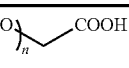 |
| Gold nano-particle (GNP-N) | Thiol-PEG-amine | 3.5 | Amine (—NH$_2$) | 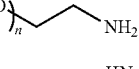 |
| Iron oxide Nanoparticle (SFP-C) | Dopamine-PEG-carboxyl | 3.5 | Carboxyl (—COOH) | 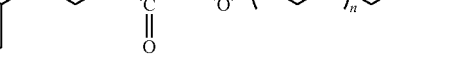 |
| Iron oxide Nanoparticle (SFP-N) | Dopamine-PEG-amine | 3.5 | Amine (—NH$_2$) | 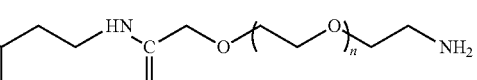 |
| Iron oxide Nanoparticle (SFP-Z) | Dopamine-PEG-azide | 3.5 | Azide (—N$_3$) | 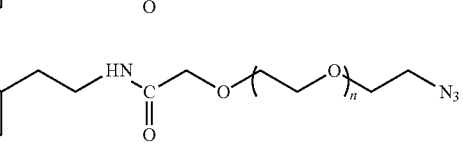 |
| Iron oxide Nanoparticle (SFP-M) | Dopamine-PEG-maleimide | 3.5 | Maleimide | 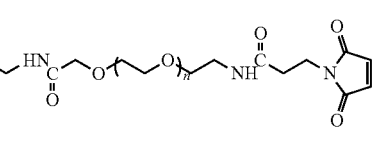 |
| Iron oxide Nanoparticle (SFP-O) | Dopamine-PEG-Orthopyridyl disulfide | 3.5 | Orthopyridyl disulfide | 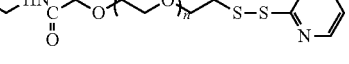 |
| Iron oxide Nano-particle (PF-C) | carboxyl-PEG-carboxyl | 3.5 | Carboxyl (—COOH) | 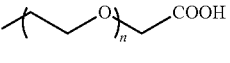 |
| Iron oxide Nano-particle (PF-N) | Methoxy-PEG-amine | 2.0 | Amine (—NH$_2$) | 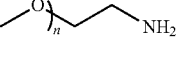 |
| Iron oxide Nano-particle (PF-M) | Methoxy-PEG-maleimide | 2.0 | Maleimide | 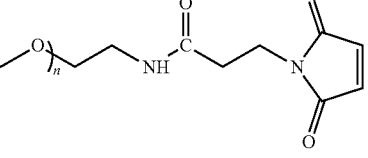 |
| Iron oxide Nano-particle (PF-O) | Methoxy-PEG-Orthopyridyl disulfide | 2.0 | Orthopyridyl disulfide | 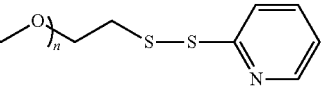 |
| Iron oxide Nano-particle (PF) | PEG | 2.0 | Hydroxyl (—OH) | 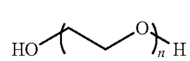 |

In order to couple the substrate or particles of the ubiquitous autoantigen-MHC to the nanoparticle, the following techniques can be applied.

The binding can be generated by chemically modifying the substrate or particle which typically involves the generation of "functional groups" on the surface, said functional groups being capable of binding to an MHC complex, and/or linking the optionally chemically modified surface of the surface or particle with covalently or non-covalently bound The functional groups or the linking molecules bearing them may be selected from amino groups, carbonic acid groups, thiols, thioethers, disulfides, guanidino, hydroxyl groups, amine groups, vicinal diols, aldehydes, alpha-haloacetyl groups, mercury organyles, ester groups, acid halide, acid thioester, acid anhydride, isocyanates, isothiocyanates, sulfonic acid halides, imidoesters, diazoacetates, diazonium salts, 1,2-diketones, phosphoric acids, phosphoric acid esters, sulfonic acids, azolides, imidazoles, indoles, N-maleimides, alpha-beta-unsaturated carbonyl compounds, arylhalogenides or their derivatives.

Non-limiting examples for other linking molecules with higher molecular weights are nucleic acid molecules, polymers, copolymers, polymerizable coupling agents, silica, proteins, and chain-like molecules having a surface with the opposed polarity with respect to the substrate or particle. Nucleic acids can provide a link to affinity molecules containing themselves nucleic acid molecules, though with a complementary sequence with respect to the linking molecule.

In some embodiments, the linking molecule comprises polyethylene glycol. In some embodiments, the linking molecule comprises polyethylene glycol and maleimide. In some embodiments, the polyethylene glycol comprises one or more of a $C_1$-$C_3$ alkoxy group, —$R^{10}$NHC(O)R—, —$R^{10}$C(O)NHR—, —$R^{10}$OC(O)R—, —$R^{10}$C(O)OR—, wherein each R is independently H or $C_1$-$C_6$ alkyl and wherein each $R_{10}$ is independently a bond or $C_1$-$C_6$ alkyl.

pMHCs can be coupled to nanoparticles by a variety of methods, one non-limiting example includes conjugation to NPs produced with PEG linkers carrying distal —NH2 or —COOH groups that can be achieved via the formation of amide bonds in the presence of 1-Ethyl-3-[3-dimethylaminopropyl]carbodiimide hydrochloride (EDC). NPs with —COOH groups are first dissolved in 20 mM MES buffer, pH 5.5. N-hydroxysulfosuccinimide sodium salt (sulpha-NHS, Thermo Scientific, Waltham, MA, final concentration 10 mM) and EDC (Thermo scientific, Waltham, MA, final concentration 1 mM) is added to the NP solution. After 20 min of stirring at room temperature, the NP solution is added drop-wise to the solution containing pMHC monomers dissolved in 20 mM borate buffer (pH 8.2). The mixture is stirred for an additional 4 hr. To conjugate MHCs to NH2-functionalized NPs pMHCs are first dissolved in 20 mM MES buffer, pH 5.5, containing 100 mM NaCl. Sulpha-NHS (10 mM) and EDC (5 mM) are then added to the MHC solution. The activated MHC molecules are then added to the NP solution in 20 mM borate buffer (pH 8.2), and stirred for 4 hr at room temperature.

To conjugate MHC to maleimide-functionalized NPs, pMHCs are first incubated with Tributylphospine (TBP, 1 mM) for 4 hr at room temperature, pMHCs engineered to encode a free carboxyterminal Cys residue are then mixed with NPs in 40 mM phosphate buffer, pH 6.0, containing 2 mM EDTA, 150 mM NaCl, and incubated overnight at room temperature. MHCs of the pMHCs are covalently bound with NPs via the formation of a carbon-sulfide bond between maleimide groups and the Cys residue.

Click chemistry can be used to conjugate pMHC or avidin to NPs functionalized with azide groups. For this reaction, MHC or avidin molecules are first incubated with dibenzocyclooctyl (DBCO, Click Chemistry Tools, Scottsdale, AZ) reagent for 2 hr at room temperature. Free DBCO molecules can be removed by dialysis overnight. MHC- or avidin-DBCO conjugates are then incubated with SFP-Z for 2 hr, resulting in formation of triazole bonds between pMHCs or avidin molecules and NPs.

Unconjugated pMHCs in the different MHC-NP conjugating reactions can be removed by extensive dialysis using methods known in the art. A non-limiting example is dialysis against PBS, pH 7.4, at 4° C. though 300 kD molecular weight cut off membranes (Spectrum labs). Alternatively, pMHC-conjugated IONPs can be purified by magnetic separation. The conjugated NPs can be concentrated by ultrafiltration through Amicon Ultra-15 units (100 kD MWCO) and stored in PBS.

The surface of the particle can be chemically modified, for instance by the binding of phosphonic acid derivatives having functional reactive groups. One example of these phosphonic acid or phosphonic acid ester derivates is iminobis(methylenephosphono) carbonic acid which can be synthesized according to the "Mannich-Moedritzer" reaction. This binding reaction can be performed with a substrate or a particle as directly obtained from the preparation process or after a pre-treatment (for instance with trimethylsilyl bromide). In the first case the phosphoric acid (ester) derivative may for instance displace components of the reaction medium which are still bound to the surface. This displacement can be enhanced at higher temperatures. Trimethylsilyl bromide, on the other hand, is believed to dealkylate alkyl group-containing phosphorous-based complexing agents, thereby creating new binding sites for the phosphonic acid (ester) derivative. The phosphonic acid (ester) derivative, or linking molecules bound thereto, may display the same functional groups as given above. A further example of the surface treatment of the substrate or particle involves heating in a diol such as ethylene glycol. It should be noted that this treatment may be redundant if the synthesis already proceeded in a diol. Under these circumstances the synthesis product directly obtained is likely to show the necessary functional groups. This treatment is, however, applicable to a substrate or a particle that was produced in N- or P-containing complexing agents. If such substrate or particle is subjected to an after-treatment with ethylene glycol, ingredients of the reaction medium (e.g. complexing agent) still binding to the surface can be replaced by the diol and/or can be dealkylated.

It is also possible to replace N-containing complexing agents still bound to the particle surface by primary amine derivatives having a second functional group. The surface of the substrate or particle can also be coated with silica. Silica allows a relatively simple chemical conjugation of organic molecules since silica easily reacts with organic linkers, such as triethoxysilane or chlorosilane. The particle surface may also be coated by homo- or copolymers. Examples for polymerizable coupling agents are: N-(3-aminopropyl)-3-mercaptobenzamidine, 3-(trimethoxysilyl) propylhydrazide and 3-trimethoxysilyl) propylmaleimide. Other non-limiting examples of polymerizable coupling agents are mentioned herein. These coupling agents can be used singly or in combination depending on the type of copolymer to be generated as a coating.

Another surface modification technique that can be used with substrates or particles containing oxidic transition metal compounds is conversion of the oxidic transition metal compounds by chlorine gas or organic chlorination agents to the corresponding oxychlorides. These oxychlorides are capable of reacting with nucleophiles, such as hydroxyl or amino groups as often found in biomolecules. This technique allows generating a direct conjugation with proteins, for instance, via the amino group of lysine side chains. The conjugation with proteins after surface modification with oxychlorides can also be effected by using a bi-functional linker, such as maleimidopropionic acid hydrazide.

For non-covalent linking techniques, chain-type molecules having a polarity or charge opposite to that of the substrate or particle surface are particularly suitable. Examples for linking molecules which can be non-covalently linked to core/shell nanoparticles involve anionic, cationic or zwitter-ionic surfactants, acid or basic proteins, polyamines, polyamides, polysulfone or polycarboxylic acid. The hydrophobic interaction between substrate or particle and amphiphilic reagent having a functional reactive group can generate the necessary link. In particular, chain-type molecules with amphiphilic character, such as phospholipids or derivatised polysaccharides, which can be crosslinked with each other, are useful. The absorption of these molecules on the surface can be achieved by coincubation. The binding between affinity molecule and substrate or particle can also be based on non-covalent, self-organizing bonds. One example thereof involves simple detection probes with biotin as linking molecule and avidin- or streptavidin-coupled molecules.

Protocols for coupling reactions of functional groups to biological molecules can be found in the literature, for instance in "Bioconjugate Techniques" (Greg T. Hermanson, Academic Press 1996). The biological molecule (e.g., MHC molecule or derivative thereof) can be coupled to the linking molecule, covalently or non-covalently, in line with standard procedures of organic chemistry such as oxidation, halogenation, alkylation, acylation, addition, substitution or amidation. These methods for coupling the covalently or non-covalently bound linking molecule can be applied prior to the coupling of the linking molecule to the substrate or particle or thereafter. Further, it is possible, by means of incubation, to effect a direct binding of molecules to correspondingly pre-treated substrate or particles (for instance by trimethylsilyl bromide), which display a modified surface due to this pre-treatment (for instance a higher charge or polar surface).

Synthesis of Nanoparticles

Nanoparticles may be formed by contacting an aqueous phase containing the pMHC complex and a polymer and a non-aqueous phase followed by evaporation of the non-aqueous phase to cause the coalescence of particles from the aqueous phase as taught in U.S. Pat. No. 4,589,330 or 4,818,542. Certain polymers for such preparations are natural or synthetic copolymers or polymers which include gelatin agar, starch, arabinogalactan, albumin, collagen, polyglycolic acid, polylactic acid, glycolide-L(-) lactide poly(epsilon-caprolactone), poly(epsilon-caprolactone-CO-lactic acid), poly(epsilon-caprolactone-CO-glycolic acid), poly(β-hydroxy butyric acid), poly(ethylene oxide), polyethylene, poly(alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate). Particularly, certain polymers are polyesters, such as polyglycolic acid, polylactic acid, glycolide-L(-) lactide poly(epsilon-caprolactone), poly(epsilon-caprolactone-CO-lactic acid), and poly(epsilon-caprolactone-CO-glycolic acid). Solvents useful for dissolving the polymer include: water, hexafluoroisopropanol, methylenechloride, tetrahydrofuran, hexane, benzene, or hexafluoroacetone sesquihydrate.

Gold nanoparticles (GNPs) are synthesized using chemical reduction of gold chloride with sodium citrate as described in Perrault, S. D. et al. (2009) Nano Lett 9:1909-1915. Briefly, 2 mL of 1% of HAuCl4 (Sigma Aldrich) is added to 100 mL H2O under vigorous stirring and the solution is heated in an oil bath. Six (for 14 nm GNPs) or two mL (for 40 nm GNPs) of 1% Na Citrate is added to the boiling HAuCl4 solution, which is stirred for an additional 10 min and then cooled down to room temperature. GNPs are stabilized by the addition of 1 µMol of thiol-PEG linkers (Nanocs, MA) functionalized with —COOH or —NH2 groups as acceptors of MHC. PEGylated GNPs are washed with water to remove free thiol-PEG, concentrated and stored in water for further analysis. NP density is determined via spectrophotometry and calculated according to Beer's law.

The SFP series of iron oxide NPs (SFP IONPs) can be produced by thermal decomposition of iron acetate in organic solvents in the presence of surfactants, then rendered solvent in aqueous buffers by pegylation (Xie, J. et al. (2007) Adv Mater 19:3163; Xie, J. et al. (2006) Pure Appl. Chem. 78:1003-1014; Xu, C. et al. (2007) Polymer International 56:821-826). Briefly, 2 mMol Fe(acac)$_3$ (Sigma Aldrich, Oakville, ON) are dissolved in a mixture of 10 mL benzyl ether and oleylamine and heated to 100° C. for 1 hr followed by 300° C. for 2 hr with reflux under the protection of a nitrogen blanket. Synthesized NPs are precipitated by addition of ethanol and resuspended in hexane. For pegylation of the IONPs, 100 mg of different 3.5 kD DPA-PEG linkers (Jenkem Tech USA) are dissolved in a mixture of $CHCl_3$ and $HCON(CH_3)_2$ (dimethylformamide (DMF)). The NP solution (20 mg Fe) is then added to the DPA-PEG solution and stirred for 4 hr at room temperature. Pegylated SFP NPs are precipitated overnight by addition of hexane and then resuspended in water. Trace amounts of aggregates are removed by high-speed centrifugation (20,000×g, 30 min), and the monodisperse SFP NPs are stored in water for further characterization and pMHC conjugation. The concentration of iron in IONP products is determined by spectrophotometry at A410 in 2N HCL. Based on the molecular structure and diameter of SFP NPs ($Fe_3O_4$; 8+1 nm diameter) (Xie, J. et al. (2007) *Adv Mater* 19:3163; Xie, J. et al. (2006) *Pure Appl. Chem.* 78:1003-1014), SFP solutions containing 1 mg of iron are estimated to contain $5 \times 10^{14}$ NPs.

The nanoparticles can also be made by thermally decomposing or heating a nanoparticle precursor. In one embodiment, the nanoparticle is a metal or a metal oxide nanoparticle. In one embodiment, the nanoparticle is an iron oxide nanoparticle. In one embodiment, the nanoparticle is a gold nanoparticle. In one embodiment, provided herein are the nanoparticles prepared in accordance with the present technology. In one embodiment, provided herein is a method of making iron oxide nanoparticles comprising a thermal decomposition reaction of iron acetyl acetonate. In one embodiment, the iron oxide nanoparticle obtained is water-soluble. In one aspect, the iron oxide nanoparticle is suitable for protein conjugation. In one embodiment, the method comprises a single-step thermal decomposition reaction.

In one aspect, the thermal decomposition occurs in the presence of functionalized PEG molecules. Certain non-limiting examples of functionalized PEG linkers are shown in Table 1.

In one aspect, the thermal decomposition comprises heating iron acetyl acetonate. In one embodiment, the thermal decomposition comprises heating iron acetyl acetonate in the presence of functionalized PEG molecules. In one embodiment, the thermal decomposition comprises heating iron acetyl acetonate in the presence of benzyl ether and functionalized PEG molecules] Without being bound by theory, in one embodiment, functionalized PEG molecules are used as reducing reagents and as surfactants. The method of making nanoparticles provided herein simplifies and improves conventional methods, which use surfactants that are difficult to be displaced, or are not displaced to completion, by PEG molecules to render the particles water-soluble. Conventionally, surfactants can be expensive (e.g., phospholipids) or toxic (e.g., Oleic acid or oleilamine). In another aspect, without being bound by theory, the method of making nanoparticles obviates the need to use conventional surfactants, thereby achieving a high degree of molecular purity and water solubility.

In one embodiment, the thermal decomposition involves iron acetyl acetonate and benzyl ether and in the absence of conventional surfactants other than those employed herein.

In one embodiment, the temperature for the thermal decomposition is about 80° C. to about 300° C., or about 80° C. to about 200° C., or about 80° C. to about 150° C., or about 100° C. to about 250° C., or about 100° C. to about 200° C., or about 150° C. to about 250° C., or about 150° C. to about 250° C. In one embodiment, the thermal decomposition occurs at about 1 to about 2 hours of time.

In one embodiment, the method of making the iron oxide nanoparticles comprises a purification step, such as by using Miltenyi Biotec LS magnet column.

In one embodiment, the nanoparticles are stable at about 4° C. in phosphate buffered saline (PBS) without any detectable degradation or aggregation. In one embodiment, the nanoparticles are stable for at least 6 months.

In one aspect, provided herein is a method of making nanoparticle complexes comprising contacting pMHC with iron oxide nanoparticles provided herein. Without being bound by theory, pMHC encodes a cysteine at its carboxy-terminal end, which can react with the maleimide group in functionalized PEG at about pH 6.2 to about pH 6.5 for about 12 to about 14 hours.

In one aspect, the method of making nanoparticle complexes comprises a purification step, such as by using Miltenyi Biotec LS magnet column.

Regulatory Immune Cell Types

The uaMHC-NP complexes of the current disclosure reprogram or differentiate autoreactive T cells into T regulatory or TR1 cells. In certain embodiments, the TR1 cells express IL-10. In certain embodiments, the TR1 cells secrete IL-10. In certain embodiments, the TR1 cells express CD49b. In certain embodiments, the TR1 cells express LAG-3. T-cells that have these phenotypic characteristics are useful to treat inflammatory or autoimmune conditions of individuals. In certain embodiments, the uaMHC-NP complexes are useful in a method to reprogram or differentiate autoreactive T cells into TR1 cells in an individual after administration. This method generates TR1 cells in an antigen specific way.

The ubiquitous autoantigen-MHCs of the current disclosure are useful for generating B regulatory cells. In certain embodiments, the ubiquitous autoantigen-MHCs of the current disclosure are deployed in a method to generate B-cells expressing high levels of CD1d, CD5, and/or the secretion of IL-10. B-regs are also identified by expression of Tim-1. In certain embodiments, the uaMHC-NP complexes are useful in a method to induce B regulatory cells in an individual after administration. This method generates B regulatory cells in an antigen specific way.

Pharmaceutical Compositions and Administration

Provided herein are pharmaceutical compositions of ubiquitous autoantigen-MHC-NPs useful for the treatment and prevention of disease. The compositions comprise, or alternatively consist essentially of, or yet further consist of, a nanoparticle complex as described herein and a carrier.

Compositions of the disclosure may be conventionally administered parenterally, by injection, for example, intravenously, subcutaneously, or intramuscularly. Additional formulations which are suitable for other modes of administration include oral formulations. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%. The preparation of an aqueous composition that contains an antigen-MHC-nanoparticle complex that modifies the subject's immune condition will be known to those of skill in the art in light of the present disclosure. In one embodiment, the ubiquitous autoantigen-MHC-nanoparticle complex is administered systemically. In specific embodiments, the ubiquitous autoantigen-MHC-NP complex or the compositions comprising a plurality of ubiquitous autoantigen-MHC-N complexes can be administered intravenously.

Typically, the ubiquitous autoantigen-MHC-NPs, described herein, are administered in a manner compatible with the dosage formulation, and in such amount as will be therapeutically effective and immune modifying. The quantity to be administered depends on the subject to be treated. Precise amounts of active ingredient required to be administered depend on the judgment of the practitioner. However, suitable dosage ranges are of the order of ten to several hundred nanograms or micrograms of antigen/MHC/nanoparticle complex per administration. Suitable regimes for initial administration and boosters are also variable, but are typified by an initial administration followed by subsequent administrations.

The manner of application may be varied widely. Any of the conventional methods for administration of a vaccine are applicable. These are believed to include oral application on a solid physiologically acceptable base or in a physiologically acceptable dispersion, parenterally, by injection and the like. The dosage of the antigen/MHC/nanoparticle complex will depend on the route of administration and will vary according to the size and health of the subject. The ubiquitous autoantigen-MHC-NPs can be administered by any suitable route including intravenous, subcutaneous, intradermal, intramuscular, rectally, or intraperitoneally. In certain embodiments, autoantigen-MHC-NPs are administered parenterally. In certain embodiments, autoantigen-MHC-NPs are administered intravenously. In certain embodiments, autoantigen-MHC-NPs are administered subcutaneously.

In many instances, it will be desirable to have multiple administrations of a ubiquitous autoantigen-MHC-NP, about, at least about, or at most about 3, 4, 5, 6, 7, 8, 9, 10 or more administrations. The administrations will normally range from 1, 2, 3, 4, 5, 6, or 7 day to twelve week intervals, more usually from one to two week intervals. Periodic boosters at intervals of every other day, twice a week, weekly, biweekly, monthly, or 0.1, 0.2, 0.3, 0.4, 0.5, 1, 2, 3, 4 or 5 years, usually two years, will be desirable to maintain the condition of the immune system. The course of the administrations may be followed by assays for autoreactive immune responses, cognate TR1 cells, and T cell activity.

In certain aspects, a single dose of the ubiquitous autoantigen-MHC-NP without including the nanoparticle core and any bioabsorbable/biocompatible outer layer comprises about 0.001 mg/kg to about 2.0 mg/kg, or about 0.001 mg/kg to about 1.5 mg/kg, or about 0.001 mg/kg to about 1.4 mg/kg, or about 0.001 mg/kg to about 1.3 mg/kg, or about 0.001 mg/kg to about 1.2 mg/kg, or about 0.001 mg/kg to about 1.1 mg/kg, or about 0.001 mg/kg to about 1.0 mg/kg. In some embodiments, the single dose comprises from about 0.004 mg/kg to about 1.014 mg/kg, or from about 0.02 mg/kg to about 0.811 mg/kg, or from about 0.041 mg/kg to about 0.608 mg/kg, or from about 0.061 mg/kg to about 0.507 mg/kg, or from about 0.081 mg/kg to about 0.405 mg/kg, or from about 0.121 mg/kg to about 0.324 mg/kg, or from about 0.162 mg/kg to about 0.243 mg/kg. In some embodiments, the single dose comprises from about 0.004 mg/kg to about 1.015 mg/kg, or from about 0.004 mg/kg to about 1.0 mg/kg, or from about 0.004 mg/kg to about 0.9 mg/kg, or from about 0.004 mg/kg to about 0.8 mg/kg, or from about 0.004 mg/kg to about 0.7 mg/kg, or from about 0.004 mg/kg to about 0.6 mg/kg, or from about 0.004 mg/kg to about 0.5 mg/kg, or from about 0.004 mg/kg to about 0.4 mg/kg, or from about 0.004 mg/kg to about 0.3 mg/kg, or from about 0.004 mg/kg to about 0.2 mg/kg, or from about 0.004 mg/kg to about 0.1 mg/kg. Herein, mg/kg refers to milligrams of ubiquitous autoantigen-MHC or ubiquitous autoantigen without considering the MHC component, administered per kg of subject body mass.

Autoimmune and Inflammatory Diseases

The ubiquitous autoantigen-MHCs of the current disclosure are useful for treating an autoimmune or inflammatory disorder. Autoimmune or inflammatory disorders include diseases or disorders arising from and directed against an individual's own tissues or organs or a manifestation thereof or a condition resulting therefrom. In one embodiment, it refers to a condition that results from, or is aggravated by, the production of T cells that are reactive with normal body tissues and antigens. In one embodiment, it refers to a condition that results from, or is aggravated by, the production by antibodies that are reactive with normal body tissues and antigens. Examples of autoimmune or inflammatory disorders include, but are not limited to arthritis (rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis (such as plaque psoriasis, gutatte psoriasis, pustular psoriasis, and psoriasis of the nails), atopy (including atopic diseases such as hay fever and Job's syndrome), dermatitis (including contact dermatitis, chronic contact dermatitis, exfoliative dermatitis, allergic dermatitis, allergic contact dermatitis, dermatitis herpetiformis, nummular dermatitis, seborrheic dermatitis, non-specific dermatitis, primary irritant contact dermatitis, and atopic dermatitis), x-linked hyper IgM syndrome, allergic intraocular inflammatory diseases, urticaria (such as chronic allergic urticaria and chronic idiopathic urticaria, including chronic autoimmune urticaria), myositis, polymyositis/dermatomyositis, juvenile dermatomyositis, toxic epidermal necrolysis, scleroderma (including systemic scleroderma), sclerosis (such as systemic sclerosis; multiple sclerosis (MS) such as spino-optical MS, primary progressive MS (PPMS), and relapsing-remitting MS (RRMS); progressive systemic sclerosis, atherosclerosis, arteriosclerosis, sclerosis disseminata, and ataxic sclerosis), neuromyelitis optica spectrum disorder (NMO, also known as Devic's Disease or Devic's Syndrome), inflammatory bowel disease (IBD) (for example, Crohn's disease; autoimmune-mediated gastrointestinal diseases; colitis such as ulcerative colitis, colitis ulcerosa, microscopic colitis, collagenous colitis, colitis polyposa, necrotizing enterocolitis, and transmural colitis; and autoimmune inflammatory bowel disease), bowel inflammation, pyoderma gangrenosum, erythema nodosum, primary sclerosing cholangitis, respiratory distress syndrome (including adult or acute respiratory distress syndrome (ARDS)), meningitis, inflammation of all or part of the uvea, iritis, choroiditis, an autoimmune hematological disorder, rheumatoid spondylitis, rheumatoid synovitis, hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis (such as anterior uveitis, acute anterior uveitis, granulomatous uveitis, non-granulomatous uveitis, phacoantigenic uveitis, posterior uveitis, or autoimmune uveitis), glomerulonephritis (GN) with and without nephrotic syndrome (such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, or proliferative nephritis), autoimmune polyglandular endocrine failure, balanitis including balanitis circumscripta plasmacellularis, balanoposthitis, erythema annulare centrifugum, erythema dyschromicum perstans, erythema multiform, granuloma annulare, lichen *nitidus*, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, allergic reaction, eczema (including allergic or atopic eczema, asteatotic eczema, dyshidrotic eczema, and vesicular palmoplantar eczema), asthma (such as asthma bronchiale, bronchial asthma, and auto-immune asthma), conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus (including lupus nephritis, lupus cerebritis, pediatric lupus, non-renal lupus, extra-renal lupus, discoid lupus and discoid lupus erythematosus, alopecia lupus, systemic lupus erythematosus (SLE) such as cutaneous SLE or subacute cutaneous SLE, neonatal lupus syndrome (NLE), and lupus erythematosus disseminatus), Type I diabetes, Type II diabetes, and latent autoimmune diabetes in adults (or Type 1.5 diabetes). Also contemplated are immune responses associated with acute and delayed hypersensitivity mediated by cytokines and T-lymphocytes, sarcoidosis, granulomatosis (including lymphomatoid granulomatosis, Wegener's granulomatosis, or agranulocytosis), vasculitides (including vasculitis, large-vessel vasculitis (including polymyalgia rheumatica and giant cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis (such as Churg-Strauss vasculitis or syndrome (CSS) and ANCA-associated small-vessel vasculitis)), temporal arteritis, aplastic anemia, autoimmune aplastic anemia, Coombs positive anemia, Diamond Blackfan anemia, hemolytic anemia, immune hemolytic anemia including autoimmune hemolytic anemia (AIHA), Addison's disease, autoimmune neutropenia, pancytopenia, leukopenia, diseases involving leukocyte diapedesis, CNS inflammatory disorders, Alzheimer's disease, Parkinson's disease, multiple organ injury syndrome (such as those secondary to septicemia, trauma, or hemorrhage), antigen-antibody complex-mediated diseases, anti-glomerular basement membrane disease, anti-phospholipid antibody syndrome, anti-phospholipid syndrome, allergic neuritis, Behcet's disease/syndrome, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including Pemphigus vulgaris, Pemphigus foliaceus, Pemphigus mucus-membrane pemphigoid, and pemphigus erythematosus), autoimmune polyendocrinopathies, Reiter's disease or syndrome, thermal injury, preeclampsia, an immune complex disorder such as immune complex nephritis, antibody-mediated nephritis, polyneuropathies, chronic neuropathy such as IgM polyneuropathies or IgM-mediated neuropathy, autoimmune or immune-mediated thrombocytopenia such as idiopathic thrombocytopenia purpura (ITP) including chronic or acute ITP, acquired thrombocytopeni purpura, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases (including thyroiditis (such as autoimmune thyroiditis, Hashimoto's disease, chronic thyroiditis (Hashimoto's thyroiditis), or subacute thyroiditis), autoimmune thyroid disease, idiopathic hypothyroidism, or Grave's disease), polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), sensory neuropathy, multifocal motor neuropathy, Sheehan's syndrome, autoimmune hepatitis, chronic hepatitis, lupoid hepatitis, giant cell hepatitis, chronic active hepatitis or autoimmune chronic active hepatitis, lymphoid interstitial pneumonitis (LIP), bronchiolitis obliterans (non-transplant) vs NSIP, Guillain-Barre syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, channelopathies of the CNS, autism, inflammatory myopathy, focal or segmental or focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia greata, alopecia totalis, CREST syndrome (calcinosis, Raynaud's phenomenon, esophageal dysmotility, sclerodactyly, and telangiectasia), male and female autoimmune infertility (e.g., due to anti-spermatozoan antibodies) mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuchs' cyclitis, Henoch-Schonlein purpura, human immunodeficiency virus (HIV) infection, SCID, acquired immune deficiency syndrome (AIDS), echovirus infection, sepsis, endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant cell polymyalgia, chronic hypersensitivity pneumonitis, keratoconjunctivitis sicca, epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders, asperniogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired splenic atrophy, non-malignant thymoma, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, autoimmune polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism, neurological disease, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritis, reperfusion injury, ischemic reperfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, emphysema, alopecia areata, adipose tissue inflammation/diabetes type II, obesity associated adipose tissue inflammation/insulin resistance, and endometriosis.

In certain embodiments, the autoimmune disease or inflammatory disorder may include, but is not limited to, diabetes mellitus Type I and Type II, pre-diabetes, transplantation rejection, multiple sclerosis, a multiple-sclerosis related disorder, premature ovarian failure, scleroderma, Sjogren's disease/syndrome, lupus, vitiligo, alopecia (baldness), polyglandular failure, Grave's disease, hypothyroidism, polymyositis, pemphigus, Crohn's disease, colitis, autoimmune hepatitis, hypopituitarism, myocarditis, Addison's disease, autoimmune skin diseases, uveitis, pernicious anemia, hypoparathyroidism, and/or rheumatoid arthritis. Other indications of interest include, but are not limited to, asthma, allergic asthma, primary biliary cirrhosis, cirrhosis, Neuromyelitis Optica Spectrum Disorder (Devic's disease, opticospinal multiple sclerosis (OSMS)), Pemphigus vulgaris, inflammatory bowel disease (IBD), arthritis, Rheumatoid arthritis, systemic lupus erythematosus (SLE), Celiac disease, psoriasis, autoimmune cardiomyopathy, idiopathic dilated cardiomyopathy (IDCM), a Myasthenia Gravis, Uveitis, Ankylosing Spondylitis, Immune Mediated Myopathies, prostate cancer, anti-phospholipid syndrome (ANCA+), atherosclerosis, dermatomyositis, chronic obstructive pulmonary disease (COPD), emphysema, spinal cord injury, traumatic injury, a tobacco-induced lung destruction, ANCA-associated vasculitis, psoriasis, sclerosing cholangitis, primary sclerosing cholangitis, and diseases of the central and peripheral nervous systems.

In certain embodiments, the autoimmune disease or inflammatory disorder may include, but is not limited to, type I diabetes, multiple sclerosis, Celiac Disease, primary biliary cirrhosis, pemphigus, pemphigus foliaceus, pemphigus vulgaris, neuromyelitis optica spectrum disorder, arthritis (including rheumatoid arthritis), allergic asthma, inflammatory bowel disease (including Crohn's disease and ulcerative colitis), systemic lupus erythematosus, atherosclerosis, chronic obstructive pulmonary disease, emphysema, psoriasis, autoimmune hepatitis, uveitis, Sjogren's Syndrome, scleroderma, anti-phospholipid syndrome, ANCA-associated vasculitis, and Stiff Man Syndrome. In a further aspect, the disease-relevant antigen is a tumor- or cancer-relevant antigen.

In certain embodiments, the autoimmune disease or inflammatory disorder may include a liver autoimmune disorder selected from primary biliary cirrhosis, autoimmune hepatitis, and primary sclerosing cholangitis. In certain embodiments, the uaMHC-NP complex is used in a method of treating primary biliary cirrhosis, autoimmune hepatitis, and/or primary sclerosing cholangitis. In certain embodiments, the method of treating primary biliary cirrhosis, autoimmune hepatitis, and/or primary sclerosing cholangitis comprises administering a uaMHC-NP complex, wherein the ubiquitous autoantigen is a polypeptide derived from any one or more of pyruvate dehydrogenase complex-E2 component (PDC-E2), cytochrome P450 2D6 (CYP2D6), soluble liver antigen (SLA), actin (ACTB), formimidoyltransferase-cyclodeaminase (FTCD), and myeloperoxidase (MPO). In certain embodiments, the method of treating primary biliary cirrhosis comprises administering a uaMHC-NP complex, wherein the ubiquitous autoantigen is a polypeptide derived from any one or more of cytochrome P450 2D6 (CYP2D6), soluble liver antigen (SLA), actin (ACTB), formimidoyltransferase-cyclodeaminase (FTCD), and myeloperoxidase (MPO). In certain embodiments, the method of treating autoimmune hepatitis comprises administering a uaMHC-NP complex, wherein the ubiquitous autoantigen is a polypeptide derived from any one or more of pyruvate dehydrogenase complex-E2 component (PDC-E2), soluble liver antigen (SLA), actin (ACTB), formimidoyltransferase-cyclodeaminase (FTCD), and myeloperoxidase (MPO). In certain embodiments, the method of treating primary sclerosing cholangitis comprises administering a uaMHC-NP complex, wherein the ubiquitous autoantigen is a polypeptide derived from any one or more of pyruvate dehydrogenase complex-E2 component (PDC-E2), cytochrome P450 2D6 (CYP2D6), soluble liver antigen (SLA), actin (ACTB), and myeloperoxidase (MPO).

In certain embodiments, the autoimmune disease or inflammatory disorder may include multiple sclerosis. In certain embodiments, the autoimmune disease or inflammatory disorder may include relapsing-remitting multiple sclerosis. In certain embodiments, the uaMHC-NP complex is used in a method of treating multiple sclerosis. In certain embodiments, the method of treating multiple sclerosis comprises administering a uaMHC-NP complex, wherein the ubiquitous autoantigen is a polypeptide derived from any one or more of pyruvate dehydrogenase complex-E2 component (PDC-E2), cytochrome P450 2D6 (CYP2D6), soluble liver antigen (SLA), actin (ACTB), formimidoyltransferase-cyclodeaminase (FTCD), and myeloperoxidase (MPO).

Pharmaceutically Acceptable Stabilizers, Excipients, and Diluents

In certain embodiments, the uaMHC-NP complexes of the current disclosure are included in a pharmaceutical composition comprising one or more pharmaceutically acceptable stabilizers excipients, carriers, and diluents. In certain embodiments, the uaMHC-NP complexes of the current disclosure are administered suspended in a sterile solution. In certain embodiments, the solution comprises 0.9% NaCl. In certain embodiments, the solution further comprises one or more of: buffers, for example, acetate, citrate, histidine, succinate, phosphate, bicarbonate and hydroxymethylaminomethane (Tris); surfactants, for example, polysorbate 80

(Tween 80), polysorbate 20 (Tween 20), and poloxamer 188; polyol/disaccharide/polysaccharides, for example, glucose, dextrose, mannose, mannitol, sorbitol, sucrose, trehalose, and dextran 40; amino acids, for example, glycine or arginine; antioxidants, for example, ascorbic acid, methionine; or chelating agents, for example, EGTA or EGTA. In certain embodiments, the uaMHC-NP complexes of the current disclosure are shipped/stored lyophilized and reconstituted before administration. In certain embodiments, the lyophilized uaMHC-NP complexes formulations comprise a bulking agent such as mannitol, sorbitol, sucrose, trehalose, or dextran 40. The lyophilized formulation can be contained in a vial comprised of glass. The uaMHC-NP complexes, when formulated, whether reconstituted or not, can be buffered at a certain pH, generally less than 7.0. In certain embodiments, the pH can be between 4.5 and 6.5, 4.5 and 6.0, 4.5 and 5.5, 4.5 and 5.0, or 5.0 and 6.0. In certain embodiments, the uaMHC-NP complexes can be formulated for intravenous injection. In certain embodiments, uaMHC-NP complexes can be formulated for oral ingestion. In certain embodiments, uaMHC-NP complexes can be formulated for parenteral, intramuscular, or intra tissue injection. In certain embodiments, uaMHC-NP complexes can be formulated and/or administered without any immunological adjuvant or other compound or polypeptide intended to increase or decrease an immune response.

EXAMPLES

The following illustrative examples are representative of embodiments of the compositions and methods described herein and are not meant to be limiting in any way.

Example 1—TR1 Like CD4+ T-Cell Formation and Expansion by PBC-Relevant pMHC Class II-NPs NOD.c3c4 mice, which carry anti-diabetogenic B6-derived chromosome 3 and 4 regions, spontaneously develop a form of autoimmune biliary ductal disease that resembles human PBC. See Irie, J., et al. *J. Exp. Med.* 203, 1209-1219. Like >90% of patients, these mice develop pathogenic T- and B-cell responses against the E2 and E3BP components of the pyruvate dehydrogenase (PDC) complex. See Kita, H. et al. *J. Clin. Invest.* 109, 1231-1240. In NOD.c3c4 mice as well as in humans, these autoimmune responses promote the destruction of biliary epithelial cells, leading to cholestasis, small bile duct proliferation, and finally liver failure.

To design PBC-relevant pMHC class II-based nanomedicines, we searched for 15mer peptides in murine PDC-E2 capable of binding to the NOD/NOD.c3c4 mouse MHC class II molecule (I-A$^{g7}$) in silico. I-A$^{g7}$-based pMHCs encoding two such epitopes (PDC-E2$_{166-181}$ and PDC-E2$_{82-96}$) were chosen for experimentation. The T1D-relevant I-A$^{g7}$-binding BDC2.5 mimotope was used as a negative control. These complexes were produced in lentiviral-transduced Chinese hamster ovary (CHO) cells, purified by sequential nickel and streptag affinity chromatography, and covalently coated via a free carboxyterminal cysteine onto iron-oxide nanoparticles produced by thermal decomposition of Iron (III) acetylacetonate (Fe(acac)$_3$) in the presence of maleimide-functionalized polyethylene glycol, as described in Singha, S. et al. *Nature Nanotechnology* 12, 701-710.

pMHC tetramer staining studies demonstrated that NOD.c3c4 (but not NOD) mice harbor increasing levels of both the PDC-E2$_{166-181}$/IA$^{g7}$ and PDC-E2$_{82-96}$/IA$^{g7}$-reactive T-cell subsets with age as shown in FIG. 1A (upside-down triangles, middle and right panels). In contrast, and unlike NOD mice, NOD.c3c4 mice contain negligible levels of the T1D-relevant BDC2.5mi/IA$^{g7}$-reactive subset as shown in FIG. 1A (triangles, middle and right panels), an outcome that is consistent with the PBC vs T1D proclivity of these two strains. Thus, progression of liver autoimmunity in NOD.c3c4 mice is accompanied by increases in the size and/or circulating activity of PDC-E2-specific CD4+ T-cells.

To ascertain if PBC-relevant pMHC class II-NPs could trigger the formation and expansion of PDC-E2-specific TR1-like CD4+ T-cells in NOD.c3c4 mice, we first treated 15 week-old NOD.c3c4 mice (when the disease is well established) with NPs displaying the PDC-E2$_{166-181}$/IA$^{g7}$ pMHC or control NPs (Cys-NPs) (twice a week intravenous for up to 13.5 weeks). Treatment triggered a rapid increase (within 2.5 weeks) in the peripheral frequency of circulating PDC-E2$_{166-181}$/IA$^{g7}$ tetramer+CD4+ T-cells as compared to mice treated with bare NPs or to untreated NOD mice as shown in FIG. 1B (squares, left and middle panels). Studies of mice at the end of follow up confirmed that the PDC-E2$_{166-181}$/IA$^{g7}$-NP-induced expansion of cognate CD4+ T-cells was systemic, with increased frequencies in spleen, bone marrow, liver and liver-draining (portal and celiac lymph nodes), but not non-draining lymph nodes (vs. mesenteric lymph nodes (MLN)) as shown in FIG. 1C.

Figure 1D:
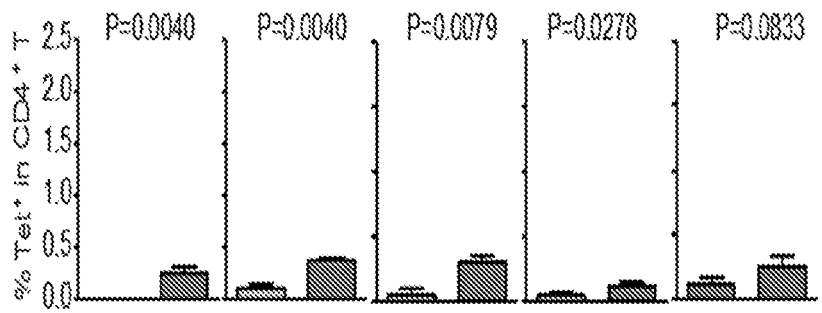
FIG. 1D shows percentages of tetramer+CD4+ T-cells in NOD.c3c4 mice treated with type 1 diabetes-relevant pMHC-NPs.

In contrast, treatment of NOD.c3c4 with NPs coated with the T1D-relevant BDC2.5/I-A$^{g7}$ pMHCs did not trigger TR1 cell formation or expansion (FIG. 1B right panel and FIG. 1D). This result is consistent with these nanomedicines exclusively operating on autoantigen-experienced T-cells; NOD.c3c4 mice do not develop islet inflammation and therefore are not expected to harbor antigen-activated BDC2.5mi/IA$^{g7}$-autoreactive CD4+ T-cells.

Figure 1E:
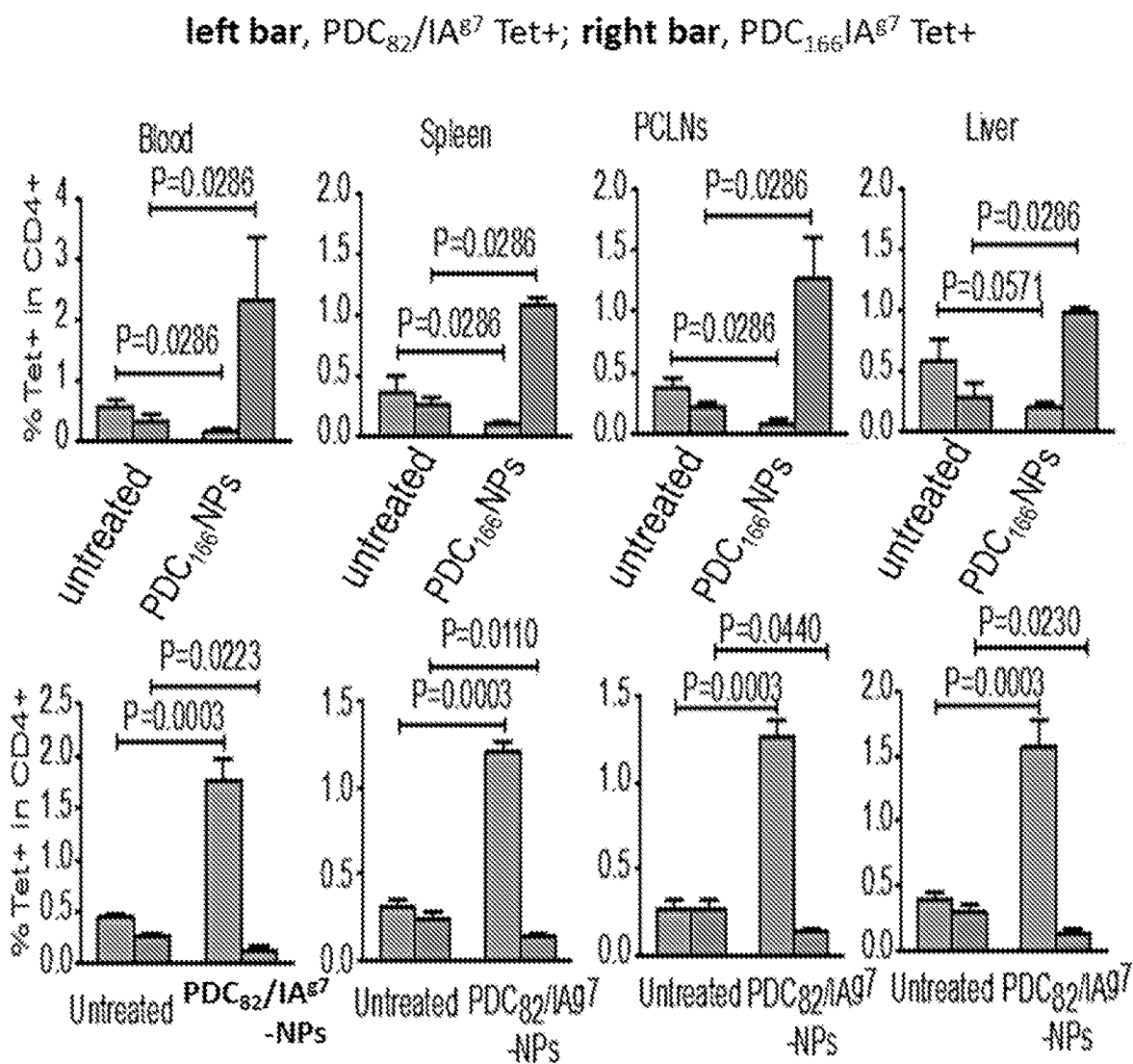
FIG. 1E shows percentages of tetramer+CD4+ T-cells in various lymphoid organs and liver of NOD.c3c4 mice treated with NPs coated with one of two different PBC-relevant pMHCs.

Experiments in additional cohorts of mice demonstrated that the PDC-E2$_{166-181}$/IA$^{g7}$-NP-induced expansion of cognate CD4+ T-cells was peptide-specific, without any detectable expansion of PDC-E2$_{82-96}$/I-A$^{g7}$-reactive CD4+ T-cells (FIG. 1E, top row). In fact, expansion of PDC-E2$_{166-181}$/IA$^{g7}$-specific CD4+ T-cells in these mice was accompanied by significant reductions in the frequency of PDC-E2$_{82-96}$/I-A$^{g7}$-reactive CD4+ T-cells in all organs examined, as compared to the levels detected in age-matched untreated mice (FIG. 1E, top row). This suggests that the PDC-E2$_{166-181}$/IA$^{g7}$-specific CD4+ T-cell subset somehow inhibited the proliferation of its PDC-E2$_{82-96}$/I-A$^{g7}$-reactive counterpart in response to endogenous autoantigen exposure.

Figure 1F:
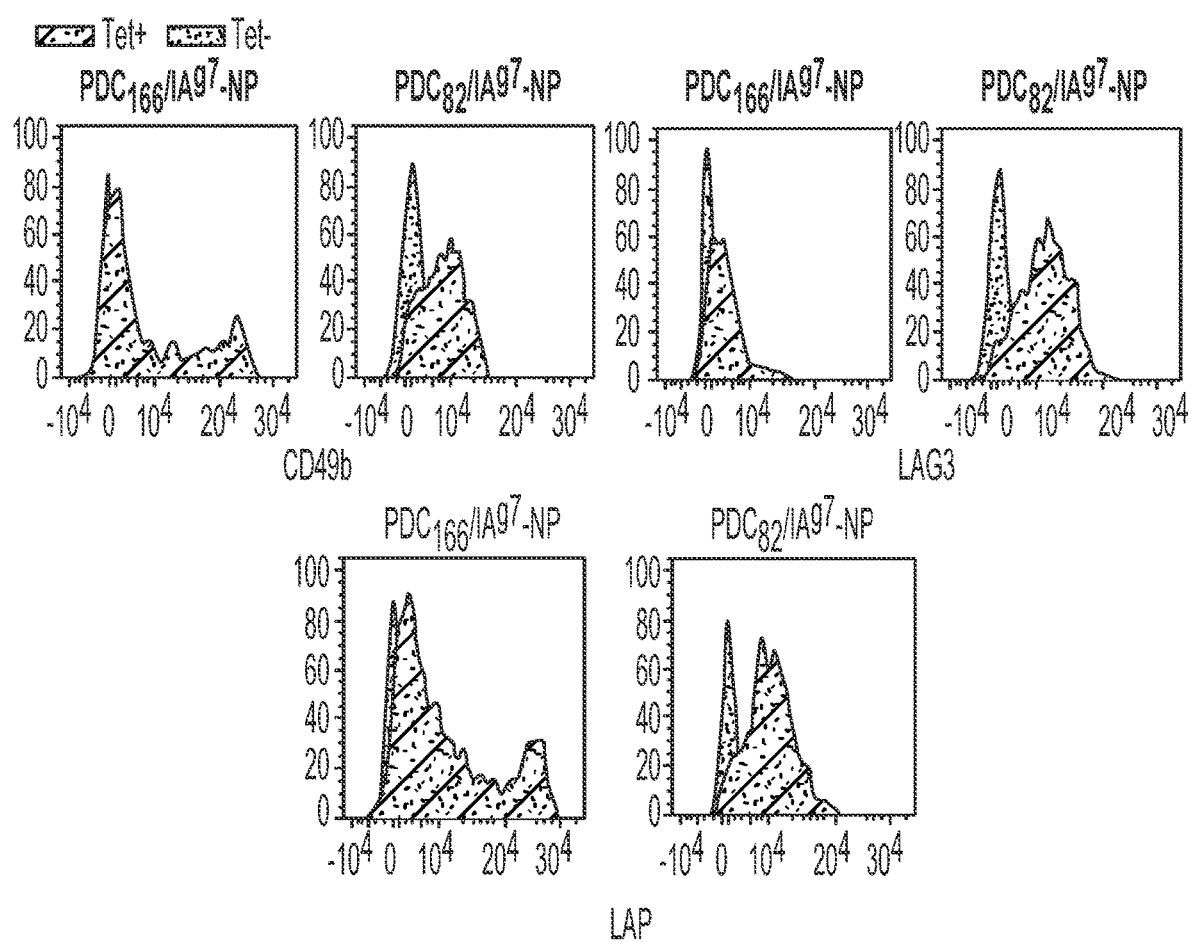
FIG. 1F shows expression of TR1-like cell surface markers by the tetramer+CD4+ T-cells expanded in NOD.c3c4 mice by pMHC-NP therapy.
Figure 1G:
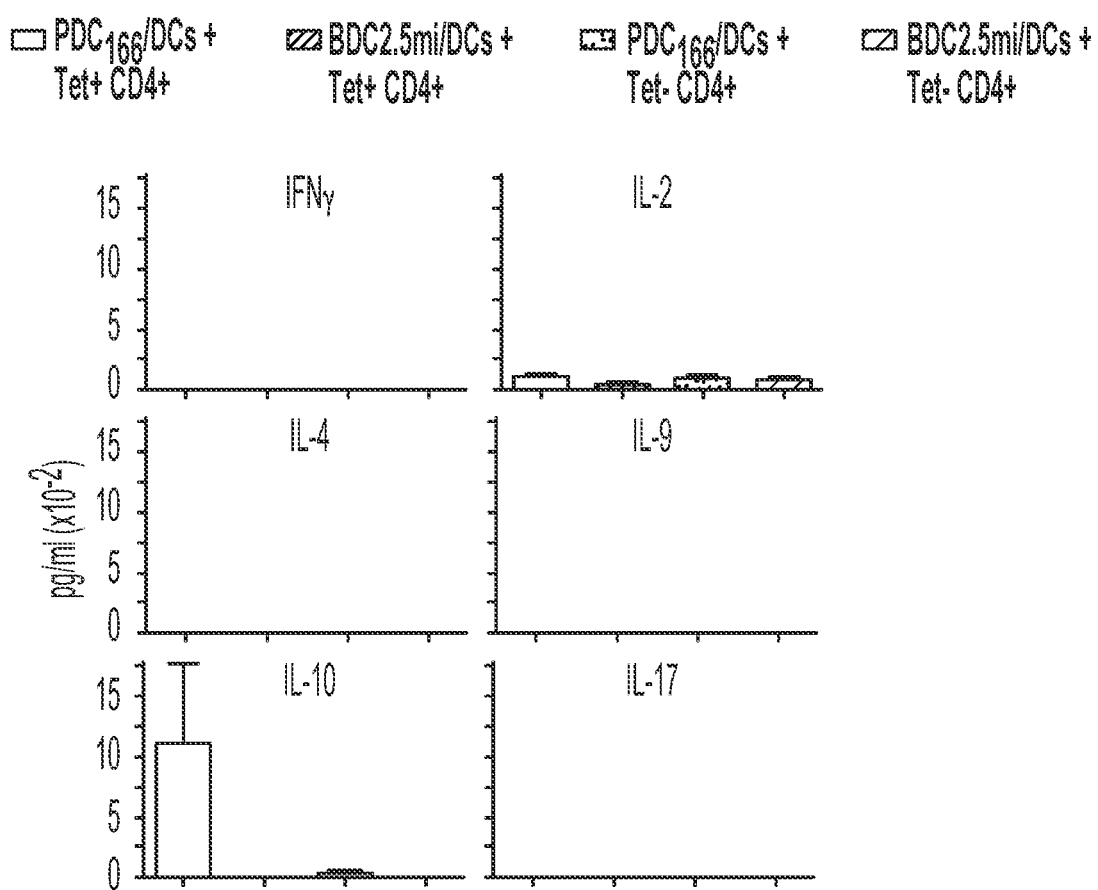
(FIG. 1G shows cytokine secretion profile of sorted tetramer+CD4+TR1-like cells vs. tetramer-negative CD4+ T-cells ex vivo upon stimulation with peptide-pulsed DCs.
Figure 2A:
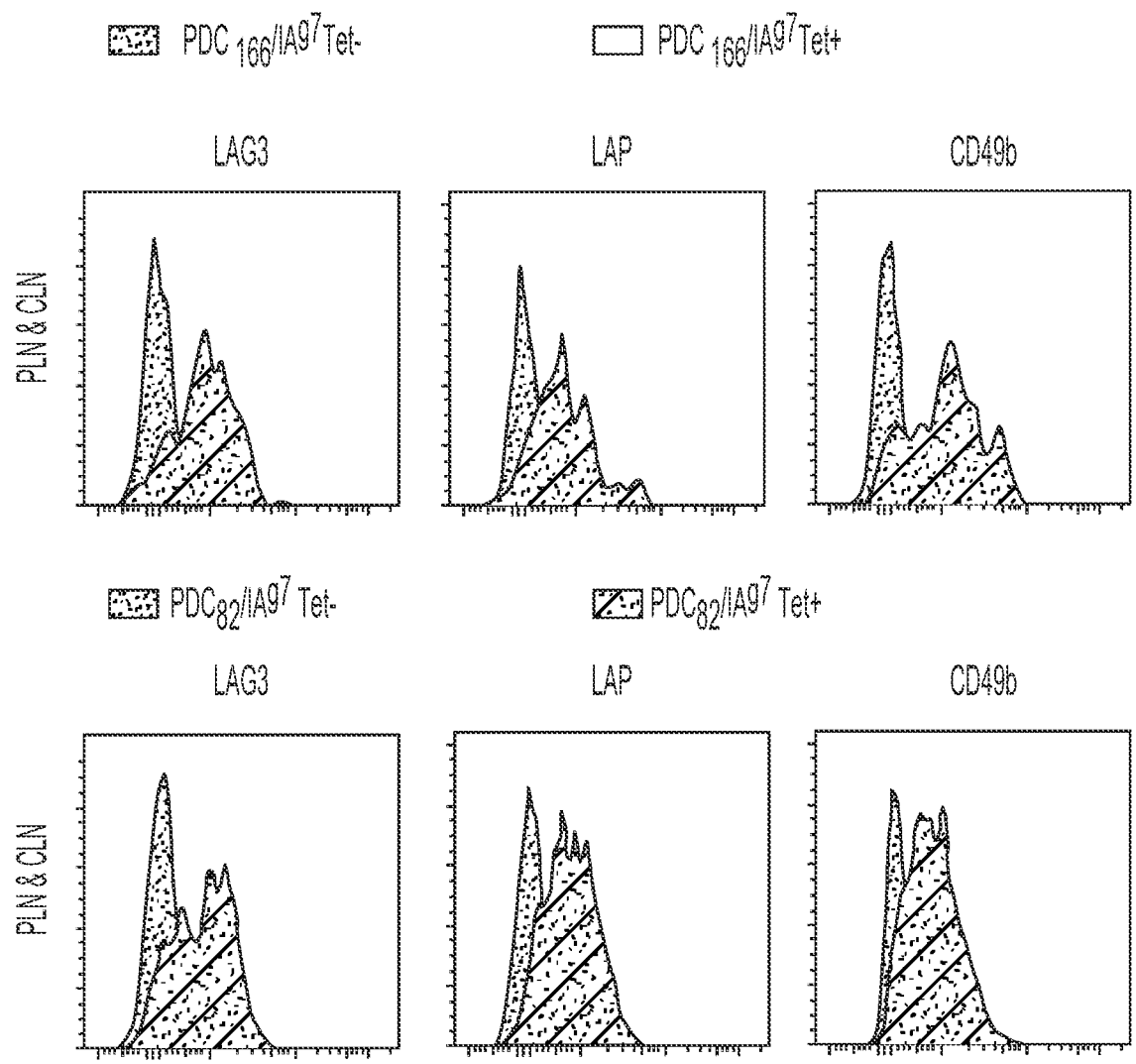
(FIGS. 2A-B) Upregulation of TR1-like markers on tetramer+CD4+ T-cells expanded in vivo in response to $PDC_{166}/IA^{g7}$- or $PDC_{82}/IA^{g7}$-NP therapy
Figure 2B:
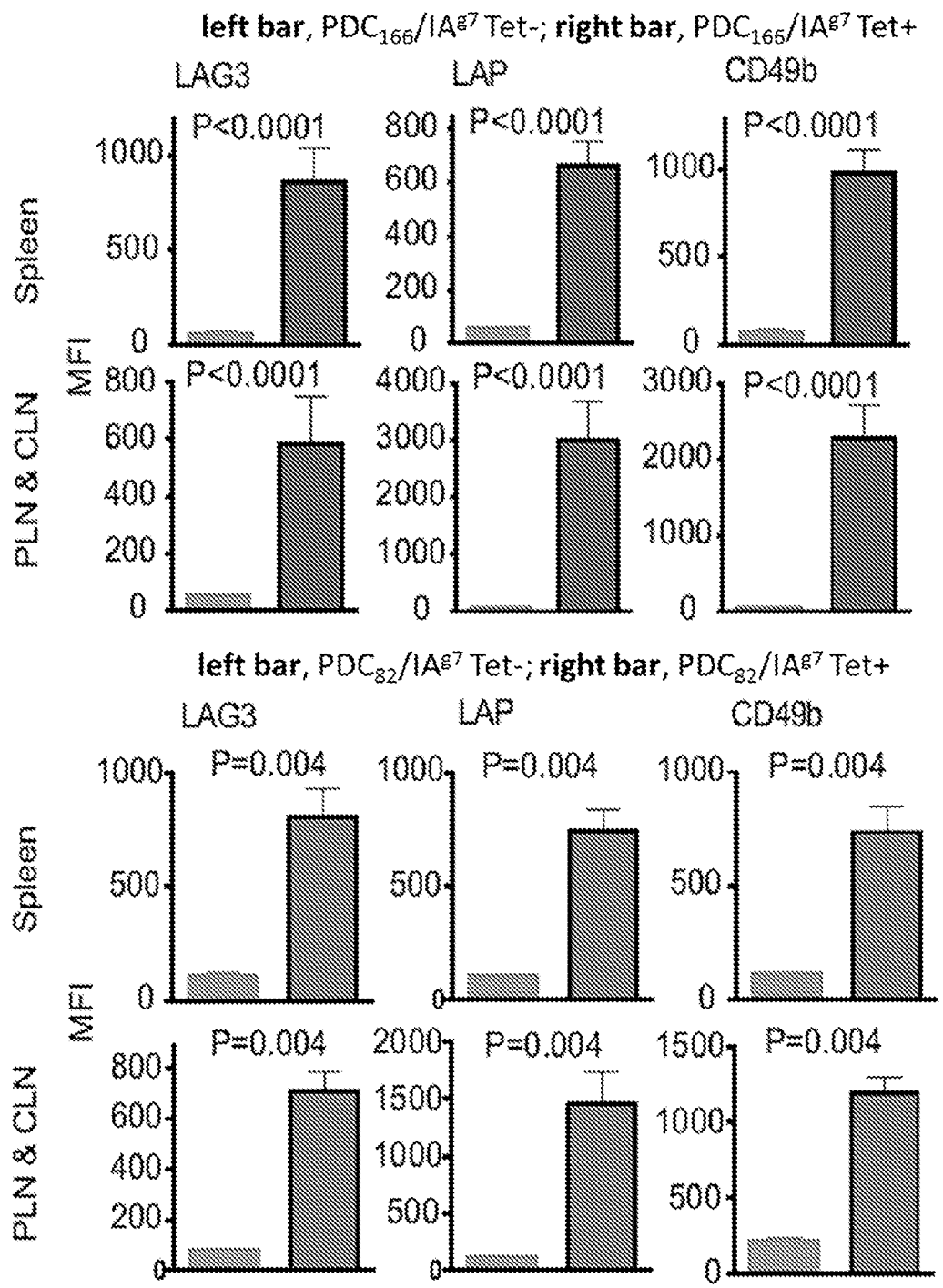

As expected, the PDC-E2$_{166-181}$/IA$^{g7}$ tetramer+CD4+ T-cells that expanded in these mice expressed the TR1 cell markers LAG-3, CD49b and LAP as shown in FIG. 1F and FIGS. 2A and 2B. Furthermore, unlike their tetramer-negative counterparts, the splenic tetramer+CD4+ T-cells of these mice produced the TR1 cytokine IL-10 but not IFNγ, IL-2, IL-4, IL-9 or IL-17 in response to PDC-E2$_{166-181}$ (but not BDC2.5) peptide-pulsed bone marrow-derived DCs (FIG. 1G). Similar results were obtained in mice treated with NPs displaying the second PDC-E2-based pMHC (PDC-E2$_{82-96}$/I-A$^{g7}$), in which there was a significant expansion of cognate PDC-E2$_{82-96}$/I-A$^{g7}$-reactive TR1-like CD4+ T-cells and significant reductions in the frequency of PDC-E2$_{166-181}$/IA$^{g7}$-reactive CD4+ T-cells as shown in FIGS. 1B (center) and 1E (bottom) and FIGS. 2A and 2B, indicating that the above outcome is not a peculiarity of any particular epitope on PDC-E2.

Together, the above data demonstrate that PDC-E2 peptide/IA$^{g7}$-NPs efficiently trigger the formation and expansion of cognate TR1-like CD4+ T-cells in NOD.c3c4 mice, as described previously for T1D-, EAE- and CIA-relevant pMHC class II-NPs in the corresponding disease models.

Example 2—Reversal of Established PBC by Disease-Relevant pMHC Class II-NPs

Figure 3A:
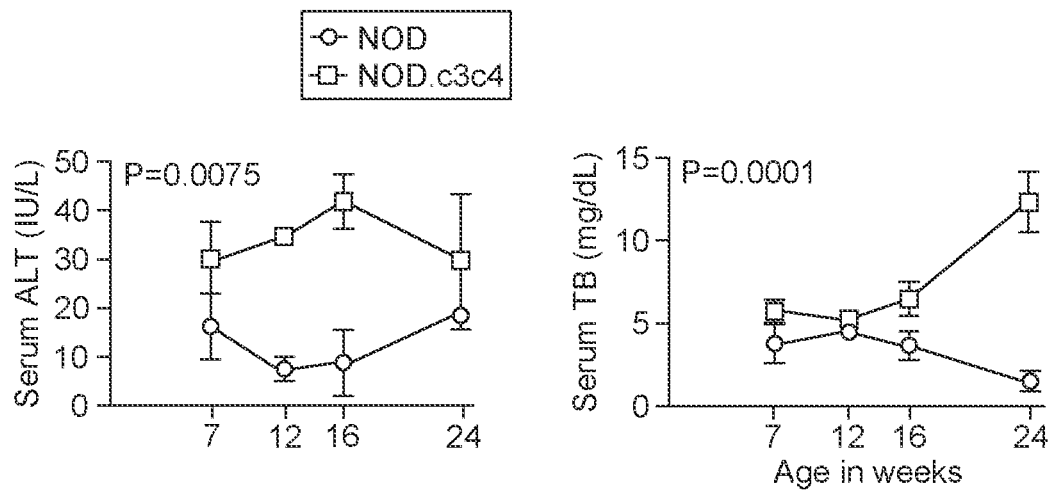
FIG. 3A shows changes in serum TB and ALT levels with age.
Figure 3B:
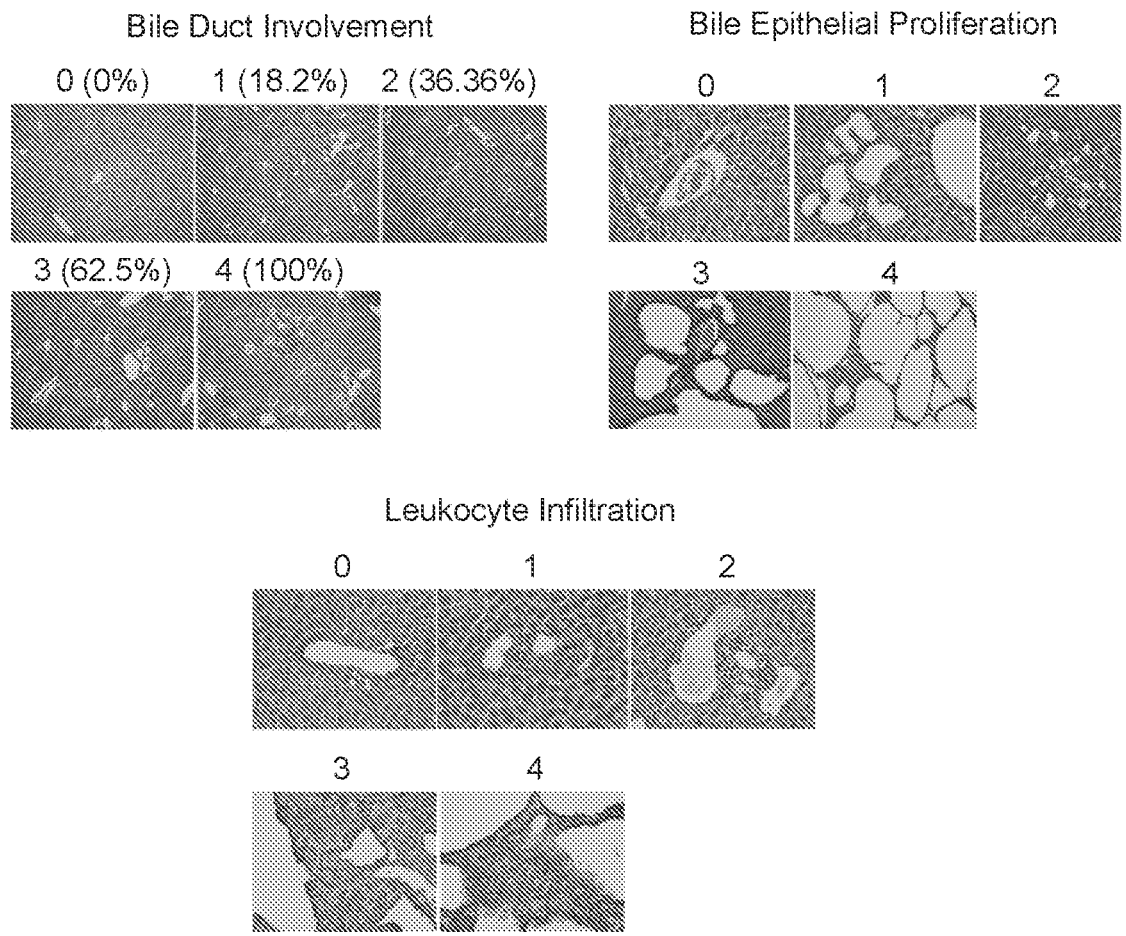
FIG. 3B shows microscopic scoring system (left) and progression of microscopic scores of disease with age (right).
Figure 3C:
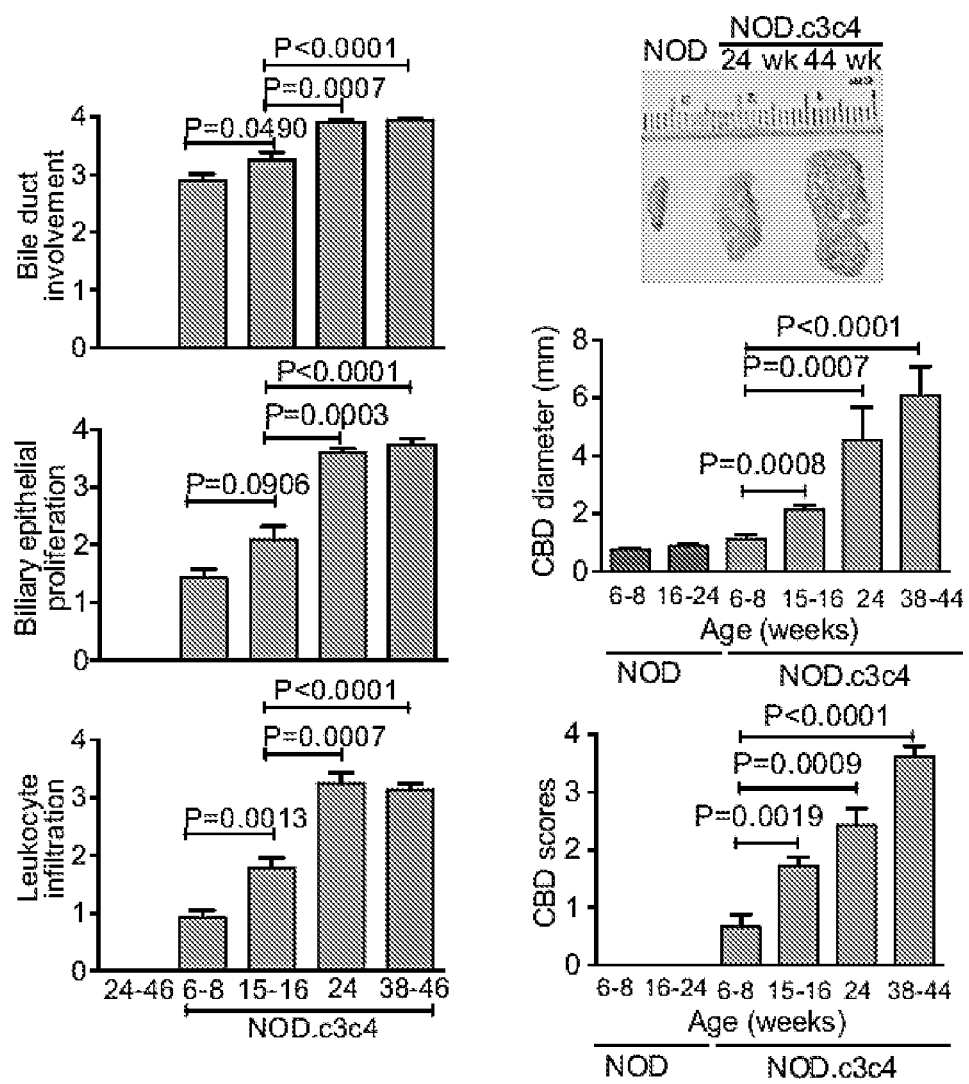
FIG. 3C shows representative CBD images and progression of CBD diameter and scores with age.
Figure 3D:
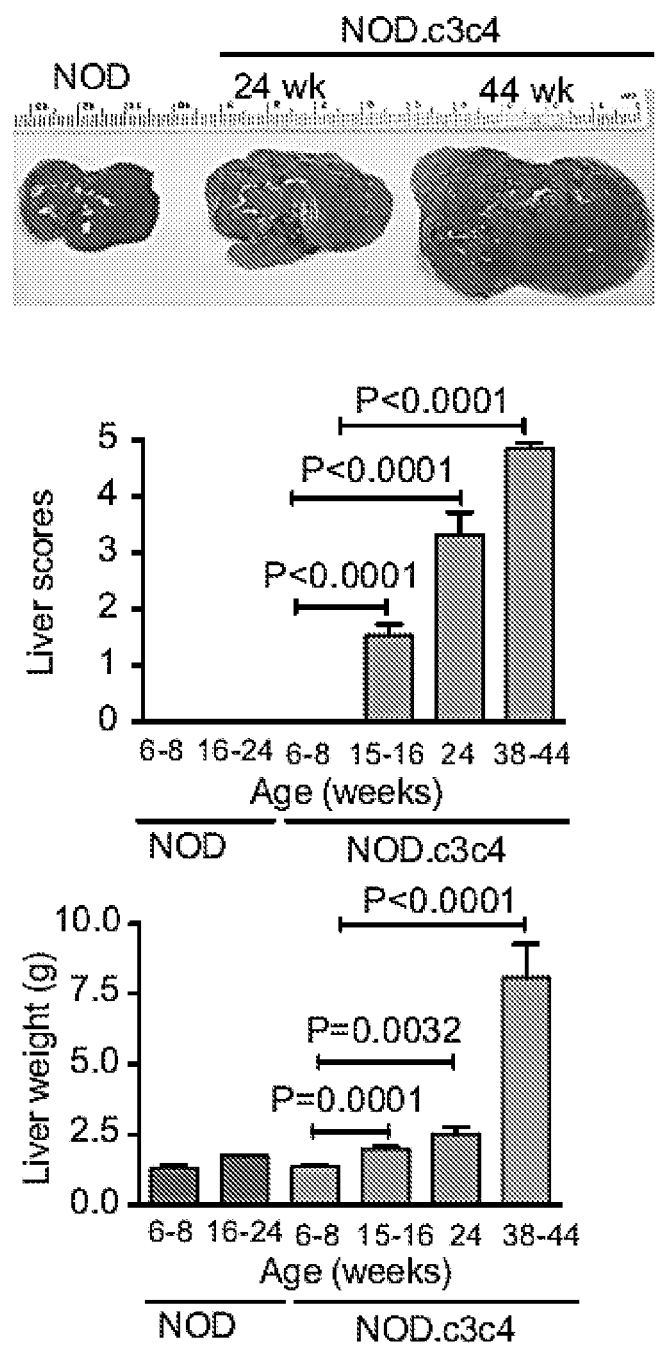
FIG. 3D shows representative liver images (top) and progression of liver scores and weight with age (bottom).
Figure 3E:
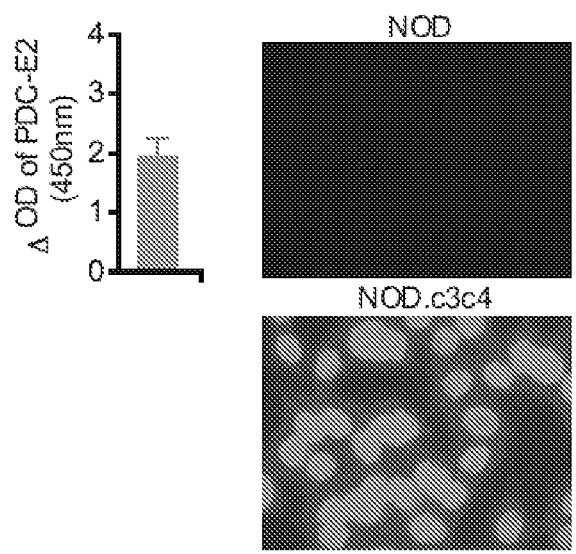
FIG. 3E shows that NOD.c3c4 mice spontaneously develop anti-PDC-E2-specific autoantibodies (left) and ANAs (right).
Figure 3F:
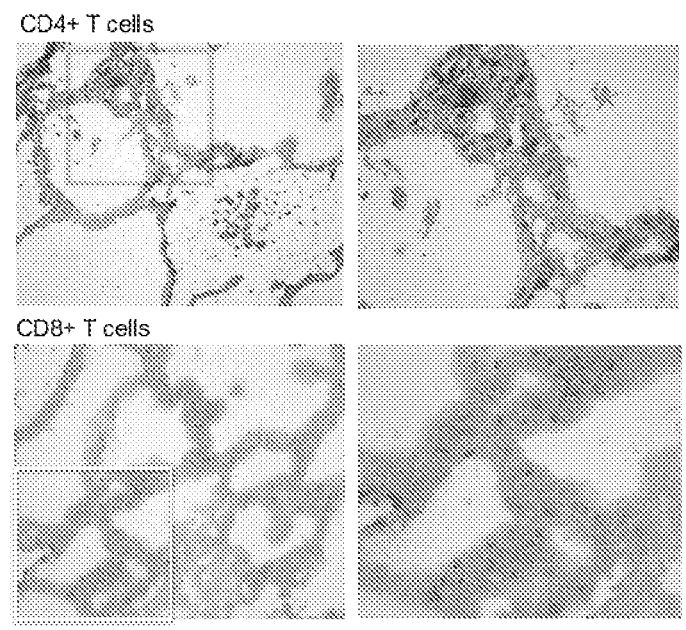
FIG. 3F depicts representative images of liver inflammation by CD4+ and CD8+ T-cells.

When compared to age-matched NOD mice, 6-8 week-old NOD.c3c4 mice begin to display elevated levels of serum alanine aminotransferase (ALT), microscopic biliary epithelial proliferation, biliary track leukocyte infiltration, massive bile duct involvement (near maximum number of portal triads affected) and macroscopic enlargement of the common biliary duct (CBD) (FIGS. 3A and 3C). FIG. 3B shows an exemplary scoring matrix to quantify microscopic analysis. By ~15-16 weeks these signs worsen and the mice begin to display increased total serum bilirubin (TB) levels (FIG. 3A) high titers of anti-mitochondrial/PDC-E2-specific autoantibodies (absent in NOD mice; FIG. 3E) and macroscopic signs of liver disease (bile cysts) (FIG. 3D). The severity of all these signs of disease peaks at ~24 weeks of age (FIGS. 3A-3D), coinciding with massive infiltration of the biliary epithelium by CD4+ and CD8+ T-cells (FIG. 3F), high titers of anti-nuclear autoantibodies (ANAs) (FIG. 3E) and a nearly three-fold increase in liver weight (FIG. 3D).

Figure 4A:
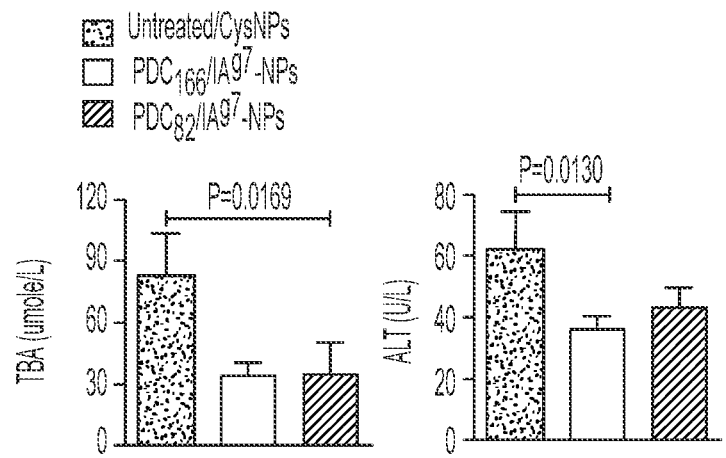
FIG. 4A shows changes in total bile acid (TBA) and alanine aminotransferase (ALT) levels in serum of NOD.c3c4 mice treated with $PDC_{166}/IA^{g7}$-NPs, $PDC_{82}/IA_{g7}$-NPs or control (Cys-NP).
Figure 4B:
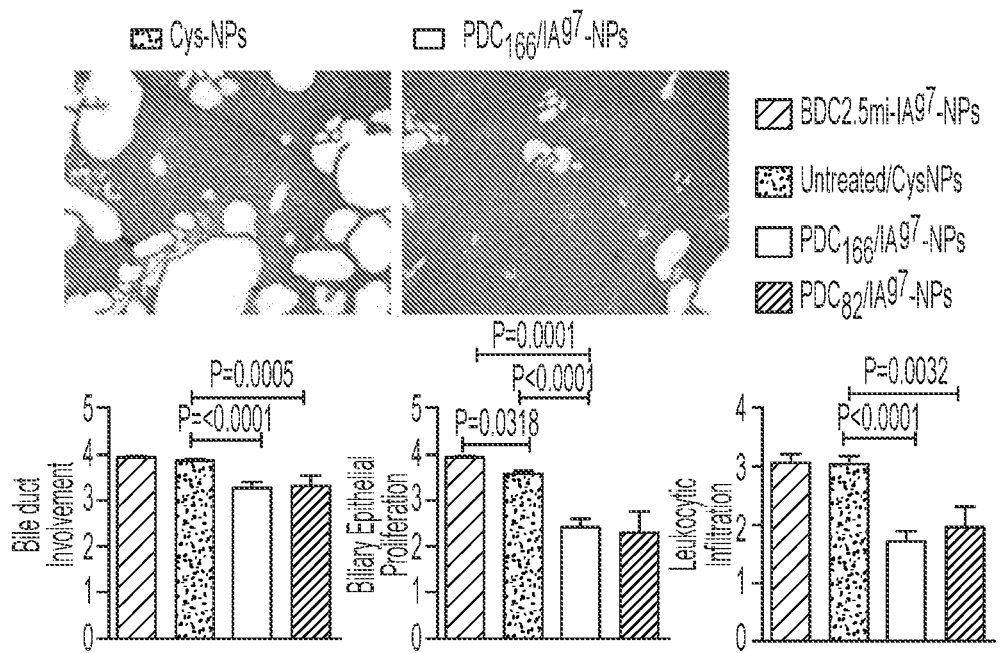
FIG. 4B shows representative histological images of livers from $PDC_{166}/IA^{g7}$-NPs, $PDC_{82}/IA^{g7}$-NPs, or Cys-NP-treated NOD.c3c4 mice (top) and average histological scores (bottom).
Figure 4C:
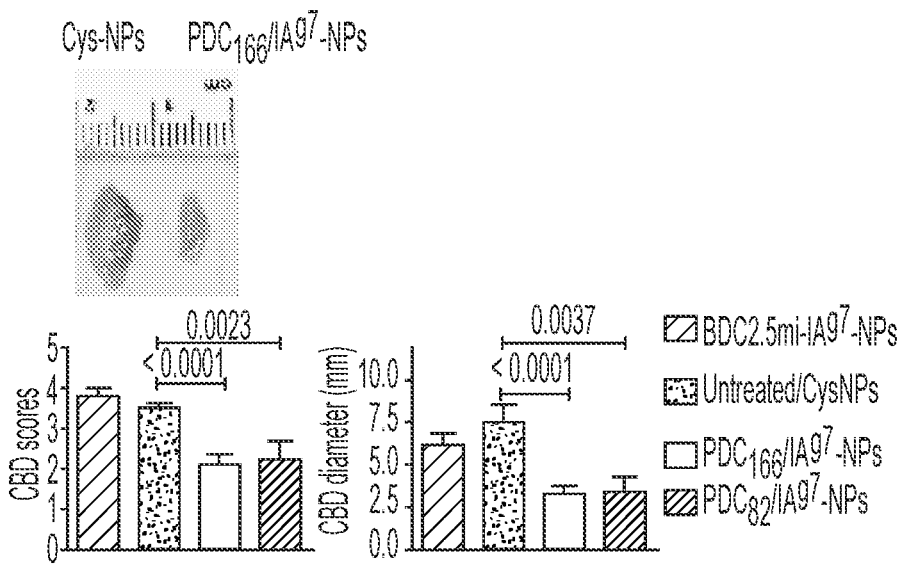
FIG. 4C shows representative macroscopic images of the common bile duct (top), and average common bile duct scores and diameters (bottom).
Figure 4D:
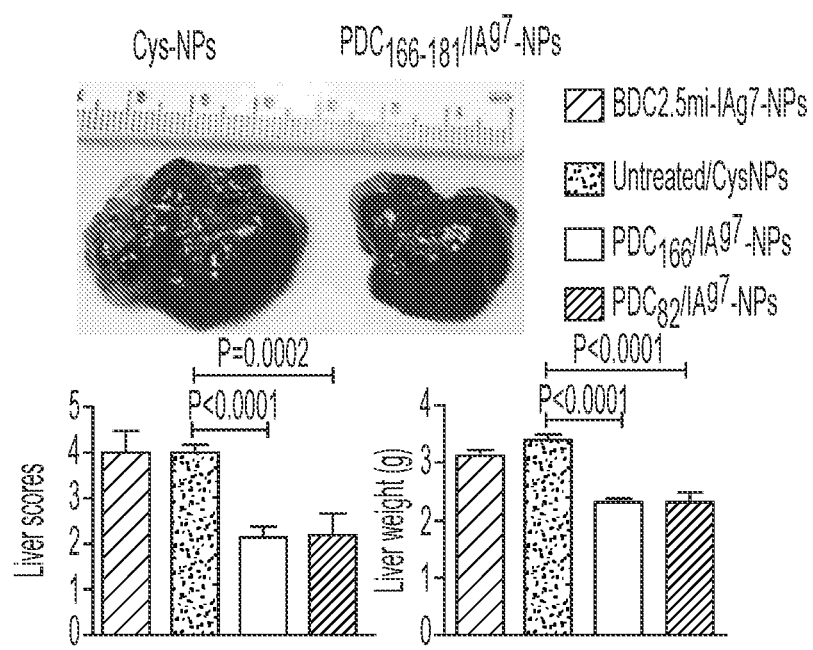
FIG. 4D shows representative macroscopic images of livers (top) and average liver scores and weight (bottom).
Figure 4E:
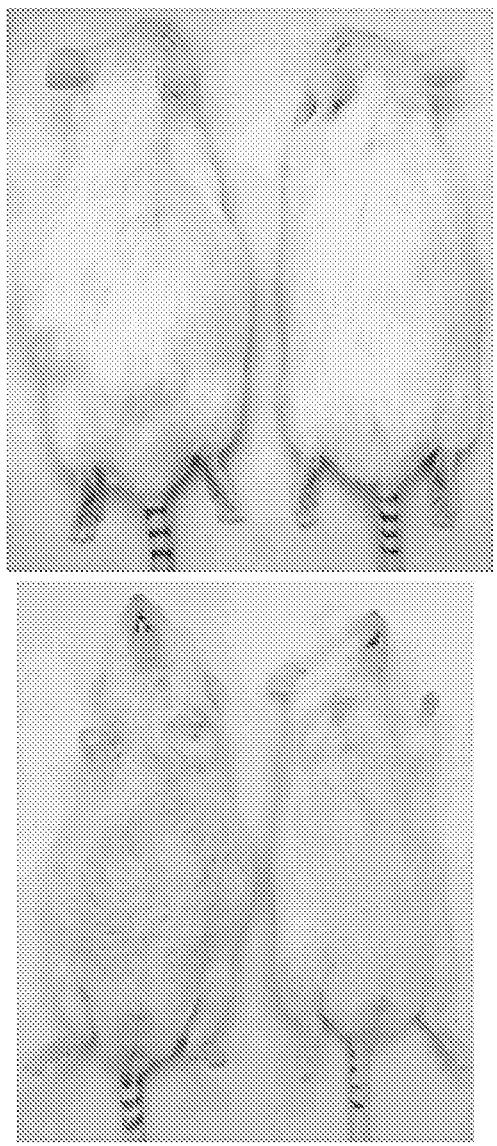
FIG. 4E shows representative whole body images of NOD.c3c4 mice treated with $PDC_{166}/IA^{g7}$-NP or control Cys-NPs.
Figure 4F:
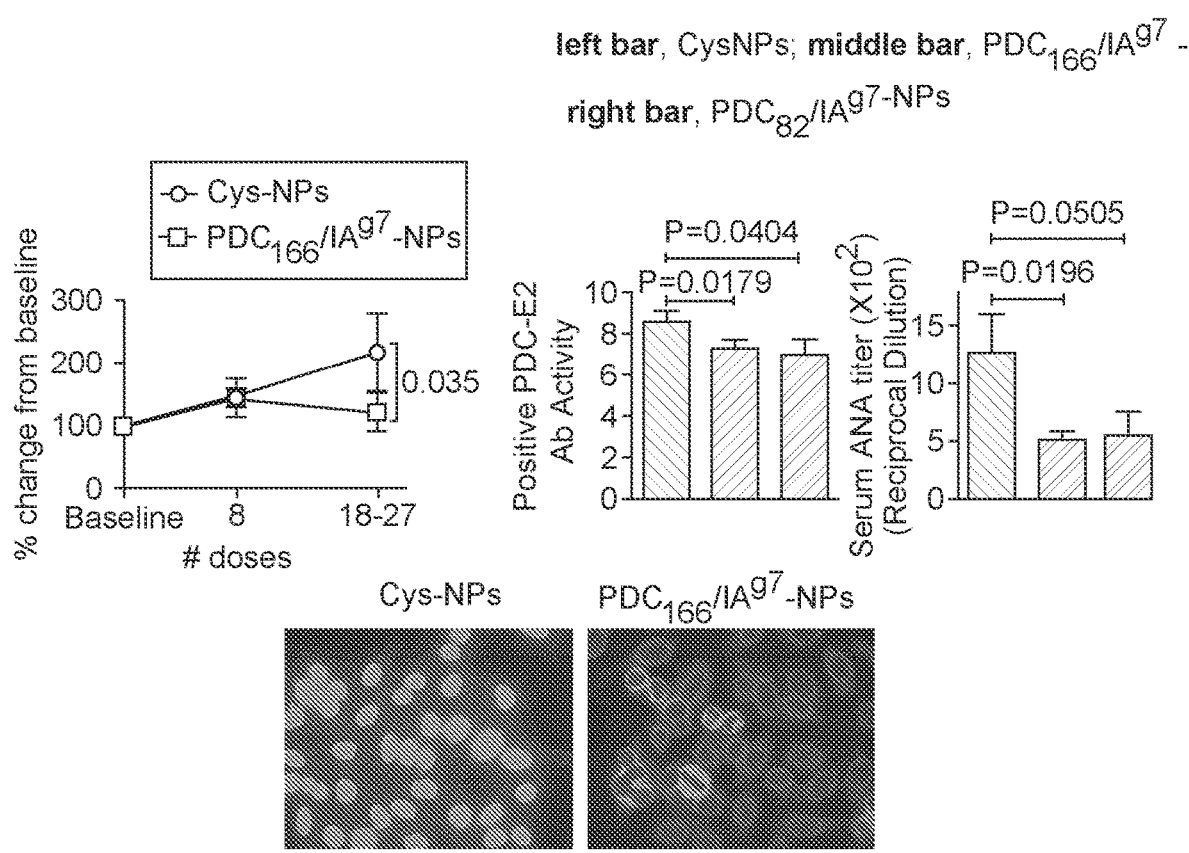
FIG. 4F shows changes in the titer of anti-mitochondrial (PDC-E2) antibodies and anti-nuclear autoantibodies (ANAs) after treatment (top left two panels and right panel, respectively), and representative images of Hep2 cells stained with sera from pMHC-NP vs Cys-NP-treated NOD.c3c4 mice (bottom).

We tested the therapeutic properties of PDC-E2$_{166\text{-}181}$/IA$^{g7}$-, PDC-E2$_{82\text{-}96}$/I-A$^{g7}$- and BDC2.5/I-A$^{g7}$-NPs in 15 week-old NOD.c3c4 mice, an age when liver autoimmunity in these mice is well established. Mice received biweekly doses of 20 ug of pMHC-NPs or an equivalent dose of control (Cys-conjugated NPs; Cys-NPs) for 9-13.5 weeks. Treatment with PDC-E2$_{166\text{-}181}$/IA$^{g7}$-NPs resulted in significant reductions in serum ALT and TB levels (FIG. 4A), bile duct involvement, bile duct epithelial proliferation and leukocyte infiltration (FIG. 4B), common bile duct diameter and macroscopic score (FIG. 4C), liver weight and macroscopic liver scores (FIG. 4D) and abdominal girth (FIG. 4E). Although treatment did not decrease the autoantibody titers found at the initiation of therapy, it clearly blunted the progression of autoantibody formation, as documented by significant reductions in anti-PDC-E2 and anti-nuclear autoantibody titers in mice treated with PDC-E2$_{166\text{-}181}$/IA$^{g7}$-NPs, PDC-E2$_{82\text{-}96}$/I-A$^{g7}$-NPs vs. control NPs (FIG. 4F). Additional studies with the second PBC-relevant pMHC-NP compound (PDC-E2$_{82\text{-}96}$/I-A$^{g7}$-NPs), and the T1D-relevant (but PBC-irrelevant) counterpart (BDC2.5/I-A$^{g7}$-NPs) confirmed the disease specificity of these compounds (FIGS. 4C and 4D).

Figure 2C:
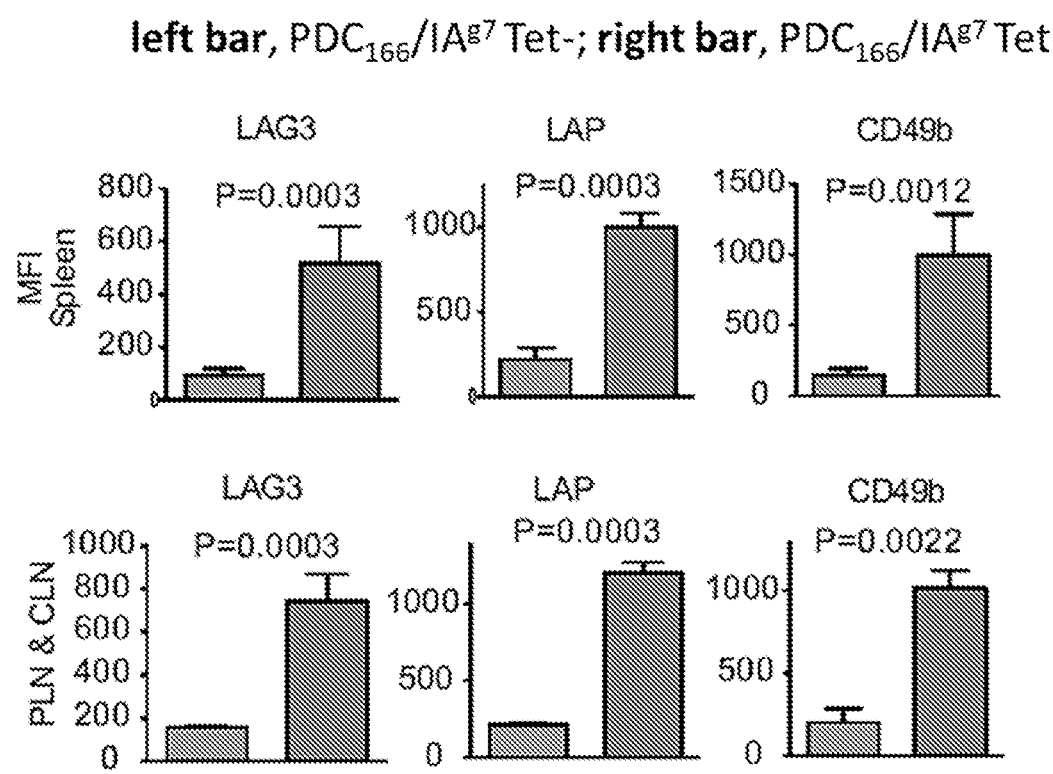
FIG. 2C shows average mean fluorescence intensity values for TR1 cell surface markers on tetramer+CD4+ T-cells arising in 38-44 week-old NOD.c3c4 mice in response to $PDC_{166}/IA^{g7}$-NP therapy.
Figure 4G:
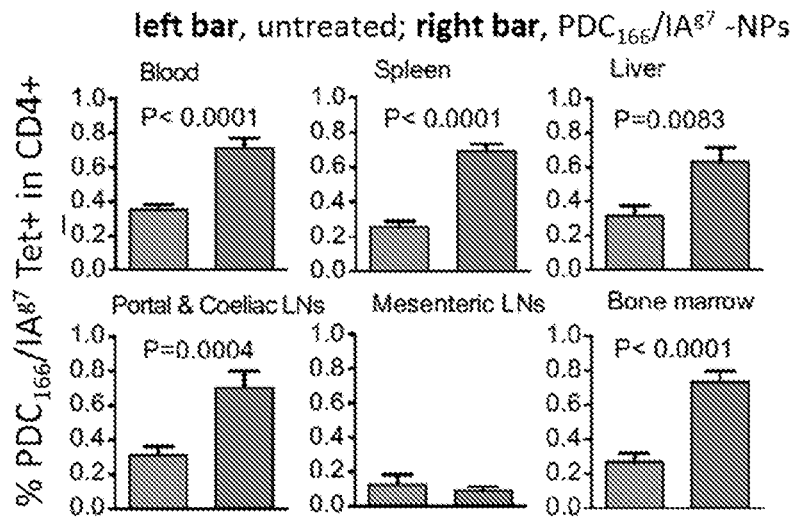
FIG. 4G shows percentages of tetramer+ cells in mice treated starting at 24 weeks of age (until week 38-44).
Figure 4H:
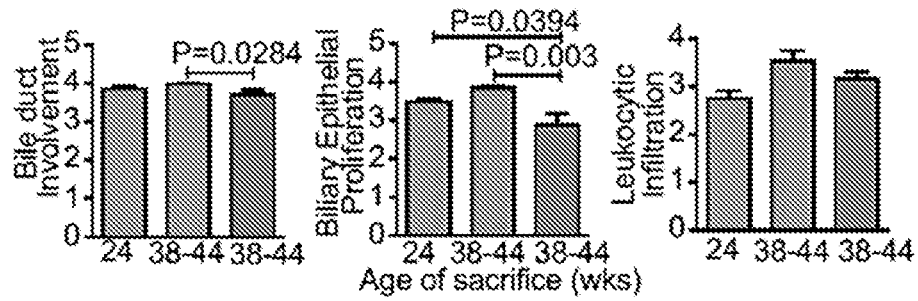
FIGS. 4H and 4I show microscopic (FIG. 4H) and macroscopic scores (FIG. 4I) for the mice studied in FIG. 4G.
Figure 4I:
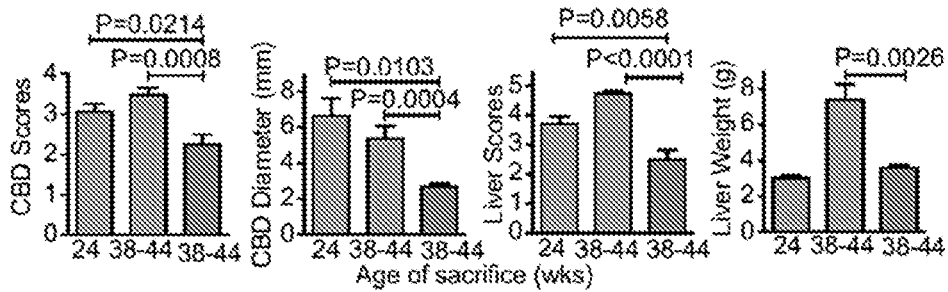

Similar results were obtained when treatment was initiated at the peak of disease severity (24 weeks of age). Analyses of mice after 14-20 weeks of therapy (38-44 weeks of age) with PDC-E2$_{166\text{-}181}$/IA$^{g7}$-NPs revealed systemic expansions of TR1-like CD4+ T-cells (FIG. 4G and FIG. 2C) and indicated that the magnitude of the signs of disease (FIGS. 4H and 4I) were significantly lower than those seen at the age when therapy was initiated, suggesting that resolution of liver inflammation by PBC-specific nanomedicines promotes repair of pre-existing liver damage.

Figure 5A:
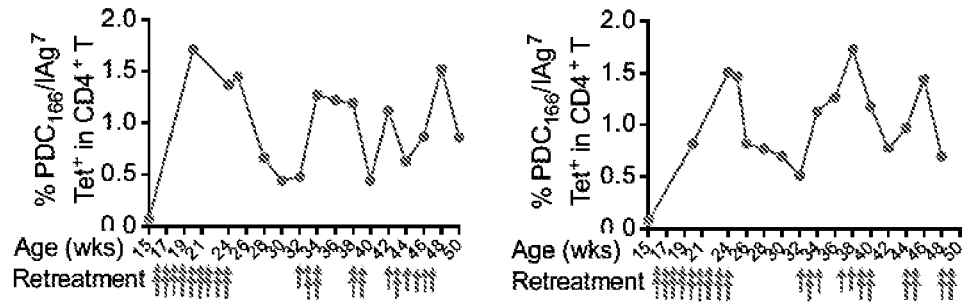
FIG. 5A shows two different mice.
Figure 5B:
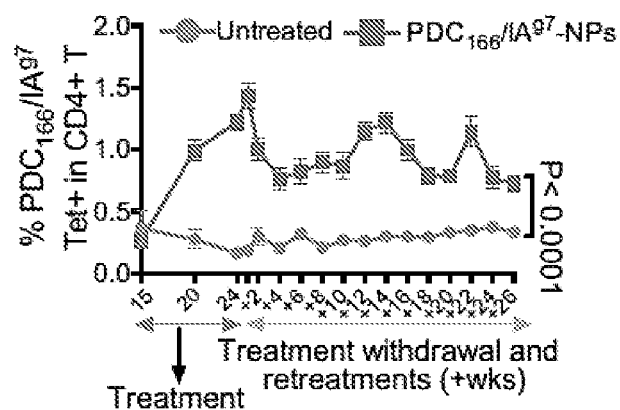
FIG. 5B shows average values corresponding to cohorts of mice treated with $PDC_{166}/IA^{g7}$-NPs or left untreated.
Figure 5C:
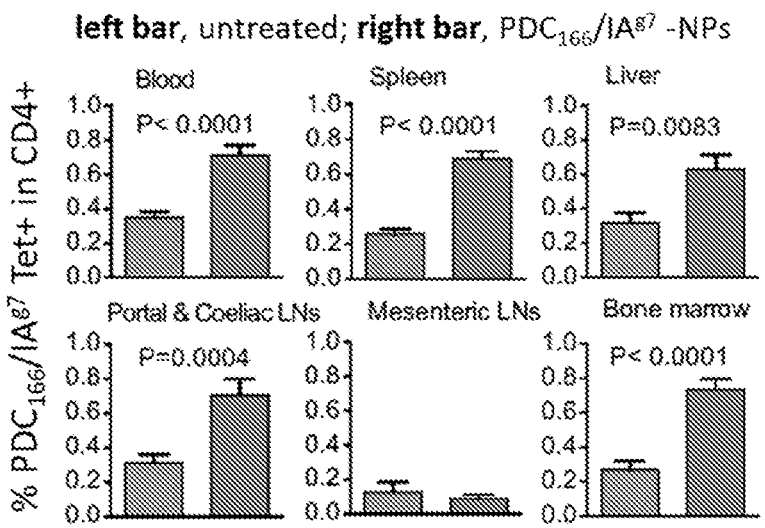
FIG. 5C shows percentage of tetramer+CD4+ T-cells.
Figure 5D:
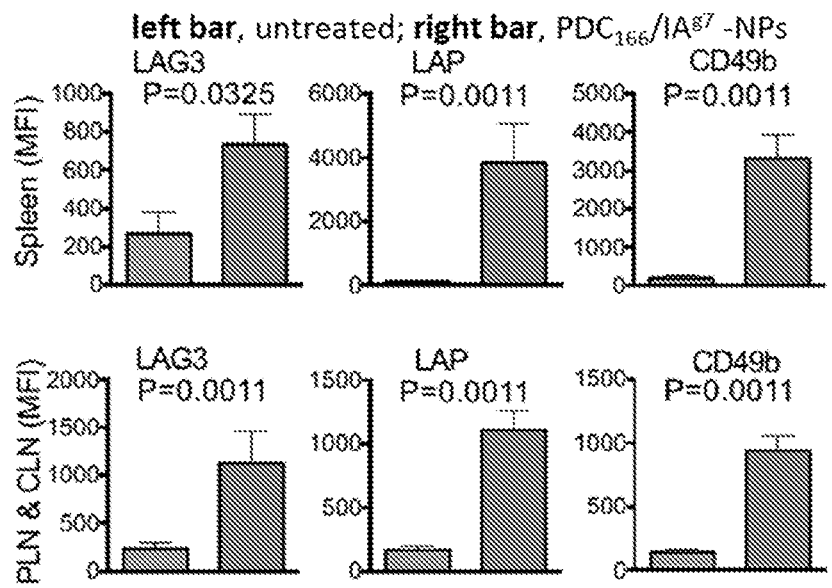
FIG. 5D shows mean fluorescence intensity staining for TR1 markers in tetramer+CD4+ T-cells from the mice studied in FIG. 5A.
Figure 5E:
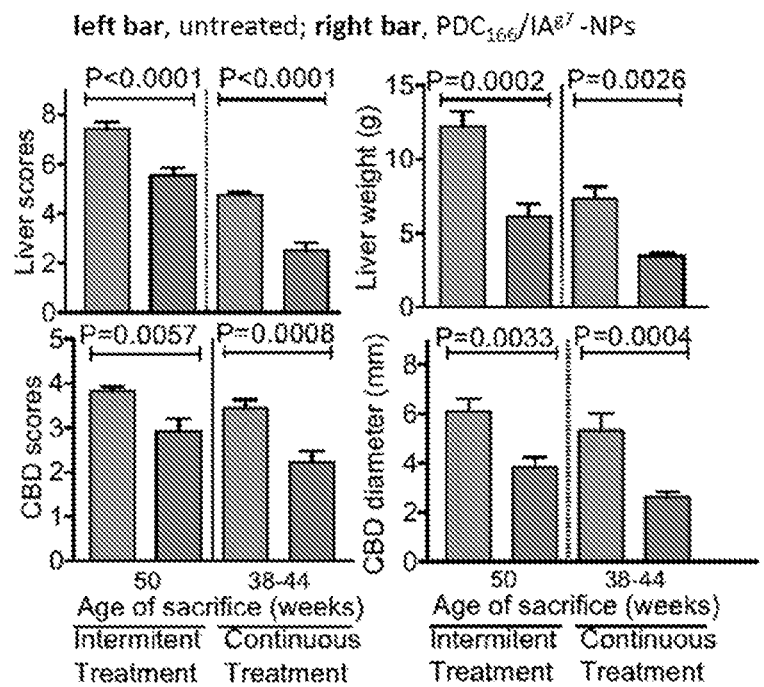
FIG. 5E shows average macroscopic CBD and liver scores for the mice studied in FIGS. 5A-D.

Example 3—Continued Versus Intermittent Treatment pMHC-NP therapy triggers the formation and expansion of cognate TR1 cells systemically, leading to accumulation of these cells in most lymphoid organs as well as at the site of autoimmune inflammation (See FIGS. 1-3). In addition, these TR1 cells circulate through the bloodstream and their presence in blood can be used as a biomarker to gauge the need for re-treatment. To investigate this, and to ascertain whether circulating levels of cognate TR1-like CD4+ T-cells can in fact be used to guide therapeutic decisions, we withdrew treatment in NOD.c3c4 mice that had been treated with PDC-E2$_{166\text{-}181}$/IA$^{g7}$-NPs from 15 week to 24 weeks of age. We then measured the percentage of PDC-E2$_{166\text{-}181}$/IA$^{g7}$ tetramer+CD4+ T-cells in peripheral blood every two weeks, and re-treated animals in which the percentage of tetramer+ cells had declined to about 50% of the value at treatment withdrawal; treatment was again withdrawn when the tetramer+ values at the next scheduled measurement had recovered, and repeated this cycle until the mice reached 50 week of age. Although there was considerable variability from mouse to mouse (FIG. 5A), in most animals the peripheral blood tetramer+ TR1 cell content progressively declined to about 50% of the original values within 4-6 weeks after treatment withdrawal but re-treatment of these animals rapidly restored these values (FIG. 5B). Intermittent treatment did not compromise the pharmacodynamic (systemic expansion of TR1-like CD4+ T-cells) (FIGS. 5C and 5D) or the therapeutic effects of treatment, including reduced common bile duct diameter/macroscopic scores and liver weight/macroscopic score (FIG. 5E), as compared to values in untreated mice or mice which had been treated continuously from 24 to 38-44 weeks of age.

Example 4—pMHC-NPs Versus the Standard of Care

Ursodeoxycholic acid (UDCA, a hydrophilic bile acid) is the standard of care for PBC. See Charatcharoenwitthaya, P. et al. Long-term survival and impact of ursodeoxycholic acid treatment for recurrent primary biliary cirrhosis after liver transplantation. Liver Transpl. 13, 1236-1245. UDCA possesses anti-cholestatic effects and stimulates hepatobiliary secretion, thus protecting cholangiocytes against the toxic effects of hydrophobic bile acids. Although effective in ~50% of patients when given early on in the disease process, it is ineffective at advanced stages of PBC.

Figure 6C:
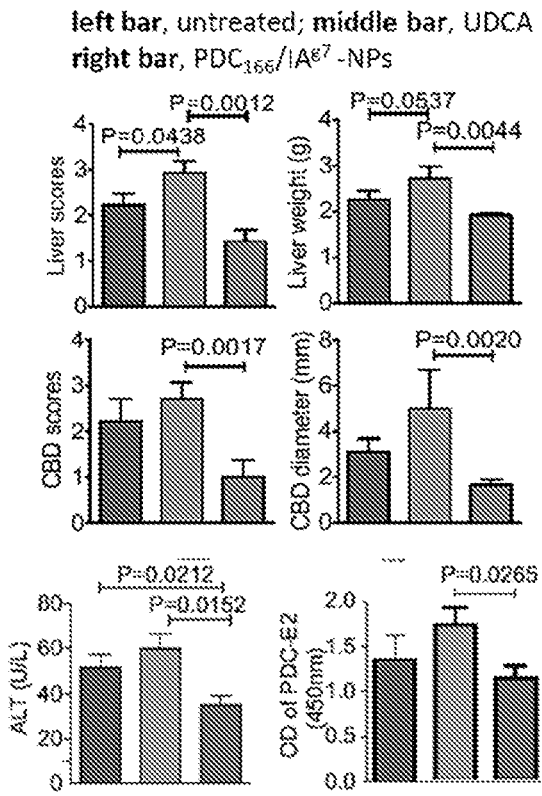
FIG. 6C shows percentages of tetramer+CD4+ T-cells in the mice studied in FIGS. 6A-B.
Figure 6C:
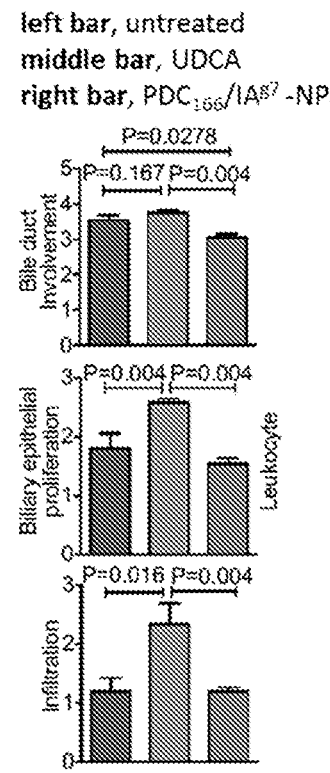
Figure 6C:
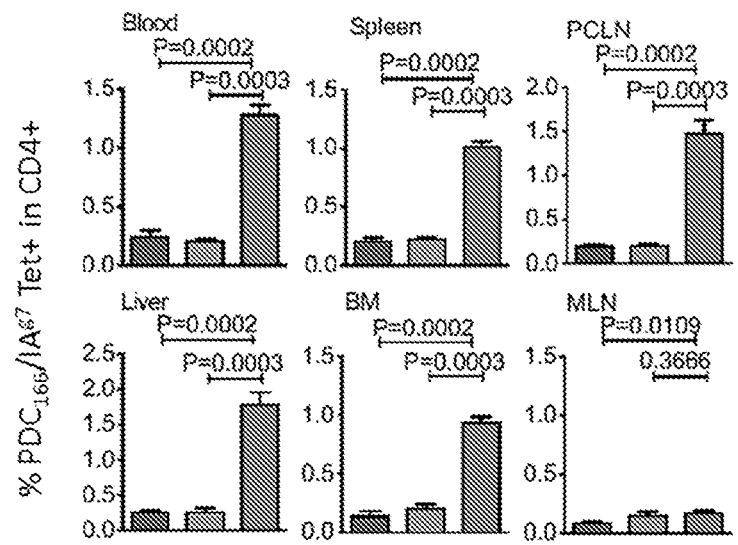
Figure 6D:
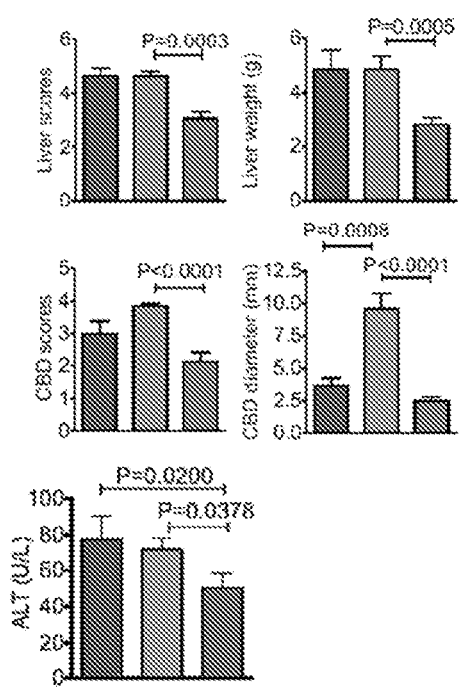
FIGS. 6D and E show effects of treatment with PBC-relevant pMHC-NPs or the standard of care in PBC (UDCA) on macroscopic (FIG. 6D) and microscopic (FIG. 6E) disease scores when treatment is initiated at advanced stages of disease.
Figure 6E:
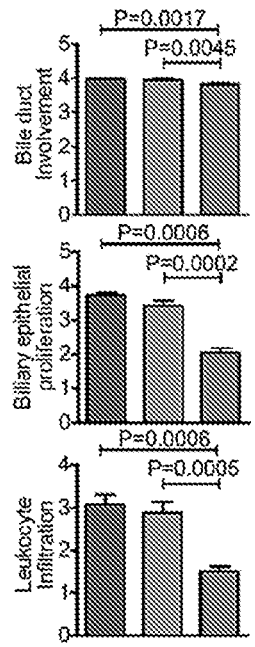
FIG. 6 illustrates effects of treatment with PBC-relevant pMHC-NPs or the standard of care in PBC (UDCA) on macroscopic and serum ALT levels (FIG. 6A) and microscopic (FIG. 6B) disease scores when treatment is initiated early on in the disease process.
FIG. 6F shows percentages of tetramer+ CD4+ T-cells in the mice studied in FIGS. 6D-E.

Oral administration of UDCA to 6 weeks-old NOD.c3c4 mice for 9 consecutive weeks via UDCA-supplemented chow had a therapeutic effect on the progression of PBC, as manifested by reductions in liver scores and liver weight, albeit not ALT, CBD scores or CBD diameter (FIG. 6A) and reductions in bile duct involvement and bile duct proliferation, albeit not leukocyte infiltration (FIG. 6B) as compared to untreated mice. However, when UDCA was given at advanced stages of disease progression (24 weeks of age), it had none of these therapeutic effects, except for a very significant reduction in CBD diameter as compared to untreated animals, possibly because of its anti-cholestatic effects (FIGS. 6D and 6E).

Figure 6F:
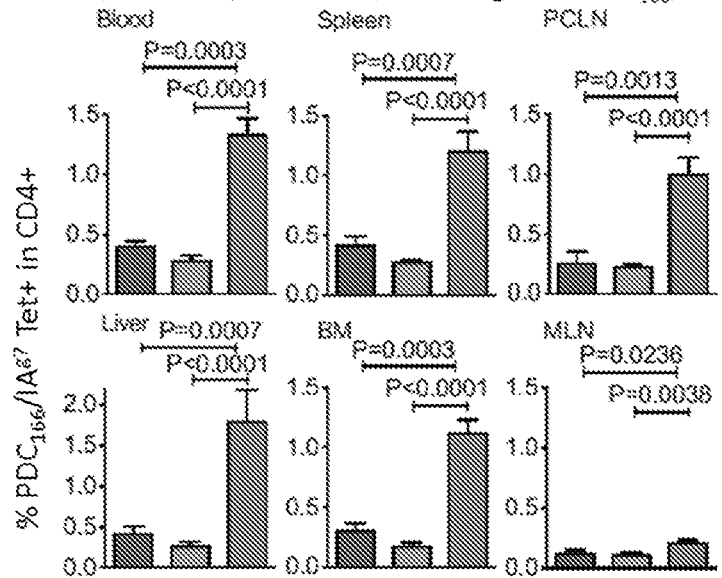

In contrast, PDC-E2$_{166\text{-}181}$/IA$^{g7}$-NP treatment had highly significant therapeutic effects in both 6 week-old and 24 week-old animals, as documented by significant reductions in the severity of all read-outs examined (FIGS. 6A-6E). As expected, this was associated with systemic expansion of cognate TR1-like CD4+ T-cells (FIG. 6F).

Example 5—Disease Suppression Requires IL-10, TGFb and CD4+ T Cells

Figure 7A:
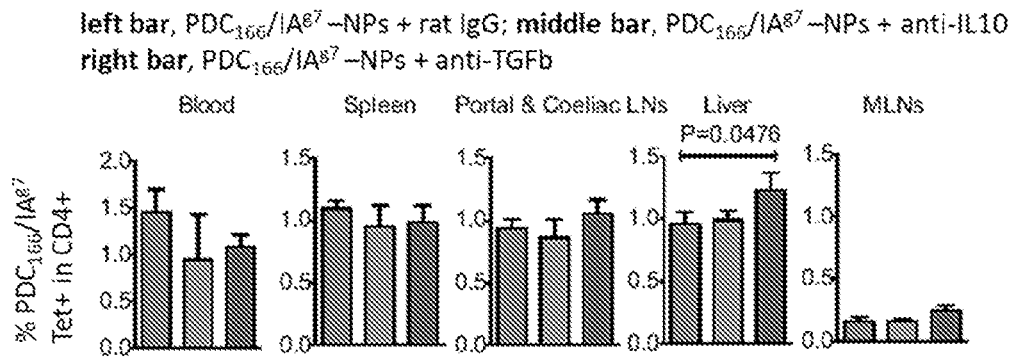
FIG. 7A shows percentages of tetramer+ CD4+ T-cells in mice treated with pMHC-NPs and rat-IgG (control) or blocking rat mAbs against mouse IL-10 or TGF-beta.
Figure 7B:
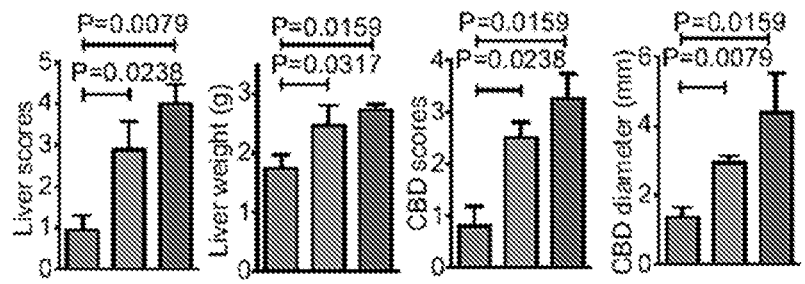
FIGS. 7B and C show macroscopic (FIG. 7B) and microscopic (FIG. 7C) scores of the mice studied in FIG. 7A.
Figure 7C:
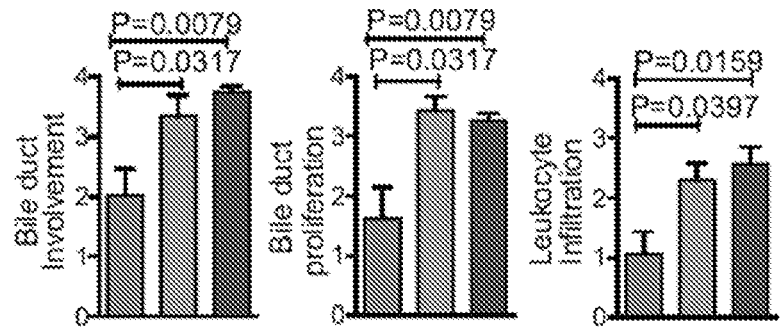
FIG. 7 illustrates that PBC-relevant pMHC-NPs expand regulatory B-cells.
FIG. 7D shows percentages of tetramer+CD4+ T cells in blood and lymphoid organs of NOD.c3c4.scid hosts reconstituted with whole splenocytes from untreated NOD.c3c4 donors and then transfused with splenic CD4+ T-cells from $PDC_{166-181}/IA^{g7}$-NP-treated NOD.c3c4 mice. The latter were either left untreated after CD4+ T-cell transfer or were treated with $PDC_{166-181}/IA^{g7}$-NPs.
FIG. 7E shows representative FACS staining histograms (top) and average mean fluorescence intensity values for TR1 markers on tetramer+ CD4+ vs. tetramer-CD4+ T-cells (bottom) of the hosts treated with $PDC_{166-181}/IA^{g7}$-NPs.
FIG. 7F shows macroscopic scores and measurements of the mice studied in A.
FIG. 7G shows the cytokine profile of LPS challenged CD11b+ cells isolated from the liver draining (PLN) or non-draining (MLN) lymph nodes of pMHC-NP vs Cys-NP-treated NOD.c3c4 mice.
FIG. 7H shows the cytokine profile of liver Kupffer cells from pMHC-NP vs Cys-NP-treated NOD.c3c4 mice.
FIG. 7I shows absolute numbers of B-cells in liver draining (PCLN) and non-draining (ILN) lymph nodes or liver of pMHC-NP vs Cys-NP-treated NOD.c3c4 mice.
FIG. 7J shows correlation between absolute numbers of B-cells and tetramer+CD4+ T-cells in pMHC-NP-treated mice. (IG. 7K shows IL-10 secretion levels of LPS-challenged B-cells isolated from liver draining and non-draining lymph nodes or liver of pMHC-NP vs Cys-NP-treated NOD.c3c4 mice.
FIG. 7L shows representative FACS plots showing conversion of B cells into IL-10-producing Breg cells only in the experiments arising in in hosts treated with pMHC-NPs.
FIG. 7M shows percentages of conventional B-cell-derived Breg cells in hosts treated with pMHC-NP or Cys-NP in liver and peripheral lymphoid organs harboring (spleen and PCLN) or lacking (MLN) pMHC-NP-induced TR1-like CD4+ T-cells.
Figure 7D:
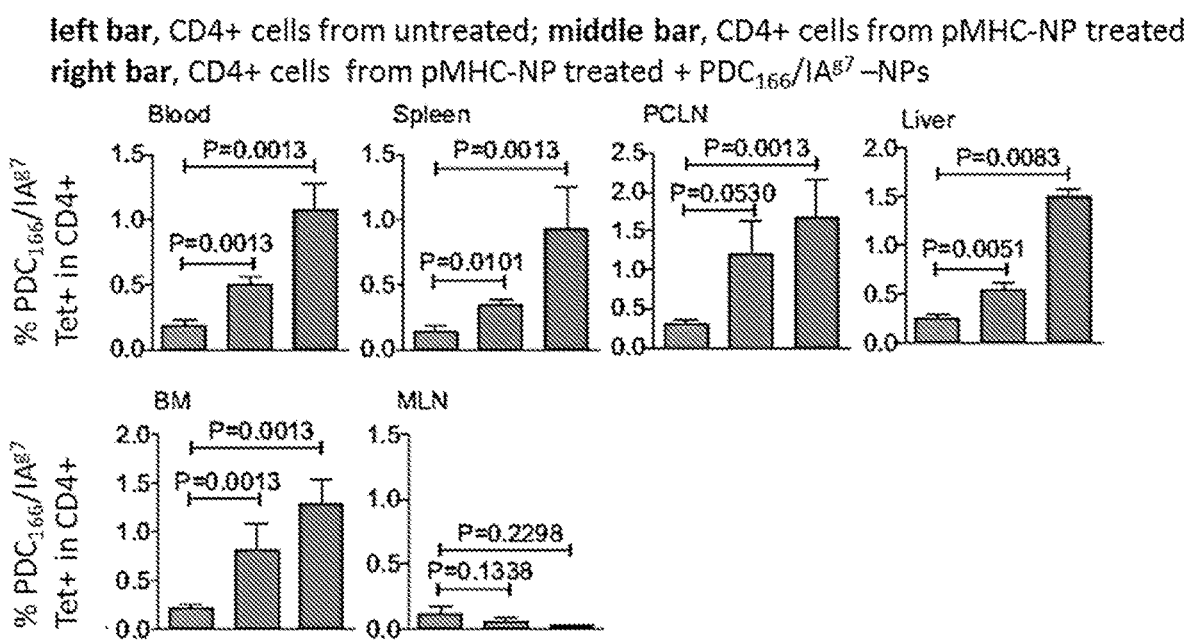
Figure 7E:
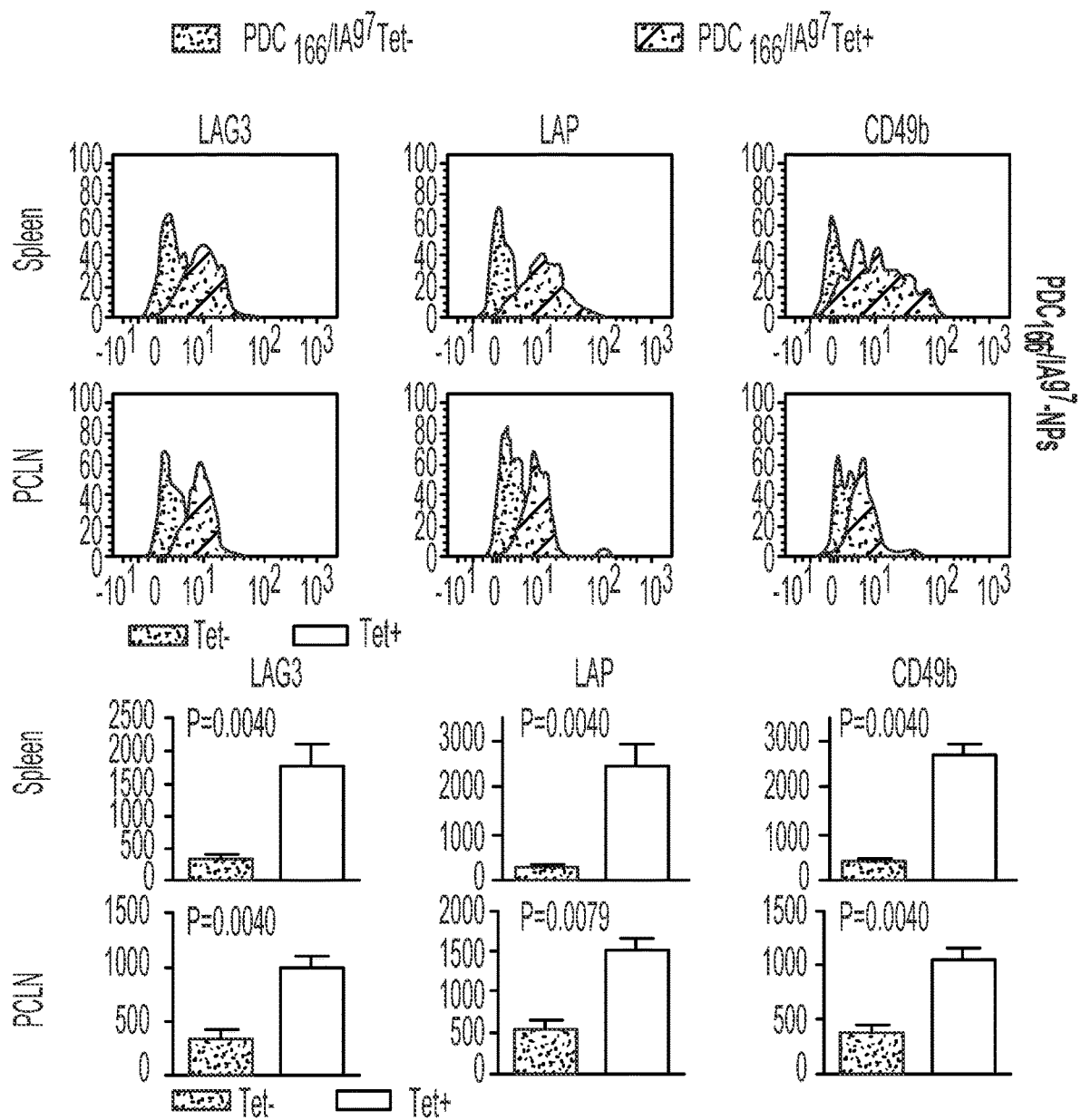
Figure 7F:
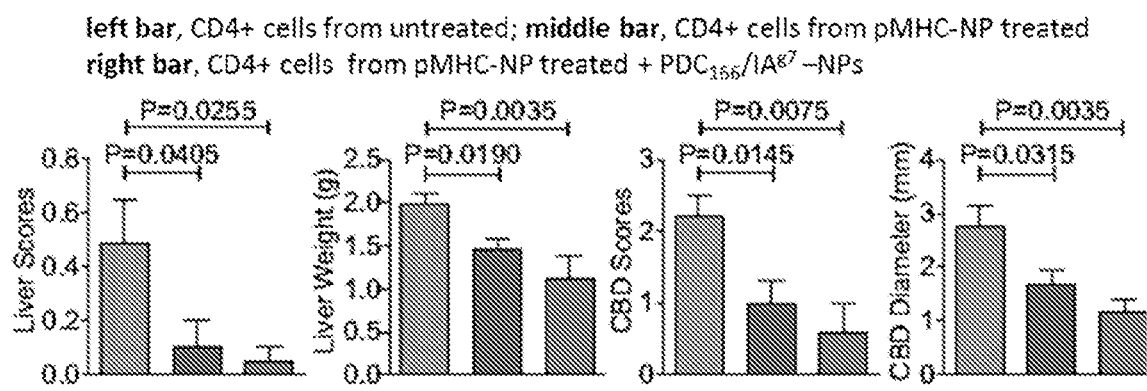

To ascertain if disease reversal by the TR1-like pMHC-NP-expanded PDC-E2$_{166\text{-}181}$/IA$^{g7}$ CD4+ T-cells was mediated by the TR1 cytokines IL-10 and/or TGFb, we compared the immunological and therapeutic effects of PDC-E2$_{166\text{-}181}$/IA$^{g7}$-NPs on 15 week-old NOD.c3c4 mice treated with blocking anti-IL10 or anti-TGFb mAbs or rat IgG for 5 weeks. Whereas cytokine blockade did not significantly inhibit the expansion of PDC-E2$_{166-181}$/IA$^{g7}$-specific TR1-like CD4+ T-cells (FIG. 7A), it suppressed their therapeutic effects, as compared to age-matched NOD.c3c4 mice treated with rat-IgG (FIGS. 7B and 7C). Purified splenic CD4+ T-cells from PDC-E2$_{166-181}$/IA$^{g7}$-NP-treated NOD.c3c4 mice could transfer disease suppression into NOD.scid.c3c4 hosts reconstituted with splenocytes from sick NOD.c3c4 mice, and treatment of the hosts with PDC-E2$_{166-181}$/IA$^{g7}$-NPs enhanced this effect as shown in FIGS. 7D-7F.

Figure 7G:
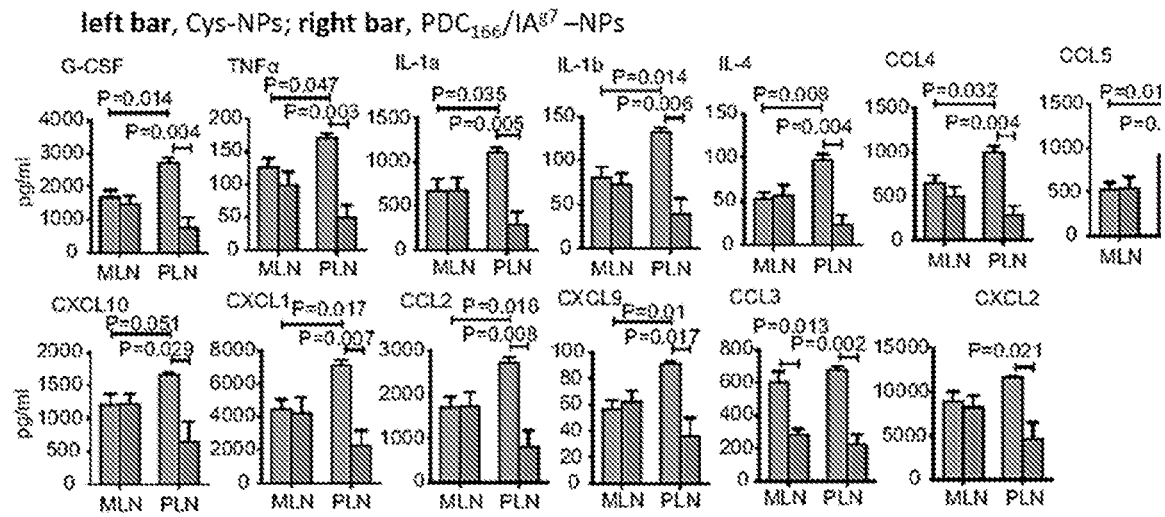
Figure 7H:
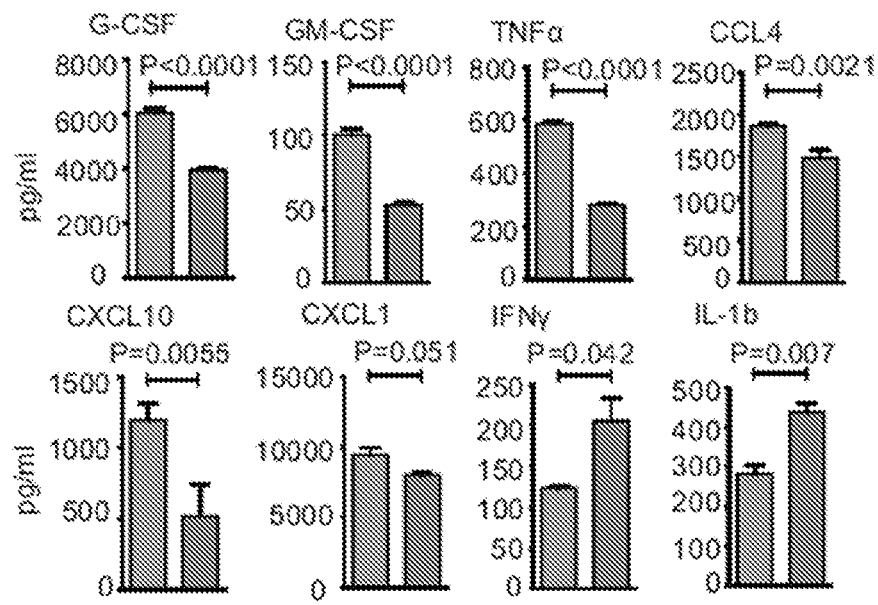

Example 6—Therapy-Induced Suppression of the Pro-Inflammatory Properties of Local and Proximal APCs To ascertain whether reversal of PBC by PDC-E2$_{166-181}$/IA$^{g7}$-NPs was associated with specific suppression of disease-fueling APCs, we compared the cytokine and chemokine profiles of portal (draining) vs. mesenteric (non-draining) lymph node CD11b+ cells and liver Kupffer cells isolated from PDC-E2$_{166-181}$/IA$^{g7}$-NP and control NP-treated animals. LPS-challenged CD11b+ cells from the portal lymph nodes of control NP-treated animals secreted significantly higher levels of a broad range of pro-inflammatory cytokines and chemokines than their mesenteric lymph node counterparts (FIG. 7G). Conversely, the portal lymph node CD11b+ cells of PDC-E2$_{166-181}$/IA$^{g7}$-NP-treated mice secreted significantly lower levels of such pro-inflammatory mediators than both their mesenteric lymph node counterparts and the CD11b+ cells isolated from control-NP-treated animals (FIG. 7G). Likewise, the Kupffer cells isolated from the livers of PDC-E2$_{166-181}$/IA$^{g7}$-NP-treated mice secreted significantly lower levels of some of these mediators (FIG. 7H). Thus, systemic expansion of PDC-E2-specific TR1 CD4+ cells in NOD.c3c4 mice by treatment with PBC-relevant pMHC class II-NPs is associated with dramatic inhibition of the pro-inflammatory properties of local and proximal APC types, likely owing to increased uptake of liver-derived PDC-E2 autoantigenic material.

Figure 7I:
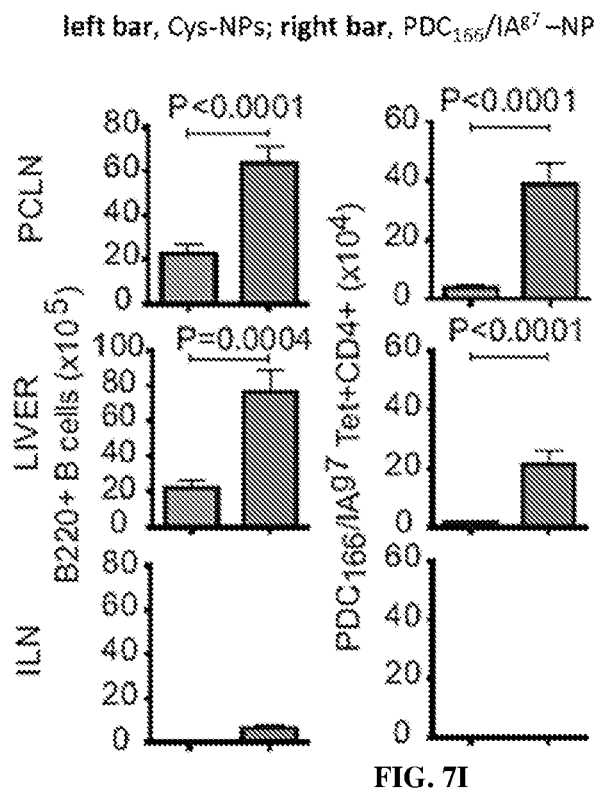
Figure 7J:
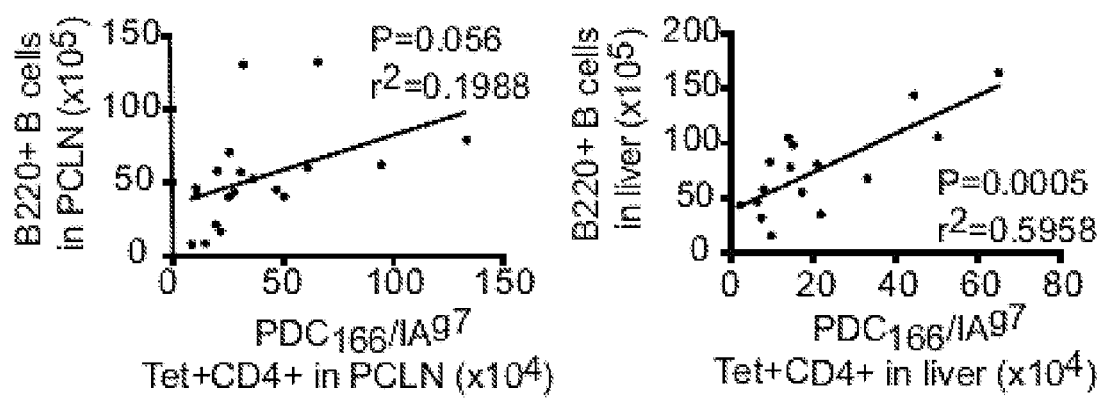

Example 7—PBC-Relevant Nanomedicines Promote Local Formation of Regulatory B Cells Pancreatic beta cell-specific TR1 CD4+ T-cells promote the recruitment of B-cells to the pancreas and its draining lymph nodes, as well as the local formation of anti-diabetogenic IL-10-producing Breg cells. To ascertain if this was also the case for PDC-E2-specific TR1 CD4+ T-cells in the context of PBC, we investigated if there were statistically significant correlations between the absolute numbers of B-cells and PDC-E2$_{166-181}$/IA$^{g7}$-specific TR1 cells in the liver, portal and mesenteric lymph nodes of PDC-E2$_{166-181}$/IA$^{g7}$-NP-treated mice. The livers and the portal, but not the mesenteric lymph nodes of PDC-E2$_{166-181}$/IA$^{g7}$-NP-treated mice harbored significantly higher numbers of PDC-E2$_{166-181}$/IA$^{g7}$-tetramer+ cells and B-cells than those from control-NP-treated animals (FIG. 7I). Furthermore, the tetramer+ and B-cell numbers in both liver and portal lymph nodes were statistically correlated; no such correlation was seen in the mesenteric lymph nodes of PDC-E2$_{166-181}$/IA$^{g7}$-NP-treated mice (FIG. 7J). Thus, enhanced recruitment of cognate TR1 cells to the liver and liver-draining lymph nodes of PDC-E2$_{166-181}$/IA$^{g7}$-NP-treated mice promotes the local accumulation of B-cells.

To ascertain whether the liver and portal lymph node B-cells of PDC-E2$_{166-181}$/IA$^{g7}$-NP-treated mice might be enriched for Breg cells, we compared the ability of the corresponding B-cells to produce IL-10 in response to LPS stimulation. The liver and portal, but not the mesenteric lymph node B-cells of PDC-E2$_{166-181}$/IA$^{g7}$-NP-treated mice produced significant levels of IL-10; neither the liver nor the portal lymph node B-cells of control NP-treated animals produced IL-10 (FIG. 7K). Thus, TR1 CD4+ T-cell-enhanced recruitment of B-cells to liver and draining lymph nodes is associated with local formation of IL-10-producing B-cells.

To further substantiate a direct relationship between TR1 cell recruitment and Breg cell formation, we ascertained the ability of PDC-E2$_{166-181}$/IA$^{g7}$-specific TR1 cells that accumulate in the spleen, liver and portal (but not mesenteric) lymph nodes of PDC-E2$_{166-181}$/IA$^{g7}$-treated mice to promote the differentiation of PDC-E2$_{166-181}$ peptide-pulsed conventional (IL-10/eGFP−) B-cells from NOD.Il10-eGFP reporter mice into CD1dhigh/CD5+/eGFP+ progeny. As shown in FIGS. 7K-7M, there was a clear formation of Breg cells in spleen, liver and portal lymph nodes (containing cognate TR1 cells) but not in the mesenteric lymph nodes (lacking cognate TR1 cells). When taken together, these results indicate that PDC-E2-specific TR1 cells promote the recruitment and differentiation of conventional B-cells into Breg-like cells.

Example 8—Systemic Immunity is Spared

Figure 8A:
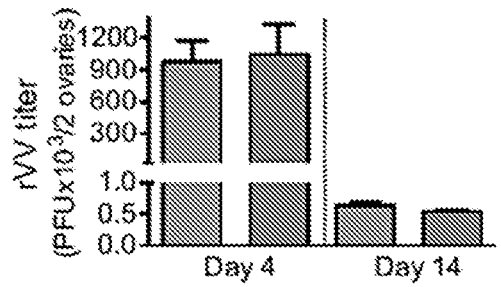
FIG. 8A shows average titers of rVV in ovaries of pMHC-NP-treated vs. untreated NOD.c3c4 female mice 4 and 14 days after a systemic rVV infection.

To ascertain if persistent expansion of PDC-E2$_{166-181}$/IA$^{g7}$-specific TR1 cells results in suppression of general immunity, we compared the ability of PDC-E2$_{166-181}$/IA$^{g7}$-NP-treated NOD.c3c4 mice to clear a systemic vaccinia virus infection, to mount effector T-cell responses against a lethal influenza infection, to mount protective immunity against an intracellular bacterial infection (Listeria), and to mount local immune responses against allogeneic tumor liver metastases. Cohorts of NOD.c3c4 mice received biweekly doses of PDC-E2$_{166-181}$/IA$^{g7}$-NPs or control NPs for 9 weeks. At the end of therapy the mice were given an intravenous injection of recombinant vaccinia virus. The viral titers in the ovaries of both cohorts of females 14 days after infection were similar in both cohorts of mice and substantially lower than those found at the peak of infection, indicating that pMHC-NP therapy did not impair cellular immunity against the virus-infected cells (FIG. 8A).

Figure 8B:
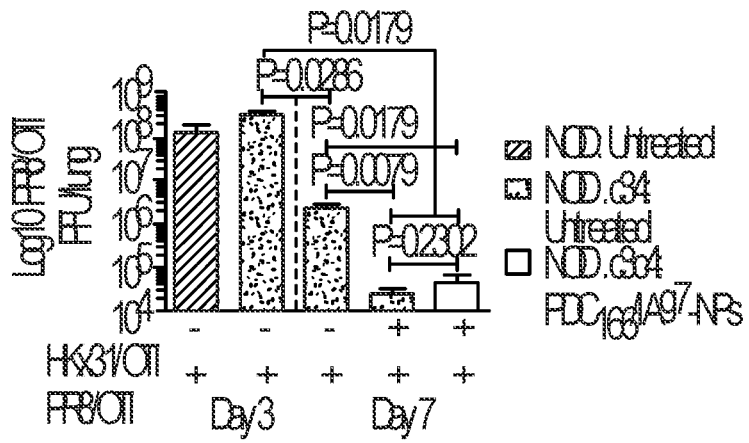
FIG. 8B shows titers of influenza virus in lungs of pMHC-NP-treated vs. untreated NOD.c3c4 female mice 3 and 7 days after infection with the PR8 strain with or without prior priming with the HKx31 strain.
Figure 8C:
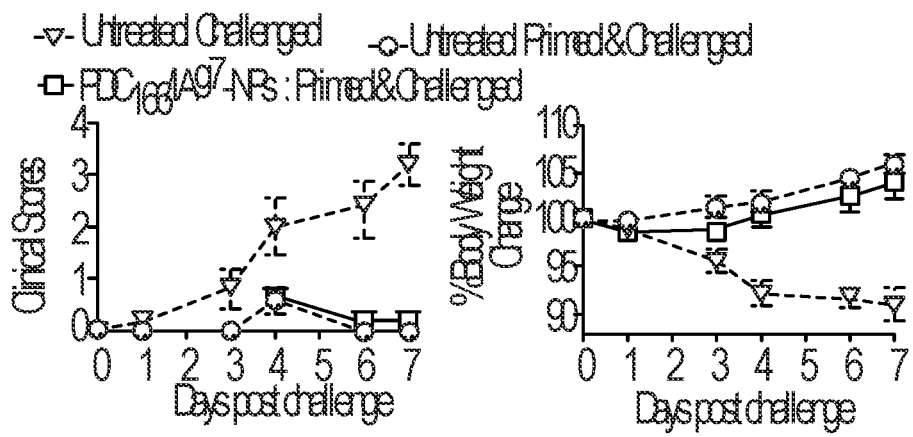
FIG. 8C shows clinical scores and body weight changes as a function of infection and treatment.

To probe this further, we infected PDC-E2$_{166-181}$/IA$^{g7}$-NP-treated or untreated NOD.c3c4 mice with a laboratory strain of influenza HKx31 (H3N2) i.p. to induce heterologous immunity against a subsequent, potentially lethal infection with an H1N1 strain of Influenza (PR8) given via the intranasal route, that shares MHC class I-restricted epitopes. As shown in FIGS. 8B and 8C, treated and untreated mice mounted protective immunity against the PR8 infection, as documented by viral load in lung tissue and clinical signs of active infection.

Figure 8D:
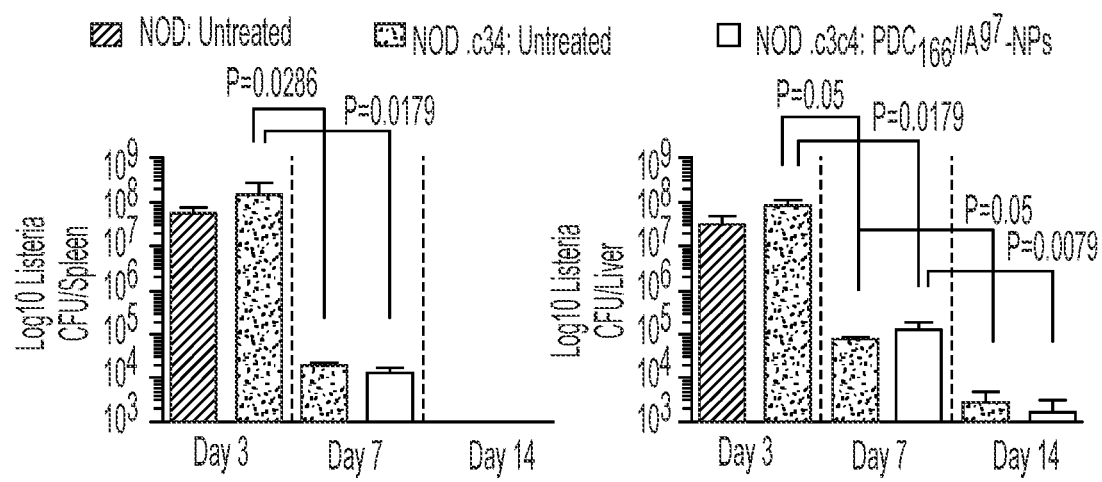
FIG. 8D shows colony-forming units of *Listeria* in the spleen or liver of pMHC-treated vs untreated NOD or NOD.c3c4 mice on days 3, 7, and 14 after a systemic *Listeria* infection.

Similar results were obtained in mice infected with the intracellular pathogen Listeria monocytogenes (LM), which does not normally cause chronic infections. LM-infected PDC-E2166-181/IA$^{g7}$-NP-treated and untreated NOD.c3c4 mice were equally efficient at clearing the bacteria from both the spleen and liver, consistent with unimpaired immunity against this intracellular pathogen (FIG. 8D).

Figure 8E:
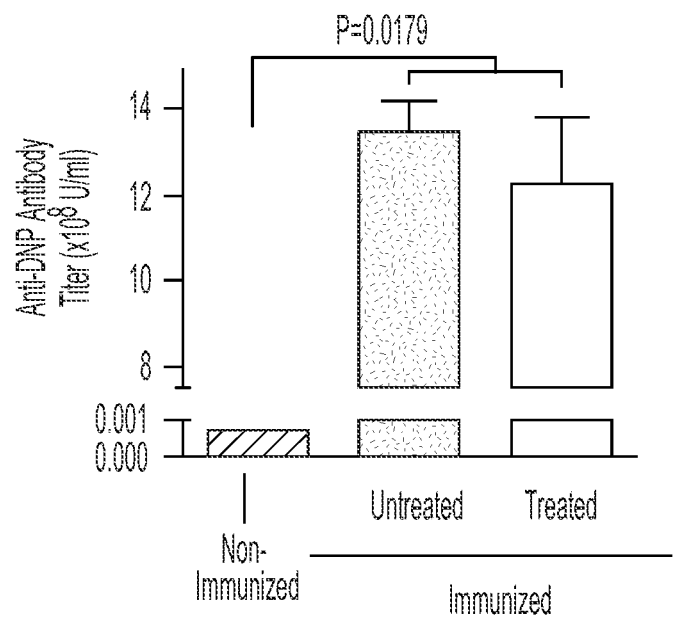
FIG. 8E shows serum anti-DNP antibody titers upon KLH-DNP immunization (n=3/group).
Figure 8F:
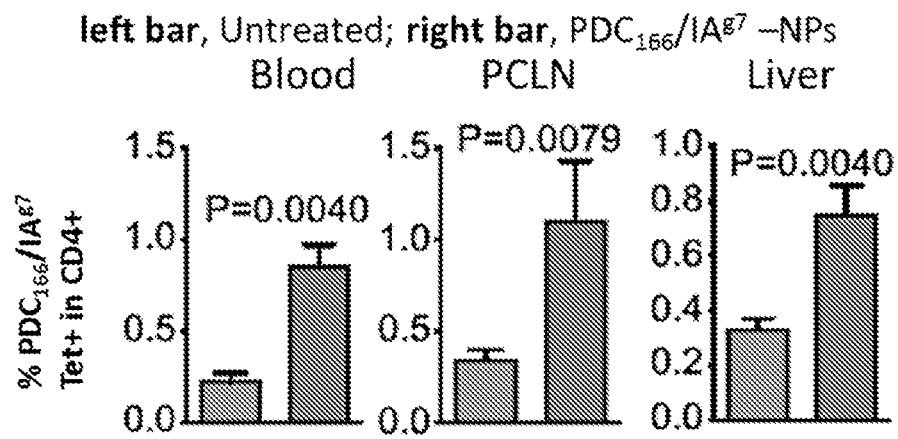
FIGS. 8F-8K show percentages of tetramer+ cells (FIG. 8F), macroscopic PBC scores and liver weight (FIG. 8G), microscopic PBC scores (FIG. 8H), liver images (FIG. 8I), microscopic tumor scores (FIG. 8J) and survival rates (FIG. 8K) of untreated vs. $PDC_{166-181}/IA^{g7}$-NP-treated NOD.c3c4 (n=5/group) or untreated Balb/c (n=7) injected with CT26 cells.
Figure 8G:
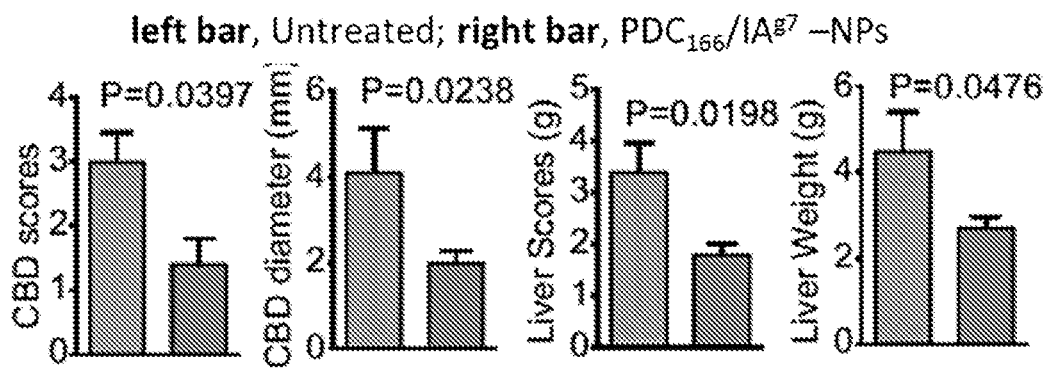
Figure 8H:
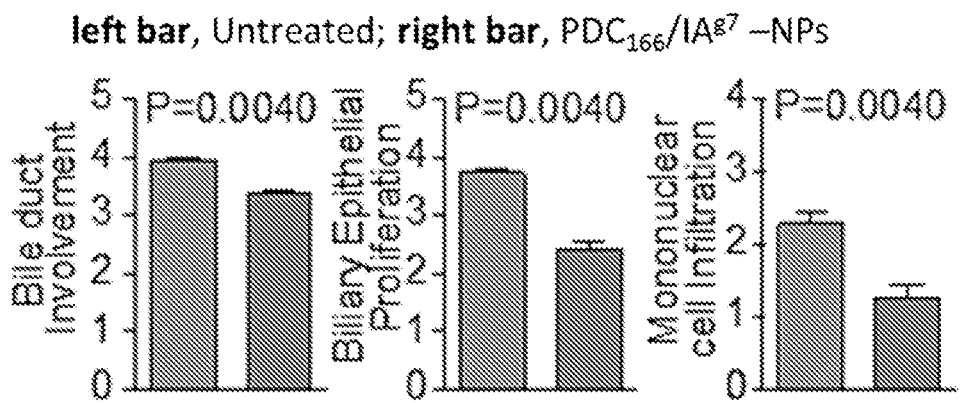
Figure 8I:
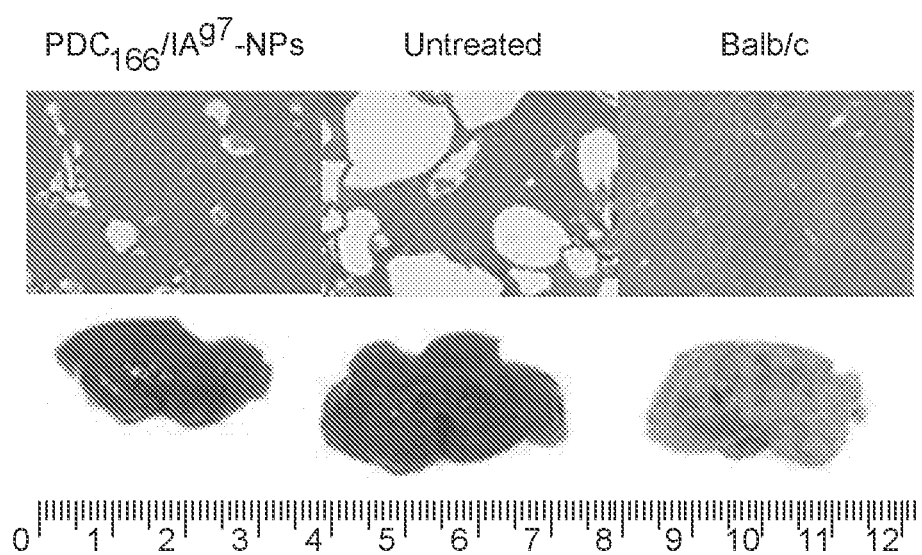
Figure 8J:
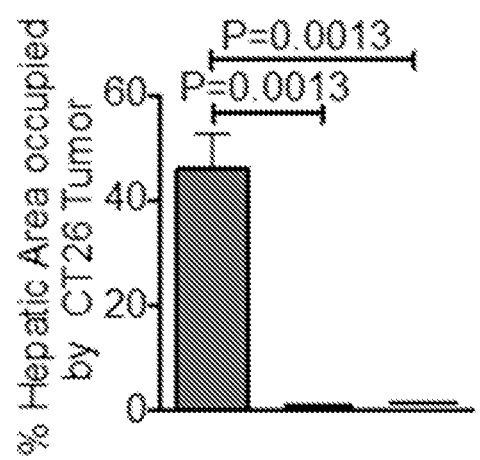
Figure 8K:
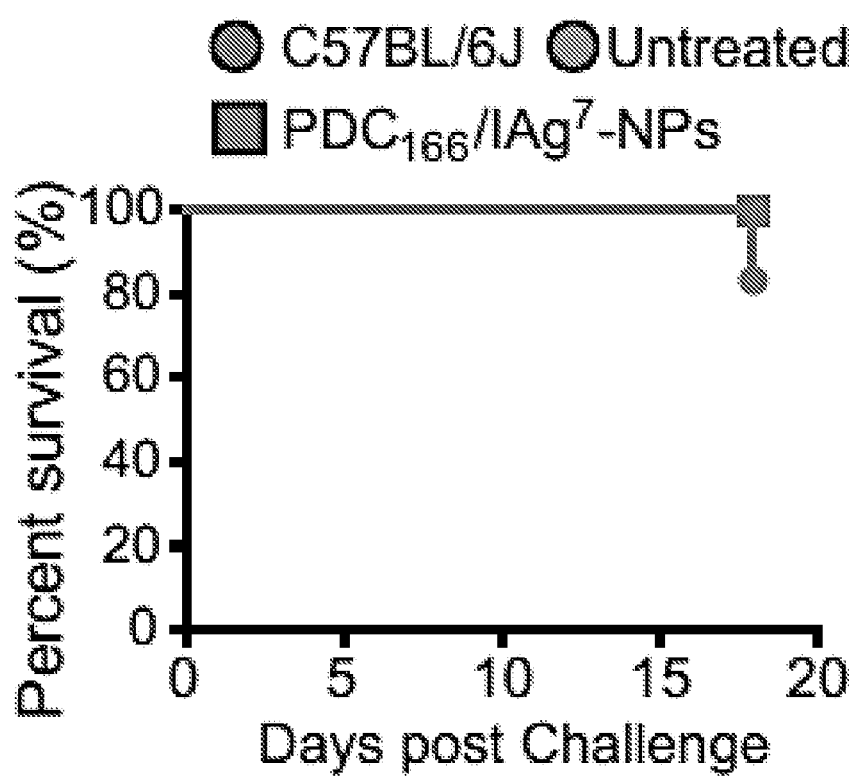
Figure 8L:
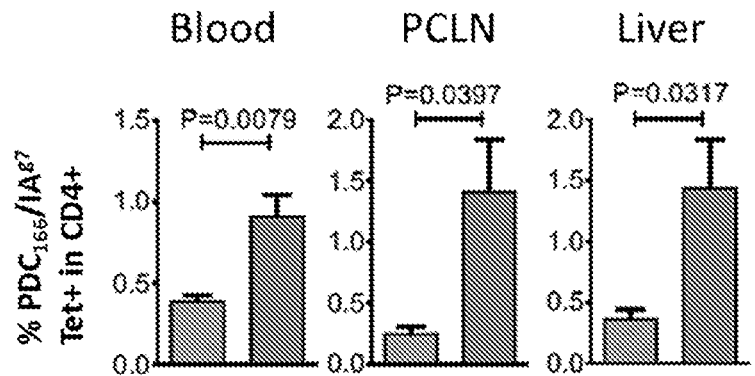
FIGS. 8L-8P show percentages of tetramer+ cells (FIG. 8L), macroscopic (FIG. 8M) and microscopic PBC scores (FIG. 8N), and liver weight and metastasis number (FIG. 8O), and liver images (FIG. 8P) of untreated vs. $PDC_{166-181}/IA^{g7}$-NP-treated NOD.c3c4 (n=5 and 4) or untreated B6 (n=6) injected with B16/F10 cells.
Figure 8M:
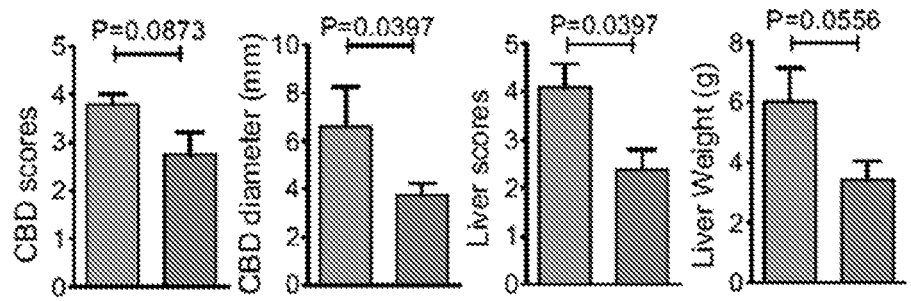
Figure 8N:
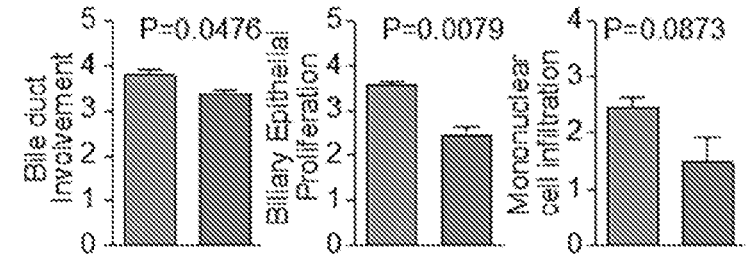
Figure 8O:
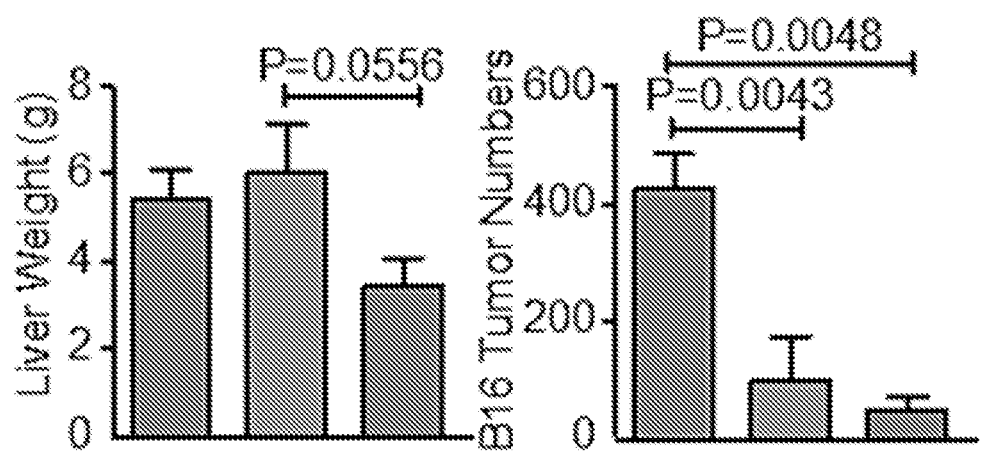
Figure 8P:
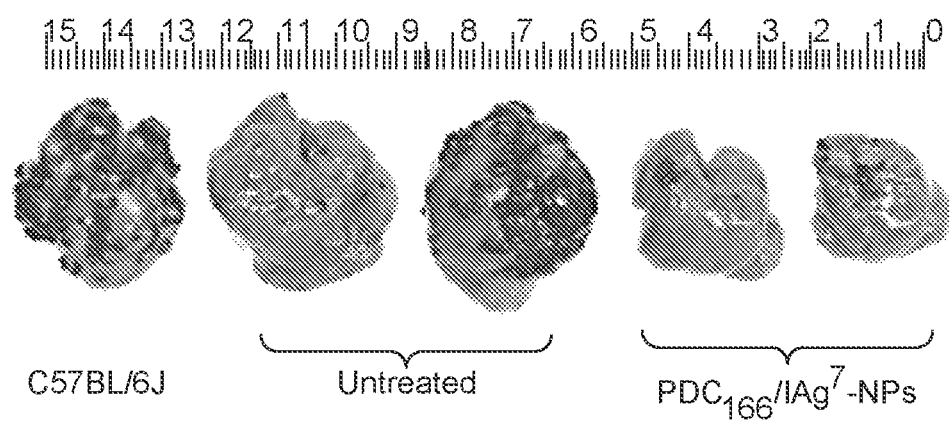
Figure 8Q:
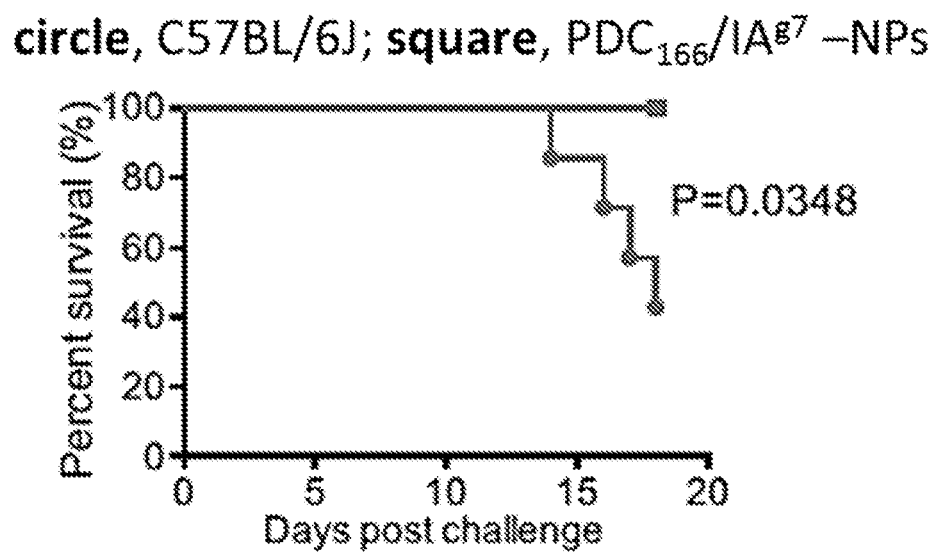
FIG. 8Q shows the survival rates of the mice in FIGS. 8L-8P. Data correspond to mean±SEM. P values were compared via Mann-Whitney U except for K, Q (log-rank) or C (two-way ANOVA).

PDC-E2$_{166-181}$/IA$^{g7}$-NP-treated and untreated NOD.c3c4 mice also produced similar titers of anti-dinitrophenyl (DNP) antibodies upon immunization with the hapten-carrier conjugate DNP-keyhole limpet haemocyanin (KLH) (FIG. 8E).

Lastly, systemic expansion and liver accumulation of PBC-suppressing PDC-E2-specific TR1-like CD4+ T-cells (FIGS. 8F and 8L) did not impair the ability of treated NOD.c3c4 mice to mount immune responses against allogeneic colon carcinoma (CT26) and melanoma (B16) liver metastases arising upon intra-splenic injection, as compared to untreated NOD.c3c4 mice or syngeneic hosts (Balb/c and C57BL/6J, respectively) (FIGS. 8F-8K and 8L-8Q). Thus, despite targeting a ubiquitously expressed antigen, PDC-E2$_{166-181}$/IA$^{g7}$-specific TR1 cells do not impair immunity against foreign or tumor antigens.

Example 9—Humanized Mice with PBC

DRB4*0101 and DRB1*0801 have been associated with PBC in some studies. To ascertain the HLA haplotypic diversity in PBC, we did high-resolution HLA-DRB1-typing of 154 patients with PBC from Spain. 40.3% of patients expressed DRB1*0701, 25% were DRB1*0301+ and 14% were DRB1*0801+. Since DRB1*0701+ and haplotypes carrying other DRB1 alleles carry the oligomorphic HLA-DRB4 locus, we also typed these patients for DRB4*0101. 61.7% of all PBC patients carried the DRB4*0101 allele.

Several T-cell epitopes from PDC-E2 binding to two of these HLA-DRB types (DRB4*0101 and DRB1*0801) have been described, including PDC-E2$_{249-262}$ (GDLLAEIETDKATI (SEQ ID NO:9); DRB4*0101-binder), PDC-E2$_{122-135}$ (GDLIAEVETDKATV (SEQ ID NO:8); also DRB4*0101-binder), PDC-E2$_{249-263}$ (GDLLAEIETDKATIG (SEQ ID NO:10); DRB1*0801) and PDC-E2$_{629-643}$ (AQWLAEFRKYLEKPI (SEQ ID NO:7); DRB1*0801). We therefore expressed and purified PDC-E2$_{122-135}$/DRB4*0101, PDC-E2$_{249-262}$/DRB4*0101, and PDC-E2$_{629-643}$/DRB1*0801 complexes and produced iron oxide nanoparticles displaying each of these complexes, as described.

Figure 9A:
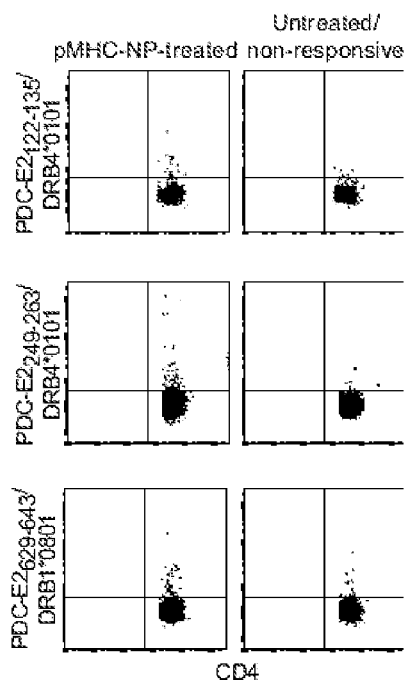
FIG. 9A shows representative tetramer stains in NSG hosts engrafted with PBMCs from DRB4*0101+ PBC patients and treated with three different PBC-relevant pMHC-NPs.
Figure 9B:
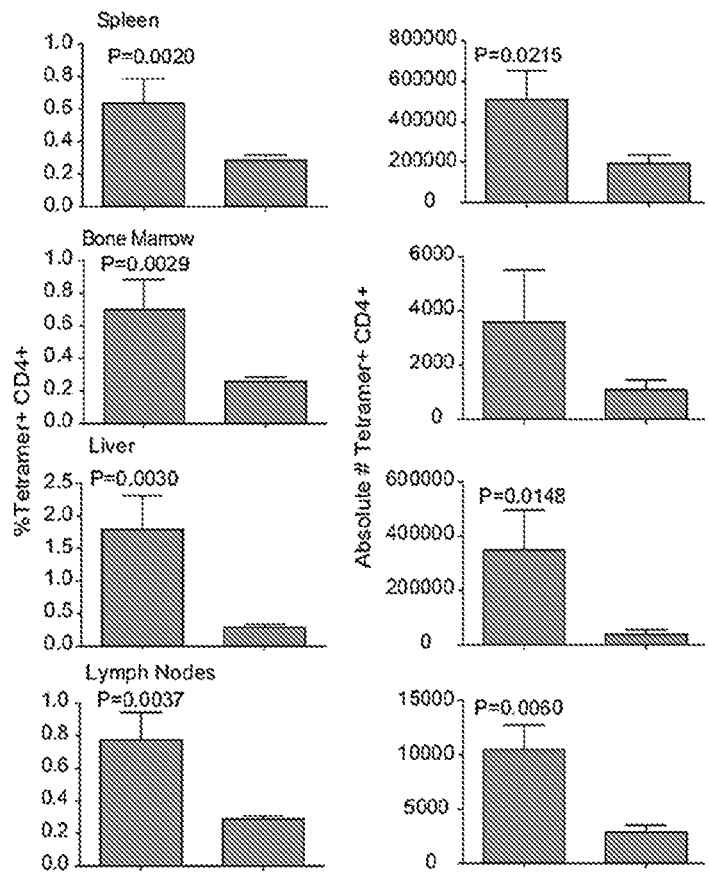
FIG. 9B shows average percentages and absolute numbers of tetramer+CD4+ cells in responsive vs. unresponsive pMHC-NP-treated mice or untreated littermates.
Figure 9C:
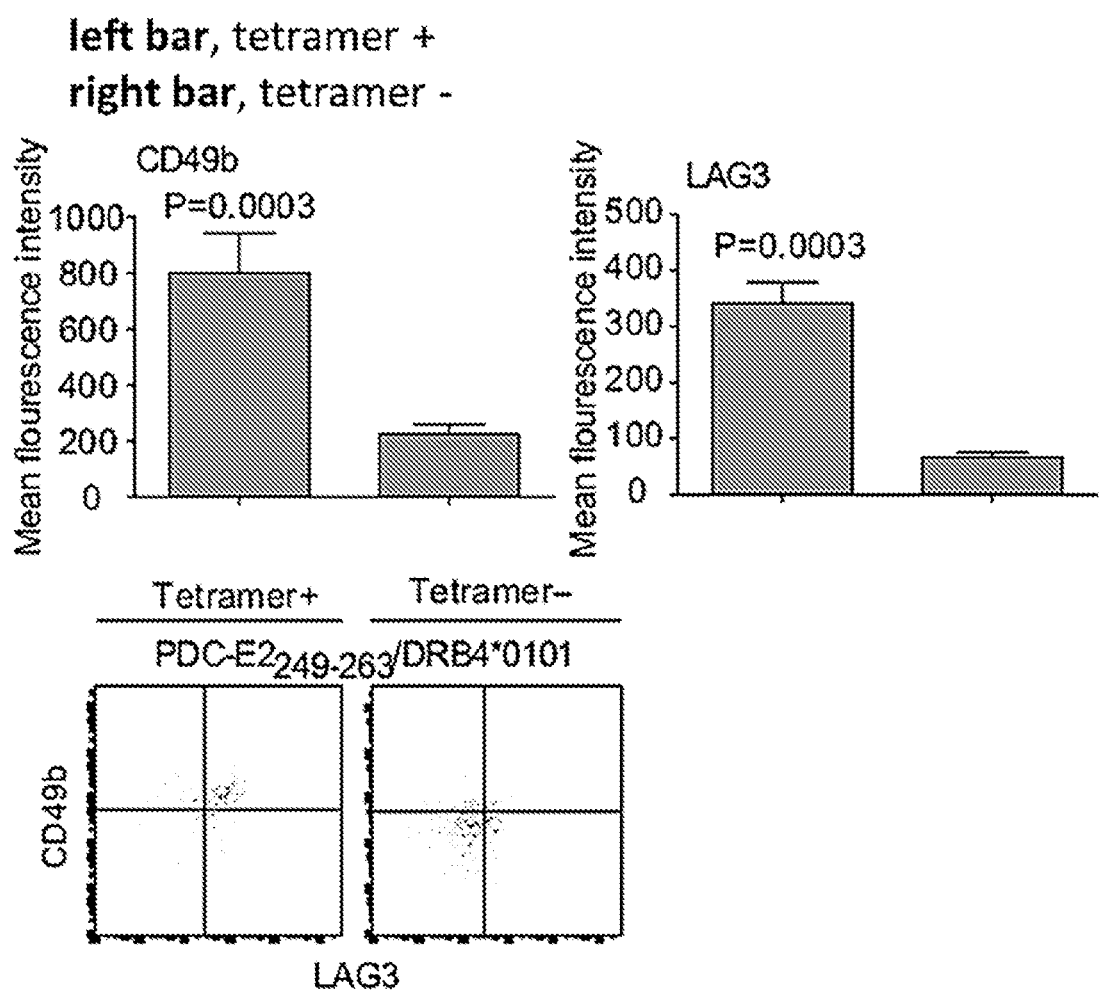
FIG. 9C shows mean fluorescence intensity values (top) and two-dimensional FACS plots (bottom) for the TR1 markers CD49b and LAG3 in the mice studied in FIGS. 9A-B.

To investigate the translational significance of the above observations, we tested the ability of these three human PBC-relevant pMHC class II-NPs to expand cognate TR1-like CD4+ T-cells in NOD.scid/Il2rg$^{-/-}$ (NSG) hosts reconstituted with PBMCs from 11 DRB4*0101+ and 5 DRB1*0801+ PBC patients (PBL-NSG mice, Tables 2, 3 and 4). PBMC-transfused NSG hosts were then treated with 8-10 doses of 20 µg pMHC-NPs intravenous (twice/week for 5 weeks). One mouse did not engraft and three others died from GvHD prior to termination of treatment. As controls, we transfused a second mouse per donor and treated it with control (non-pMHC-coated NPs). Expansions of cognate CD4+ T-cells were analyzed in the spleens, liver, portal/celiac and axillary lymph nodes. We saw expansion of tetramer+CD49b+LAG-3+CD4+ T-cells in the spleen and/or liver and LNs from all 6/6 PBL-NSG mice treated with PDC-E2$_{122-135}$/DRB4*0101-NPs, 5/6 PBL-NSG mice treated with PDC-E2$_{249-262}$/DRB4*0101-NPs and 4/5 PBL-NSG mice treated with PDC-E2$_{629-643}$/DRB1*0801-NPs vs. the untreated controls (Tables 2, 3, and 4). Treated responsive mice had significantly higher percentages and absolute numbers of tetramer+ cells in spleen, liver and lymph nodes (FIGS. 9A and 9B) than control NP-treated or unresponsive mice, and these cells expressed the TR1 markers CD49b and LAG-3 (FIG. 9C).

TABLE 2

Table 2 hPDC-E2(122-135)-DRB4-PFM-010616 (30 mcg/dose).

| | | | | Spleen | | Liver | | LN | | |
|---|---|---|---|---|---|---|---|---|---|---|
| ID | Gender | Age (yr) | Anti-mitochondrial Abs | % hCD4 Treated # of cells | % hCD4 Untreated # of cells | % hCD4 Treated # of cells | % hCD4 Untreated # of cells | % hCD4 Treated # of cells | % hCD4 Untreated # of cells | Outcome |
| B013 | F | 79 | + | 0.055 | 0.303 | 2.288 | 0.302 | 0.863 | 0.274 | + |
| | | | | | | | | (A) | | |
| | | | | 63756 | 141561 | 300444 | 39069 | 23760 | 154 | |
| B009 | F | 76 | + | 1.253 | 0.291 | 0.199 | 0.307 | * | | + |
| | | | | | (249-NP) | | (249-NP) | | | |
| | | | | 732729 | 308949 | 7047 | 11853 | * | | |
| B005 | M | 74 | + | | | No engraftment | | | | |
| B001 | M | 59 | + | 0.319 | 0.296 | 1.625 | 0.296 | 1.082 | 0.312 | + |
| | | | | | | | | (A) | | |
| | | | | 186539 | 291863 | 256354 | 62871 | 28524 | 1874 | |
| B021 | F | 68 | + | 0.767 | 0.309 | 0.343 | 0.296 | 0.728 | 0.3 | + |
| | | | | | | | | (A) | | |
| | | | | 849816 | 509331 | 18691 | 28993 | 15072 | 5721 | |
| B011 | F | 71 | + | 0.169 | 0.304 | 0.091 | 0.294 | 0.425 | 0.291 | + |
| | | | | | | | | (L) | | |
| | | | | 202383 | 209370 | 6658 | 151772 | 120 | 755 | |
| B018 | F | 56 | + | | | Dead | | | | |
| B012 | F | 71 | + | 0.709 | 0.298 | | | 0.722 | 0.290 | + |
| | | | | | | | | (A) | (A) | |
| | | | | 341920 | 124050 | ND | | 5602 | 2101 | |

DRB4*01:01 patients

TABLE 3

Table 3 hPDC-E2(249-262)-DRB4-PFM-010616 (40 mcg/dose).

| | | | | Spleen | | Liver | | LN | | |
|---|---|---|---|---|---|---|---|---|---|---|
| ID | Gender | Age (yr) | Anti-mitochondrial Abs | % hCD4 Treated # of cells | % hCD4 Untreated # of cells | % hCD4 Treated # of cells | % hCD4 Untreated # of cells | % hCD4 Treated # of cells | % hCD4 Untreated # of cells | Outcome |
| B013 | F | 79 | + | 0.078 | 0.31 | 4.925 | 0.295 | 0.621 (L) | 0.245 | + |
| | | | | 105174 | 164589 | 1124257 | 35712 | 33121 | 275 | |
| B009 | F | 76 | + | 0.028 | 0.307 (122-NP) | 0.515 | 0.297 (122-NP) | * | | + |
| | | | | 31807 | 192099 | 20215 | 10866 | * | | |
| B004 | F | 63 | + | 0.427 | 0.294 | 0.094 | 0.315 | 0.089 (A) | 0.293 | + |
| | | | | 268565 | 228575 | 2990 | 299574 | 526 | 11251 | |
| B012 | F | 70 | + | 0.264 | 0.297 | 0.078 | 0.3 | 0.059 (L) | 0.313 | − |
| | | | | 41467 | 147568 | 1034 | 24584 | 1513 | 6160 | |
| B001 | M | 59 | + | | | Dead | | | | |
| B021 | F | 68 | + | 1.612 | 0.31 | 1.943 | 0.289 | 2.589 (L) | 0.32 | + |
| | | | | 1368420 | 514802 | 1174100 | 35690 | 9491 | 788 | |
| B019 | F | 73 | + | | | Dead | | | | |
| B014 | F | 72 | + | 0.709 | 0.295 | 0.588 | 0.305 | 1.096 (A) | 0.299 | + |
| | | | | 604820 | 162521 | 76559 | 30198 | 5557 | 1271 | |
| | | | | 416501 | 181855 | 4960 | 4517 | 3740 | 2232 | |

DRB4*01:01 patients

TABLE 4

Table 4 hPDC-E2(629-643)-DR8-PFM-010616 (30 mcg/dose).

| | | | | Spleen | | Liver | | LN | | |
|---|---|---|---|---|---|---|---|---|---|---|
| ID | Gender | Age (yr) | Anti-mitochondrial Abs | % hCD4 Treated # of cells | % hCD4 Untreated # of cells | % hCD4 Treated # of cells | % hCD4 Untreated # of cells | % hCD4 Treated # of cells | % hCD4 Untreated # of cells | Outcome |
| B022 | F | 72 | + | 0.024 | 0.3 | 0.619 | 0.293 | No cells | 0.295 (L) | + |
| | | | | 662 | 48190 | 26 | 29984 | | 260 | |
| B021 | F | 68 | + | 0.725 | 0.317 | 3.185 | 0.3 | 1.103 (A) | 0.301 | + |
| | | | | 1095456 | 562089 | 455716 | 36134 | 22752 | 8080 | |
| B020 | F | 70 | + | 0.303 | 0.308 | 0.18 | 0.297 | No cells | | − |
| | | | | 38207 | 114160 | 19765 | 46701 | | | |
| B025 | F | 69 | + | 0.404 | 0.308 | 2.895 | 0.294 | 0.501 (A) | 0.319 (A) | + |
| | | | | 59552 | 49721 | 78551 | 8747 | 740 | 466 | |
| B023 | F | 75 | + | 0.745 | 0.292 | 0.283 | 0.292 | 0.371 (A) | 0.297 | + |

DRB1*08:01 patients

Example 10—Disease Versus Organ Specificity

Given the large autoantigenic load of an organ such as the liver as compared to smaller organs, like the endocrine pancreas, and the fact that PDC-E2 is an autoantigen expressed in virtually all cell types, our results begged the question of whether PBC-relevant nanomedicines (i.e. PDC-E2$_{166-181}$/IA$^{g7}$-NP) are disease (PBC)- or organ (liver)- specific, or also able to blunt liver-distal autoimmune inflammation.

Primary sclerosing cholangitis (PSC) is a chronic cholestatic disease characterized by inflammation of intra- and extra-hepatic bile ducts leading to a fibro-obliterative cholangitis with periductal fibrosis around medium and large bile ducts and degenerative changes of the biliary epithelium, which progresses to portal and biliary cirrhosis and finally liver cirrhosis. Human PSC is frequently associated with inflammatory bowel disease and accompanied by a high prevalence of atypical perinuclear anti-neutrophil cytoplasmic (pANCA) but not anti-mitochondrial autoantibodies. See Fickert, P. et al. Characterization of animal models for primary sclerosing cholangitis (PSC). *J. Hepatol.* 60, 1290-1303. Abcb4 gene knockout mice spontaneously develop a form of sclerosing cholangitis that is remarkably similar to human PSC and is caused by damage of bile duct cells by impaired biliary phospholipid secretion. See Pollheimer, M. J. & Fickert, P. Animal models in primary biliary cirrhosis and primary sclerosing cholangitis. *Clin. Rev. Allergy Immunol.* 48, 207-217, doi: 10.1007/s12016-014-8442-y (2015).

Autoimmune Hepatitis (AIH) is characterized by a portal mononuclear cell infiltration of the liver parenchyma that is associated with presence of anti-nuclear and/or smooth muscle (AIH type 1) or anti-liver kidney microsomal or anti-liver cytosol type 1 autoantibodies, which specifically target the microsomal cytochrome P450IID6 (CYP2D6) or formiminotransferase cyclodeaminase (FTCD), respectively (AIH Type 2). See Longhi, M. S. et al. Aetiopathogenesis of autoimmune hepatitis. *J. Autoimmun.* 34, 7-14. Recently, it has been shown that infection of NOD mice with replication-defective adenoviruses encoding the human liver autoantigen formiminotransferase cyclodeaminase (Ad-FTCD) triggers a form of chronic autoimmune hepatitis that resembles AIH type 2. See Hardtke-Wolenski, M. et al. Genetic predisposition and environmental danger signals initiate chronic autoimmune hepatitis driven by CD4+ T cells. *Hepatology* 58, 718-728.

The large bile duct and parenchymal liver damage that underlie PSC and AIH may trigger the release of PDC-E2 and the priming of cognate autoreactive CD4+ T-cells capable of responding to PDC-E2$_{166-181}$/IA$^{g7}$-NP therapy. If so, therapy should trigger the expansion of TR1-like PDC-E2$_{166-181}$/IA$^{g7}$-specific CD4+ T-cells and suppression of local inflammation upon recognition of local and proximal PDC-E2-loaded APCs. Alternatively, the amount of PDC-E2 shed into the inflammatory milieu in PSC and/or AIH may be insufficient to generate PDC-E2166-181/IA$^{g7}$-experienced CD4+ T-cells, hence an immunological and therapeutic response to PDC-E2$_{166-181}$/IA$^{g7}$-NPs.

To test these alternative possibilities, we first investigated the ability of PDC-E2$_{166-181}$/IA$^{g7}$-NPs to trigger the expansion of cognate TR1-like CD4+ T-cells and revert PSC in NOD.Abcb4$^{-/-}$ mice. Remarkably, PDC-E2$_{166-181}$/IA$^{g7}$-NP triggered the systemic expansion of cognate TR1-like CD4+ T-cells in these animals and reverted established disease, as compared to control NP-treated controls as shown in FIGS. 10A-10B and FIGS. 11A and 11B.

Figure 10A:
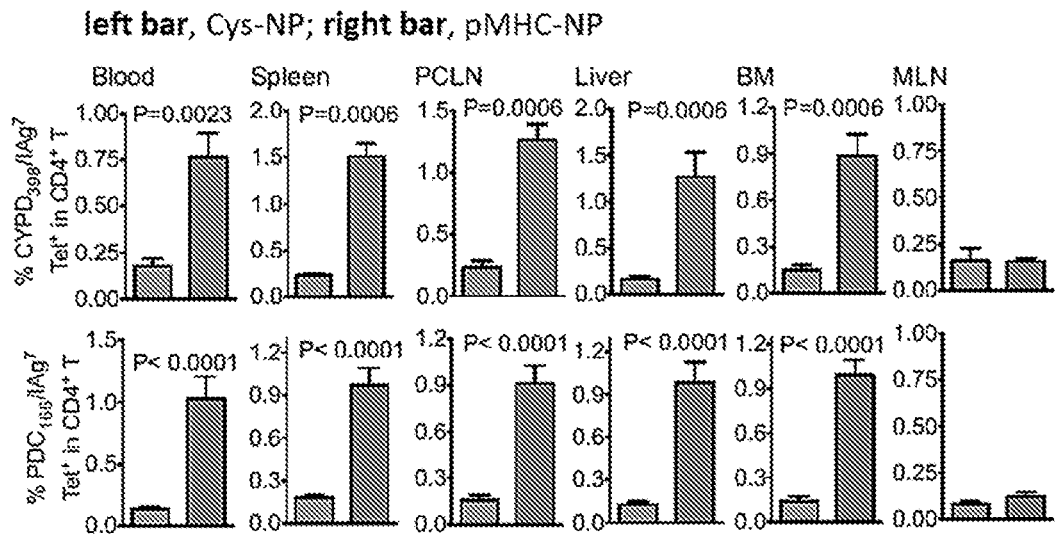
FIG. 10A shows percentage of tetramer+CD4+ T-cells in NOD.Abcb4-/- mice in response to pMHC-NP therapy.
Figure 10B:
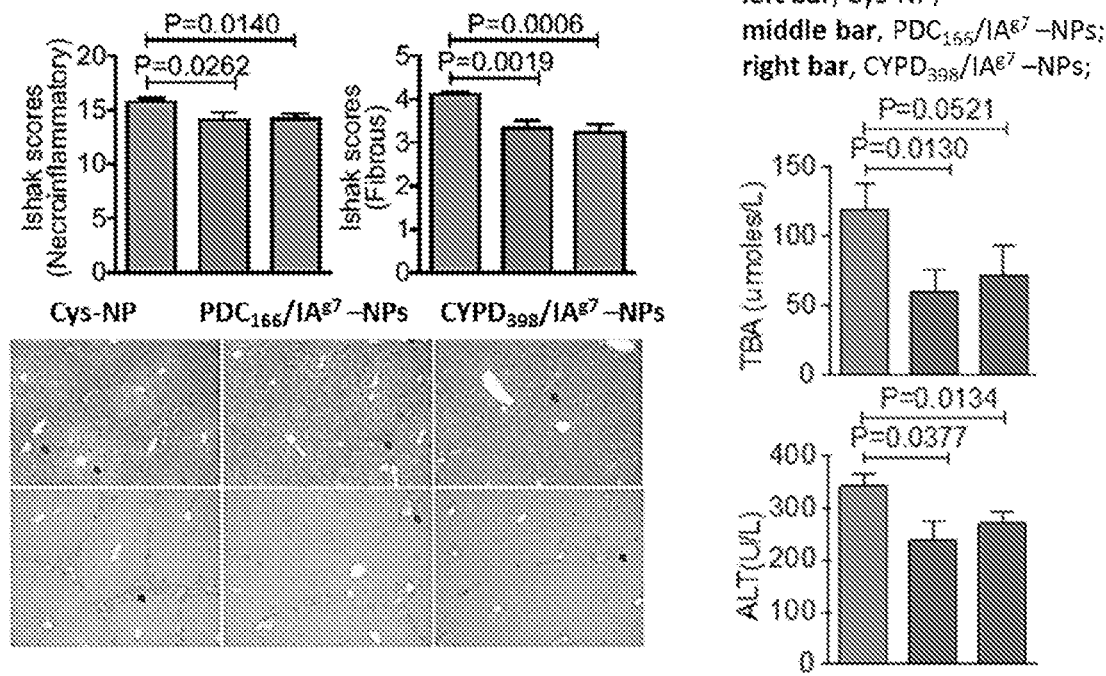
FIG. 10B shows average Primary Sclerosing Cholangitis scores (top) and representative H&E stained or picrosirius-stained liver sections (bottom), and TBA and ALT (right column) corresponding to the mice studied in FIG. 10A.
Figure 10C:
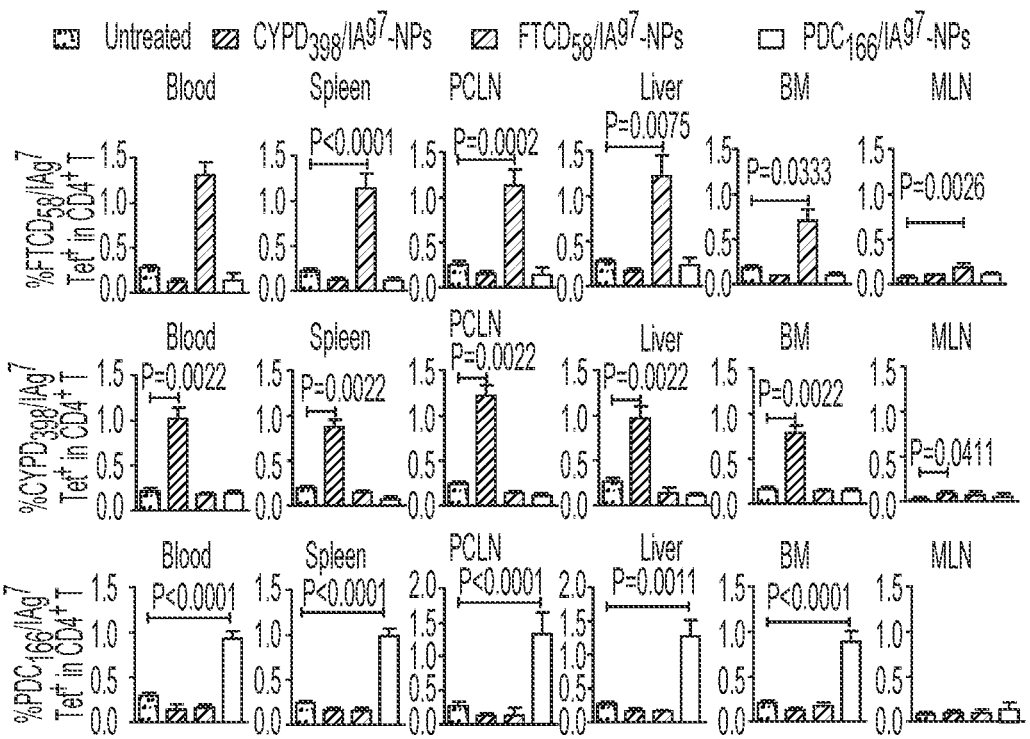
FIG. 10C shows percentage of tetramer+CD4+ T-cells in NOD mice infected with an hFTCD-encoding Adenovirus (developing AIH) and treated with three different pMHC-NP types.
Figure 10D:
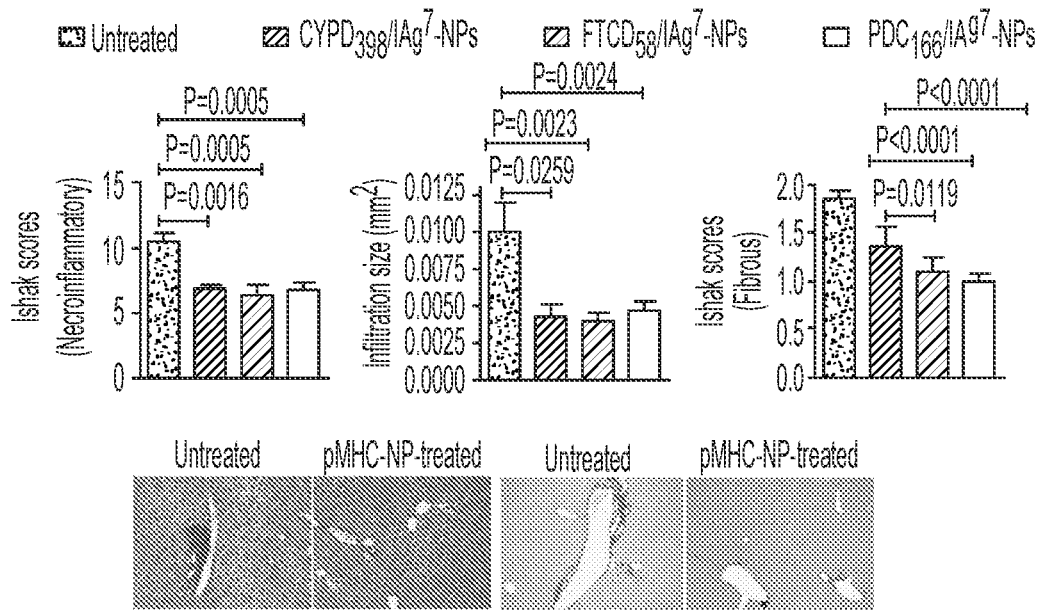
FIG. 10D shows autoimmune hepatitis histopathological scores (top) and representative H&D and picrosirius liver stained sections (bottom) for the mice studied in FIG. 10C.
Figure 10E:
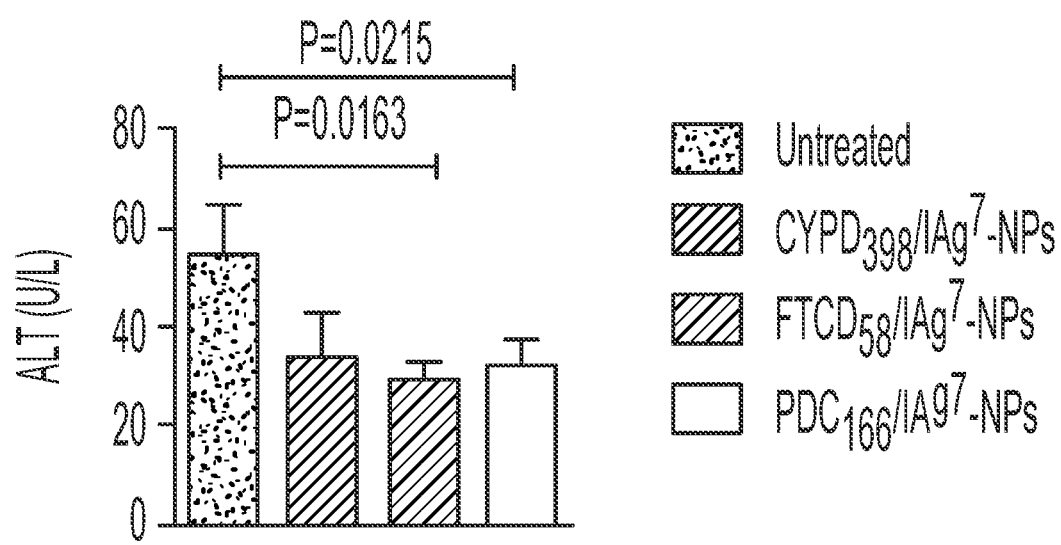
FIG. 10E shows serum ALT levels in the mice in FIG. 10C [n=11, 5, 9 and 10 mice (left to right); 2-3 experiments].
Figure 11A:
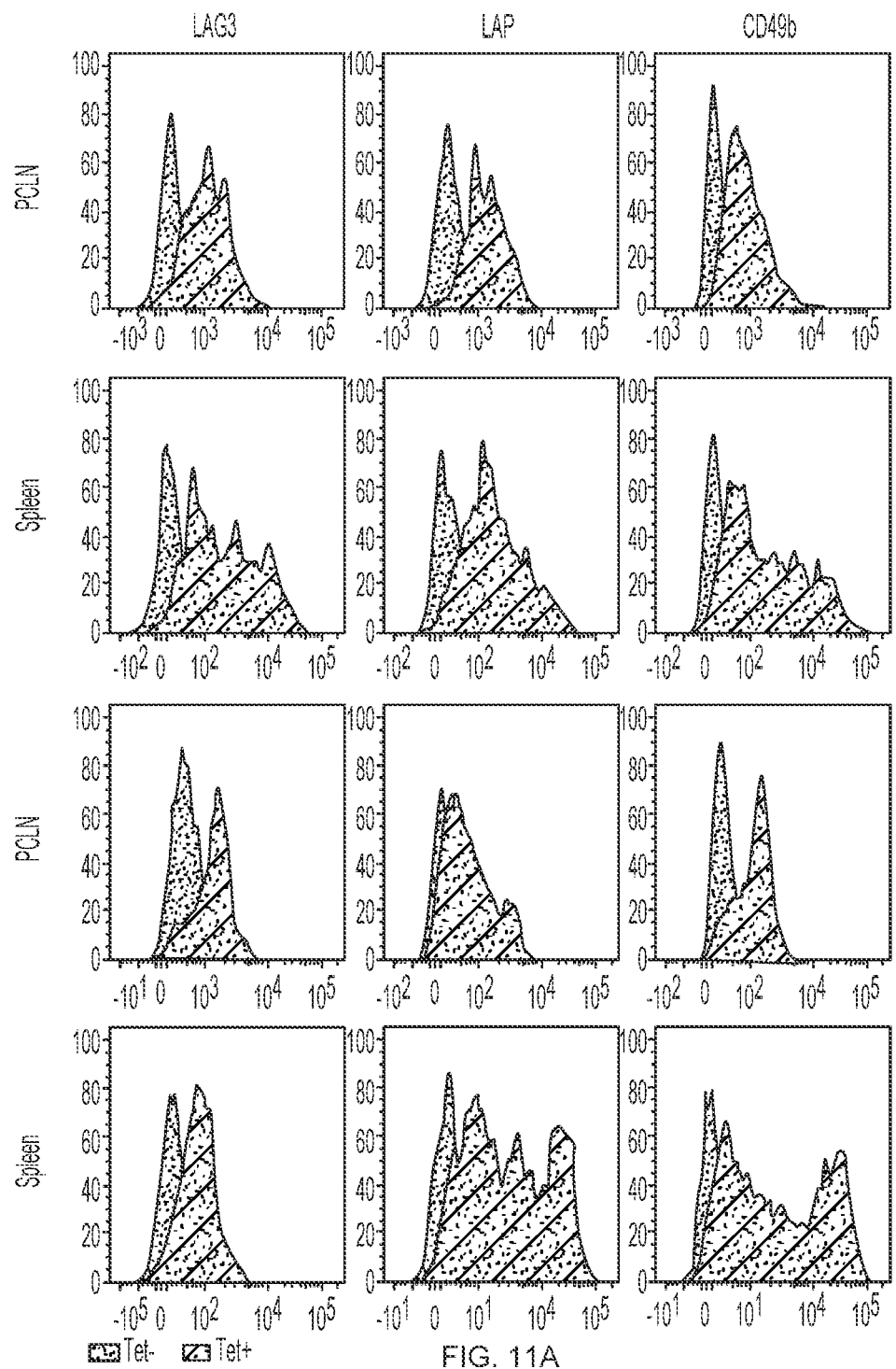
FIG. 11A shows representative FACS staining histograms.
Figure 11B:
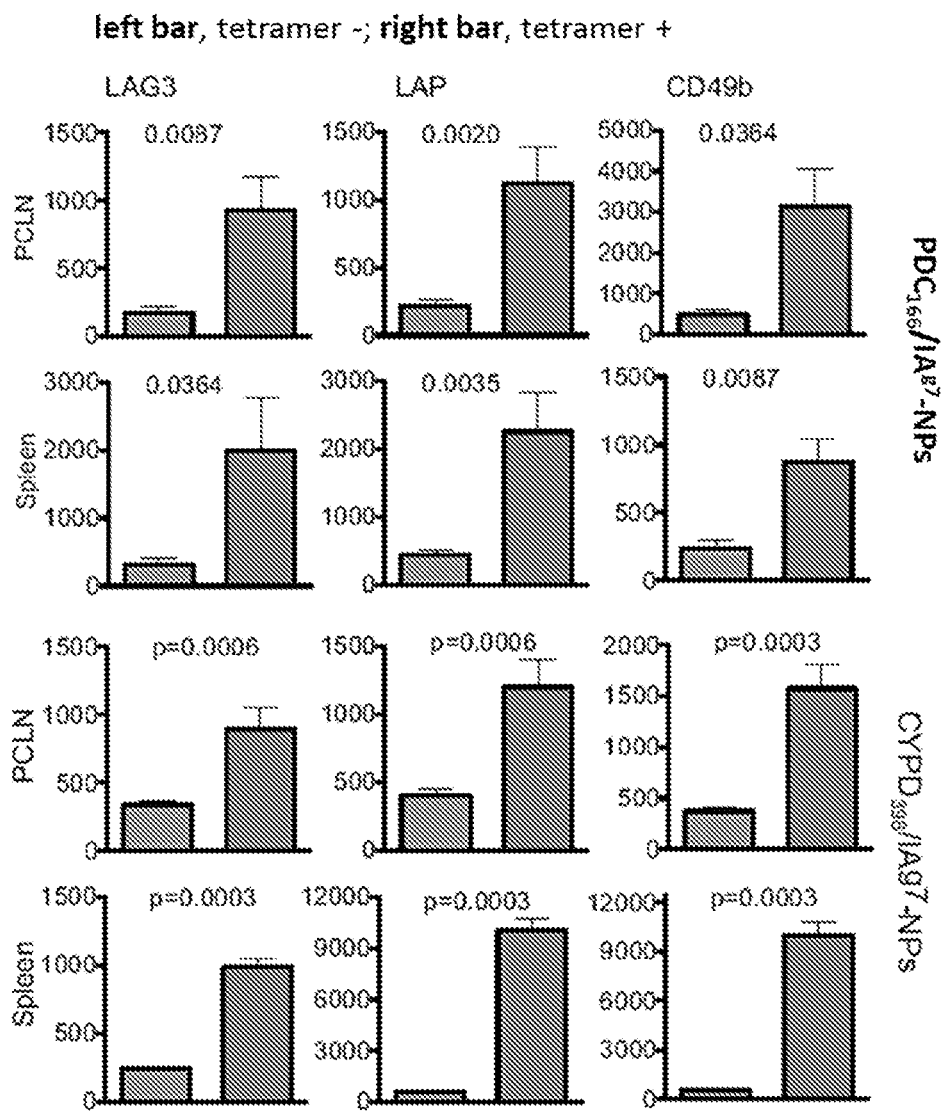
FIG. 11B shows average mean fluorescence intensity values for TR1 markers on tetramer+CD4+ vs. tetramer-CD4+ T-cells of NOD.Abcb4-/- mice (spontaneously developing PSC) treated with PBC- or AIH-relevant pMHC-NPs.
Figure 12A:
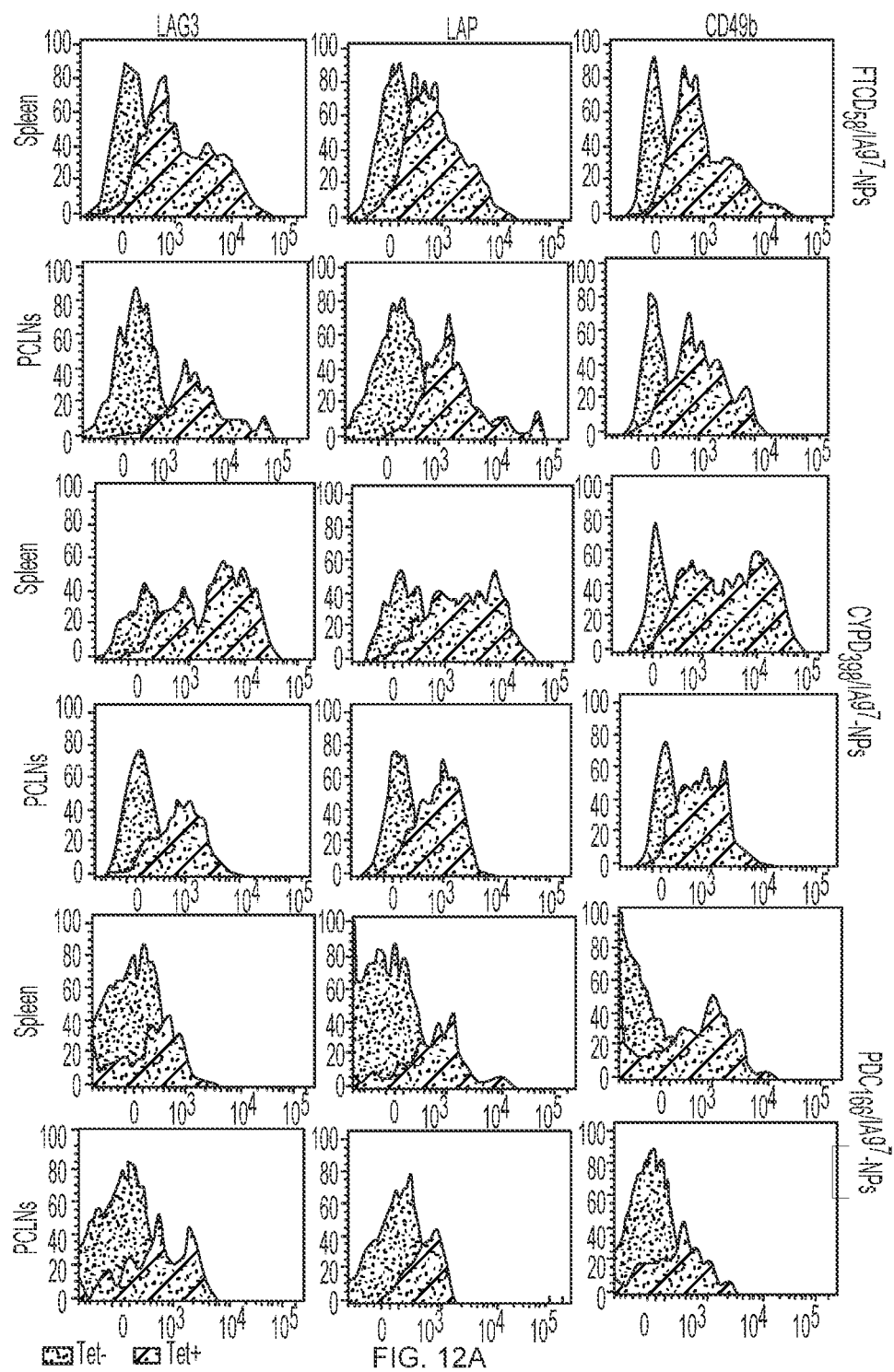
FIG. 12A shows representative FACS staining histograms.
Figure 12B:
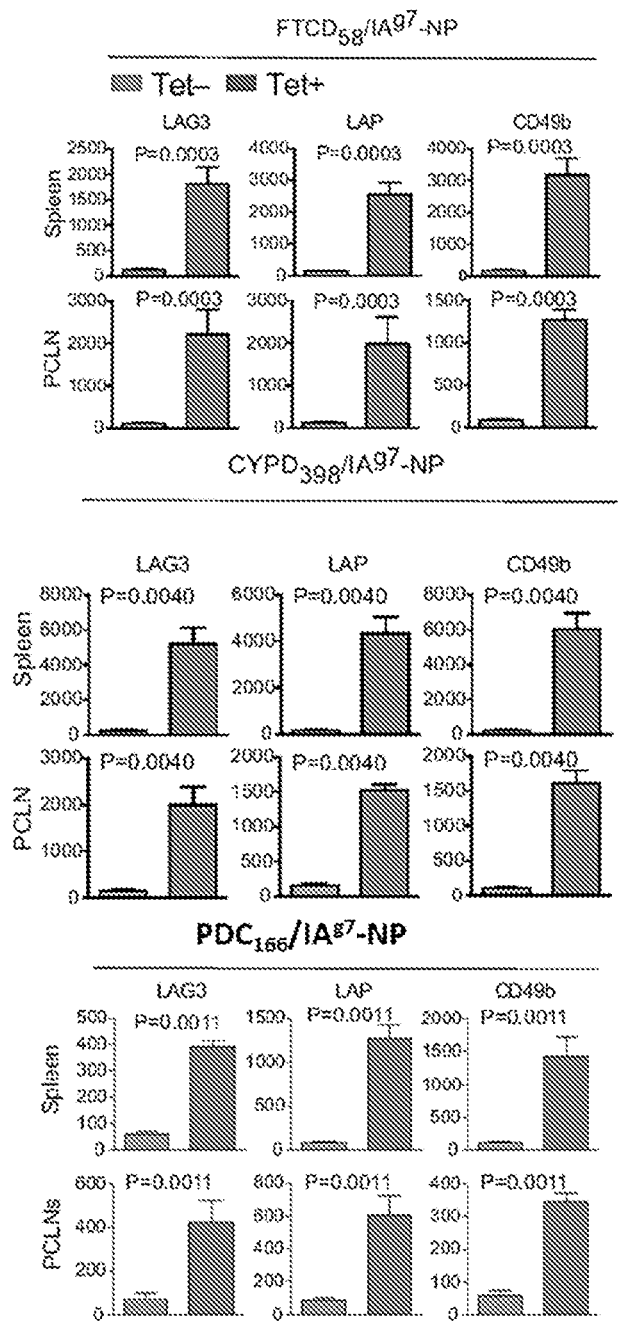
FIG. 12B shows average mean fluorescence intensity values for TR1 markers on tetramer+CD4+ vs. tetramer-CD4+ T-cells of NOD mice infected with an adenovirus encoding hFTCD (spontaneously developing AIH) treated with PBC- or AIH-relevant pMHC-NPs.

We next investigated whether this was also true in Ad-FTCD-induced AIH. We compared the pharmacodynamic and therapeutic activities of both mFTCD$_{58-72}$/IA$^{g7}$-NPs and CYPD$_{398-412}$/IA$^{g7}$-NPs (AIH-relevant) with those of PDC-E2$_{166-181}$/IA$^{g7}$-NPs (PBC-relevant) in NOD mice infected with Ad-FTCD. All three compounds triggered the formation and expansion of cognate TR1-like CD4+ T-cells in these animals to a similar extent (FIG. 10C and FIGS. 12A and 12B) as compared to untreated Ad-FTCD-infected animals, and this was accompanied by significant reductions in liver inflammation as shown in FIGS. 10C and 10D, and serum ALT levels as shown in FIG. 10E.

Figure 13A:
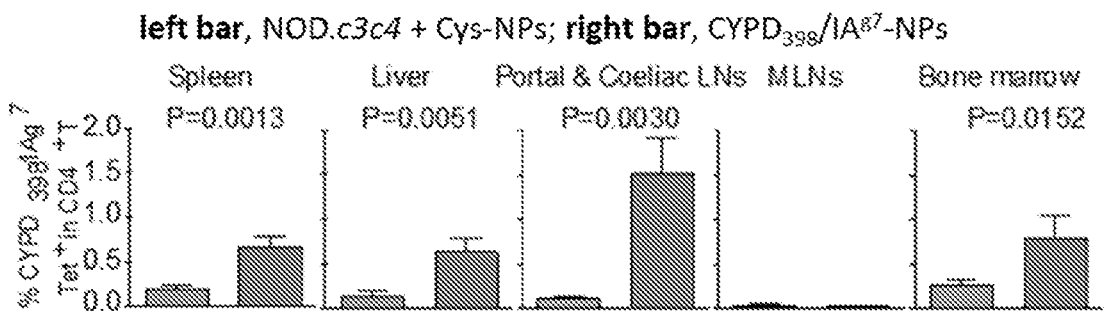
FIG. 13A shows percentage of tetramer+CD4+ T-cells in NOD.c3c4 mice treated with an AIH relevant pMHC-NP type.
Figure 13B:
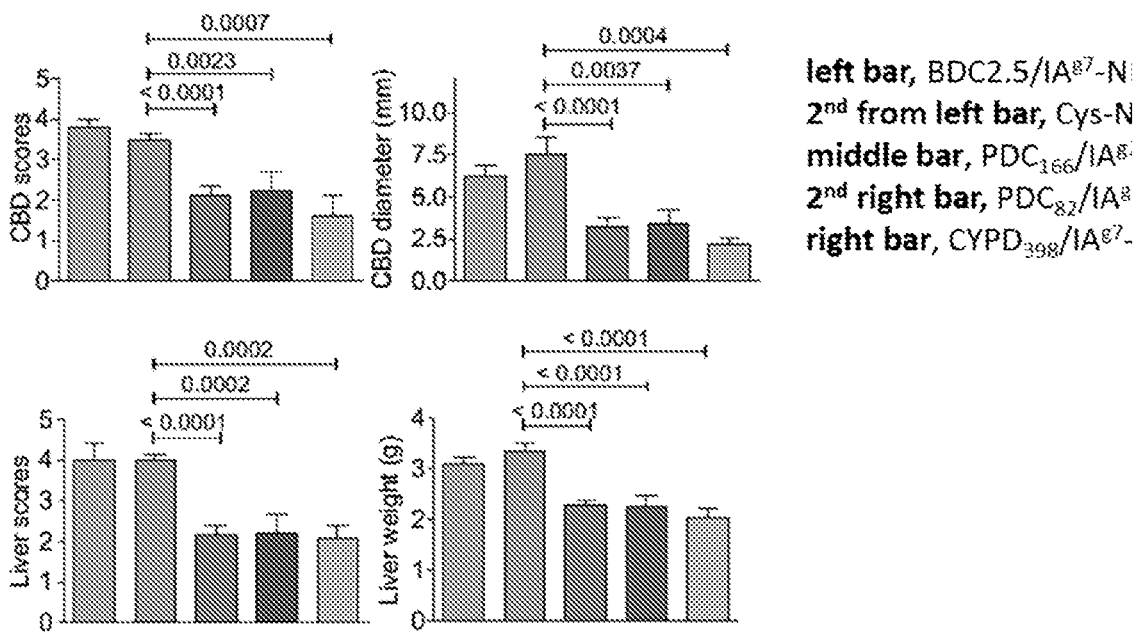
FIG. 13B shows average macroscopic liver scores in NOD.c3c4 mice treated with PBC-AIH- or TID-relevant pMHC-NP types.
Figure 13C:
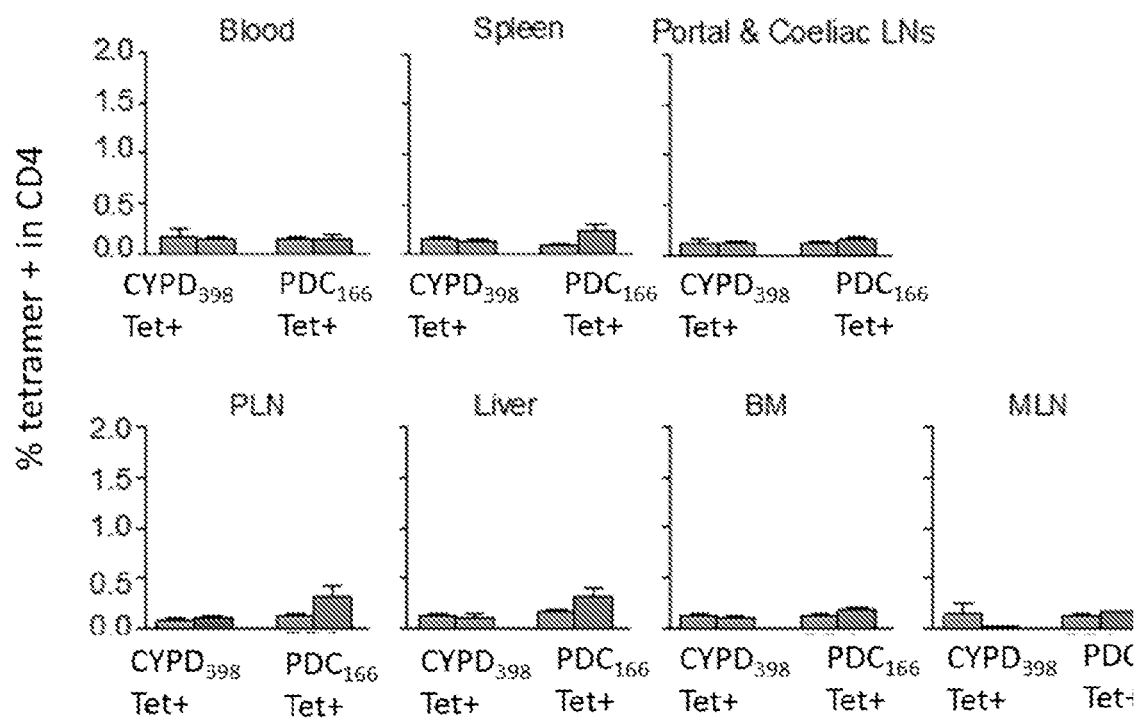
FIG. 13C shows percentage of tetramer+CD4+ T-cells in NOD mice treated with PBC- or AIH-relevant pMHC-NP types.

This ability of ubiquitous autoantigen-based pMHC-nanomedicines to blunt liver autoimmunity in an organ rather than disease-specific manner also occurred in NOD.c3c4 mice treated with CYPD$_{398-412}$/IA$^{g7}$-NPs (FIGS. 13A-13C). In fact, the latter were as efficient as PDC-E2$_{166-181}$/IA$^{g7}$-NPs at expanding cognate TR1 cells (FIG. 13A), and blunting PBC in 15 week-old mice (FIG. 13B). In contrast, neither PDC-E2$_{166-181}$/IA$^{g7}$-NPs nor CYPD$_{398-412}$/IA$^{g7}$-NPs triggered the expansion of cognate TR1 CD4+ T-cells in 10 week-old pre-diabetic NOD mice (FIG. 13C), unlike the case for beta cell-specific BDC2.5/IA$^{g7}$-, IGRP$_{4-22}$/IA$^{g7}$- or IGRP$_{128-145}$/IA$^{g7}$-NPs, presumably because the PDC-E2 and CYPD content in beta cells is insufficient to prime the activation of cognate CD4+ T-cells.

Collectively, these observations suggest that abundant levels of PDC-E2 (mitochondrial), CYPD2D6 and FTCD antigens (Golgi-resident or cytoplasmic, respectively) are delivered to local and proximal APCs upon hepatocyte (AIH) or bile duct epithelial cell damage (PBC and PSC), enabling autoreactive CD4+ T-cell priming, cognate TR1 cell generation by pMHC-NPs and suppression of local and proximal autoantigen-loaded APCs.

Example 11—Therapeutic Effects in Another PBC Model

Figure 14A:
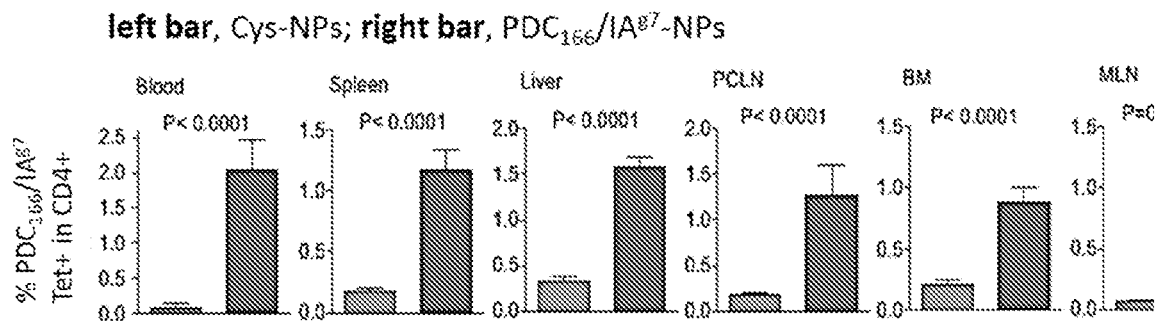
FIG. 14A shows percentages of tetramer+CD4+ T-cells in mice (males and females pooled) treated with Cys-NPs or $PDC_{166-181}/IA^{g7}$-NPs.
Figure 14B:
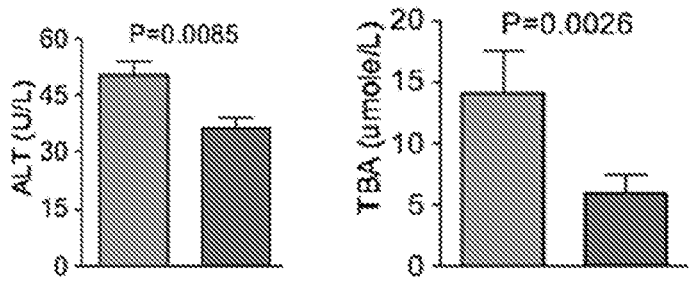
FIG. 14B shows serum TBA and ALT levels in the mice studied in A.
Figure 14C:
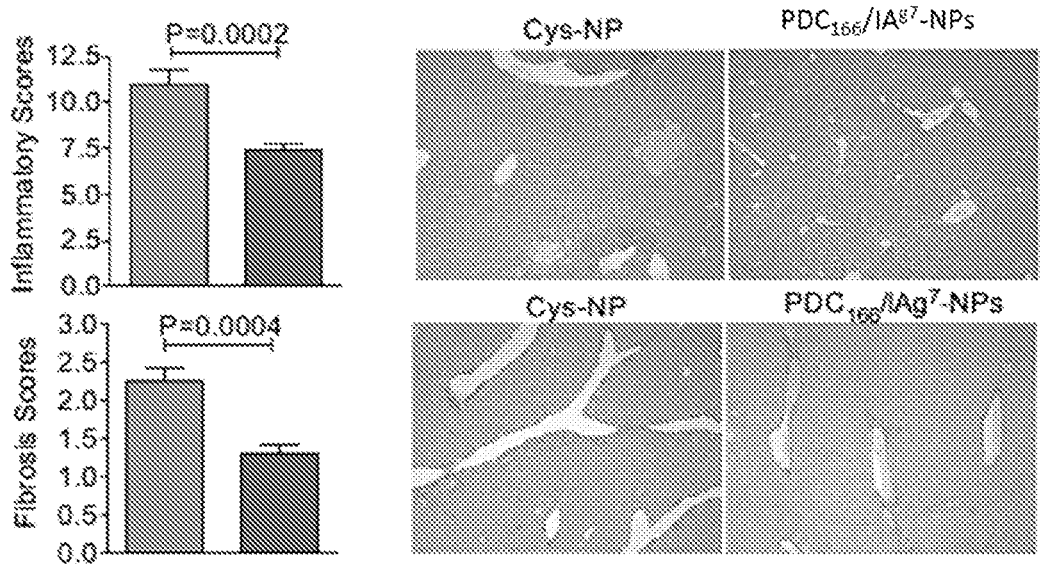
FIG. 14C shows microscopic scores of the female mice studied in A (left) and representative H&E (top right) and picrosirius-red-stained liver sections (bottom right). Data in FIGS. 14A-C correspond to n=7 and 12 mice/treatment type, respectively, from 2-3 experiments.

The NOD.c3c4 model does not fully recapitulate the immunopathology of human PBC, characterized by female prevalence, progression to liver fibrosis and absence of liver cyst formation. B6 mice carrying a deletion of the IFNγ 3'-untranslated region adenylate uridylate-rich element (ARE) (ARE-Del+/−) have a dysregulated Ifng locus, and develop a form of PBC that, like the human disease, primarily affects females and is associated with up-regulation of TBA, production of anti-PDC-E2 autoantibodies, portal duct and lobular liver inflammation, bile duct damage, granuloma formation and fibrosis. FIG. 14A-C show that treatment of (NODxB6.ARE-Del−/−) F1 mice with PDC-E2$_{166-181}$/IA$^{g7}$-NPs suppressed the upregulation of TBA and ALT levels, liver inflammation and fibrosis, as compared to mice treated with control NPs.

Figure 15A:
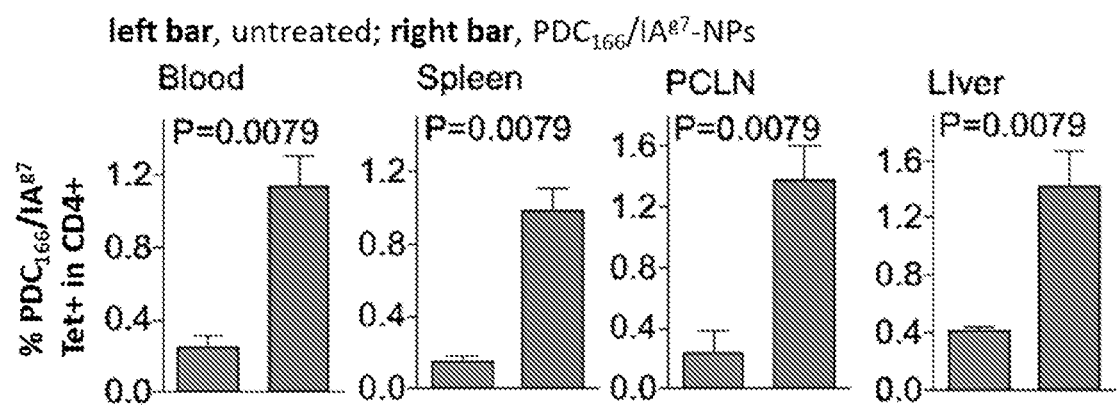
FIG. 15A shows average percentages of $PDC_{166-181}/IA^{g7}$ tetramer+CD4+ T-cells in blood and lymphoid organs of $PDC_{166-181}/IA^{g7}$ in NP-treated NOD.c3c4 mice 7 days after priming with HKx31 strain. Data correspond to n=4 and 5, respectively.

Example 12-Ubiquitous Autoantigen pMHCII-NPs Spare General Immunity Despite Harboring PDC-E2 Autoreactive TR1-Like CD4+ T-Cells PDC-E2$_{166-181}$/IA$^{g7}$-NP-treated or untreated NOD.c3c4 mice were infected with a laboratory strain of influenza (HKx31-H3N2-) i.p. to induce heterologous immunity against a lethal infection with an H1N1 strain of Influenza (PR8) given via the intranasal route. As shown in FIGS. 8B-8C, pMHCII-NP treated NOD.c3c4 mice mounted protective immunity against the PR8 infection, as documented by viral load in lung tissue and clinical signs of active infection, despite systemic presence of cognate TR1-like CD4+ T-cells as shown in FIG. 15A.

Figure 15B:
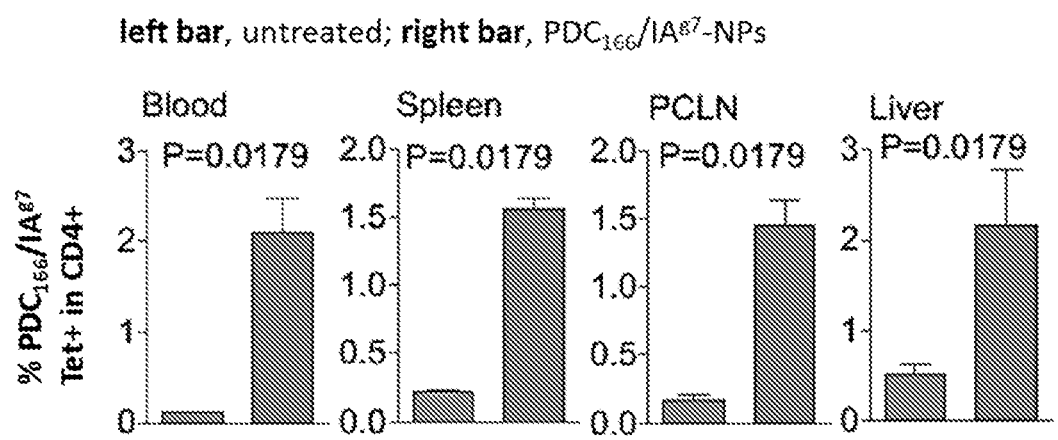
FIG. 15B shows average percentages of $PDC_{166-181}/IA^{g7}$ tetramer+CD4+ T-cells in blood and lymphoid organs of $PDC_{166-181}/A87$ in NP-treated NOD.c3c4 mice 14 days after infection with *Listeria*. Data correspond to n=3 and 5 mice, respectively. Data correspond the mean±SEM. P values were compared via Mann-Whitney U.

Similar results were obtained in mice infected with the intracellular pathogen *Listeria Monocytogenes* (LM). LM-infected PDC-E2$_{166-181}$/IA$^{g7}$-NP-treated and untreated NOD.c3c4 mice were equally efficient at clearing the bacteria from both the spleen and liver as shown in FIG. 8D, consistent with unimpaired immunity against this intracellular pathogen as shown in FIG. 15B.

Example 13—Ubiquitous Autoantigen pMHC-NPs Treat EAE in Mice

One question unanswered was whether these liver disease-relevant nanomedicines, displaying epitopes from ubiquitous antigens, were liver-specific or, alternatively, also able to blunt extra-hepatic autoimmunity. To investigate this, the ability of PDC-E2$_{166-181}$/IA$^{g7}$-NPs and CYPD$_{398-412}$/IA$^{g7}$-NPs (displaying ubiquitous epitopes) vs. BDC2.5/IA$^{g7}$-NPs (displaying a beta cell-specific epitope) and MOG$_{36-50}$/IA$^{g7}$-NPs (displaying a central nervous system-specific epitope) were compared to see if any could blunt a MOG$_{36-55}$-induced relapsing-remitting form of EAE in NOD mice. BDC2.5/IA$^{g7}$-NPs expanded cognate TR1-like CD4+ T-cells in these animals (in blood and spleen) to a similar extent as they do in non-EAE-affected NOD mice, but these cells were absent from the CNS-draining cervical lymph nodes (CLNs) (FIG. 16B), and had no anti-encephalitogenic activity, as shown in FIG. 16C (oligodendrocytes do not express chromogranin A).

Figure 16A:
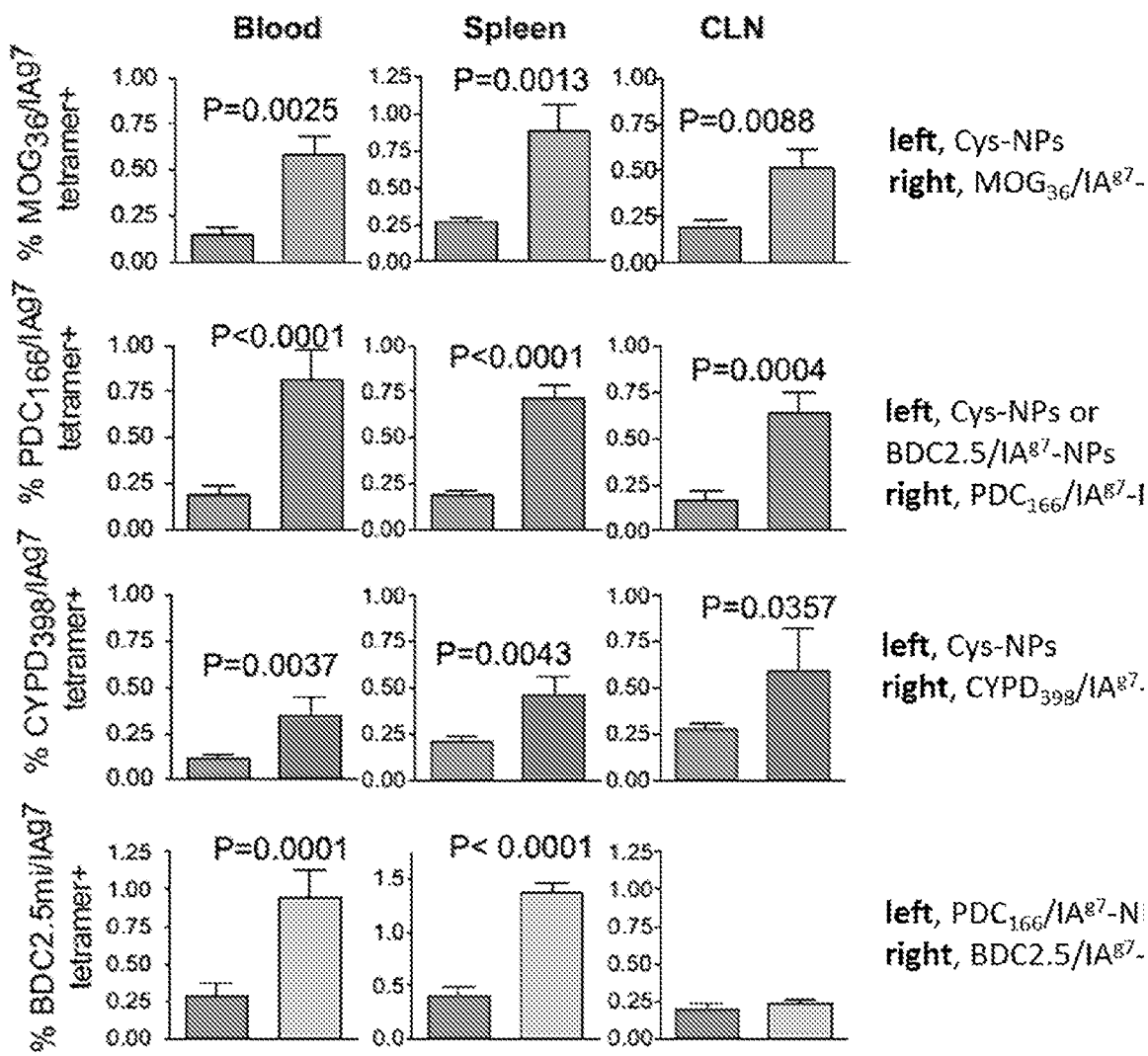
FIG. 16A shows percentage of tetramer+CD4+ cells in blood, spleen and cervical LNs of pMHCII-NP-treated NOD mice with EAE. Data correspond to (from top): (i) $MOG_{36-50}/IA^{g7}$ tetramer staining for 5 Cys-NP- and 7 $MOG_{36-50}/IA^{g7}$-NP-treated mice; (ii) $PDC_{166-181}/IA^{g7}$ tetramer staining for 11 Cys-NP-plus 14 $BDC_{2.5mi}/IA^{g7}$-NP- and 22 $PDC_{166-181}/IA^{g7}$-NP-treated mice (pooled from 2 experiments); (iii) $CYPD_{398-412}/IA^{g7}$ tetramer staining for 11 Cys-NP- and 8 $CYPD_{398-412}/IA^{g7}$-NP-treated mice (pooled from 2 experiments); and (iv) $BDC_{2.5mi}/IA^{g7}$ tetramer staining for 14
Figure 16B:
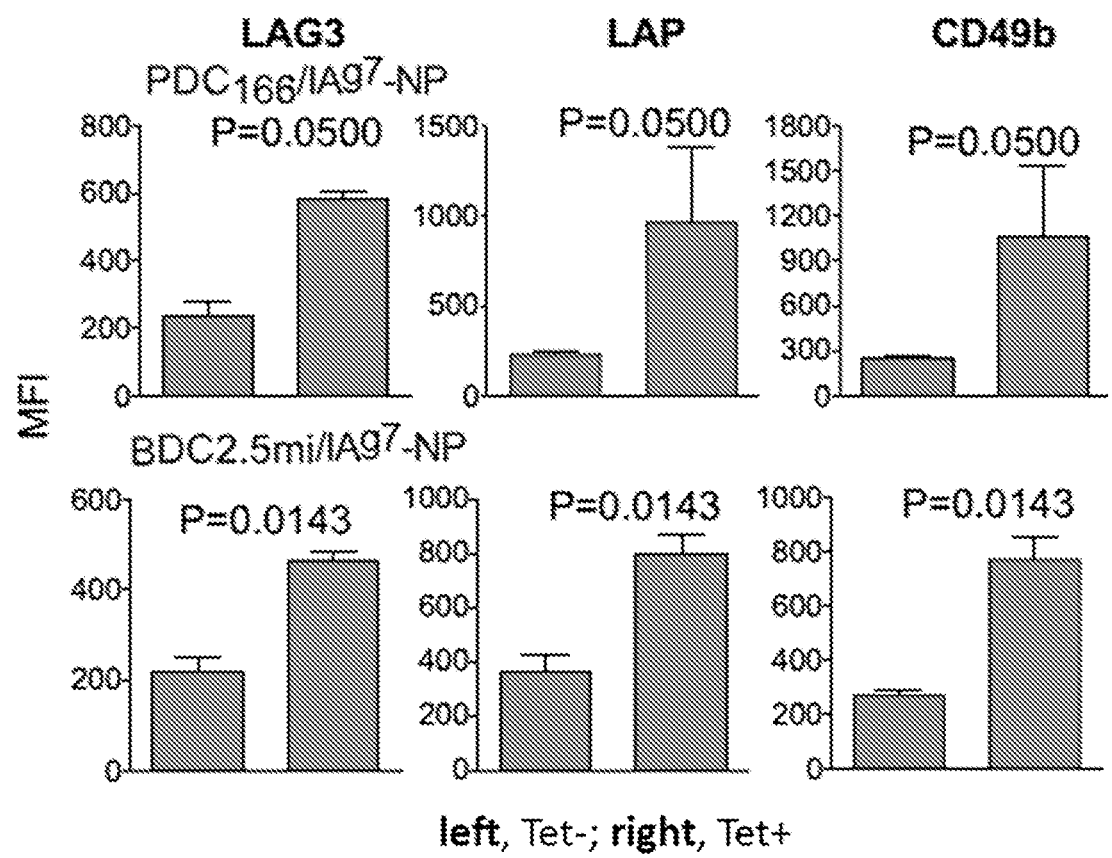
FIG. 16B shows and MFI for TR1 markers in splenic tetramer+CD4+ cells. Data in FIG. 16B correspond to 3 PDC$_{166-181}$/IA$^{g7}$-NP- and 4 BDC$_{2.5mi}$/IA$^{g7}$-NP-treated mice.
Figure 16C:
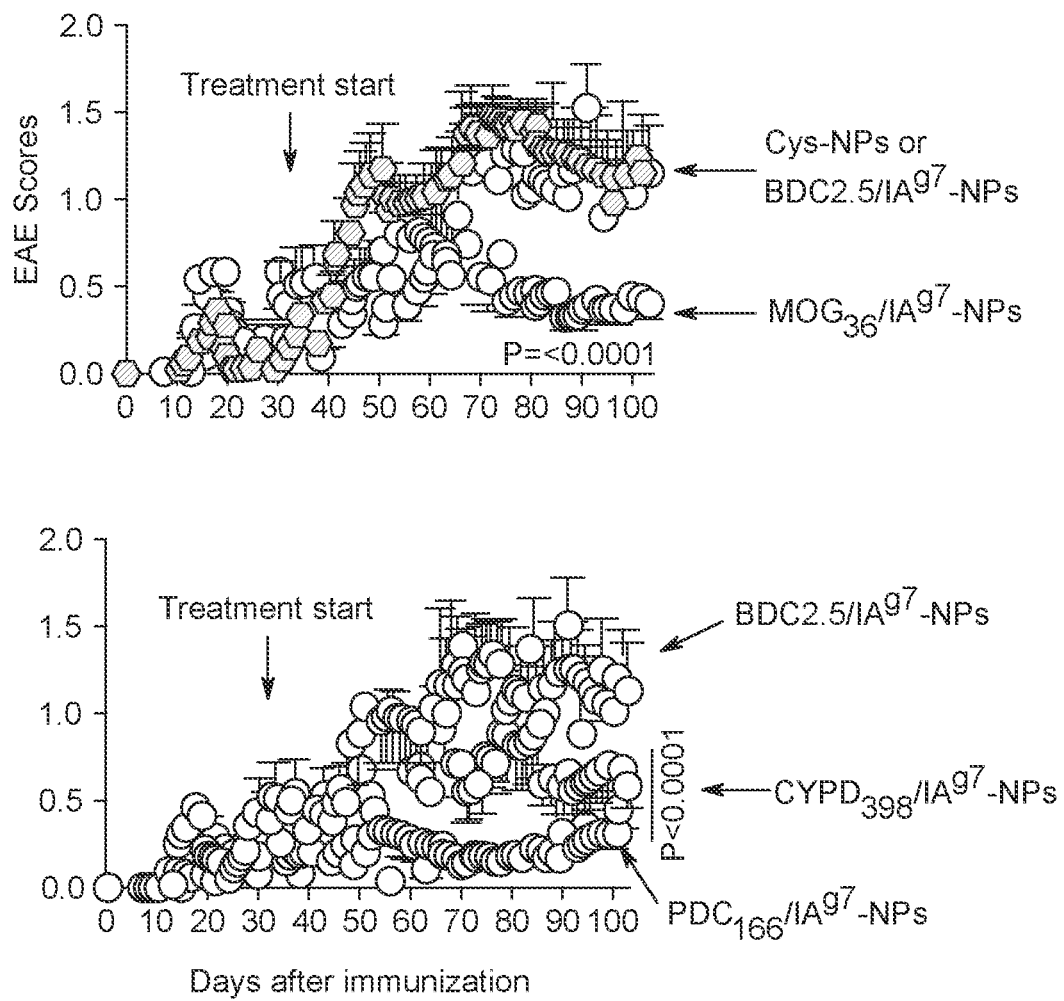
FIG. 16C shows EAE scores in NOD mice treated with: (i) Cys-NPs (n=9), BDC$_{2.5mi}$/IA$^{g7}$-NPs (n=14), or MOG$_{36-50}$/IA$^{g7}$-NPs (n=8) (top); and (ii) Cys-NPs (n=11, from 2 experiments) PDC$_{166-181}$/IA$^{g7}$-NPs (n=22, from 2 experiments) or CYPD$_{398-412}$/IA$^{g7}$-NPs (n=8) (bottom).
Figure 16D:
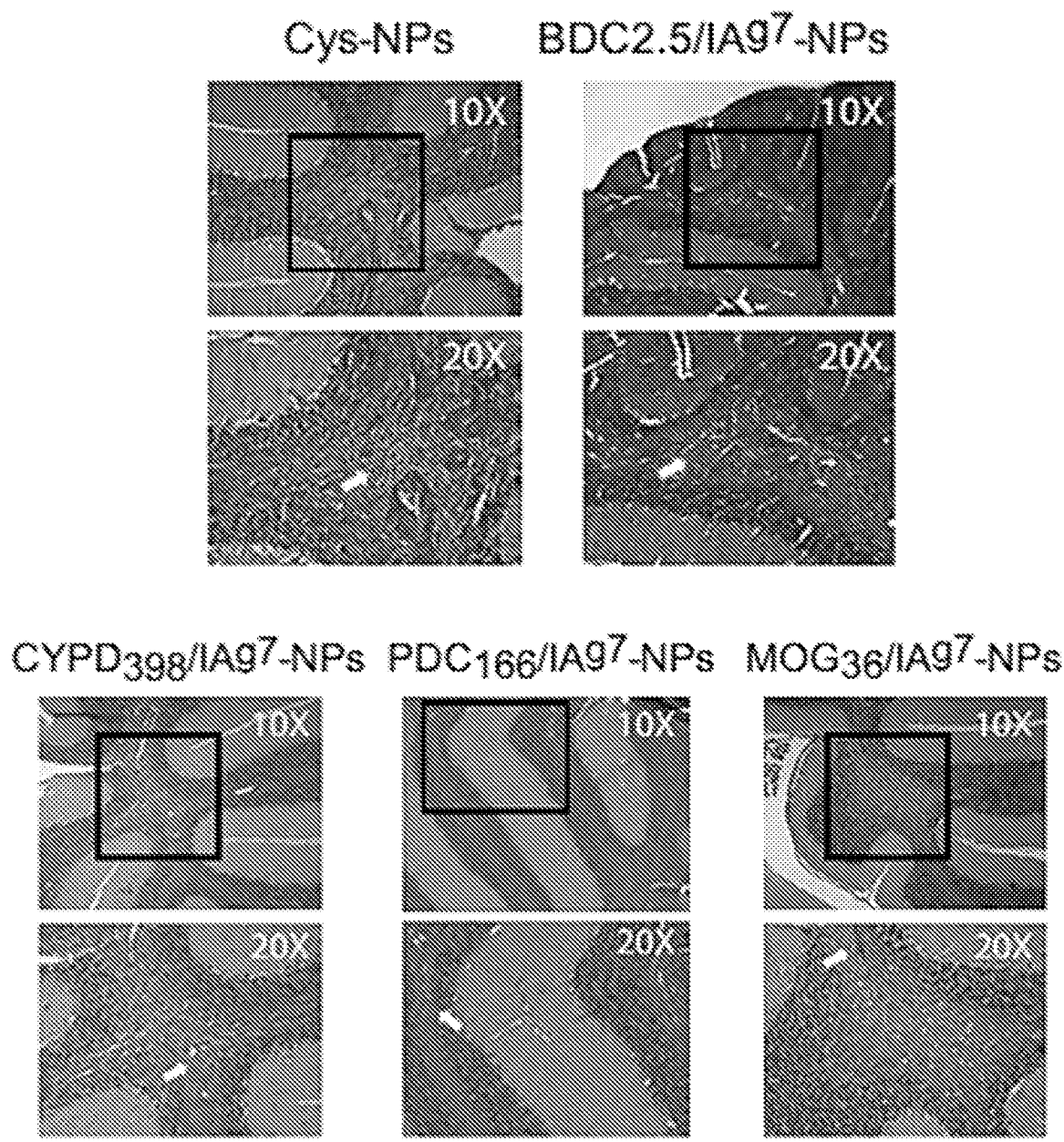
FIG. 16D shows representative luxol fast blue (LFB)/H&E staining pictures of cerebellum from the mice in FIG. 16C showing infiltration of inflammatory cells and areas of demyelination (white arrows).
Figure 16E:
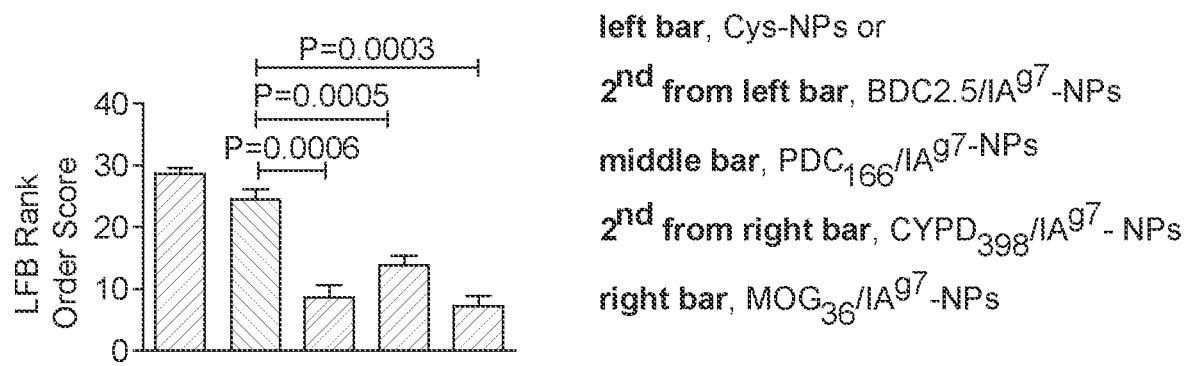
FIG. 16E shows average blinded histopathological rank order LFB scores for the mice in FIG. 16D. Data correspond to n=5, 7, 6, 8 and 7/NP type, from left to right in the bar diagram. Data correspond to the mean±SEM. P values were calculated using two-way ANOVA (FIG. 16C) or Mann-Whitney U test (FIGS. 16A, B, and E).
Figure 17A:
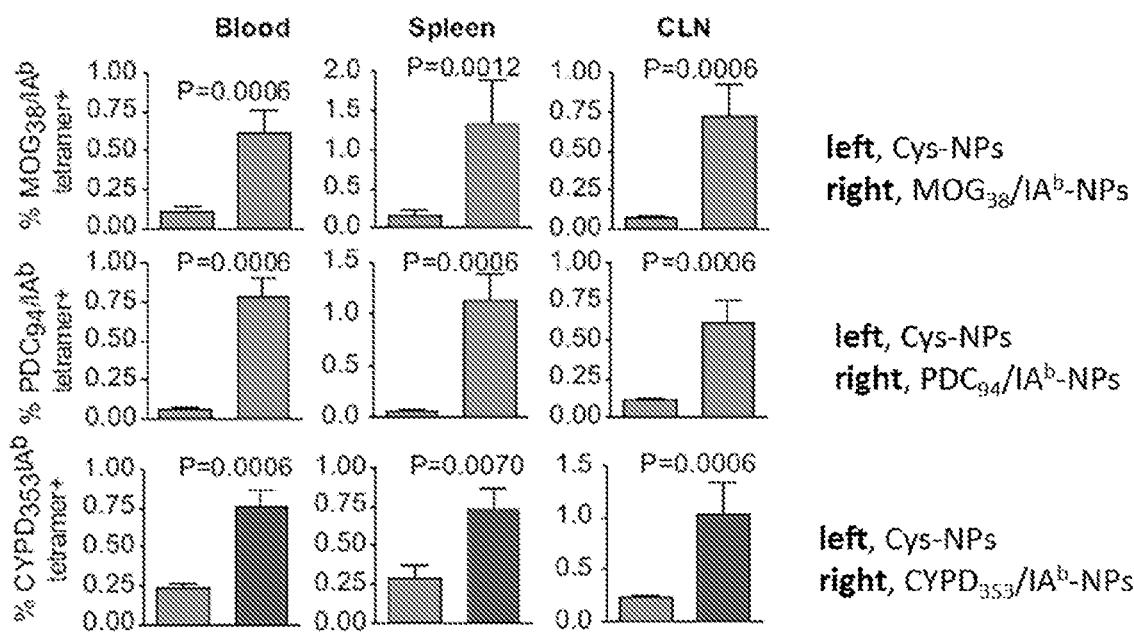
FIG. 17A shows percentages of tetramer+CD4+ cells in in blood, spleen and cervical LNs of pMHCII-NP-treated C57BL/6J mice with EAE. Data correspond to samples from 6 Cys-NP- and 7 pMHCII-NP-treated mice per panel, stained with cognate pMHC tetramers (top: MOG$_{38-49}$/IA$^b$; middle: PDC$_{94}$-108/IA$^b$; and bottom: CYPD$_{353-367}$/IA$^b$).
Figure 17B:
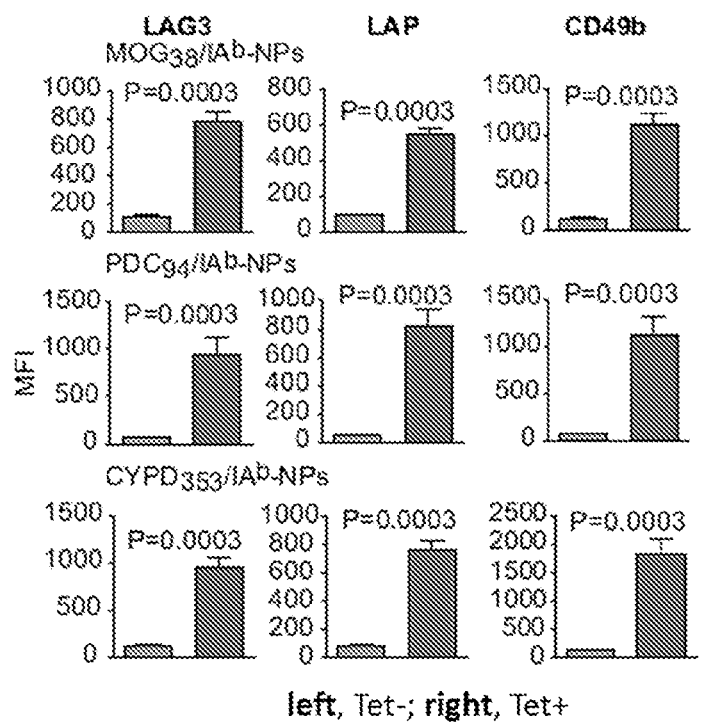
FIG. 17B shows and MFI of TR1 markers in splenic tetramer+CD4+ cells. Data in FIG. 17B correspond to 7 pMHCII-NP-treated mice in each panel.
Figure 17C:
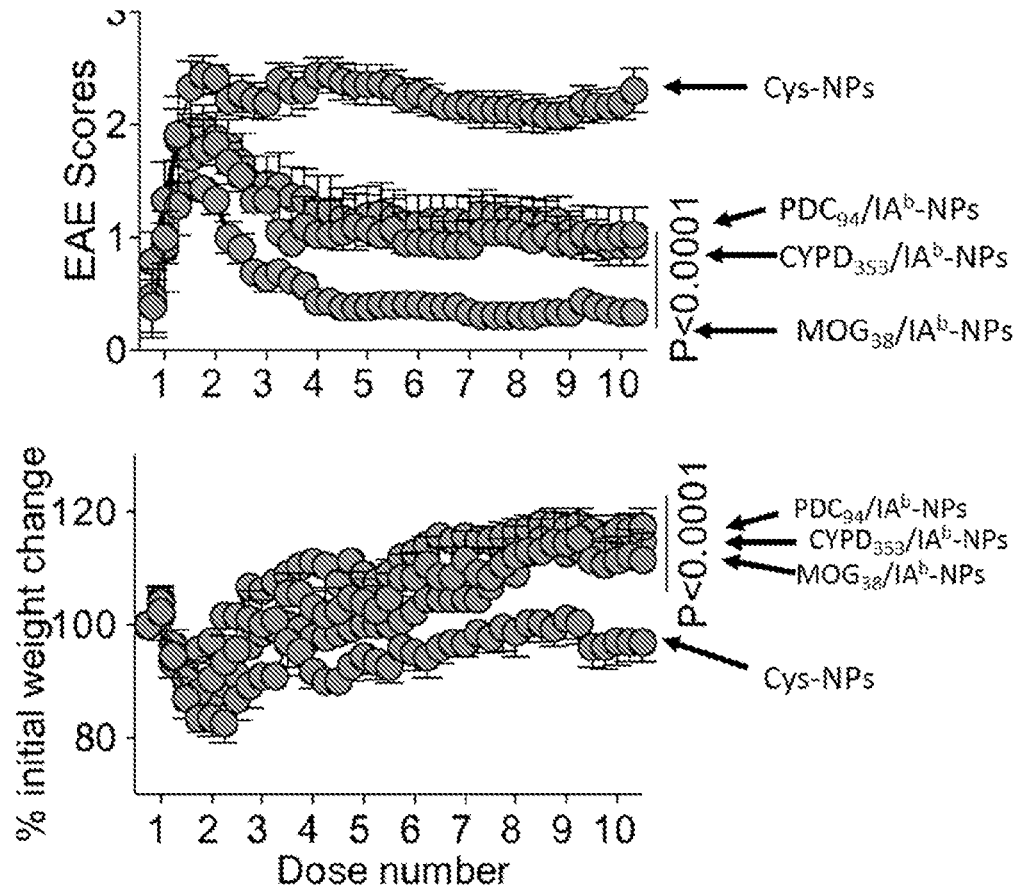
FIG. 17C shows EAE scores and % initial body weight changes in pMHCII-NP-treated C57BL/6J mice with EAE. Data corresponds to 6 Cys-NP, 7 MOG$_{38-49}$/IA$^b$-NP-, 7 PDC$_{94}$-108/IA$^b$-NP- and 7 CYPD$_{353-367}$/IA$^b$-NP-treated mice.
Figure 17D:
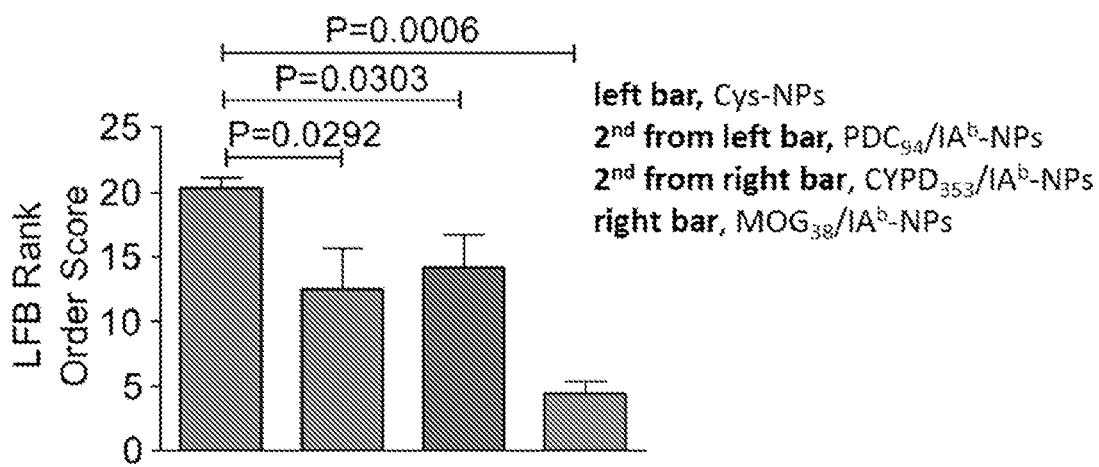
FIG. 17D shows average blinded histopathological rank order LFB scores for the mice in FIG. 17D. Data correspond to n=6, 6, 6 and 7/pMHC-NP type, from left to right in the bar diagram. Data correspond to the mean±SEM. P values were calculated using two-way ANOVA (FIG. 17C) or Mann-Whitney U test (FIGS. 17A, B, and D).

Notably, both CYPD$_{398-412}$/IA$^{g7}$-NPs and PDC-E2$_{166-181}$/IA$^{g7}$-NPs also triggered cognate TR1-like cell expansion in these mice (FIG. 16B) but, unlike BDC2.5/IA$^{g7}$-NPs, suppressed CNS inflammation and demyelination and the progression and severity of EAE relapses (FIGS. 16C, D and 16E). This was associated with an accumulation of cognate TR1-like cells in the CLNs as shown in FIG. 16A. Importantly, these effects were not NOD genetic background-specific, because they were also seen in C57BL/6 mice treated with CYPD and PDC epitope/IA$^b$-based nanomedicines: PDC$_{94-108}$/IA$^b$-NPs and CYPD$_{353-367}$/IA$^b$-NPs expanded cognate TR1-like CD4+ T-cells in blood, spleen and CLNs (FIGS. 17A and B) and blunted the progression of a chronic form of MOG$_{35-55}$-induced EAE in these mice, as compared to Cys-NPs and MOG$_{36-49}$/IA$^b$-NPs (negative and positive controls, respectively) as shown in FIGS. 17C and D.

Collectively, these observations suggested that significant levels of two different ubiquitously expressed autoantigens, PDC-E2 and CYPD2D6, are delivered to local and proximal APCs upon oligodendrocyte cell damage (in EAE), enabling autoreactive CD4+ T-cell priming, cognate TR1 cell generation by pMHC-NPs, recruitment and accumulation of these TR1 cells in the CNS-draining lymph nodes, and suppression of local inflammation.

Figure 18A:
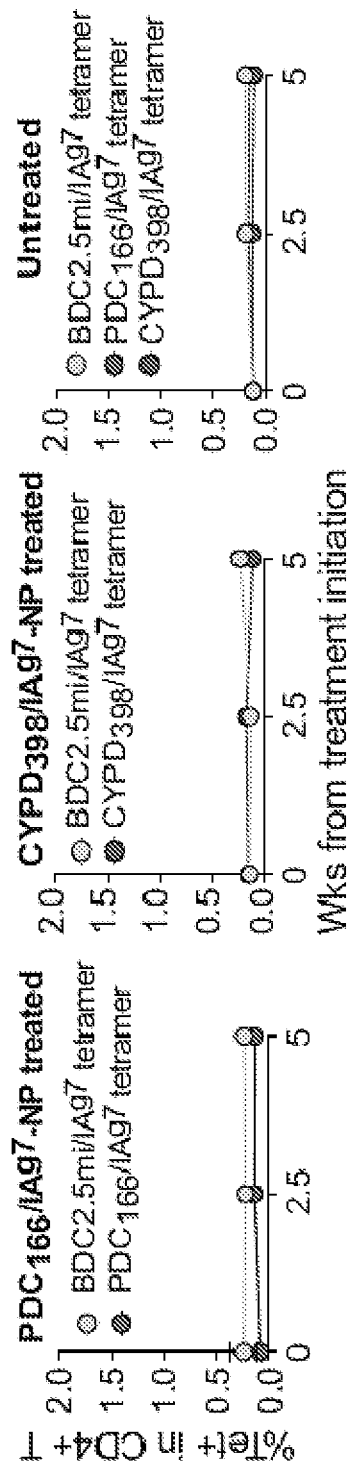
FIG. 18A shows percentage of tetramer+CD4+ cells in the blood of pMHCII-NP-treated vs. untreated NOD mice before (time 0) and 2.5 and 5 weeks after treatment initiation. Data correspond to (from left to right panels): (i) 5 PDC$_{166-181}$/IA$^{g7}$-NP treatment (2 experiments); (ii) 5 CYPD$_{398-412}$/IA$^{g7}$-NP treatment; and (iii) 5 untreated mice (2 experiments). Blood samples were stained with BDC$_{2.5mi}$/IA$^{g7}$, PDC$_{166-181}$/IA$^{g7}$ and CYPD$_{398-412}$/IA$^{g7}$ tetramers.
Figure 18B:
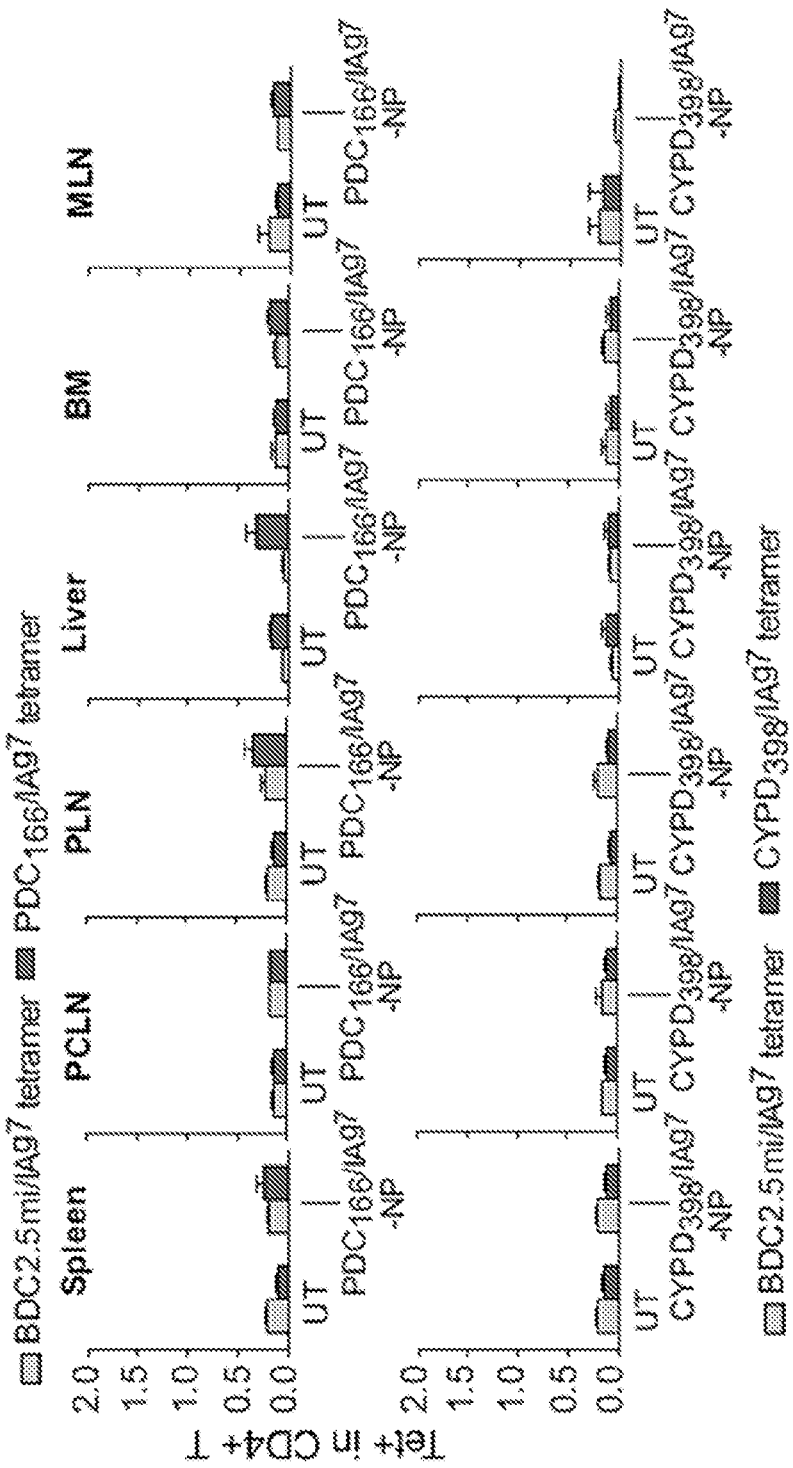
FIG. 18B shows percentages of tetramer+CD4+ cells in different lymphoid organs and liver of NOD mice treated with PDC$_{166-181}$/IA$^{g7}$-NPs or CYPD$_{398-412}$/IA$^{g7}$-NPs. PCLN, portal and celiac LNs; PLN: pancreatic LNs; MLN, mesenteric LNs; BM, bone marrow. Data corresponds to 9 untreated (2 experiments), 5 PDC$_{166-181}$/IA$^{g7}$-NP-treated (2 experiments) and 5 CYPD$_{398-412}$/IA$^{g7}$-NP-treated mice.

Example 14—Induction of Beta Cell Apoptosis Renders NOD Mice Responsive to Ubiquitous Autoantigen pMHC-NPs Treatment of pre-diabetic 10 wk-old NOD mice with PDC-E2$_{166-181}$/IA$^{g7}$-NPs (PBC-relevant) and CYPD$_{398-412}$/IA$^{g7}$-NPs (AIH-relevant) did not trigger the expansion of cognate TR1-like CD4+ T-cells relative to endogenous BDC2.5/IA$^{g7}$-specific CD4+ T-cells, as measured with pMHC tetramers, in blood (FIG. 18A) or any of the organs examined, including liver (FIG. 18B).

These results suggested that spontaneous beta cell killing in pre-diabetic NOD mice does not trigger the formation of PDC-E2 or CYPD autoantigen-experienced T-cells capable of responding to the corresponding nanomedicines. Three alternative possibilities could explain these results: 1) these antigens are released from cholangiocytes and hepatocytes (in liver autoimmune diseases) but not from dying beta cells (in T1D); 2) the antigens are released from NOD beta cells, but NOD mice do not export cognate autoreactive T-cells capable of responding to these ubiquitous autoantigens; or 3) the antigens are released from beta cells and the mice harbor cognate autoreactive T-cells, but the antigens are released in amounts insufficient to prime these T-cells.

Figure 18C:
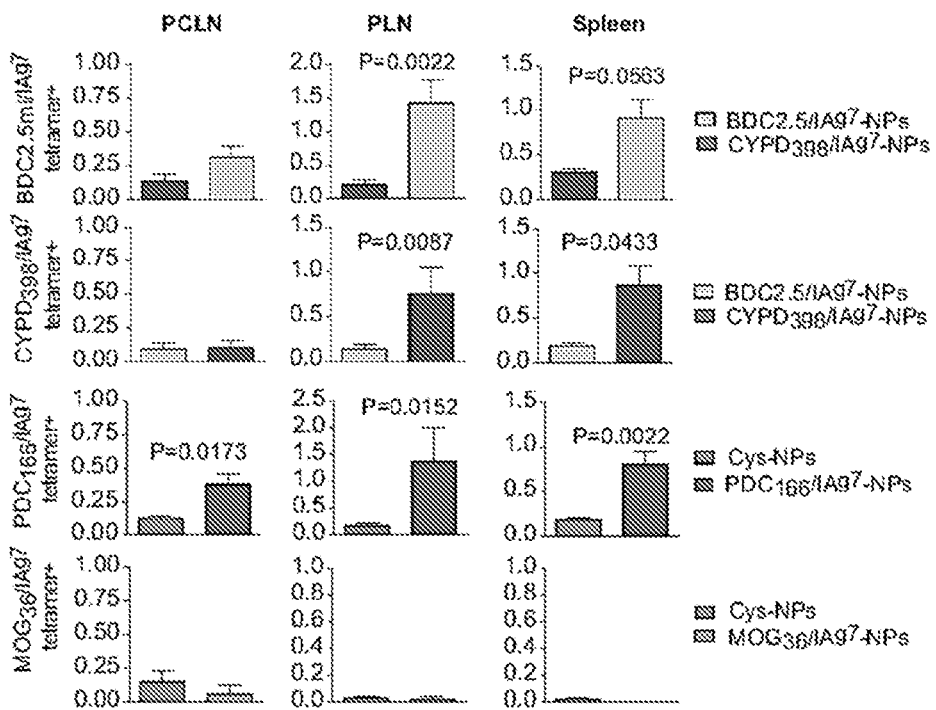
FIG. 18C shows percentages of tetramer+CD4+ cells in PCLN, PLN and spleen of DT-treated RIP-DTR-transgenic NOD mice following pMHCII-NP therapy. Data correspond to 6 Cys-NP-, 5 BDC$_{2.5mi}$/IA$^{g7}$-NP-, 5 PDC$_{166-181}$/IA$^{g7}$-NP- and 5 CYPD$_{398-412}$/IA$^{g7}$-NP-treated mice from 2 independent experiments. Samples from mice treated with BDC$_{2.5mi}$/IA$^{g7}$-NPs and CYPD$_{398-412}$/IA$^{g7}$-NPs were stained with both pMHCII tetramers (cognate and non-cognate). Samples from mice treated with Cys-NPs, PDC$_{166-181}$/IA$^{g7}$-NPs and MOG$_{36-50}$/IA$^{g7}$-NPs were stained with PDC$_{166-181}$/IA$^{g7}$ or MOG$_{36-50}$/IA$^{g7}$ tetramers, respectively.
Figure 18:
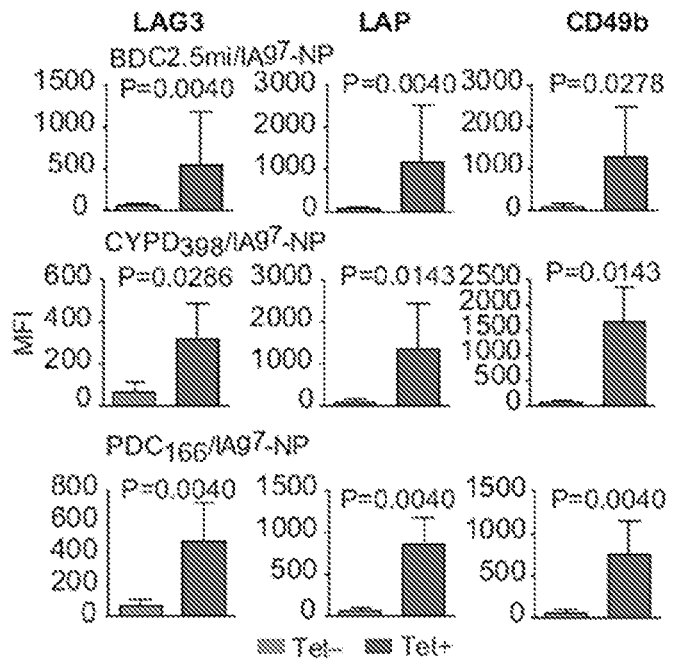
FIG. 18 illustrates autoantigen shedding renders peripheral autoreactive T-cells responsive to pMHCII-NP therapy.

To distinguish among the above three possibilities, an X-chromosome-linked rat-insulin promoter-driven human diphtheria toxin receptor (hDTR) transgene was expressed in the pancreatic beta cells of non-diabetic female NOD mice. These mice were then treated with DT to simultaneously kill 50% of beta cells (due to X-chromosome inactivation, only 50% of beta cells express the hDTR). We then treated DT-treated and DT-untreated mice with PDC-E2$_{166-181}$/IA$^{g7}$-NPs, CYPD$_{398-412}$/IA$^{g7}$-NPs (liver autoimmunity-relevant), BDC2.5/IA$^{g7}$-NPs (T1D-relevant, positive control), MOG$_{36-50}$/IA$^{g7}$-NPs (central nervous system autoimmune disease-specific, negative control) or Cys-coated NPs (negative control) and enumerated the presence of cognate autoreactive T-cells in spleen, liver-draining lymph nodes (portal and celiac LNs, PCLNs) and pancreatic LNs (PLNs), using pMHC tetramers. As expected, MOG$_{36-50}$/IA$^{g7}$-NPs did not trigger the expansion of cognate tetramer+ CD4+ T-cells in these mice (MOG is an oligodendrocyte-specific protein that is not expressed in pancreatic beta cells) (FIG. 18C, bottom right panel). In contrast, both PDC-E2$_{166-181}$/IA$^{g7}$- and CYPD$_{398-412}$/IA$^{g7}$-NPs triggered the expansion and accumulation of significant numbers of cognate tetramer+CD4+ T-cells expressing the TR1 markers LAG3, LAP and CD49b in the spleen and PLNs of the DT-treated mice, to an extent similar to that seen for BDC2.5/IA$^{g7}$ tetramer+ T-cells in BDC2.5/IA$^{g7}$-NP-treated animals (FIG. 18C, bottom left and top panels, and FIG. 18D).

These findings corroborate our previous observations that pMHC-NP-induced TR1 cell formation and expansion requires the presence of autoantigen-experienced T-cells, that priming of such cells requires antigen shedding from expressing cell types and that the peripheral repertoire of NOD mice normally harbors naïve CD4+ T-cell specificities targeting ubiquitously-expressed antigens.

Figure 19A:
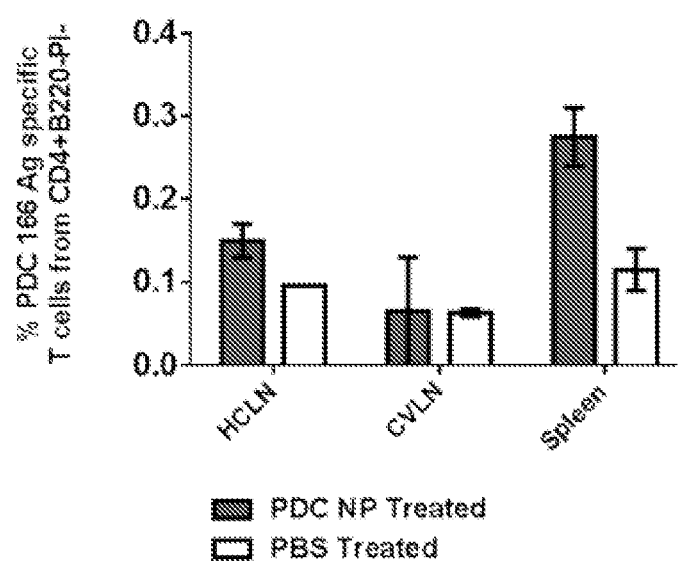
FIG. 19A shows percent tetramer staining of PDC$_{166-181}$/IA$^{g7}$ T cells.
Figure 19B:
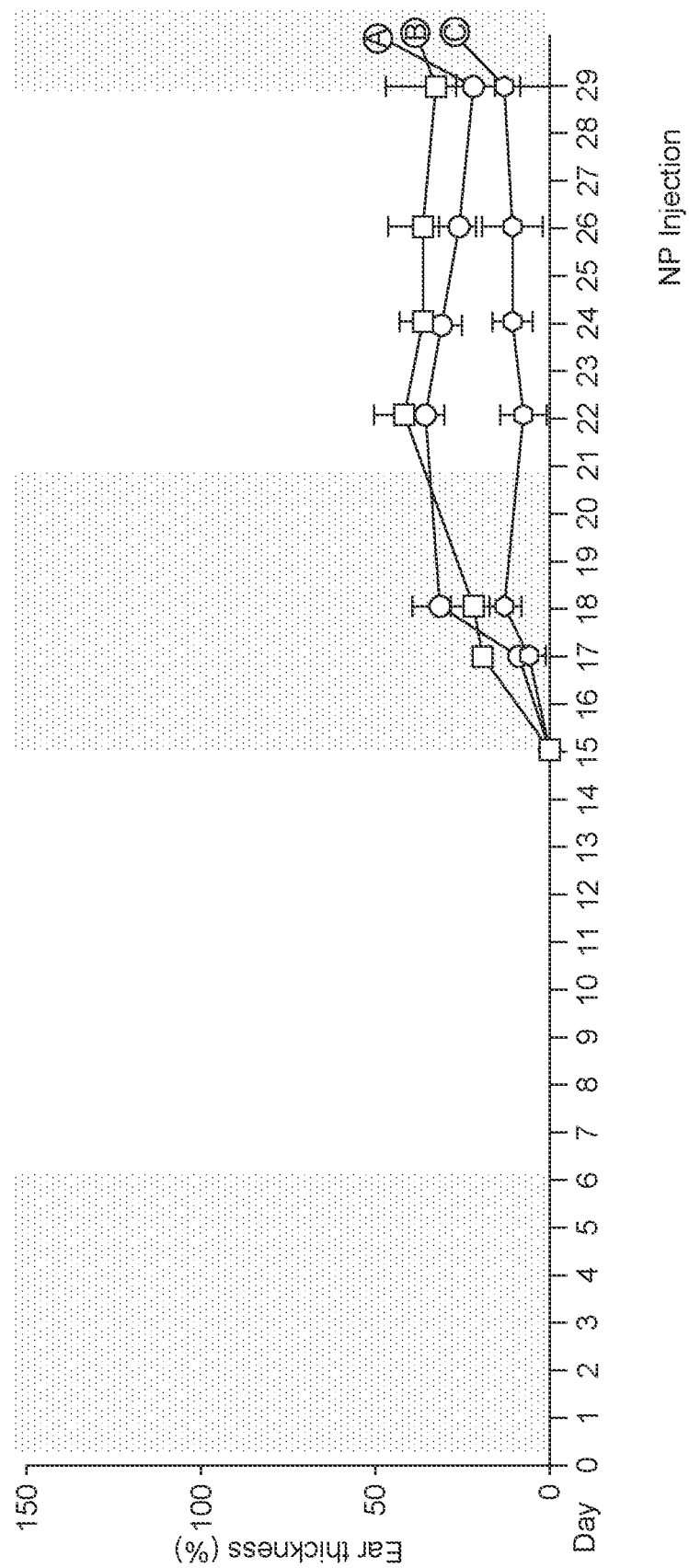
FIG. 19B shows improvements of ear thickness in mice administered, PDC$_{166-181}$/IA$^{g7}$-NPs.
Figure 19B:
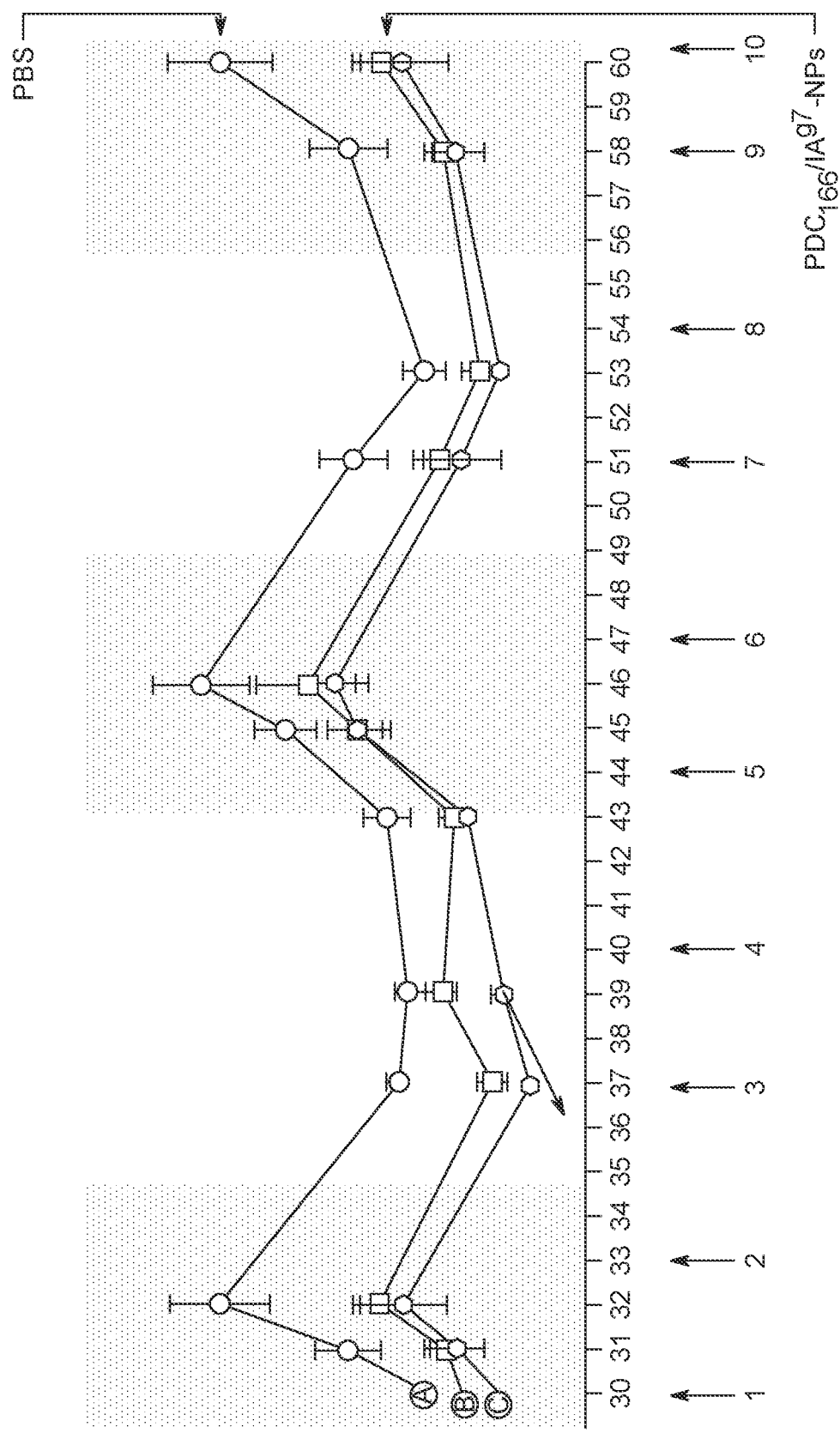

Example 15—Ubiquitous Autoantigen pMHC-NPs Suppress Signs of Psoriasis in a Mouse Model of Induced Psoriasis The ability of ubiquitous autoimmune disease relevant pMHC-NPs was tested in a relevant mouse model of psoriasis, the imiquimod (IMQ) induced model. This mouse model is one of the most widely used mouse models in preclinical psoriasis studies. NOD/Ltj mice were treated with 5% topical IMQ for 6 days with 8 day rest intervals. The first application was made to the back of the mice and subsequent applications on the ear. Mice were administered either PDC-E2$_{166-181}$/IA$^{g7}$- or CYPD$_{398-412}$/IA$^{g7}$-NPs starting after the second application to the ear. Mice were assayed for symptoms of psoriasis following the PASI (Psoriasis Area and Severity Index) criteria which measures erythema, scaling and skin thickness; and mice were evaluated for expansion of PDC and CYPD tetramer+CD4 T cells in spleen, cervical lymph nodes (CV LN), and hepato-celiac lymph nodes (HC LN). As shown in FIG. 19A PDC-E2$_{166-181}$/IA$^{g7}$ were expanded in this model, indicating that these cells were primed by the induction of inflammation brought on by IMQ treatment. FIG. 19B shows that ear thickness was improved by treatment with PDC-E2$_{166-181}$/IA$^{g7}$- or CYPD$_{398-412}$/IA$^{g7}$-NPs, while scaling and erythema were not (not shown). These experiments are preliminary, but indicate that different models of autoimmune/inflammatory disease prime T cells to ubiquitous autoantigens that are able to be modified by ubiquitous autoantigen-relevant pMHC-NPs Example 16—Select Methods Utilized Herein Mice NOD/LtJ, BALB/c, C57BL/6, NOD.scid.Il2rg−/−(NSG), NOD.c3c4 and FVB/N.Abcb4−/− (Abcb4 or ATP-binding cassette transporter, sub-family B, member 4) mice were purchased from the Jackson Laboratory (Bar Harbor, ME). IFNγ ARE-Del−/− B6 mice were obtained from H. Young (NIH, Bethesda, MD). NOD.c3c4.scid mice were generated by backcrossing (NOD.c3c4×NOD.scid) F1 mice with NOD.c3c4 mice for five generations, followed by intercrossing of mice heterozygous for the scid mutation and homozygous for the B6 chromosome 3 and 4 intervals from NOD.c3c4 mice. NOD.Abcb4−/− mice were obtained by backcrossing the mutant Abcb4 allele from FVB/N-Abcb4−/− mice onto the NOD/Ltj background for six generations, followed by intercrossing. (NODxB6.IFNg ARE- Del–/–) F1 mice were generated by intercrossing IFNγ ARE-Del–/– and NOD/LtJ mice. NOD.Il10tm1Flv (Tiger) mice were obtained by backcrossing the Il10tm1Flv allele from C57BL/6.Il10tm1Flv mice (Jackson Lab) onto the NOD/Ltj background for 10 generations. RIP-DTR.NOD transgenic mice were generated by backcrossing an X-chromosome-linked rat-insulin promoter-driven human diphtheria toxin receptor (RIP-DTR) transgene from transgenic B6 mice into the NOD background for more than 10 generations.

Cell Lines, Pathogens, and Tumors

CHO—S, BSC-1, MDCK, 293T, B16/F10 and CT26 cell lines were purchased from the ATCC (Manassas, VA). *Listeria monocytogenes* was obtained from DMX Corporation (Philadelphia, PA).

Antibodies and Flow Cytometry

FITC, PE, APC, PerCP or biotin-conjugated mAbs against mouse CD4 (RM4-5), CD5 (53-7.3), CD19 (1D3), B220 (RA36B2) and CD49b (HMa2) and streptavidin-PerCP were purchased from BD Biosciences (San Diego, CA). Anti-murine LAG-3 mAb (C9B7W) was purchased from eBioscience (San Diego, CA). Anti-latent-associated-TGF-β (LAP) antibody (TW7-16B4) was from BioLegend (San Diego, CA). PE-conjugated pMHC class II tetramers were produced using biotinylated pMHC monomers. pMHC class II tetramer staining and phenotypic marker analysis were done essentially as described with minor modifications. Briefly, after avidin incubation (15 min at RT), blood leukocytes, and single cell suspensions from spleen, lymph node, liver mononuclear cells, and bone marrow cells were stained first with pMHC tetramer (5 μg ml$^{-1}$) in FACS buffer (0.05% sodium azide and 1% FBS in PBS) for 60 min at 37° C., and later with FITC-conjugated anti-mouse CD4 (5 μg ml$^{-1}$) and PerCP-conjugated anti-mouse B220 (2 μg ml$^{-1}$; as a 'dump' channel) for 30 min at 4° C. After washing, cells were fixed (1% paraformaldehyde in PBS) and analyzed with FACScan, FACSaria, or BD LSRII flow cytometers. For phenotypic analyses, the cells were incubated with anti-FcR Abs, and then stained with cell surface marker antibodies diluted 1:100 in FACS buffer (at 4° C. for anti-CD49b and anti-LAP Abs, and at 37° C. for anti-LAG-3 Abs) followed by pMHC tetramer, FITC-conjugated anti-mouse CD4 (5 μg ml$^{-1}$) and PerCP-conjugated anti-mouse B220. Upon staining, cells were washed, fixed, and analyzed by flow cytometry. FlowJo software was used for all analyses.

NSG-engrafted human T cells were analyzed using the following mAbs: FITC-conjugated anti-CD4 (OKT4, BioLegend), APC-conjugated anti-CD19 (HIB19, BD Biosciences, San Jose, CA), PerCP-conjugated polyclonal goat anti-LAG-3 IgG (R&D Systems, Minneapolis, MN), biotin-conjugated anti-CD49b (AK7, Pierce Antibodies, Thermo Fisher Scientific, Waltham, MA), and eFluor 450-conjugated streptavidin (eBioscience). Briefly, splenocytes and pancreatic lymph node cells were incubated with avidin (0.25 mg ml$^{-1}$ in FACS buffer) for 30 min at room temperature, washed and stained with tetramer (5 μg ml$^{-1}$) for 1 h at 37° C., washed, and incubated with FITC-conjugated anti-CD4 (2/100), APC-conjugated anti-CD19 (5/100; used as a 'dump' channel), PerCP-conjugated anti-LAG-3 (8/100) and biotin-conjugated anti-CD49b (4/100) at 4° C. for 45 min. After washing, the cells were incubated with eFluor 450-conjugated streptavidin for 30 min at 4° C., washed, fixed in 1% PFA in PBS and cells within the hCD4$^+$/hCD19$^-$ gate analysed with a FACSCanto II (BD Bioscience).

pMHC Monomers and Peptides

Recombinant pMHC class II monomers were purified from supernatants of CHO—S cells transduced with lentiviruses encoding a monocistronic message in which the peptide-MHCb and MHCa chains of the complex were separated by the ribosome skipping P2A sequence. The peptide was tethered to the amino terminal end of the MHCb chain via a flexible GS linker and the MHCa chains were engineered encode a BirA site, a 6×His tag, a twin strep-tag and a free Cys at their carboxyterminal end. The secreted, self-assembled pMHC class II complexes were purified by sequential nickel and Strep-Tactin® chromatography and used for coating onto NPs or processed for biotinylation and tetramer formation as described above. The epitopes encoded in the murine monomeric constructs were selected based on predicted MHCII-binding capacity using RANK-PEP (http://imed.med.ucm.es/cgi-bin/rankpep_mif.cgi) using 7.54 as the threshold score. PDC-E2$_{166-181}$ had a score that fell below the threshold but was selected for experimentation because it is contained within one of the lipoyl-binding domains of PDC-E2, an antigenic target for AMAs. For CYPD and FTCD epitope prediction, we used a second online algorithm (GPS-MBA) (mba.biocuckoo.org/) and peptides predicted by both RANKPEP and GPS-MBA were selected for experimentation. hPDC-E2$_{122-135}$, hPDC-E2$_{249-262}$ (both contained within the lipoyl-binding domain of PDC-E2), and hPDC-E2$_{629-643}$ have been described previously. The sequences of the different epitopes are: PDC-E2$_{166-181}$/IA$^{g7}$ (LAEIETDKATIGFEVQ, (SEQ ID NO: 105), PDC-E2$_{82-96}$/IA$^{g7}$ (EKPQDIEAFKNYTLD, (SEQ ID NO: 106), FTCD$_{58-72}$/IA$^{g7}$ (VVEGALHAARTASQL, (SEQ ID NO:107), CYPD$_{398-412}$/IA$^{g7}$ (LITNLSSALKDETVW, (SEQ ID NO:108), 2.5 mi/IA$^{g7}$ (AHHPIWARMDA, (SEQ ID NO: 109), hPDC-E2$_{122-135}$/DRB4*0101 (GDLIAE-VETDKATV, (SEQ ID NO:8), hPDC-E2$_{249-262}$/DRB4*0101 (GDLLAEIETDKATI, (SEQ ID NO:9), and hPDC-E2$_{629-643}$/DRB1*0801 (AQWLAEFRKYLEKPI, (SEQ ID NO:7). Synthetic PDC-E2$_{166-181}$, 2.5 mi, and mMOG$_{36-55}$ (EVGWYRSPFSRVVHLYRNGK, (SEQ ID NO:110) peptides were purchased from Genscript (Piscataway, NJ). The amino acid residue numbers for each peptide correspond to those found in the mature form of the corresponding antigens.

Nanoparticles, pMHCII-NP Synthesis, and Purification pMHCs were coated onto pegylated iron oxide NPs (PFM-NPs), produced as described (2). Briefly, PFM-NPs were produced by thermal decomposition of Fe(acac)$_3$ in the presence of 2 kD methoxy-PEG-maleimide. The NPs were purified using magnetic (MACS) columns (Miltenyi Biotec, Auburn, CA). Free Cysteines (controls) or pMHCs, carrying a free carboxyterminal Cys, were conjugated to the maleimide-functionalized PFMs in 40 mM phosphate buffer, pH 6.0, containing 2 mM EDTA, 150 mM NaCl overnight at room temperature. The pMHC-conjugated NPs were separated from free pMHC using magnetic columns, sterilized by filtration through 0.2 μm filters and stored in water or PBS at 4° C. Quality control was done using transmission electron microscopy, dynamic light scattering, and native and denaturing gel electrophoresis. pMHC content was measured using Bradford assay (Thermo Fisher Scientific) and SDS-PAGE.

Generation of FTCD-Expressing Adenovirus

A replication-deficient adenovirus expressing human formiminotransferase cyclodeaminase (Ad-hFTCD) (a target autoantigen in AIH Type 2) was generated by cloning the hFTCD DNA sequence directly into Adeno-X Adenoviral System 3 (CMV) using In-Fusion® HD cloning technology and Stellar Competent cells (Clontech, Mountain View, CA).

Cloned Ad-FTCD was amplified in Ad-293 T cells and purified using Adeno-X Maxi Purification Kit (Clontech). The viral titer was measured using the End-point Dilution Assay or Adeno-X Rapid Titer Kit (Clontech).

Ursodeoxycholic Acid Treatment

Cohorts of 5-6 or 24 wk-old male and/or female NOD.c3c4 mice were left untreated, fed a diet supplemented with 0.5% UDCA (BOC Sciences, Upton, NY; TestDiet, Richmond, IN), or treated with pMHCII-NPs for 14 or 9 wk, respectively, and sacrificed for pMHCII tetramer staining, PBC scoring and biochemical testing.

pMHCII-NP Therapy in NOD.c3c4, (NOD×B6.IFNg ARE-Del−/−) F1 and NOD/Ltj Mice

Cohorts of 15 wk-old male and/or female NOD.c3c4 mice with established PBC were left untreated or treated with 20 mg of pMHCII-NPs or Cys-NPs (i.v.) twice weekly for 9 wk unless indicated otherwise. Liver disease scoring involved macroscopic evaluation of cyst content (0-5), liver weight and CBD diameter (0-4), as well as microscopic evaluation of bile duct involvement (0-4), bile duct proliferation (0-4) and mononuclear cell infiltration (0-4), essentially as described (23). In other experiments, treatment was initiated at the peak of disease (24 wk of age) and given twice a week for 14-20 wk. Intermittent treatment involved treating mice twice a wk from 15 to 24 wk of age, then withdrawing treatment until the percentages of tetramer+ cells dropped to ~50% of the levels seen at treatment withdrawal (measurements in peripheral blood were done once every two wk), re-treating mice twice a wk until the percentages of tetramer+ cells reached original values, and repeating this cycle until 50 wk of age.

In in vivo cytokine blocking experiments, mAbs against HRPN (rIgG1), IL-10 (JES5-2A5) or TGF-β (1D11) (BioXcell, West Lebanon, NH) were given i.p. twice a week at 500 mg per dose for 2 wk, followed by 200 mg per dose for 7 additional wk. Mice were randomized into cytokine-neutralizing mAb-treatment (anti-IL-10 or -TGFβ) or HRPN rat-IgG1 groups.

In experiments involving (NOD×B6.IFNg ARE-Del$^{-/-}$) F1 mice, 10-wk-old male and female mice were treated for 5-6 wk. Histopathologic scoring in the liver was performed as described. Briefly, severity scores were obtained by scoring portal inflammation, lobular inflammation and granuloma formation from 0-4, and bile duct damage from 0-2. The extent of portal inflammation and bile duct damage were scored from 0-4 based on the ratio between affected vs unaffected area. The extent of lobular inflammation and granuloma formation were scored from 0-4 based on number of lesions per specimen. The severity of fibrosis was scored on a 0-6 scale.

Studies using NOD mice involved treating cohorts of 10-wk-old pre-diabetic female NOD/Ltj mice with 20 mg of pMHCII-NPs or Cys-NPs i.v. twice weekly for 5 wk.

pMHCII-NP Therapy for EAE in NOD.c3c4 Mice

Male and female 12-14 wk-old NOD.c3c4 mice were immunized with 250 mg of pMOG$_{36-55}$ in CFA s.c. on either side of the flank region above the base of the tail under isofluorane anesthesia. The mice received 350 ng of Pertussis toxin i.v. on days 0 and 2 relative to peptide immunization. Mice were weighed and scored on day 0 and then daily starting on day 14 after immunization, and scores were plotted on a 5-point scale. On day 32 of immunization, all the mice having scores <3 were randomized into treatment with Cys-NPs or pMHCII-NPs. All mice were treated twice a week for 9 wk. Scoring of mice for signs of PBC was done as described above.

pMHCII-NP Therapy for PSC in NOD.Abcb4−/− Mice

Cohorts of 5-6 wk-old male and/or female NOD.Abcb4$^{-/-}$ mice with established PSC were treated with 20 mg of pMHCII-NPs or Cys-NPs i.v. twice weekly for 5-6 wk. Histopathologic lesions were graded using the Ishak scoring system, which evaluates both fibrosis (0-6) as well as necroinflammatory sequelae of biliary cholangitis, including interface hepatitis (0-4), confluent necrosis (0-6), lobular inflammation (0-4) and portal inflammation (0-4).

pMHCII-NP Therapy for AIH in NOD Mice

AIH was induced by infecting 5-6 wk-old female NOD/Ltj mice with an adenovirus encoding human FTCD (Ad-hFTCD, 1010 plaque forming units (PFU) i.v.). Four wks later, cohorts of mice with established AIH were treated with 20 mg of pMHCII-NPs or Cys-NPs (i.v.) twice weekly for 5-6 wk. Histopathological scoring was done using the Ishak scale as above.

pMHCII-NP Therapy in Human PBMC-Reconstituted NSG Hosts

PBMCs from HLA-DRB4*0101+ PBC patients (recruited under informed consent approved by the Institutional Review Board at Hospital Clinic) were depleted of CD8+ T-cells using anti-CD8 mAb-coated magnetic beads (Miltenyi Biotech, Auburn, CA) and injected i.v. ($2\times10^7$) into 8-10 wk-old NSG hosts. Mice were treated with 30-40 mg pMHC-NPs starting on day 5 after PBMC transfusion, twice a wk for 5 consecutive wks, or left untreated. Therapy-induced expansion of cognate CD4+ T-cells was measured in liver, peripheral LNs, spleen and bone marrow (not shown). A mouse was considered a responder if the percentage of tetramer+ T-cells in at least two different organs were higher than the mean±10 standard deviation values seen in untreated hosts.

Evaluation of General Adaptive Immunity pMHCII-NP-treated and untreated female mice were injected i.v. with $2\times10^6$ PFU of recombinant Vaccinia Virus (rVV) and sacrificed on days 4 and 14 after infection. Samples were processed for pMHCII tetramer staining and rVV titer measurements. Briefly, both ovaries were collected in DMEM containing 2% FBS, homogenized, freeze-thawed 3 times followed by sonication (3 rounds, 20 sec each). Serial dilutions of the lysates were added to confluent BSC-1 cell cultures at 37° C. for 1 h, washed twice with serum free DMEM and then overlaid with DMEM containing 2% FCS and 0.4% carboxymethyl cellulose (CMC; Sigma, Saint Louis, MO). On day 3, the overlay was discarded, and the cell layers were stained with crystal violet to count the number of plaques.

To evaluate cellular responses to Influenza infection, pMHCII-NP-treated and untreated mice were first primed i.p. with the HKx31 (H3N2) strain at $10^6$ EID$_{50}$ per mouse. One cohort of mice was sacrificed 7d after priming and processed for tetramer staining to confirm presence of pMHC-NP-specific TR1-like cells during priming. Other cohorts of primed mice were re-infected 30d later with an intranasal dose of PR8 virus, a lethal H1N1 strain of Influenza ($8\times10^4$ EID$_{50}$ per mouse), under anesthesia. PR8-challenged mice were weighed daily and scored clinically from 0-4 based on the extent of ruffled fur, reduced motility, huddled appearance, and rapid and/or labored breathing. Mice were sacrificed 7d later and processed for tetramer staining and influenza titer measurement. Briefly, lungs were collected in serum free DMEM, homogenized and freeze-thawed 3 times. Serial dilutions of the lysates were added to confluent MDCK cell cultures at RT for 1 h and washed. Cultures were then overlaid with DMEM containing 0.4% CMC for 2-3 days, washed, fixed and stained with crystal violet to count the number of plaques.

Cellular immunity to intracellular bacteria was determined by infecting pMHCII-NP-treated and untreated mice i.v. with 103 colony forming units (cfu) of *Listeria monocytogenes*. Mice were sacrificed 7d or 14d after infection and samples processed for tetramer staining and bacterial load measurements. Briefly, spleen and liver were cut into several pieces, weighed and homogenized in PBS containing 0.35% Triton X-100. Serial dilutions of the lysates were then plated onto Bovine Heart Infusion agar containing 5 mg/ml erythromycin, incubated for 24-48 h at 37° C. and the number of colonies counted.

Cellular immunity to liver metastatic tumors was ascertained upon intra-splenic injections of B16/F10 melanoma and CT26 colon carcinoma tumors into syngeneic (C57BL/6J or Balb/c, respectively) or allogeneic hosts (pMHC-NP-treated or untreated NOD.c3c4 mice). A small incision was made in the abdomen, under isofluorane inhalational anesthesia, to partially expose the spleen. Tumor cells ($0.2 \times 10^6$ and $0.1 \times 10^6$ for B16/F10 and CT26, respectively, in 100 mL of PBS) were injected slowly for 1min into the exposed spleen. Ten minutes later, the spleen was removed and the peritoneal and skin layers sutured. pMHCII-NP therapy was resumed within 5-7d after surgery and continued until the end of follow-up. Mice were monitored for up to 19-21d and euthanized for tetramer staining, PBC scoring, and tumor burden measurements. In B16/F10-injected mice, tumor burden was assessed by measuring liver weight and counting the number of metastases, easily distinguishable from liver parenchyma. In CT26-injected animals, tumor burden was scored histologically by measuring the hepatic area (HPA) occupied by metastatic tumors.

To evaluate humoral immunity, pMHCII-NP-treated and untreated mice were immunized i.p. with 100 mg of DNP-KLH (Alpha Diagnostic International, San Antonio, TX) in CFA and boosted again 3 wk later. Mice were sacrificed 10d later, to measure serum anti-DNP antibody titers using an anti-DNP Ig ELISA Kit (Alpha Diagnostic International).

Cytokine Secretion Assays

Splenic and portal/celiac lymph node (PCLN) cell suspensions from pMHCII-NP-treated mice were enriched for CD4+ T-cells depleting CD19+ B-cells (EasySep™ Mouse CD19 Positive Selection Kit, Stem Cell Technologies, Vancouver, BC) and CD8+ T-cells (CD8 Magnetic Particles, BD Biosciences). Cells were stained with pMHCII tetramers and sorted by flow cytometry. The sorted cells ($2-3 \times 10^4$) were challenged with bone marrow-derived DCs ($2 \times 10^4$) pulsed with 2 μg ml$^{-1}$ peptide. Forty-eight hours later, supernatants were harvested for measurement of cytokine content via Luminex®.

To ascertain whether pMHCII-NP therapy promoted the recruitment/formation of IL-10-secreting B-cells, mesenteric LNs, PCLNs and liver cell suspensions were enriched for B-cells using a CD19 enrichment kit (Stem Cell Technologies). The cells ($2-3 \times 10^5$ in 200 mL/well) were stimulated in duplicate with LPS (1 μg ml$^{-1}$, Sigma) for 24 h in RPMI-1640 media containing 10% FCS. The levels of IL-10 in the supernatants were measured via Luminex®.

Isolation and In Vitro Stimulation of Lymph Node CD11b+ Cells and Liver Kupffer Cells CD11b+ cells from LNs were obtained by digestion in collagenase D (1.25 μg mL$^{-1}$) and DNAse I (0.1 μg mL-1) for 15 min at 37° C., washed, incubated with anti-FcR Abs, and purified using anti-CD11b mAb-coated magnetic beads (BD Biosciences). The purified cells ($2-3 \times 10^5$ in 200 mL/well) were stimulated with LPS (2 μg ml$^{-1}$) for 3 days, and the supernatants analyzed for cytokine content using a Luminex® multiplex cytokine assay.

To isolate Kupffer cells (KCs), livers from treated and untreated mice were minced and digested in 15 ml of 0.05% collagenase solution in HBSS for 20-30 min at 37° C. The resulting cell suspension was filtered through a nylon mesh (0.7 μm) and centrifuged at 50×g for 3 min at 4° C., to remove tissue debris and hepatocytes. Cells in the supernatant were pelleted by centrifugation at 300×g for 5 min at 4° C. The cell pellet, mainly composed of non-parenchymal liver immune cells, KCs, sinusoidal endothelial cells and stellate cells, was re-suspended in 33% Percoll® solution and centrifuged at 350×g for 30 min to isolate mononuclear cells. The pellets were re-suspended in DMEM containing 10% FCS ($5 \times 10^6$ cells ml$^{-1}$) and plated in 6-well plate at $1-3 \times 10^7$ cells/well and incubated for 2-3 h in a 5% $CO_2$ atmosphere at 37° C. Non-adherent cells were removed by gentle washing with PBS. The adherent fraction (enriched for KCs) was harvested by trypsin digestion (5 min, 0.25% trypsin). The resulting cell suspension was plated in 96 well plates at $1-2 \times 10^5/200$ mL/well and stimulated with LPS (2 mg ml$^{-1}$) for 3 d. The supernatants were analyzed for cytokine content using a Luminex® multiplex cytokine assay.

Adoptive Transfer of Suppression

Splenic CD4+ T-cells ($10^7$) from untreated mice or mice treated with 12 doses of PDC-E2$_{166-181}$/IA$^{g7}$-NPs were adoptively transferred (i.v.) into 10-14 wk-old, sex-matched NOD.c3c4.scid hosts. One day later, the recipients were adoptively transferred with $4 \times 10^7$ whole splenocytes from sex-matched NOD.c3c4 donor mice with established PBC (>35 wk-old). One of the cohorts of mice transfused with CD4+ T-cells from pMHCII-NP-treated donors was further treated with 12 doses of PDC-E2$_{166-181}$/IA$^{g7}$-NPs. The recipients were sacrificed 6 wk later for tetramer staining and PBC scoring.

In Vivo Breg Induction Assay

Splenic B-cells from NOD.Il10$^{tm1Flv}$ (Tiger) mice were enriched using an EasySep Mouse B-cell Isolation Kit (Stem Cell Technologies) and pulsed with BDC2.5 mi or PDC$_{166-181}$ peptides (10 μg ml$^{-1}$) for 2 h at 37° C. The peptide-pulsed B-cells were washed twice with PBS, labeled with PKH26 (Sigma) and transfused ($3 \times 10^6$) into pMHC-NP-treated or untreated mice. The hosts were killed 7d later and their spleens, MLNs, PCLNs and liver mononuclear cells were labeled with anti-B220-APC and biotinylated anti-CD1d or anti-CD5 mAbs followed by Streptavidin-PerCP. PKH26+ B-cells were analyzed for presence of eGFP+/CD1d$^{high}$ and eGFP+/CD5+ cells by flow cytometry.

Histology and Immunohistochemistry

Livers were fixed in 10% formalin for 2d, embedded in paraffin, cut into 5 μm sections and stained with H&E or Picrosirius Red. For immunohistochemistry, liver tissues were embedded in Tissue-Tek OCT, sectioned into 30 μm cryosections and stored on slides at −80° C. Slides were fixed in chilled acetone, washed with PBS, treated with a 1:10 dilution of 30% $H_2O_2$ in PBS, washed with PBS, blocked with 10% normal goat serum in PBS, washed again, and stained with anti-mouse CD4 (GK1.5) or CD8 (Lyt-2) antibodies (1.5 h, 4° C.). After washing, the slides were stained with a biotinylated goat anti-rat secondary antibody (1:200 dilution), incubated with Horseradish Peroxidase (HRP)-conjugated streptavidin, followed by 3,3-diaminobenzidine (DAB) substrate. Slides were counterstained with hematoxylin before mounting.

ALT and TBA Assays

Alanine aminotransferase (ALT) levels in serum were determined using a kit from Thermo Fisher Scientific following the manufacturer's protocol. Briefly, serum samples were mixed with pre-warmed (37° C.) Infinity™ ALT (GPT) Liquid Stable Reagent at 1:10 ratio and OD readings were taken for 3 min at 1 min intervals in a nanodrop at a 340 nm wavelength, 37° C. The slope was calculated by plotting absorbance vs. time using linear regression and multiplied with a factor to obtain ALT levels in serum (U/L) as described in the kit. Serum total bile acid (TBA) levels were analyzed using a TBA Enzymatic Cycling Assay Kit (Diazyme, Poway, CA) following a modified manufacturer's protocol as described.

Anti-Nuclear and Anti-Mitochondrial Autoantibody Measurements

Presence of anti-nuclear autoantibodies (ANAs) in serum was ascertained using NOVA Lite®HEp-2 Slides kit (Inova Diagnostics, San Diego, CA). A semi-quantitative approach was followed to measure ANA titers. Briefly, serum samples were serially diluted in PBS (at 1:160, 1:320, 1:640, 1:1280 and 1:2560) and then added to pre-fixed Hep-2 substrate slides, washed, stained with FITC-conjugated goat anti-mouse IgG in PBS containing 5% normal donkey serum (1:200 dilution), washed, mounted and read under a fluorescent microscope.

Serum levels of anti-mitochondrial PDC-E2 antibodies were determined via ELISA. Briefly, ELISA plates were coated with PDC-E2 protein (5 μg ml$^{-1}$, 100 mL) (SurModics Inc., Eden Prairie, MN) overnight at RT. Plates were washed, blocked using 3% dry skim milk in PBS (pH 7.4, 150 ml), and incubated with serially-diluted serum samples (100 ml, at 1:250 dilutions prepared using reagent diluent) for 2 h at RT. Wells were washed and incubated with 100 mL of HRP-conjugated anti-mouse IgG (1:2000 in reagent diluent) for 2 h at RT, and washed. Finally, wells were incubated in the dark with 100 mL of DAB substrate for 20 min at RT. Upon stopping the enzymatic reaction with 50 mL 2N $H_2SO_4$, the absorption was measured at a 450 nm wavelength using an ELISA plate reader. The Positive Antibody Activity (PAA) levels were calculated by calculating the mean OD±2 SD of the control NOD serum samples (positive index) and by dividing the OD values corresponding to NOD.c3c4 serum samples by the positive index, whereby values >1.0 correspond to PAA.

Statistical Analyses

Unless specified, sample size values mentioned in the figure legends correspond to the total number of mice examined, pooled from different experiments. Data were compared in GraphPad Prism 6 using Mann-Whitney U-test, Chi-Square, Log-Rank (Mantel-Cox), Pearson correlation, two-way ANOVA or multiple t test analyses using the Holm-Sidak correction. P values <0.05 were considered statistically significant. Only statistically significant P values are displayed on Figures.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Embodiments of the Current Description

The following embodiments provide a non-exhaustive list of specific compositions and uses of the current invention.

1. In a certain aspect described herein is a composition comprising:
   a) a plurality of antigen-major histocompatibility complexes (MHCs), each antigen-MHC of the plurality comprising a ubiquitous autoantigen, that is not a tissue specific antigen, associated with a binding groove of an MHC molecule; and
   b) a nanoparticle core possessing a diameter of between 1 and 100 nanometers;
   wherein the antigen-MHCs are coupled to the nanoparticle core.

2. An embodiment of the composition of embodiment 1, wherein the MHC molecule is an MHC class II molecule.

3. An embodiment of the composition of embodiment 1, wherein the nanoparticle core is a metal or metal oxide.

4. An embodiment of the composition of embodiment 3, wherein the metal is iron.

5. An embodiment of the composition of embodiment 3, wherein the metal oxide is iron oxide.

6. An embodiment of the composition of any one of embodiments 1 to 5, wherein the diameter is between about 5 nanometers and about 50 nanometers.

7. An embodiment of the composition of embodiment 6, wherein the diameter is between about 5 nanometers and about 25 nanometers.

8. An embodiment of the composition of any one of embodiments 1 to 7, wherein the plurality of antigen-MHCs is coupled to the nanoparticle core at an antigen-MHC to nanoparticle core ratio of at least 10:1.

9. An embodiment of the composition of any one of embodiments 1 to 8, wherein the plurality of antigen-MHCs is coupled to the nanoparticle core at an antigen-MHC to nanoparticle core ratio of no more than 150:1.

10. An embodiment of the composition of any one of embodiments 1 to 9, wherein the plurality of antigen-MHCs is coupled to the nanoparticle core at a density from about 0.4 to about 13 antigen-MHCs per 100 $nm^2$ of nanoparticle core surface area.

11. An embodiment of the composition of any one of embodiments 1 to 10, wherein the antigen-MHCs are covalently coupled to the nanoparticle core.

12. An embodiment of the composition of any one of embodiments 1 to 11, wherein the antigen-MHCs are covalently coupled to the nanoparticle core by a polyethylene glycol (PEG) linker having a mass of less than about 5 kilodaltons.

13. An embodiment of the composition of any one of embodiments 1 to 12, wherein the nanoparticle core further comprises a biocompatible coating.

14. An embodiment of the composition of any one of embodiments 1 to 13, wherein the ubiquitous autoantigen comprises a polypeptide derived from a protein that at steady-state exists in or on an intracellular compartment.

15. An embodiment of the composition of embodiment 14, wherein the intracellular compartment is cytosol, mitochondria, Golgi apparatus, endoplasmic reticulum, nucleus, or plasma membrane.

16. An embodiment of the composition of embodiment 14, wherein the intracellular compartment is a mitochondrion.

17. An embodiment of the composition of any one of embodiments 1 to 13, wherein the ubiquitous autoantigen is pyruvate dehydrogenase complex-E2 component (PDC-E2).

18. The composition of any one of embodiments 1 to 13, wherein the ubiquitous autoantigen is Cytochrome P450 2D6 (CYP2D6).

19. An embodiment of the composition of any one of embodiments 1 to 13, wherein the ubiquitous autoantigen is actin (ACTB).

20. An embodiment of the composition of any one of embodiments 1 to 13, wherein the ubiquitous autoantigen is soluble liver antigen (SLA).

21. An embodiment of the composition of any one of embodiments 1 to 13, wherein the ubiquitous autoantigen is formimidoyltransferase-cyclodeaminase (FTCD).

22. An embodiment of the composition of any one of embodiments 1 to 13, wherein the ubiquitous autoantigen is myeloperoxidase (MPO).

23. An embodiment of the composition of embodiment 17, wherein the ubiquitous autoantigen is selected from the group consisting of: $PDC-E2_{353-367}$; $PDC-E2_{72-86}$; $PDC-E2_{422-436}$; $PDC-E2_{353-367}$; $PDC-E2_{80-94}$; $PDC-E2_{535-549}$; $PDC-E2_{629-648}$; $PDC-E2_{122-135}$ $PDC-E2_{249-263}$; and $PDC-E2_{249-263}$.

24. An embodiment of the composition of embodiment 17, wherein the ubiquitous autoantigen is selected from the group consisting of: $PDC-E2_{422-436}$ and $PDC-E2_{80-94}$.

25. An embodiment of the composition of embodiment 18, wherein the ubiquitous autoantigen is selected from the group consisting of: $CYP2D6_{284-298}$ $CYP2D6_{289-303}$; $CYP2D6_{318-332}$; $CYP2D6_{313-332}$; $CYP2D6_{393-412}$; $CYP2D6_{192-206}$; $CYP2D6_{5-19}$; $CYP2D6_{293-307}$; $CYP2D6_{219-233}$; $CYP2D6_{237-251}$; $CYP2D6_{15-29}$; $CYP2D6_{235-249}$; $CYP2D6_{317-331}$; $CYP2D6_{293-307}$; $CYP2D6_{428-442}$; $CYP2D6_{237-251}$; $CYP2D6_{14-28}$; $CYP2D6_{199-213}$; $CYP2D6_{450-464}$; $CYP2D6_{301-315}$; $CYP2D6_{452-466}$; $CYP2D6_{59-73}$; $CYP2D6_{130-144}$; $CYP2D6_{193-212}$; $CYP2D6_{305-324}$; and $CYP2D6_{15-29}$.

26. An embodiment of the composition of embodiment 19, wherein the ubiquitous autoantigen is selected from the group consisting of: $ACTB_{202-216}$; $ACTB_{170-184}$; $ACTB_{245-259}$; $ACTB_{187-201}$; $ACTB_{172-186}$; $ACTB_{131-145}$; $ACTB_{131-145}$; $ACTB_{171-185}$; $ACTB_{129-143}$; $ACTB_{164-178}$; $ACTB_{25-39}$; and $ACTB_{323-337}$.

27. An embodiment of the composition of embodiment 19, wherein the ubiquitous autoantigen is selected from the group consisting of: $ACTB_{146-160}$; $ACTB_{18-32}$; and $ACTB_{171-185}$.

28. An embodiment of the composition of embodiment 20, wherein the ubiquitous autoantigen is selected from the group consisting of: $SLA_{334-348}$; $SLA_{196-210}$; $SLA_{115-129}$; $SLA_{373-386}$; $SLA_{186-197}$; $SLA_{342-256}$; $SLA_{110-124}$; $SLA_{299-313}$; $SLA_{49-63}$; $SLA_{260-274}$; $SLA_{119-133}$; $SLA_{86-100}$; $SLA_{26-40}$; $SLA_{331-345}$; $SLA_{317-331}$; $SLA_{171-185}$; $SLA_{417-431}$; $SLA_{359-373}$; $SLA_{215-229}$; and $SLA_{111-125}$.

29. An embodiment of the composition of embodiment 21, wherein the ubiquitous autoantigen is selected from the group consisting of: $FTCD_{439-453}$; $FTCD_{381-395}$; $FTCD_{297-311}$; $FTCD_{525-539}$; $FTCD_{218-232}$; $FTCD_{495-509}$; $FTCD_{262-276}$; $FTCD_{300-314}$; $FTCD_{259-273}$; $FTCD_{490-504}$; $FTCD_{389-403}$; and FTCD 295-309.

30. An embodiment of the composition of embodiment 21, wherein the ubiquitous autoantigen is selected from the group consisting of: $FTCD_{271-285}$; $FTCD_{498-512}$; and $FTCD_{301-315}$.

31. An embodiment of the composition of embodiment 22, wherein the ubiquitous autoantigen is selected from the group consisting of: $MPO_{322-336}$; $MPO_{714-728}$; $MPO_{617-631}$; $MPO_{504-518}$; $MPO_{462-476}$; $MPO_{617-631}$; $MPO_{444-458}$; $MPO_{689-703}$; $MPO_{248-262}$; $MPO_{511-525}$; $MPO_{97-111}$; and $MPO_{616-630}$.

32. An embodiment of the composition of any one of embodiments 1 to 31, further comprising a second plurality of antigen-major histocompatibility complexes (MHCs) coupled to the nanoparticle core, each antigen-MHC of the second plurality comprising an antigen.

33. An embodiment of the composition of embodiment 32, wherein the antigen of the second plurality of antigen-major histocompatibility complexes (MHCs) is a second ubiquitous autoantigen.

34. An embodiment of the composition of embodiment 32, wherein the second ubiquitous autoantigen comprises a polypeptide derived from a protein that at steady-state exists in or on an intracellular compartment.

35. An embodiment of the composition of embodiment 34, wherein the intracellular compartment is cytosol, mitochondria, Golgi apparatus, endoplasmic reticulum, nucleus, or plasma membrane.

36. An embodiment of the composition of embodiment 34, wherein the intracellular compartment is a mitochondrion.

37. An embodiment of the composition of embodiment 34, wherein the second ubiquitous autoantigen is selected from the group consisting of: $PDC-E2_{353-367}$; $PDC-E2_{72-86}$; $PDC-E2_{422-436}$; $PDC-E2_{353-367}$; $PDC-E2_{80-94}$; $PDC-E2_{535-549}$; $PDC-E2_{629-648}$; $PDC-E2_{122-135}$ $PDC-E2_{249-263}$; and $PDC-E2_{249-263}$.

38. An embodiment of the composition of embodiment 34, wherein the second ubiquitous autoantigen is selected from the group consisting of: $PDC-E2_{422-436}$ and $PDC-E2_{80-94}$.

39. An embodiment of the composition of embodiment 34, wherein the second ubiquitous autoantigen is selected from the group consisting of: $CYP2D6_{284-298}$; $CYP2D6_{289-303}$; $CYP2D6_{318-332}$; $CYP2D6_{313-332}$; $CYP2D6_{393-412}$; $CYP2D6_{192-206}$; $CYP2D65-19$; $CYP2D6_{293-307}$; $CYP2D6_{219-233}$; $CYP2D6_{237-251}$; $CYP2D6_{15-29}$; $CYP2D6_{235-249}$; $CYP2D6_{317-331}$; $CYP2D6_{293-307}$; $CYP2D6_{428-442}$; $CYP2D6_{237-251}$; $CYP2D6_{14-28}$; $CYP2D6_{199-213}$; $CYP2D6_{450-464}$; $CYP2D6_{301-315}$; $CYP2D6_{452-466}$; $CYP2D6_{59-73}$; $CYP2D6_{130-144}$; $CYP2D6_{193-212}$; $CYP2D6_{305-324}$; and $CYP2D6_{15-29}$.

40. An embodiment of the composition of embodiment 34, wherein the second ubiquitous autoantigen is selected from the group consisting of: $ACTB_{202-216}$; $ACTB_{170-184}$; $ACTB_{245-259}$; $ACTB_{187-201}$; $ACTB_{172-186}$; $ACTB_{131-145}$; $ACTB_{131-145}$; $ACTB_{171-185}$; $ACTB_{129-143}$; $ACTB_{164-178}$; $ACTB_{25-39}$; and $ACTB_{323-337}$.

41. An embodiment of the composition of embodiment 34, wherein the second ubiquitous autoantigen is selected from the group consisting of: $ACTB_{146-160}$; $ACTB_{18-32}$; and $ACTB_{171-185}$.

42. An embodiment of the composition of embodiment 34, wherein the second ubiquitous autoantigen is selected from the group consisting of: $SLA_{334-348}$; $SLA_{196-210}$; $SLA_{115-129}$; $SLA_{373-386}$; $SLA_{186-197}$; $SLA_{342-256}$; $SLA_{110-124}$; $SLA_{299-313}$; $SLA_{49-63}$; $SLA_{260-274}$; $SLA_{119-133}$; $SLA_{86-100}$; $SLA_{26-40}$; $SLA_{331-345}$; $SLA_{317-331}$; $SLA_{171-185}$; $SLA_{417-431}$; $SLA_{359-373}$; $SLA_{215-229}$; and $SLA_{111-125}$.

43. An embodiment of the composition of embodiment 34, wherein the second ubiquitous autoantigen is selected from the group consisting of: $FTCD_{439-453}$; $FTCD_{381-395}$; $FTCD_{297-311}$; $FTCD_{525-539}$; $FTCD_{218-232}$; $FTCD_{495-509}$;

FTCD$_{262-276}$; FTCD$_{300-314}$; FTCD$_{259-273}$; FTCD$_{490-504}$; FTCD$_{389-403}$; and FTCD$_{295-309}$.

44. An embodiment of the composition of embodiment 34, wherein the second ubiquitous autoantigen is selected from the group consisting of: FTCD$_{271-285}$; FTCD$_{498-512}$; and FTCD$_{301-315}$.

45. An embodiment of the composition of embodiment 34, wherein the second ubiquitous autoantigen is selected from the group consisting of: MPO$_{322-336}$; MPO$_{714-728}$; MPO$_{617-631}$; MPO$_{504-518}$; MPO$_{462-476}$; MPO$_{617-631}$; MPO$_{444-458}$; MPO$_{689-703}$; MPO$_{248-262}$; MPO$_{511-525}$; MPO$_{97-111}$; and MPO$_{616-630}$.

46. An embodiment of the composition of any one of embodiments 1 to 45, further comprising a pharmaceutically acceptable stabilizer, excipient, diluent, or combination thereof.

47. An embodiment of the composition of any one of embodiments 1 to 46, formulated for intravenous administration.

48. An embodiment of the composition of any one of embodiments 1 to 47, for use in a method of treating an autoimmune or inflammatory disease.

49. Use of the composition of any one of embodiments 1 to 47, in the manufacture of a medicament for treating an autoimmune or inflammatory disease.

50. An embodiment of the composition or use of embodiment 49, wherein the ubiquitous autoantigen or the second ubiquitous autoantigen is not a polypeptide derived from myelin basic protein, myelin associated glycoprotein, myelin oligodendrocyte protein (MOG), proteolipid protein, oligodendrocyte myelin oligoprotein, myelin associated oligodendrocyte basic protein, oligodendrocyte specific protein, heat shock proteins, an oligodendrocyte specific protein, NOGO A, glycoprotein Po, peripheral myelin protein 22, or 2'3'-cyclic nucleotide 3'-phosphodiesterase.

51. An embodiment of the composition or use of embodiment 49, wherein the ubiquitous autoantigen or the second ubiquitous autoantigen is not a polypeptide derived from pre-proinsulin, proinsulin, islet-specific glucose-6-phosphatase (IGRP), glutamate decarboxylase (GAD), islet cell autoantigen-2 (ICA2), or insulin.

TABLE 5 additional ubiquitous autoantigens

| Cellular location | Uniprot Code | | Description |
|---|---|---|---|
| Cytoplasm | P14152 | Mdh1 | Malate dehydrogenase, cytoplasmic (EC 1.1.1.37) (Cytosolic malate dehydrogenase) |
| Cytoplasm | P63260 | Actg1 | Actin, cytoplasmic 2 (Gamma-actin) [Cleaved into: Actin, cytoplasmic 2, N-terminally processed] |
| Cytoplasm | P20152 | Vim | Vimentin |
| Cytoplasm | P06151 | Ldha | L-lactate dehydrogenase A chain (LDH-A) (EC 1.1.1.27) (LDH muscle subunit) (LDH-M) |
| Cytoplasm | P16858 | Gapdh | Glyceraldehyde-3-phosphate dehydrogenase (GAPDH) (EC 1.2.1.12) (Peptidyl-cysteine S-nitrosylase GAPDH) (EC 2.6.99.—) |
| Cytoplasm | P63101 | Ywhaz | 14-3-3 protein zeta/delta (Protein kinase C inhibitor protein 1) (KCIP-1) (SEZ-2) |
| Cytoplasm | P11404 | Fabp3 | Fatty acid-binding protein, heart (Fatty acid-binding protein 3) (Heart-type fatty acid-binding protein) (H-FABP) (Mammary-derived growth inhibitor) (MDGI) |
| Cytoplasm | O08997 | Atox1 | Copper transport protein ATOX1 (Metal transport protein ATX1) |
| Cytoplasm | P35700 | Prdx1 | Peroxiredoxin-1 (EC 1.11.1.15) (Macrophage 23 kDa stress protein) (Osteoblast-specific factor 3) (OSF-3) (Thioredoxin peroxidase 2) (Thioredoxin-dependent peroxide reductase 2) |
| Cytoplasm | Q9CQM5 | Txndc17 | Thioredoxin domain-containing protein 17 (14 kDa thioredoxin-related protein) (TRP14) (Protein 42-9-9) (Thioredoxin-like protein 5) |
| Nucleus | P09405 | Ncl | Nucleolin (Protein C23) |
| Nucleus | Q9Z2X1 | Hnrnpf | Heterogeneous nuclear ribonucleoprotein F (hnRNP F) [Cleaved into: Heterogeneous nuclear ribonucleoprotein F, N-terminally processed] |
| Nucleus | Q3U898 | Cops9 | COP9 signalosome complex subunit 9 |
| Nucleus | P62322 | Lsm5 | U6 snRNA-associated Sm-like protein LSm5 |
| Nucleus | P17918 | Pcna | Proliferating cell nuclear antigen (PCNA) (Cyclin) |
| Nucleus | O88569 | Hnrnpa2b1 | Heterogeneous nuclear ribonucleoproteins A2/B1 (hnRNP A2/B1) |
| Nucleus | P40142 | Tkt | Transketolase (TK) (EC 2.2.1.1) (P68) |

TABLE 5-continued additional ubiquitous autoantigens

| Cellular location | Uniprot Code | | Description |
|---|---|---|---|
| Nucleus | Q60972 | Rbbp4 | Histone-binding protein RBBP4 (Chromatin assembly factor 1 subunit C) (CAF-1 subunit C) (Chromatin assembly factor I p48 subunit) (CAF-I 48 kDa subunit) (CAF-I p48) (Nucleosome-remodeling factor subunit RBAP48) (Retinoblastoma-binding protein 4) (RBBP-4) (Retinoblastoma-binding protein p48) |
| Nucleus | Q60973 | Rbbp7 | Histone-binding protein RBBP7 (Histone acetyltransferase type B subunit 2) (Nucleosome-remodeling factor subunit RBAP46) (Retinoblastoma-binding protein 7) (RBBP-7) (Retinoblastoma-binding protein p46) |
| Nucleus | P15532 | Nme1 | Nucleoside diphosphate kinase A (NDK A) (NDP kinase A) (EC 2.7.4.6) (Metastasis inhibition factor NM23) (NDPK-A) (Tumor metastatic process-associated protein) (nm23-M1) |
| Plasma Membrane | More Abundant | | |
| Plasma Membrane | P68040 | Rack1 | Receptor of activated protein C kinase 1 (12-3) (Guanine nucleotide-binding protein subunit beta-2-like 1) (Receptor for activated C kinase) (Receptor of activated protein kinase C 1) (p205) [Cleaved into: Receptor of activated protein C kinase 1, N-terminally processed (Guanine nucleotide-binding protein subunit beta-2-like 1, N-terminally processed)] |
| Plasma Membrane | Q62351 | Tfrc | Transferrin receptor protein 1 (TR) (TfR) (TfR1) (Trfr) (CD antigen CD71) |
| Plasma Membrane | Q9QYY0 | Gab1 | GRB2-associated-binding protein 1 (GRB2-associated binder 1) (Growth factor receptor bound protein 2-associated protein 1) |
| Plasma Membrane | P42703 | Lifr | Leukemia inhibitory factor receptor (LIF receptor) (LIF-R) (D-factor/LIF receptor) (CD antigen CD118) |
| Plasma Membrane | Q01279 | Egfr | Epidermal growth factor receptor (EC 2.7.10.1) |
| Plasma Membrane | Q62351 | Tfrc | Transferrin receptor protein 1 (TR) (TfR) (TfR1) (Trfr) (CD antigen CD71) |
| Plasma Membrane | P14069 | S100a6 | Protein S100-A6 (5B10) (Calcyclin) (Prolactin receptor-associated protein) (S100 calcium-binding protein A6) |
| Plasma Membrane | Q61160 | Fadd | FAS-associated death domain protein (FAS-associating death domain-containing protein) (Mediator of receptor induced toxicity) (Protein FADD) |
| Plasma Membrane | Q5M8N0 | Cnrip1 | CB1 cannabinoid receptor-interacting protein 1 (CRIP-1) |
| Plasma Membrane | Q60902 | Eps15l1 | Epidermal growth factor receptor substrate 15-like 1 (Epidermal growth factor receptor pathway substrate 15-related sequence) (Eps15-rs) (Eps15-related protein) (Eps15R) |
| Plasma Membrane | P97300 | Nptp | Nuroplastin |
| Mitochondria | Q64433 | Hspe1 | 10 kDa heat shock protein, mitochondrial (Hsp10) (10 kDa chaperonin) (Chaperonin 10) (CPN10) |

TABLE 5-continued additional ubiquitous autoantigens

| Cellular location | Uniprot Code | | Description |
|---|---|---|---|
| Mitochondria | Q07813 | Bax | Apoptosis regulator BAX |
| Mitochondria | P38647 | Hspa9 | Stress-70 protein, mitochondrial (75 kDa glucose-regulated protein) (GRP-75) (Heat shock 70 kDa protein 9) (Mortalin) (Peptide-binding protein 74) (PBP74) (p66 MOT) |
| Mitochondria | P19157 | Gstp1 | Glutathione S-transferase P 1 (Gst P1) (EC 2.5.1.18) (GST YF-YF) (GST class-pi) (GST-piB) (Preadipocyte growth factor) |
| Mitochondria | Q9CR21 | Ndufab1 | Acyl carrier protein, mitochondrial (ACP) (CI-SDAP) (NADH-ubiquinone oxidoreductase 9.6 kDa subunit) |
| Mitochondria | P08249 | Mdh2 | Malate dehydrogenase, mitochondrial (EC 1.1.1.37) |
| Mitochondria | P63038 | Hspd1 | 60 kDa heat shock protein, mitochondrial (EC 3.6.4.9) (60 kDa chaperonin) (Chaperonin 60) (CPN60) (HSP-65) (Heat shock protein 60) (HSP-60) (Hsp60) (Mitochondrial matrix protein P1) |
| Mitochondria | Q03265 | Atp5f1a | ATP synthase subunit alpha, mitochondrial (ATP synthase F1 subunit alpha) |
| Mitochondria | P63038 | Hspd1 | 60 kDa heat shock protein, mitochondrial (EC 3.6.4.9) (60 kDa chaperonin) (Chaperonin 60) (CPN60) (HSP-65) (Heat shock protein 60) (HSP-60) (Hsp60) (Mitochondrial matrix protein P1) |
| Mitochondria | P56382 | Atp5f1e | ATP synthase subunit epsilon, mitochondrial (ATPase subunit epsilon) (ATP synthase F1 subunit epsilon) |
| Golgi | | More Abundant | |
| Golgi | P61205 | Arf3 | ADP-ribosylation factor 3 |
| Golgi | P61750 | Arf4 | ADP-ribosylation factor 4 |
| Golgi | P84084 | Arf5 | ADP-ribosylation factor 5 |
| Golgi | Q99LT0 | Dpy30 | Protein dpy-30 homolog (Dpy-30-like protein) (Dpy-30L) |
| Golgi | P53811 | Pitpnb | Phosphatidylinositol transfer protein beta isoform (PI-TP-beta) (PtdIns transfer protein beta) (PtdInsTP beta) |
| Golgi | O35643 | Ap1b1 | AP-1 complex subunit beta-1 (Adaptor protein complex AP-1 subunit beta-1) (Adaptor-related protein complex 1 subunit beta-1) (Beta-1-adaptin) (Beta-adaptin 1) (Clathrin assembly protein complex 1 beta large chain) (Golgi adaptor HA1/AP1 adaptin beta subunit) |
| Golgi | P61211 | Arl1 | ADP-ribosylation factor-like protein 1 |
| Golgi | Q3UPH1 | Prrc1 | Protein PRRC1 (Proline-rich and coiled-coil-containing protein 1) |
| Golgi | P61924 | Copz1 | Coatomer subunit zeta-1 (Zeta-1-coat protein) (Zeta-1 COP) |
| Golgi | Q9CQC9 | Sar1b | GTP-binding protein SAR1b |
| ER | O55022 | Pgrmc1 | Membrane-associated progesterone receptor component 1 (mPR) |
| ER | P33267 | Cyp2f2 | Cytochrome P450 2F2 (EC 1.14.14.—) (CYPIIF2) (Cytochrome P450-NAH-2) (Naphthalene dehydrogenase) (Naphthalene hydroxylase) |
| ER | O55143 | Atp2a2 | Sarcoplasmic/endoplasmic reticulum calcium ATPase 2 (SERCA2) (SR Ca(2+)-ATPase 2) (EC 3.6.3.8) (Calcium pump 2) (Calcium-transporting ATPase sarcoplasmic reticulum type, slow twitch skeletal muscle isoform) (Endoplasmic reticulum class 1/2 Ca(2+) ATPase) |
| ER | P45878 | Fkbp2 | Peptidyl-prolyl cis-trans isomerase FKBP2 (PPIase FKBP2) (EC 5.2.1.8) (13 kDa FK506-binding protein) (13 kDa FKBP) (FKBP-13) (FK506-binding protein 2) (FKBP-2) (Immunophilin FKBP13) (Rotamase) |
| ER | P56395 | Cyb5a | Cytochrome b5 |
| ER | Q9D1Q6 | Erp44 | Endoplasmic reticulum resident protein 44 (ER protein 44) (ERp44) (Thioredoxin domain-containing protein 4) |

TABLE 5-continued additional ubiquitous autoantigens

| Cellular location | Uniprot Code | | Description |
|---|---|---|---|
| ER | P35564 | Canx | Calnexin |
| ER | P08113 | Hsp90b1 | Endoplasmin (94 kDa glucose-regulated protein) (GRP-94) (Endoplasmic reticulum resident protein 99) (ERp99) (Heat shock protein 90 kDa beta member 1) (Polymorphic tumor rejection antigen 1) (Tumor rejection antigen gp96) |
| ER | Q01853 | Vcp | Transitional endoplasmic reticulum ATPase (TER ATPase) (EC 3.6.4.6) (15S Mg(2+)-ATPase p97 subunit) (Valosin-containing protein) (VCP) |
| | Q9D0F3 | Lman1 | Protein ERGIC-53 (ER-Golgi intermediate compartment 53 kDa protein) (Lectin mannose-binding 1) (p58) |

Also contemplated are the human proteins or human homologues disclosed in this table

SEQUENCES DISCLOSED HEREIN

| HLA Allele bound | Position in protein start | end | Amino Acid Sequence PDC-E2 derived peptides | SEQ. ID NO: |
|---|---|---|---|---|
| DRB3*0202 | 353 | 367 | GRVFVSPLAKKLAVE | 1 |
| DRB3*0202 | 72 | 86 | RLLLQLLGSPGRRYY | 2 |
| DRB3*0202 | 422 | 436 | DIPISNIRRVIAQRL | 3 |
| DRB5*0101 | 353 | 367 | GRVFVSPLAKKLAVE | 4 |
| DRB5*0101 | 80 | 94 | SPGRRYYSLPPHQKV | 5 |
| DRB5*0101 | 535 | 549 | ETIANDVVSLATKAR | 6 |
| DRB4*0101 | 629 | 643 | AQWLAEFRKYLEKPI | 7 |
| DRB4*0101 | 122 | 135 | GDLIAEVETDKATV | 8 |
| DRB4*0101 | 249 | 262 | GDLLAEIETDKATI | 9 |
| DRB1*0801 | 249 | 263 | GDLLAEIETDKATIG | 10 |
| DRB3*0202 | 422 | 436 | DIPISNIRRVIAQRL | 11 |
| DRB5*0101 | 80 | 94 | SPGRRYYSLPPHQKV | 12 |
| | | | | 13 |

CYP2D6 derived peptides

| | | | | |
|---|---|---|---|---|
| DRB3*01:01 | 284 | 298 | GNPESSFNDENLRIV | 14 |
| DRB3*01:01 | 289 | 303 | SFNDENLRIVVADLF | 15 |
| DRB3*01:01 | 318 | 332 | LLLMILHPDVQRRVQ | 16 |
| DRB1*03:01 | 313 | 332 | TLAWGLLLMILHPDVQRRVQ | 17 |
| DRB1*03:01 | 393 | 412 | TTLITNLSSVLKDEAVWEKP | 18 |
| DRB1*03:01 | 192 | 206 | GRRFEYDDPRFLRLL | 19 |
| DRB1*03:01 | 5 | 19 | ALVPLAVIVAIFLLL | 20 |
| DRB1*03:01 | 293 | 307 | ENLRIVVADLFSAGM | 21 |
| DRB3*0202 | 219 | 233 | FLREVLNAVPVLLHI | 22 |
| DRB3*0202 | 237 | 251 | AGKVLRFQKAFLTQL | 23 |

-continued

| SEQUENCES DISCLOSED HEREIN | | | | |
|---|---|---|---|---|
| HLA Allele bound | Position in protein start | end | Amino Acid Sequence PDC-E2 derived peptides | SEQ. ID NO: |
| DRB3*0202 | 15 | 29 | IFLLLVDLMHRRQRW | 24 |
| DRB4*0101 | 235 | 249 | ALAGKVLRFQKAFLT | 25 |
| DRB4*0101 | 317 | 331 | GLLLMILHPDVQRRV | 26 |
| DRB4*0101 | 293 | 307 | ENLRIVVADLFSAGM | 27 |
| DRB5*0101 | 428 | 442 | VKPEAFLPFSAGRRA | 28 |
| DRB5*0101 | 237 | 251 | AGKVLRFQKAFLTQL | 29 |
| DRB5*0101 | 14 | 28 | AIFLLLVDLMHRRQR | 30 |
| DRB1*04:01 | 199 | 213 | DPRFLRLLDLAQEGL | 31 |
| DRB1*04:01 | 450 | 464 | RMELFLFFTSLLQHF | 32 |
| DRB1*04:01 | 301 | 315 | DLFSAGMVTTSTTLA | 33 |
| DRB1*07:01 | 452 | 466 | ELFLFFTSLLQHFSF | 34 |
| DRB1*07:01 | 59 | 73 | DQLRRRFGDVFSLQL | 35 |
| DRB1*07:01 | 130 | 144 | EQRRFSVSTLRNLGL | 36 |
| DRB1*07:01 | 193 | 212 | RRFEYDDPRFLRLLDLAQEG | 37 |
| DRB1*07:01 | 305 | 324 | AGMVTTSTTLAWGLLLMILH | 38 |
| ACTB derived peptides | | | | |
| DRB1*0301 | 202 | 216 | TTAEREIVRDIKEKL | 39 |
| DRB1*0301 | 170 | 184 | ALPHAILRLDLAGRD | 40 |
| DRB1*0301 | 245 | 259 | SGRTTGIVMDSGDGV | 41 |
| DRB3*02:02 | 187 | 201 | DYLMKILTERGYSFT | 42 |
| DRB3*02:02 | 172 | 186 | PHAILRLDLAGRDLT | 43 |
| DRB3*02:02 | 131 | 145 | AMYVAIQAVLSLYAS | 44 |
| DRB4*0101 | 131 | 145 | AMYVAIQAVLSLYAS | 45 |
| DRB4*0101 | 171 | 185 | LPHAILRLDLAGRDL | 46 |
| DRB4*0101 | 129 | 143 | TPAMYVAIQAVLSLY | 47 |
| DRB5*0101 | 164 | 178 | PIYEGYALPHAILRL | 48 |
| DRB5*0101 | 25 | 39 | DAPRAVFPSIVGRPR | 49 |
| DRB5*0101 | 323 | 337 | STMKIKIIAPPERKY | 50 |
| DRB3*0101 | 146 | 160 | GRTTGIVMDSGDGVT | 51 |
| DRB3*0101 | 18 | 32 | KAGFAGDDAPRAVFP | 52 |
| DRB4*0101 | 171 | 185 | LPHAILRLDLAGRDL | 53 |
| SLA derived peptides | | | | |
| DRB1*0301 | 334 | 348 | YKKLLKERKEMFSYL | 54 |
| DRB1*0301 | 196 | 210 | DELRTDLKAVEAKVQ | 55 |
| DRB1*0301 | 115 | 129 | NKITNSLVLDIIKLA | 56 |
| DRB1*0301 | 373 | 386 | NRLDRCLKAVRKER | 57 |

SEQUENCES DISCLOSED HEREIN

| HLA Allele bound | Position in protein start | end | Amino Acid Sequence | SEQ. ID NO: |
|---|---|---|---|---|
| | | | PDC-E2 derived peptides | |
| DRB1*0301 | 186 | 197 | LIQQGARVGRID | 58 |
| DRB3*0202 | 342 | 356 | KEMFSYLSNQIKKLS | 59 |
| DRB3*0202 | 110 | 124 | GSSLLNKITNSLVLD | 60 |
| DRB3*0202 | 299 | 313 | NDSFIQEISKMYPGR | 61 |
| DRB4*0101 | 49 | 63 | STLELFLHELAIMDS | 62 |
| DRB4*0101 | 260 | 274 | SKCMHLIQQGARVGR | 63 |
| DRB4*0101 | 119 | 133 | NSLVLDIIKLAGVHT | 64 |
| DRB5*0101 | 86 | 100 | RRHYRFIHGIGRSGD | 65 |
| DRB5*0101 | 26 | 40 | RSHEHLIRLLLEKGK | 66 |
| DRB5*0101 | 331 | 345 | SNGYKKLLKERKEMF | 67 |
| DRB1*0401 | 317 | 331 | SPSLDVLITLLSLGS | 68 |
| DRB1*0401 | 171 | 185 | DQKSCFKSMITAGFE | 69 |
| DRB1*0401 | 417 | 431 | YTFRGFMSHTNNYPC | 70 |
| DRB1*0701 | 359 | 373 | YNERLLHTPHNPISL | 71 |
| DRB1*0701 | 215 | 229 | DCILCIHSTTSCFAP | 72 |
| DRB1*0701 | 111 | 125 | SSLLNKITNSLVLDI | 73 |
| | | | FTCD derived peptides | |
| DRB3*0202 | 439 | 453 | ALQEGLRRAVSVPLT | 74 |
| DRB3*0202 | 381 | 395 | RRQFQSLDTTMRRLI | 75 |
| DRB3*0202 | 297 | 311 | EQRIRLVVSRLGLDS | 76 |
| DRB1*0301 | 525 | 539 | AKTQAALVLDCLETR | 77 |
| DRB1*0301 | 218 | 232 | KVQGIGWYLDEKNLA | 78 |
| DRB1*0301 | 495 | 509 | YFNVLINLRDITDEA | 79 |
| DRB4*0101 | 262 | 276 | LPVVGSQLVGLVPLK | 80 |
| DRB4*0101 | 300 | 314 | IRLVVSRLGLDSLCP | 81 |
| DRB4*0101 | 259 | 273 | ELSLPVVGSQLVGLV | 82 |
| DRB5*0101 | 490 | 504 | GVFGAYFNVLINLRD | 83 |
| DRB5*0101 | 389 | 403 | TTMRRLIPPFREASA | 84 |
| DRB5*0101 | 295 | 309 | EEEQRIRLVVSRLGL | 85 |
| DRB3*0101 | 271 | 285 | GLVPLKALLDAAAFY | 86 |
| DRB3*0101 | 498 | 512 | VLINLRDITDEAFKD | 87 |
| DRB3*0101 | 301 | 315 | RLVVSRLGLDSLCPF | 88 |
| | | | MPO derived peptides | |
| DRB3*0202 | 322 | 336 | SNITIRNQINALTSF | 89 |
| DRB3*0202 | 714 | 728 | KNNIFMSNSYPRDFV | 90 |
| DRB3*0202 | 617 | 631 | LGTVLRNLKLARKLM | 91 |

SEQUENCES DISCLOSED HEREIN

| HLA Allele bound | Position in protein start | Position in protein end | Amino Acid Sequence PDC-E2 derived peptides | SEQ. ID NO: |
|---|---|---|---|---|
| DRB1*0301 | 504 | 518 | LIQPFMFRLDNRYQP | 92 |
| DRB1*0301 | 462 | 476 | YLPLVLGPTAMRKYL | 93 |
| DRB1*0301 | 617 | 631 | LGTVLRNLKLARKLM | 94 |
| DRB4*0101 | 444 | 458 | QEARKIVGAMVQIIT | 95 |
| DRB4*0101 | 689 | 703 | QQRQALAQISLPRII | 96 |
| DRB4*0101 | 248 | 262 | RSLMFMQWGQLLDHD | 97 |
| DRB5*0101 | 511 | 525 | RLDNRYQPMEPNPRV | 98 |
| DRB5*0101 | 97 | 111 | ELLSYFKQPVAATRT | 99 |
| DRB5*0101 | 616 | 630 | QLGTVLRNLKLARKL | 100 |

Any of the peptides described herein may encompass a naturally occurring variant that does not affect binding to an MHC class II molecule or recognition by a T cell receptor. Such variants are contemplated herein and included with reference to the sequence.

| SEQ ID NO: | |
|---|---|
| 103 | MAIIYLILLFTAVRGIKEEHVIIQAEFYLNPDQSGEFMFDFD GDEIFHVDMAKKETVWRLEEFGRFASFEAQGALANIAVDKAN LEIMTKRSNYTPITNVPPEVTVLTNSPVELREPNVLICFIDK FTPPVVNVTWLRNGKPVTTGVSETVFLPREDHLFRKFHYLPF LPSTEDVYDCRVEHWGLDEPLLKHWEFDAPSPLPETTESGGG GGDKTHTCPPCPAPEAAGGPSVFLEPPKPKDTLMISRTPEVT CVVVDVSHEDPEVKFNWYVDGVEVHNAKTKPREEQYNSTYRV VSVLTVLHQDWLNGKEYKCKVSNKALPAPIEKTISKAGQPR EPQVYTLPPCRDELTKNQVSLWCLVKGFYPSDIAVEWESNGQ PENNYKTTPPVLDSDGSFFLYSKLTVDKSRWQQGNVFSCSVM HEALHNHYTQKSLSLSPGKGSGSGSGSC |
| 104 | MGSLQPLATLYLLGMLVASSLGGDLIAEVETDKATVGGGGGS GGGSGGSGDTQPRFLEQAKCECHFLNGTERVWNLIRYIYNQE EYARYNSDLGEYQAVTELGRPDAEYWNSQKDLLERRRAEVDT YCRYNYGVVESFTVQRRVQPKVTVYPSKTQPLQHHNLLVCSV NGFYPGSIEVRWFRNSQEEKAGVVSTGLIQNGDWTFQTLVML ETVPRSGEVYTCQVEHPSMMSPLTVQWSARSESAQSKSGGGG GDKTHTCPPCPAPEAAGGPSVFLEPPKPKDTLMISRTPEVTC VVVDVSHEDPEVKFNWYVDGVEVHNAKTKPREEQYNSTYRVV SVLTVLHQDWLNGKEYKCKVSNKALPAPIEKTISKAKGQPRE PQVCTLPPSRDELTKNQVSLSCAVKGFYPSDIAVEWESNGQP ENNYKTTPPVLDSDGSFFLVSKLVDKSRWQQGNVFSCSVMHE ALHNHYTQKSLSLSPGK |

What is claimed is:

1. A method for treating an autoimmune or inflammatory disease in a patient in need thereof, comprising administering to the patient a composition comprising:
   a) a plurality of antigen-major histocompatibility class II complexes (antigen-MHCIIs), each antigen-MHCII of the plurality comprising a ubiquitous autoantigen associated with a binding groove of an MHC class II molecule, wherein the ubiquitous autoantigen is chosen from PDC-E2$_{353-367}$, PDC-E2$_{72-86}$, and PDC-E2$_{422-436}$ for DRB3*0202; PDC-E2$_{353-367}$, PDC-E2$_{80-94}$, and PDC-E2$_{535-549}$ for DRB5*0101; PDC-E2$_{629-648}$, PDC-E2$_{122-135}$, and PDC-E2$_{249-263}$ for DRB4*0101; and PDC-E2$_{249-263}$ for DRB1*0801; and
   b) a nanoparticle core possessing a diameter of between 1 and about 100 nanometers;
   wherein the antigen-MHCs are coupled to the nanoparticle core or a biocompatible layer surrounding the nanoparticle core; and
   wherein the autoimmune or inflammatory disease is chosen from multiple sclerosis and psoriasis.

2. The method of claim 1, wherein the nanoparticle core is a metal or metal oxide.

3. The method of claim 2, wherein the metal is iron.

4. The method of claim 2, wherein the metal oxide is iron oxide.

5. The method of claim 1, wherein the diameter is between about 5 nanometers and about 50 nanometers.

6. The method of claim 5, wherein the diameter is between about 5 nanometers and about 25 nanometers.

7. The method of claim 1, wherein the plurality of antigen-MHCs is coupled to the nanoparticle core at an antigen-MHC to nanoparticle core ratio of at least 10:1.

8. The method of claim 1, wherein the plurality of antigen-MHCs is coupled to the nanoparticle core at an antigen-MHC to nanoparticle core ratio of no more than about 150:1.

9. The method of claim 1, wherein the plurality of antigen-MHCs is coupled to the nanoparticle core at a density from about 0.4 to about 13 antigen-MHCs per 100 nm$^2$ of nanoparticle core surface area.

10. The method of claim 1, wherein the antigen-MHCs are covalently coupled to the nanoparticle core.

11. The method of claim 1, wherein the antigen-MHCs are coupled to the nanoparticle core by a polyethylene glycol (PEG) linker having a mass of less than about 5 kilodaltons.

12. The method of claim 1, wherein the nanoparticle core further comprises a biocompatible coating.

13. The method of claim 1, wherein the ubiquitous autoantigen is selected from the group consisting of: PDC-E2$_{422-436}$ and PDC-E2$_{80-94}$.

14. The method of claim 1 further comprising a pharmaceutically acceptable stabilizer, excipient, diluent, or combination thereof.

15. The method of claim 1, formulated for intravenous administration.

16. A method of treating an autoimmune or inflammatory disease in an individual comprising administering to an individual a composition comprising:
   a) a plurality of antigen-major histocompatibility class II complexes (antigen-MHCIIs), each antigen-MHCII of the plurality comprising a ubiquitous autoantigen associated with a binding groove of an MHC class II molecule, wherein the ubiquitous autoantigen is chosen from PDC-E2353-367, PDC-E2$_{72-86}$, and PDC-E2$_{422-436}$ for DRB3*0202; PDC-E2$_{353-367}$, PDC-E2$_{80-94}$, and PDC-E2$_{535-549}$ for DRB5*0101; PDC-E2$_{629-648}$, PDC-E2122-135, and PDC-E2$_{249-263}$ for DRB4*0101; and PDC-E2$_{249-263}$ for DRB1*0801; and
   b) a nanoparticle core possessing a diameter of between 1 and about 100 nanometers;
   wherein the antigen-MHCs are coupled to the nanoparticle core or a biocompatible layer surrounding the nanoparticle core; and
   wherein the autoimmune or inflammatory disease is chosen from multiple sclerosis and psoriasis.

* * * * *

SEQUENCE LISTING

```
<160> NUMBER OF SEQ ID NOS: 110

<210> SEQ ID NO 1
<211> LENGTH: 15
<212> TYPE: PRT
<213> ORGANISM: Homo sapiens

<400> SEQUENCE: 1

Gly Arg Val Phe Val Ser Pro Leu Ala Lys Lys Leu Ala Val Glu
1               5                   10                  15

<210> SEQ ID NO 2
<211> LENGTH: 15
<212> TYPE: PRT
<213> ORGANISM: Homo sapiens

<400> SEQUENCE: 2

Arg Leu Leu Leu Gln Leu Leu Gly Ser Pro Gly Arg Arg Tyr Tyr
1               5                   10                  15
```

-continued

```
<210> SEQ ID NO 3
<211> LENGTH: 15
<212> TYPE: PRT
<213> ORGANISM: Homo sapiens

<400> SEQUENCE: 3

Asp Ile Pro Ile Ser Asn Ile Arg Arg Val Ile Ala Gln Arg Leu
1               5                   10                  15

<210> SEQ ID NO 4
<211> LENGTH: 15
<212> TYPE: PRT
<213> ORGANISM: Homo sapiens

<400> SEQUENCE: 4

Gly Arg Val Phe Val Ser Pro Leu Ala Lys Lys Leu Ala Val Glu
1               5                   10                  15

<210> SEQ ID NO 5
<211> LENGTH: 15
<212> TYPE: PRT
<213> ORGANISM: Homo sapiens

<400> SEQUENCE: 5

Ser Pro Gly Arg Arg Tyr Tyr Ser Leu Pro Pro His Gln Lys Val
1               5                   10                  15

<210> SEQ ID NO 6
<211> LENGTH: 15
<212> TYPE: PRT
<213> ORGANISM: Homo sapiens

<400> SEQUENCE: 6

Glu Thr Ile Ala Asn Asp Val Val Ser Leu Ala Thr Lys Ala Arg
1               5                   10                  15

<210> SEQ ID NO 7
<211> LENGTH: 15
<212> TYPE: PRT
<213> ORGANISM: Homo sapiens

<400> SEQUENCE: 7

Ala Gln Trp Leu Ala Glu Phe Arg Lys Tyr Leu Glu Lys Pro Ile
1               5                   10                  15

<210> SEQ ID NO 8
<211> LENGTH: 14
<212> TYPE: PRT
<213> ORGANISM: Homo sapiens

<400> SEQUENCE: 8

Gly Asp Leu Ile Ala Glu Val Glu Thr Asp Lys Ala Thr Val
1               5                   10

<210> SEQ ID NO 9
<211> LENGTH: 14
<212> TYPE: PRT
<213> ORGANISM: Homo sapiens

<400> SEQUENCE: 9

Gly Asp Leu Leu Ala Glu Ile Glu Thr Asp Lys Ala Thr Ile
1               5                   10

<210> SEQ ID NO 10
<211> LENGTH: 15
```

```
<212> TYPE: PRT
<213> ORGANISM: Homo sapiens

<400> SEQUENCE: 10

Gly Asp Leu Leu Ala Glu Ile Glu Thr Asp Lys Ala Thr Ile Gly
1               5                   10                  15

<210> SEQ ID NO 11
<211> LENGTH: 15
<212> TYPE: PRT
<213> ORGANISM: Homo sapiens

<400> SEQUENCE: 11

Asp Ile Pro Ile Ser Asn Ile Arg Arg Val Ile Ala Gln Arg Leu
1               5                   10                  15

<210> SEQ ID NO 12
<211> LENGTH: 15
<212> TYPE: PRT
<213> ORGANISM: Homo sapiens

<400> SEQUENCE: 12

Ser Pro Gly Arg Arg Tyr Tyr Ser Leu Pro Pro His Gln Lys Val
1               5                   10                  15

<210> SEQ ID NO 13
<211> LENGTH: 15
<212> TYPE: PRT
<213> ORGANISM: Homo sapiens

<400> SEQUENCE: 13

Gly Asn Pro Glu Ser Ser Phe Asn Asp Glu Asn Leu Arg Ile Val
1               5                   10                  15

<210> SEQ ID NO 14
<211> LENGTH: 15
<212> TYPE: PRT
<213> ORGANISM: Homo sapiens

<400> SEQUENCE: 14

Gly Asn Pro Glu Ser Ser Phe Asn Asp Glu Asn Leu Arg Ile Val
1               5                   10                  15

<210> SEQ ID NO 15
<211> LENGTH: 15
<212> TYPE: PRT
<213> ORGANISM: Homo sapiens

<400> SEQUENCE: 15

Ser Phe Asn Asp Glu Asn Leu Arg Ile Val Val Ala Asp Leu Phe
1               5                   10                  15

<210> SEQ ID NO 16
<211> LENGTH: 15
<212> TYPE: PRT
<213> ORGANISM: Homo sapiens

<400> SEQUENCE: 16

Leu Leu Leu Met Ile Leu His Pro Asp Val Gln Arg Arg Val Gln
1               5                   10                  15

<210> SEQ ID NO 17
<211> LENGTH: 20
<212> TYPE: PRT
<213> ORGANISM: Homo sapiens
```

<400> SEQUENCE: 17

Thr Leu Ala Trp Gly Leu Leu Leu Met Ile Leu His Pro Asp Val Gln
1               5                   10                  15

Arg Arg Val Gln
            20

<210> SEQ ID NO 18
<211> LENGTH: 20
<212> TYPE: PRT
<213> ORGANISM: Homo sapiens

<400> SEQUENCE: 18

Thr Thr Leu Ile Thr Asn Leu Ser Ser Val Leu Lys Asp Glu Ala Val
1               5                   10                  15

Trp Glu Lys Pro
            20

<210> SEQ ID NO 19
<211> LENGTH: 15
<212> TYPE: PRT
<213> ORGANISM: Homo sapiens

<400> SEQUENCE: 19

Gly Arg Arg Phe Glu Tyr Asp Asp Pro Arg Phe Leu Arg Leu Leu
1               5                   10                  15

<210> SEQ ID NO 20
<211> LENGTH: 15
<212> TYPE: PRT
<213> ORGANISM: Homo sapiens

<400> SEQUENCE: 20

Ala Leu Val Pro Leu Ala Val Val Ala Ile Phe Leu Leu Leu
1               5                   10                  15

<210> SEQ ID NO 21
<211> LENGTH: 15
<212> TYPE: PRT
<213> ORGANISM: Homo sapiens

<400> SEQUENCE: 21

Glu Asn Leu Arg Ile Val Val Ala Asp Leu Phe Ser Ala Gly Met
1               5                   10                  15

<210> SEQ ID NO 22
<211> LENGTH: 15
<212> TYPE: PRT
<213> ORGANISM: Homo sapiens

<400> SEQUENCE: 22

Phe Leu Arg Glu Val Leu Asn Ala Val Pro Val Leu Leu His Ile
1               5                   10                  15

<210> SEQ ID NO 23
<211> LENGTH: 15
<212> TYPE: PRT
<213> ORGANISM: Homo sapiens

<400> SEQUENCE: 23

Ala Gly Lys Val Leu Arg Phe Gln Lys Ala Phe Leu Thr Gln Leu
1               5                   10                  15

<210> SEQ ID NO 24
<211> LENGTH: 15
<212> TYPE: PRT
<213> ORGANISM: Homo sapiens

<400> SEQUENCE: 24

Ile Phe Leu Leu Leu Val Asp Leu Met His Arg Arg Gln Arg Trp
1               5                   10                  15

<210> SEQ ID NO 25
<211> LENGTH: 15
<212> TYPE: PRT
<213> ORGANISM: Homo sapiens

<400> SEQUENCE: 25

Ala Leu Ala Gly Lys Val Leu Arg Phe Gln Lys Ala Phe Leu Thr
1               5                   10                  15

<210> SEQ ID NO 26
<211> LENGTH: 15
<212> TYPE: PRT
<213> ORGANISM: Homo sapiens

<400> SEQUENCE: 26

Gly Leu Leu Leu Met Ile Leu His Pro Asp Val Gln Arg Arg Val
1               5                   10                  15

<210> SEQ ID NO 27
<211> LENGTH: 15
<212> TYPE: PRT
<213> ORGANISM: Homo sapiens

<400> SEQUENCE: 27

Glu Asn Leu Arg Ile Val Val Ala Asp Leu Phe Ser Ala Gly Met
1               5                   10                  15

<210> SEQ ID NO 28
<211> LENGTH: 15
<212> TYPE: PRT
<213> ORGANISM: Homo sapiens

<400> SEQUENCE: 28

Val Lys Pro Glu Ala Phe Leu Pro Phe Ser Ala Gly Arg Arg Ala
1               5                   10                  15

<210> SEQ ID NO 29
<211> LENGTH: 15
<212> TYPE: PRT
<213> ORGANISM: Homo sapiens

<400> SEQUENCE: 29

Ala Gly Lys Val Leu Arg Phe Gln Lys Ala Phe Leu Thr Gln Leu
1               5                   10                  15

<210> SEQ ID NO 30
<211> LENGTH: 15
<212> TYPE: PRT
<213> ORGANISM: Homo sapiens

<400> SEQUENCE: 30

Ala Ile Phe Leu Leu Leu Val Asp Leu Met His Arg Arg Gln Arg
1               5                   10                  15

<210> SEQ ID NO 31
<211> LENGTH: 15

```
<212> TYPE: PRT
<213> ORGANISM: Homo sapiens

<400> SEQUENCE: 31

Asp Pro Arg Phe Leu Arg Leu Leu Asp Leu Ala Gln Glu Gly Leu
1               5                   10                  15

<210> SEQ ID NO 32
<211> LENGTH: 15
<212> TYPE: PRT
<213> ORGANISM: Homo sapiens

<400> SEQUENCE: 32

Arg Met Glu Leu Phe Leu Phe Phe Thr Ser Leu Leu Gln His Phe
1               5                   10                  15

<210> SEQ ID NO 33
<211> LENGTH: 15
<212> TYPE: PRT
<213> ORGANISM: Homo sapiens

<400> SEQUENCE: 33

Asp Leu Phe Ser Ala Gly Met Val Thr Ser Thr Thr Leu Ala
1               5                   10                  15

<210> SEQ ID NO 34
<211> LENGTH: 15
<212> TYPE: PRT
<213> ORGANISM: Homo sapiens

<400> SEQUENCE: 34

Glu Leu Phe Leu Phe Phe Thr Ser Leu Leu Gln His Phe Ser Phe
1               5                   10                  15

<210> SEQ ID NO 35
<211> LENGTH: 15
<212> TYPE: PRT
<213> ORGANISM: Homo sapiens

<400> SEQUENCE: 35

Asp Gln Leu Arg Arg Arg Phe Gly Asp Val Phe Ser Leu Gln Leu
1               5                   10                  15

<210> SEQ ID NO 36
<211> LENGTH: 15
<212> TYPE: PRT
<213> ORGANISM: Homo sapiens

<400> SEQUENCE: 36

Glu Gln Arg Arg Phe Ser Val Ser Thr Leu Arg Asn Leu Gly Leu
1               5                   10                  15

<210> SEQ ID NO 37
<211> LENGTH: 20
<212> TYPE: PRT
<213> ORGANISM: Homo sapiens

<400> SEQUENCE: 37

Arg Arg Phe Glu Tyr Asp Asp Pro Arg Phe Leu Arg Leu Leu Asp Leu
1               5                   10                  15

Ala Gln Glu Gly
            20

<210> SEQ ID NO 38
```

```
<211> LENGTH: 20
<212> TYPE: PRT
<213> ORGANISM: Homo sapiens

<400> SEQUENCE: 38

Ala Gly Met Val Thr Thr Ser Thr Thr Leu Ala Trp Gly Leu Leu Leu
1               5                   10                  15

Met Ile Leu His
            20

<210> SEQ ID NO 39
<211> LENGTH: 15
<212> TYPE: PRT
<213> ORGANISM: Homo sapiens

<400> SEQUENCE: 39

Thr Thr Ala Glu Arg Glu Ile Val Arg Asp Ile Lys Glu Lys Leu
1               5                   10                  15

<210> SEQ ID NO 40
<211> LENGTH: 15
<212> TYPE: PRT
<213> ORGANISM: Homo sapiens

<400> SEQUENCE: 40

Ala Leu Pro His Ala Ile Leu Arg Leu Asp Leu Ala Gly Arg Asp
1               5                   10                  15

<210> SEQ ID NO 41
<211> LENGTH: 15
<212> TYPE: PRT
<213> ORGANISM: Homo sapiens

<400> SEQUENCE: 41

Ser Gly Arg Thr Thr Gly Ile Val Met Asp Ser Gly Asp Gly Val
1               5                   10                  15

<210> SEQ ID NO 42
<211> LENGTH: 15
<212> TYPE: PRT
<213> ORGANISM: Homo sapiens

<400> SEQUENCE: 42

Asp Tyr Leu Met Lys Ile Leu Thr Glu Arg Gly Tyr Ser Phe Thr
1               5                   10                  15

<210> SEQ ID NO 43
<211> LENGTH: 15
<212> TYPE: PRT
<213> ORGANISM: Homo sapiens

<400> SEQUENCE: 43

Pro His Ala Ile Leu Arg Leu Asp Leu Ala Gly Arg Asp Leu Thr
1               5                   10                  15

<210> SEQ ID NO 44
<211> LENGTH: 15
<212> TYPE: PRT
<213> ORGANISM: Homo sapiens

<400> SEQUENCE: 44

Ala Met Tyr Val Ala Ile Gln Ala Val Leu Ser Leu Tyr Ala Ser
1               5                   10                  15
```

<210> SEQ ID NO 45
<211> LENGTH: 15
<212> TYPE: PRT
<213> ORGANISM: Homo sapiens

<400> SEQUENCE: 45

Ala Met Tyr Val Ala Ile Gln Ala Val Leu Ser Leu Tyr Ala Ser
1               5                   10                  15

<210> SEQ ID NO 46
<211> LENGTH: 15
<212> TYPE: PRT
<213> ORGANISM: Homo sapiens

<400> SEQUENCE: 46

Leu Pro His Ala Ile Leu Arg Leu Asp Leu Ala Gly Arg Asp Leu
1               5                   10                  15

<210> SEQ ID NO 47
<211> LENGTH: 15
<212> TYPE: PRT
<213> ORGANISM: Homo sapiens

<400> SEQUENCE: 47

Thr Pro Ala Met Tyr Val Ala Ile Gln Ala Val Leu Ser Leu Tyr
1               5                   10                  15

<210> SEQ ID NO 48
<211> LENGTH: 15
<212> TYPE: PRT
<213> ORGANISM: Homo sapiens

<400> SEQUENCE: 48

Pro Ile Tyr Glu Gly Tyr Ala Leu Pro His Ala Ile Leu Arg Leu
1               5                   10                  15

<210> SEQ ID NO 49
<211> LENGTH: 15
<212> TYPE: PRT
<213> ORGANISM: Homo sapiens

<400> SEQUENCE: 49

Asp Ala Pro Arg Ala Val Phe Pro Ser Ile Val Gly Arg Pro Arg
1               5                   10                  15

<210> SEQ ID NO 50
<211> LENGTH: 15
<212> TYPE: PRT
<213> ORGANISM: Homo sapiens

<400> SEQUENCE: 50

Ser Thr Met Lys Ile Lys Ile Ile Ala Pro Pro Glu Arg Lys Tyr
1               5                   10                  15

<210> SEQ ID NO 51
<211> LENGTH: 15
<212> TYPE: PRT
<213> ORGANISM: Homo sapiens

<400> SEQUENCE: 51

Gly Arg Thr Thr Gly Ile Val Met Asp Ser Gly Asp Gly Val Thr
1               5                   10                  15

<210> SEQ ID NO 52
<211> LENGTH: 15

-continued

<212> TYPE: PRT
<213> ORGANISM: Homo sapiens

<400> SEQUENCE: 52

Lys Ala Gly Phe Ala Gly Asp Asp Ala Pro Arg Ala Val Phe Pro
1               5                   10                  15

<210> SEQ ID NO 53
<211> LENGTH: 15
<212> TYPE: PRT
<213> ORGANISM: Homo sapiens

<400> SEQUENCE: 53

Leu Pro His Ala Ile Leu Arg Leu Asp Leu Ala Gly Arg Asp Leu
1               5                   10                  15

<210> SEQ ID NO 54
<211> LENGTH: 15
<212> TYPE: PRT
<213> ORGANISM: Homo sapiens

<400> SEQUENCE: 54

Tyr Lys Lys Leu Leu Lys Glu Arg Lys Glu Met Phe Ser Tyr Leu
1               5                   10                  15

<210> SEQ ID NO 55
<211> LENGTH: 15
<212> TYPE: PRT
<213> ORGANISM: Homo sapiens

<400> SEQUENCE: 55

Asp Glu Leu Arg Thr Asp Leu Lys Ala Val Glu Ala Lys Val Gln
1               5                   10                  15

<210> SEQ ID NO 56
<211> LENGTH: 15
<212> TYPE: PRT
<213> ORGANISM: Homo sapiens

<400> SEQUENCE: 56

Asn Lys Ile Thr Asn Ser Leu Val Leu Asp Ile Ile Lys Leu Ala
1               5                   10                  15

<210> SEQ ID NO 57
<211> LENGTH: 14
<212> TYPE: PRT
<213> ORGANISM: Homo sapiens

<400> SEQUENCE: 57

Asn Arg Leu Asp Arg Cys Leu Lys Ala Val Arg Lys Glu Arg
1               5                   10

<210> SEQ ID NO 58
<211> LENGTH: 12
<212> TYPE: PRT
<213> ORGANISM: Homo sapiens

<400> SEQUENCE: 58

Leu Ile Gln Gln Gly Ala Arg Val Gly Arg Ile Asp
1               5                   10

<210> SEQ ID NO 59
<211> LENGTH: 15
<212> TYPE: PRT
<213> ORGANISM: Homo sapiens

<400> SEQUENCE: 59

Lys Glu Met Phe Ser Tyr Leu Ser Asn Gln Ile Lys Lys Leu Ser
1               5                   10                  15

<210> SEQ ID NO 60
<211> LENGTH: 15
<212> TYPE: PRT
<213> ORGANISM: Homo sapiens

<400> SEQUENCE: 60

Gly Ser Ser Leu Leu Asn Lys Ile Thr Asn Ser Leu Val Leu Asp
1               5                   10                  15

<210> SEQ ID NO 61
<211> LENGTH: 15
<212> TYPE: PRT
<213> ORGANISM: Homo sapiens

<400> SEQUENCE: 61

Asn Asp Ser Phe Ile Gln Glu Ile Ser Lys Met Tyr Pro Gly Arg
1               5                   10                  15

<210> SEQ ID NO 62
<211> LENGTH: 15
<212> TYPE: PRT
<213> ORGANISM: Homo sapiens

<400> SEQUENCE: 62

Ser Thr Leu Glu Leu Phe Leu His Glu Leu Ala Ile Met Asp Ser
1               5                   10                  15

<210> SEQ ID NO 63
<211> LENGTH: 15
<212> TYPE: PRT
<213> ORGANISM: Homo sapiens

<400> SEQUENCE: 63

Ser Lys Cys Met His Leu Ile Gln Gln Gly Ala Arg Val Gly Arg
1               5                   10                  15

<210> SEQ ID NO 64
<211> LENGTH: 15
<212> TYPE: PRT
<213> ORGANISM: Homo sapiens

<400> SEQUENCE: 64

Asn Ser Leu Val Leu Asp Ile Ile Lys Leu Ala Gly Val His Thr
1               5                   10                  15

<210> SEQ ID NO 65
<211> LENGTH: 15
<212> TYPE: PRT
<213> ORGANISM: Homo sapiens

<400> SEQUENCE: 65

Arg Arg His Tyr Arg Phe Ile His Gly Ile Gly Arg Ser Gly Asp
1               5                   10                  15

<210> SEQ ID NO 66
<211> LENGTH: 15
<212> TYPE: PRT
<213> ORGANISM: Homo sapiens

<400> SEQUENCE: 66

Arg Ser His Glu His Leu Ile Arg Leu Leu Glu Lys Gly Lys
1               5                   10                  15

<210> SEQ ID NO 67
<211> LENGTH: 15
<212> TYPE: PRT
<213> ORGANISM: Homo sapiens

<400> SEQUENCE: 67

Ser Asn Gly Tyr Lys Lys Leu Leu Lys Glu Arg Lys Glu Met Phe
1               5                   10                  15

<210> SEQ ID NO 68
<211> LENGTH: 15
<212> TYPE: PRT
<213> ORGANISM: Homo sapiens

<400> SEQUENCE: 68

Ser Pro Ser Leu Asp Val Leu Ile Thr Leu Leu Ser Leu Gly Ser
1               5                   10                  15

<210> SEQ ID NO 69
<211> LENGTH: 15
<212> TYPE: PRT
<213> ORGANISM: Homo sapiens

<400> SEQUENCE: 69

Asp Gln Lys Ser Cys Phe Lys Ser Met Ile Thr Ala Gly Phe Glu
1               5                   10                  15

<210> SEQ ID NO 70
<211> LENGTH: 15
<212> TYPE: PRT
<213> ORGANISM: Homo sapiens

<400> SEQUENCE: 70

Tyr Thr Phe Arg Gly Phe Met Ser His Thr Asn Asn Tyr Pro Cys
1               5                   10                  15

<210> SEQ ID NO 71
<211> LENGTH: 15
<212> TYPE: PRT
<213> ORGANISM: Homo sapiens

<400> SEQUENCE: 71

Tyr Asn Glu Arg Leu Leu His Thr Pro His Asn Pro Ile Ser Leu
1               5                   10                  15

<210> SEQ ID NO 72
<211> LENGTH: 15
<212> TYPE: PRT
<213> ORGANISM: Homo sapiens

<400> SEQUENCE: 72

Asp Cys Ile Leu Cys Ile His Ser Thr Thr Ser Cys Phe Ala Pro
1               5                   10                  15

<210> SEQ ID NO 73
<211> LENGTH: 15
<212> TYPE: PRT
<213> ORGANISM: Homo sapiens

<400> SEQUENCE: 73

Ser Ser Leu Leu Asn Lys Ile Thr Asn Ser Leu Val Leu Asp Ile

```
1               5                   10                  15
```

<210> SEQ ID NO 74
<211> LENGTH: 15
<212> TYPE: PRT
<213> ORGANISM: Homo sapiens

<400> SEQUENCE: 74

```
Ala Leu Gln Glu Gly Leu Arg Arg Ala Val Ser Val Pro Leu Thr
1               5                   10                  15
```

<210> SEQ ID NO 75
<211> LENGTH: 15
<212> TYPE: PRT
<213> ORGANISM: Homo sapiens

<400> SEQUENCE: 75

```
Arg Arg Gln Phe Gln Ser Leu Asp Thr Thr Met Arg Arg Leu Ile
1               5                   10                  15
```

<210> SEQ ID NO 76
<211> LENGTH: 15
<212> TYPE: PRT
<213> ORGANISM: Homo sapiens

<400> SEQUENCE: 76

```
Glu Gln Arg Ile Arg Leu Val Val Ser Arg Leu Gly Leu Asp Ser
1               5                   10                  15
```

<210> SEQ ID NO 77
<211> LENGTH: 15
<212> TYPE: PRT
<213> ORGANISM: Homo sapiens

<400> SEQUENCE: 77

```
Ala Lys Thr Gln Ala Ala Leu Val Leu Asp Cys Leu Glu Thr Arg
1               5                   10                  15
```

<210> SEQ ID NO 78
<211> LENGTH: 15
<212> TYPE: PRT
<213> ORGANISM: Homo sapiens

<400> SEQUENCE: 78

```
Lys Val Gln Gly Ile Gly Trp Tyr Leu Asp Glu Lys Asn Leu Ala
1               5                   10                  15
```

<210> SEQ ID NO 79
<211> LENGTH: 15
<212> TYPE: PRT
<213> ORGANISM: Homo sapiens

<400> SEQUENCE: 79

```
Tyr Phe Asn Val Leu Ile Asn Leu Arg Asp Ile Thr Asp Glu Ala
1               5                   10                  15
```

<210> SEQ ID NO 80
<211> LENGTH: 15
<212> TYPE: PRT
<213> ORGANISM: Homo sapiens

<400> SEQUENCE: 80

```
Leu Pro Val Val Gly Ser Gln Leu Val Gly Leu Val Pro Leu Lys
1               5                   10                  15
```

```
<210> SEQ ID NO 81
<211> LENGTH: 15
<212> TYPE: PRT
<213> ORGANISM: Homo sapiens

<400> SEQUENCE: 81

Ile Arg Leu Val Val Ser Arg Leu Gly Leu Asp Ser Leu Cys Pro
1               5                   10                  15

<210> SEQ ID NO 82
<211> LENGTH: 15
<212> TYPE: PRT
<213> ORGANISM: Homo sapiens

<400> SEQUENCE: 82

Glu Leu Ser Leu Pro Val Val Gly Ser Gln Leu Val Gly Leu Val
1               5                   10                  15

<210> SEQ ID NO 83
<211> LENGTH: 15
<212> TYPE: PRT
<213> ORGANISM: Homo sapiens

<400> SEQUENCE: 83

Gly Val Phe Gly Ala Tyr Phe Asn Val Leu Ile Asn Leu Arg Asp
1               5                   10                  15

<210> SEQ ID NO 84
<211> LENGTH: 15
<212> TYPE: PRT
<213> ORGANISM: Homo sapiens

<400> SEQUENCE: 84

Thr Thr Met Arg Arg Leu Ile Pro Pro Phe Arg Glu Ala Ser Ala
1               5                   10                  15

<210> SEQ ID NO 85
<211> LENGTH: 15
<212> TYPE: PRT
<213> ORGANISM: Homo sapiens

<400> SEQUENCE: 85

Glu Glu Glu Gln Arg Ile Arg Leu Val Val Ser Arg Leu Gly Leu
1               5                   10                  15

<210> SEQ ID NO 86
<211> LENGTH: 15
<212> TYPE: PRT
<213> ORGANISM: Homo sapiens

<400> SEQUENCE: 86

Gly Leu Val Pro Leu Lys Ala Leu Leu Asp Ala Ala Ala Phe Tyr
1               5                   10                  15

<210> SEQ ID NO 87
<211> LENGTH: 15
<212> TYPE: PRT
<213> ORGANISM: Homo sapiens

<400> SEQUENCE: 87

Val Leu Ile Asn Leu Arg Asp Ile Thr Asp Glu Ala Phe Lys Asp
1               5                   10                  15

<210> SEQ ID NO 88
```

```
<211> LENGTH: 15
<212> TYPE: PRT
<213> ORGANISM: Homo sapiens

<400> SEQUENCE: 88

Arg Leu Val Val Ser Arg Leu Gly Leu Asp Ser Leu Cys Pro Phe
1               5                   10                  15

<210> SEQ ID NO 89
<211> LENGTH: 15
<212> TYPE: PRT
<213> ORGANISM: Homo sapiens

<400> SEQUENCE: 89

Ser Asn Ile Thr Ile Arg Asn Gln Ile Asn Ala Leu Thr Ser Phe
1               5                   10                  15

<210> SEQ ID NO 90
<211> LENGTH: 15
<212> TYPE: PRT
<213> ORGANISM: Homo sapiens

<400> SEQUENCE: 90

Lys Asn Asn Ile Phe Met Ser Asn Ser Tyr Pro Arg Asp Phe Val
1               5                   10                  15

<210> SEQ ID NO 91
<211> LENGTH: 15
<212> TYPE: PRT
<213> ORGANISM: Homo sapiens

<400> SEQUENCE: 91

Leu Gly Thr Val Leu Arg Asn Leu Lys Leu Ala Arg Lys Leu Met
1               5                   10                  15

<210> SEQ ID NO 92
<211> LENGTH: 15
<212> TYPE: PRT
<213> ORGANISM: Homo sapiens

<400> SEQUENCE: 92

Leu Ile Gln Pro Phe Met Phe Arg Leu Asp Asn Arg Tyr Gln Pro
1               5                   10                  15

<210> SEQ ID NO 93
<211> LENGTH: 15
<212> TYPE: PRT
<213> ORGANISM: Homo sapiens

<400> SEQUENCE: 93

Tyr Leu Pro Leu Val Leu Gly Pro Thr Ala Met Arg Lys Tyr Leu
1               5                   10                  15

<210> SEQ ID NO 94
<211> LENGTH: 15
<212> TYPE: PRT
<213> ORGANISM: Homo sapiens

<400> SEQUENCE: 94

Leu Gly Thr Val Leu Arg Asn Leu Lys Leu Ala Arg Lys Leu Met
1               5                   10                  15

<210> SEQ ID NO 95
<211> LENGTH: 15
<212> TYPE: PRT
```

<213> ORGANISM: Homo sapiens

<400> SEQUENCE: 95

Gln Glu Ala Arg Lys Ile Val Gly Ala Met Val Gln Ile Ile Thr
1               5                   10                  15

<210> SEQ ID NO 96
<211> LENGTH: 15
<212> TYPE: PRT
<213> ORGANISM: Homo sapiens

<400> SEQUENCE: 96

Gln Gln Arg Gln Ala Leu Ala Gln Ile Ser Leu Pro Arg Ile Ile
1               5                   10                  15

<210> SEQ ID NO 97
<211> LENGTH: 15
<212> TYPE: PRT
<213> ORGANISM: Homo sapiens

<400> SEQUENCE: 97

Arg Ser Leu Met Phe Met Gln Trp Gly Gln Leu Leu Asp His Asp
1               5                   10                  15

<210> SEQ ID NO 98
<211> LENGTH: 15
<212> TYPE: PRT
<213> ORGANISM: Homo sapiens

<400> SEQUENCE: 98

Arg Leu Asp Asn Arg Tyr Gln Pro Met Glu Pro Asn Pro Arg Val
1               5                   10                  15

<210> SEQ ID NO 99
<211> LENGTH: 15
<212> TYPE: PRT
<213> ORGANISM: Homo sapiens

<400> SEQUENCE: 99

Glu Leu Leu Ser Tyr Phe Lys Gln Pro Val Ala Ala Thr Arg Thr
1               5                   10                  15

<210> SEQ ID NO 100
<211> LENGTH: 15
<212> TYPE: PRT
<213> ORGANISM: Homo sapiens

<400> SEQUENCE: 100

Gln Leu Gly Thr Val Leu Arg Asn Leu Lys Leu Ala Arg Lys Leu
1               5                   10                  15

<210> SEQ ID NO 101
<211> LENGTH: 5
<212> TYPE: PRT
<213> ORGANISM: Homo sapiens

<400> SEQUENCE: 101

Ser Ser Ser Ser Ser
1               5

<210> SEQ ID NO 102
<211> LENGTH: 5
<212> TYPE: PRT
<213> ORGANISM: Homo sapiens -continued

<400> SEQUENCE: 102

Asp Asp Asp Asp Asp
1               5

<210> SEQ ID NO 103
<211> LENGTH: 448
<212> TYPE: PRT
<213> ORGANISM: Homo sapiens

<400> SEQUENCE: 103

Met Ala Ile Ile Tyr Leu Ile Leu Leu Phe Thr Ala Val Arg Gly Ile
1               5                   10                  15

Lys Glu Glu His Val Ile Ile Gln Ala Glu Phe Tyr Leu Asn Pro Asp
            20                  25                  30

Gln Ser Gly Glu Phe Met Phe Asp Phe Asp Gly Asp Glu Ile Phe His
        35                  40                  45

Val Asp Met Ala Lys Lys Glu Thr Val Trp Arg Leu Glu Glu Phe Gly
    50                  55                  60

Arg Phe Ala Ser Phe Glu Ala Gln Gly Ala Leu Ala Asn Ile Ala Val
65                  70                  75                  80

Asp Lys Ala Asn Leu Glu Ile Met Thr Lys Arg Ser Asn Tyr Thr Pro
                85                  90                  95

Ile Thr Asn Val Pro Pro Glu Val Thr Val Leu Thr Asn Ser Pro Val
            100                 105                 110

Glu Leu Arg Glu Pro Asn Val Leu Ile Cys Phe Ile Asp Lys Phe Thr
        115                 120                 125

Pro Pro Val Val Asn Val Thr Trp Leu Arg Asn Gly Lys Pro Val Thr
    130                 135                 140

Thr Gly Val Ser Glu Thr Val Phe Leu Pro Arg Glu Asp His Leu Phe
145                 150                 155                 160

Arg Lys Phe His Tyr Leu Pro Phe Leu Pro Ser Thr Glu Asp Val Tyr
                165                 170                 175

Asp Cys Arg Val Glu His Trp Gly Leu Asp Glu Pro Leu Leu Lys His
            180                 185                 190

Trp Glu Phe Asp Ala Pro Ser Pro Leu Pro Glu Thr Thr Glu Ser Gly
        195                 200                 205

Gly Gly Gly Gly Asp Lys Thr His Thr Cys Pro Pro Cys Pro Ala Pro
    210                 215                 220

Glu Ala Ala Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser His Glu Asp Pro Glu Val Lys Phe Asn Trp Tyr Val Asp
            260                 265                 270

Gly Val Glu Val His Asn Ala Lys Thr Lys Pro Arg Glu Glu Gln Tyr
        275                 280                 285

Asn Ser Thr Tyr Arg Val Val Ser Val Leu Thr Val Leu His Gln Asp
    290                 295                 300

Trp Leu Asn Gly Lys Glu Tyr Lys Cys Lys Val Ser Asn Lys Ala Leu
305                 310                 315                 320

Pro Ala Pro Ile Glu Lys Thr Ile Ser Lys Ala Lys Gly Gln Pro Arg
                325                 330                 335

Glu Pro Gln Val Tyr Thr Leu Pro Pro Cys Arg Asp Glu Leu Thr Lys
            340                 345                 350

Asn Gln Val Ser Leu Trp Cys Leu Val Lys Gly Phe Tyr Pro Ser Asp
            355                 360                 365

Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Asn His Tyr Thr Gln Lys Ser
            420                 425                 430

Leu Ser Leu Ser Pro Gly Lys Gly Ser Gly Ser Gly Ser Gly Ser Cys
            435                 440                 445

<210> SEQ ID NO 104
<211> LENGTH: 479
<212> TYPE: PRT
<213> ORGANISM: Homo sapiens

<400> SEQUENCE: 104

Met Gly Ser Leu Gln Pro Leu Ala Thr Leu Tyr Leu Leu Gly Met Leu
1               5                   10                  15

Val Ala Ser Ser Leu Gly Gly Asp Leu Ile Ala Glu Val Glu Thr Asp
            20                  25                  30

Lys Ala Thr Val Gly Gly Gly Gly Ser Gly Gly Gly Ser Gly Gly
            35                  40                  45

Ser Gly Asp Thr Gln Pro Arg Phe Leu Glu Gln Ala Lys Cys Glu Cys
        50                  55                  60

His Phe Leu Asn Gly Thr Glu Arg Val Trp Asn Leu Ile Arg Tyr Ile
65                  70                  75                  80

Tyr Asn Gln Glu Glu Tyr Ala Arg Tyr Asn Ser Asp Leu Gly Glu Tyr
                85                  90                  95

Gln Ala Val Thr Glu Leu Gly Arg Pro Asp Ala Glu Tyr Trp Asn Ser
            100                 105                 110

Gln Lys Asp Leu Leu Glu Arg Arg Ala Glu Val Asp Thr Tyr Cys
        115                 120                 125

Arg Tyr Asn Tyr Gly Val Val Glu Ser Phe Thr Val Gln Arg Arg Val
    130                 135                 140

Gln Pro Lys Val Thr Val Tyr Pro Ser Lys Thr Gln Pro Leu Gln His
145                 150                 155                 160

His Asn Leu Leu Val Cys Ser Val Asn Gly Phe Tyr Pro Gly Ser Ile
                165                 170                 175

Glu Val Arg Trp Phe Arg Asn Ser Gln Glu Glu Lys Ala Gly Val Val
            180                 185                 190

Ser Thr Gly Leu Ile Gln Asn Gly Asp Trp Thr Phe Gln Thr Leu Val
        195                 200                 205

Met Leu Glu Thr Val Pro Arg Ser Gly Glu Val Tyr Thr Cys Gln Val
    210                 215                 220

Glu His Pro Ser Met Met Ser Pro Leu Thr Val Gln Trp Ser Ala Arg
225                 230                 235                 240

Ser Glu Ser Ala Gln Ser Lys Ser Gly Gly Gly Gly Gly Asp Lys Thr
                245                 250                 255

His Thr Cys Pro Pro Cys Pro Ala Pro Glu Ala Ala Gly Gly Pro Ser
            260                 265                 270

Val Phe Leu Phe Pro Pro Lys Pro Lys Asp Thr Leu Met Ile Ser Arg
        275                 280                 285

-continued

```
Thr Pro Glu Val Thr Cys Val Val Asp Val Ser His Glu Asp Pro
    290                 295                 300
Glu Val Lys Phe Asn Trp Tyr Val Asp Gly Val Glu Val His Asn Ala
305                 310                 315                 320
Lys Thr Lys Pro Arg Glu Glu Gln Tyr Asn Ser Thr Tyr Arg Val Val
                325                 330                 335
Ser Val Leu Thr Val Leu His Gln Asp Trp Leu Asn Gly Lys Glu Tyr
            340                 345                 350
Lys Cys Lys Val Ser Asn Lys Ala Leu Pro Ala Pro Ile Glu Lys Thr
        355                 360                 365
Ile Ser Lys Ala Lys Gly Gln Pro Arg Glu Pro Gln Val Cys Thr Leu
370                 375                 380
Pro Pro Ser Arg Asp Glu Leu Thr Lys Asn Gln Val Ser Leu Ser Cys
385                 390                 395                 400
Ala Val Lys Gly Phe Tyr Pro Ser Asp Ile Ala Val Glu Trp Glu Ser
                405                 410                 415
Asn Gly Gln Pro Glu Asn Asn Tyr Lys Thr Thr Pro Pro Val Leu Asp
            420                 425                 430
Ser Asp Gly Ser Phe Phe Leu Val Ser Lys Leu Val Asp Lys Ser Arg
        435                 440                 445
Trp Gln Gln Gly Asn Val Phe Ser Cys Ser Val Met His Glu Ala Leu
450                 455                 460
His Asn His Tyr Thr Gln Lys Ser Leu Ser Leu Ser Pro Gly Lys
465                 470                 475

<210> SEQ ID NO 105
<211> LENGTH: 16
<212> TYPE: PRT
<213> ORGANISM: Homo sapiens

<400> SEQUENCE: 105

Leu Ala Glu Ile Glu Thr Asp Lys Ala Thr Ile Gly Phe Glu Val Gln
1               5                   10                  15

<210> SEQ ID NO 106
<211> LENGTH: 15
<212> TYPE: PRT
<213> ORGANISM: Homo sapiens

<400> SEQUENCE: 106

Glu Lys Pro Gln Asp Ile Glu Ala Phe Lys Asn Tyr Thr Leu Asp
1               5                   10                  15

<210> SEQ ID NO 107
<211> LENGTH: 15
<212> TYPE: PRT
<213> ORGANISM: Homo sapiens

<400> SEQUENCE: 107

Val Val Glu Gly Ala Leu His Ala Ala Arg Thr Ala Ser Gln Leu
1               5                   10                  15

<210> SEQ ID NO 108
<211> LENGTH: 15
<212> TYPE: PRT
<213> ORGANISM: Homo sapiens

<400> SEQUENCE: 108

Leu Ile Thr Asn Leu Ser Ser Ala Leu Lys Asp Glu Thr Val Trp
```

```
1               5               10              15

<210> SEQ ID NO 109
<211> LENGTH: 11
<212> TYPE: PRT
<213> ORGANISM: Homo sapiens

<400> SEQUENCE: 109

Ala His His Pro Ile Trp Ala Arg Met Asp Ala
1               5                   10

<210> SEQ ID NO 110
<211> LENGTH: 20
<212> TYPE: PRT
<213> ORGANISM: Homo sapiens

<400> SEQUENCE: 110

Glu Val Gly Trp Tyr Arg Ser Pro Phe Ser Arg Val Val His Leu Tyr
1               5                   10                  15

Arg Asn Gly Lys
            20
```